(12) United States Patent
Bumcrot

(10) Patent No.: US 8,802,639 B2
(45) Date of Patent: Aug. 12, 2014

(54) RNA INTERFERENCE MODULATORS OF HEDGEHOG SIGNALING AND USES THEREOF

(75) Inventor: David A. Bumcrot, Belmont, MA (US)

(73) Assignees: Curis, Inc., Lexington, MA (US); Genentech, Inc., South San Francisco, CA (US)

(*) Notice: Subject to any disclaimer, the term of this patent is extended or adjusted under 35 U.S.C. 154(b) by 1612 days.

(21) Appl. No.: 11/088,691

(22) Filed: Mar. 24, 2005

(65) Prior Publication Data

US 2005/0256076 A1 Nov. 17, 2005

Related U.S. Application Data

(60) Provisional application No. 60/556,661, filed on Mar. 26, 2004.

(51) Int. Cl.
C12N 15/11 (2006.01)

(52) U.S. Cl.
USPC ........................................................ 514/44 A

(58) Field of Classification Search
USPC ........................................ 514/44 A; 536/24.5
See application file for complete search history.

(56) References Cited

U.S. PATENT DOCUMENTS

| | | |
|---|---|---|
| 4,426,330 A | 1/1984 | Sears |
| 4,534,899 A | 8/1985 | Sears |
| 5,013,556 A | 5/1991 | Woodle et al. |
| 5,108,921 A | 4/1992 | Low et al. |
| 5,213,804 A | 5/1993 | Martin et al. |
| 5,227,170 A | 7/1993 | Sullivan |
| 5,264,221 A | 11/1993 | Tagawa et al. |
| 5,354,844 A | 10/1994 | Beug et al. |
| 5,356,633 A | 10/1994 | Woodle et al. |
| 5,395,619 A | 3/1995 | Zalipsky et al. |
| 5,416,016 A | 5/1995 | Low et al. |
| 5,417,978 A | 5/1995 | Tari et al. |
| 5,459,127 A | 10/1995 | Felgner et al. |
| 5,462,854 A | 10/1995 | Coassin et al. |
| 5,469,854 A | 11/1995 | Unger et al. |
| 5,512,295 A | 4/1996 | Kornberg et al. |
| 5,521,291 A | 5/1996 | Curiel et al. |
| 5,527,528 A | 6/1996 | Allen et al. |
| 5,534,259 A | 7/1996 | Zalipsky et al. |
| 5,538,892 A | 7/1996 | Donahoe et al. |
| 5,543,152 A | 8/1996 | Webb et al. |
| 5,543,158 A | 8/1996 | Gref et al. |
| 5,547,932 A | 8/1996 | Curiel et al. |
| 5,556,948 A | 9/1996 | Tagawa et al. |
| 5,580,575 A | 12/1996 | Unger et al. |
| 5,583,020 A | 12/1996 | Sullivan |
| 5,591,721 A | 1/1997 | Agrawal et al. |
| 5,595,756 A | 1/1997 | Bally et al. |
| 5,681,278 A | 10/1997 | Igo et al. |
| 5,759,811 A | 6/1998 | Epstein et al. |
| 5,789,543 A | 8/1998 | Ingham et al. |
| 5,837,538 A | 11/1998 | Scott et al. |
| 5,844,079 A | 12/1998 | Ingham et al. |
| 6,027,882 A | 2/2000 | Scott et al. |
| 6,165,747 A | 12/2000 | Ingham et al. |
| 6,172,200 B1 | 1/2001 | Scott et al. |
| 6,261,786 B1 | 7/2001 | Marigo et al. |
| 6,271,363 B1 | 8/2001 | Ingham et al. |
| 6,384,192 B1 | 5/2002 | Ingham et al. |
| 6,429,354 B1 | 8/2002 | Scott et al. |
| 6,432,970 B2 | 8/2002 | Beachy et al. |
| 6,492,139 B1 * | 12/2002 | Rosenthal et al. ........... 435/69.1 |
| 6,545,005 B1 | 4/2003 | Baxter et al. |
| 6,551,782 B1 | 4/2003 | Scott et al. |
| 6,552,016 B1 | 4/2003 | Baxter et al. |
| 6,576,237 B1 | 6/2003 | Ingham et al. |
| 6,607,913 B1 | 8/2003 | Ingham et al. |
| 6,610,507 B2 | 8/2003 | Scott et al. |
| 6,610,656 B1 | 8/2003 | Ingham et al. |
| 6,613,798 B1 | 9/2003 | Porter |
| 6,630,148 B1 | 10/2003 | Ingham et al. |
| 6,639,051 B2 | 10/2003 | Wang |
| 6,664,075 B2 | 12/2003 | Ingham et al. |
| 6,867,216 B1 * | 3/2005 | Beachy et al. ................ 514/278 |
| 6,884,775 B1 | 4/2005 | Tabin et al. |
| 6,921,646 B2 | 7/2005 | Scott et al. |
| 6,946,257 B1 | 9/2005 | Scott et al. |
| 7,060,450 B1 | 6/2006 | Tabin et al. |
| 7,144,732 B2 | 12/2006 | Ingham et al. |

(Continued)

FOREIGN PATENT DOCUMENTS

| | | |
|---|---|---|
| WO | WO-95/18856 | 7/1995 |
| WO | WO 95/23223 | 8/1995 |

(Continued)

OTHER PUBLICATIONS

Dahmane et al., "Activation of the transcription factor Gli1 and the sonic hedgehog signalling pathway in skin tumors," *Nature, Nature Publishing Group*, London, 389 (23): 876-881 (1997).

McManus et al., "Gene silencing in mammals by small interfering RNAs," *Nature Reviews Genetics*, 3 (10): 737-747 (2002).

Michelson, Alan M., "Running interference for hedgehog signaling," *Science's Stke Electronic Reource!: Signal Transduction Knowledge Environment*, 2003 (192): PE30 (2003).

Ruiz et al., "Gli and Hedgehog in cancer. Tumours, embryos, and stem cells," *Nature Reviews Cancer*, 2 (5): 361-372 (2002).

Ruiz et al., "Hedgehog-Gli1 signaling in brain tumors: Stem cells and paradevelopmental programs in cancer," *Cancer Letters*, 204 (2): 145-157 (2004).

Sanchez, et al., "Inhibition of Prostate Cancer Proliferation by Interference with SONIC HEDGEHOG—GLI1 Signaling," *Proceedings of the National Academy of Sciences of the United States of America*, 101(34): 12561-12566 (2004).

(Continued)

*Primary Examiner* — Jon E Angell
(74) *Attorney, Agent, or Firm* — Ropes & Gray LLP

(57) ABSTRACT

The instant application relates to methods and reagents for modulating the Hedgehog signaling pathway using RNA interference technology (RNAi). The application provides potential targets of the Hedgehog RNAi, methods to identify additional Hedgehog signaling pathway components, methods to inhibit Hedgehog signaling targets using siRNA, and their uses in the treatment of a number of disease conditions.

22 Claims, 55 Drawing Sheets

(56) References Cited

U.S. PATENT DOCUMENTS

| | | | |
|---|---|---|---|
| 7,445,778 | B2 | 11/2008 | Burkly et al. |
| 7,498,304 | B2 | 3/2009 | Kotkow et al. |
| 7,666,676 | B2 | 2/2010 | Lawman et al. |
| 2002/0015702 | A1 | 2/2002 | Burkly et al. |
| 2003/0022819 | A1 | 1/2003 | Ling et al. |
| 2004/0060568 | A1 | 4/2004 | Dudek et al. |
| 2004/0072345 | A1 | 4/2004 | Altaba et al. |
| 2004/0110663 | A1 | 6/2004 | Dudek et al. |
| 2004/0171546 | A1 | 9/2004 | Pepicelli et al. |
| 2004/0259247 | A1* | 12/2004 | Tuschl et al. .......... 435/375 |
| 2005/0002933 | A1 | 1/2005 | Baron et al. |
| 2005/0054568 | A1 | 3/2005 | Ling et al. |
| 2005/0080138 | A1 | 4/2005 | Guicherit et al. |
| 2007/0110698 | A1 | 5/2007 | Wang |

FOREIGN PATENT DOCUMENTS

| | | |
|---|---|---|
| WO | WO-96/17924 | 6/1996 |
| WO | WO 98/21227 A1 | 5/1998 |
| WO | WO 98/35020 | 8/1998 |
| WO | WO 99/10004 A2 | 3/1999 |
| WO | WO 99/20298 | 4/1999 |
| WO | WO 00/15246 | 3/2000 |
| WO | WO 00/18428 | 4/2000 |
| WO | WO 00/25725 | 5/2000 |
| WO | WO 00/41545 | 7/2000 |
| WO | WO 00/74706 | 12/2000 |
| WO | WO 01/19800 | 3/2001 |
| WO | WO 01/26644 | 4/2001 |
| WO | WO-01/68836 | 9/2001 |
| WO | WO 01/74344 | 10/2001 |
| WO | WO-01/75164 | 10/2001 |
| WO | WO-01/77350 | 10/2001 |
| WO | WO 02/30462 | 4/2002 |
| WO | WO 02/80952 A2 | 10/2002 |
| WO | WO 03/011219 | 2/2003 |
| WO | WO-2004/020599 A2 | 3/2004 |

OTHER PUBLICATIONS

Thayer et al., "Hedgehog is an early and late mediator of pancreatic cancer tumorigenesis," Nature, Nature Publishing Group, London, 425 (23): 851-856 (2003).
Apelqvist, A., et al., "Sonic hedgehog directs specialized mesoderm differentiation in the intestine and pancreas," Current Biology, 7:801-804 (1997).
Bale, A.E., "Hedgehog Signaling and Human Disease," Annu. Rev. Genomics Hum. Genet., 3:47-65 (2002).
Bellusci, S., et al., "Involvement of Sonic hedgehog (Shh) in mouse embryonic lung growth and morphogenesis," Development, 124:53-63 (1997).
Berger, C.S., et al., "Chromosomes in Kidney, Ureter, and Bladder Cancer," Cancer Genetics and Cytogenetics, 23:1-24 (1986).
Brown, et al., Am. J. Hum. Genet., 57:859 (1995).
Brown, S.A., et al., "Holoprosencephaly due to mutations in ZIC2, a homologue of Drosophila odd-paired," Nature Genet., 20:180 (1998).
Brummelkamp, T.R., et al., "A System for Stable Expression of Short Interfering RNAs in Mammalian Cells," Science, 296:550-553 (2002).
Cairns, et al., Oncogene, 8:1083-1085 (1992).
Caplen, N.J., et al., "Specific inhibition of gene expression by small double-stranded RNAs in invertebrate and vertebrate systems," Proc. Natl. Acad. Sci., 98:9742-9747 (2001).
Carter, B.S., et al., "Allelic loss of chromosomes 16q and 10q in human prostate cancer," PNAS, 87:8751-8755 (1990).
Chen, J.K., et al., "Synthesis of oligodeoxyribonucleotide N3'→P5' phosphoramidates," Nucleic Acids Res., 23:2661-2668 (1995).
Chen, Y., et al., "Dual Roles for Patched in Sequestering and Transducing Hedgehog," Cell, 87:553-563 (1996).
Chiang, C., et al., "Cyclopia and defective axial patterning in mice lacking Sonic hedgehog gene function," Nature, 383:407-413 (1996).
Cole, F., et al., "Microform Holoprosencephaly in Mice that Lack the Ig Superfamily Member Cdon," Curr. Biol., 13:411-415 (2003).
Dalbagni, et al., Lancet, 342: 469-471 (1993).
De Cat, B., "Developmental roles of the glypicans," Semin. Cell Dev. Biol., 12:117-125 (2001).
Elbashir, S.M., et al., "Duplexes of 21-nucleotides RNAs mediate RNA interference in cultured mammalian cells," Nature, 411:494-498 (2001).
Elbashir, S.M., et al., "Functional anatomy of siRNAs for mediating efficient RNAi in Drosophila melanogaster embryo lysate," EMBO J., 20:6877-6888 (2001).
Fujita, E., et al., "Involvement of Sonic hedgehog in the Cell Growth of LK-2 Cells, Human Lung Squamous Carcinoma Cells," Biochem. Biophys. Res. Commun., 238:658-664 (1997).
Gibas, et al., Cancer Research, 44:1257-1264 (1984).
Gil, et al., Apoptosis, 5:107-114 (2000).
Gomez-Skarmeta and Modolell, Genes Dev., 10:2935-2945 (1996).
Hahn, H., et al., "Mutations of the Human Homolog of Drosophila patched in the Nevoid Basal Cell Carcinoma Syndrome," Cell, 85:841-851 (1996).
Heidenreich, O., et al., "RNase H-independent antisense activity of oligonucleotide N3'→P5' phosphoramidates," Nucleic Acids Res., 25:776-780 (1997).
Hirschbein, et al., Antisense Nucleic Acid Drug Dev., 7:55-61 (1997).
Ho, K.S., et al., "Sonic hedgehog in the nervous system: functions, modifications and mechanisms," Curr. Opin. Neurobiol., 12:57-63 (2002).
Hooper, J.E., et al., "The Drosophila patched Gene Encodes a Putative Membrane Protein Required for Segmental Patterning," Cell, 59:751-765 (1989).
Ingham, P.W., et al., "Hedgehog signaling in animal development: paradigms and principles," Genes Dev., 15:3059-3087 (2001).
Jarov, A., et al., "A dual role for Sonic hedgehog in regulating adhesion and differentiation of neuroepithelial cells," Dev. Biol., 261(2):520-536 (2003).
Jensen, A.M., et al., "Expression of Sonic hedgehog and its putative role as a precursor cell mitogen in the developing mouse retina," Development, 124:363-371 (1997).
Johnson, R.L., et al., Science, 272:1668 (1996).
Levine, E.M., et al., "Sonic Hedgehog Promotes Rod Photoreceptor Differentation in Mammalian Retinal Cells In Vitro," J. Neurosci., 17:6277-6288 (1997).
Li, J., et al., "PTEN, a Putative Protein Tyrosine Phosphatase Gene Mutated in Human Brain, Breast, and Prostate Cancer," Science, 275:1943-1947 (1997).
Lum, L., et al., "Identification of Hedgehog Pathway Components by RNAi in Drosophila Cultured Cells," Science, 299:2039-2045 (2003).
McCaffrey, A.P., et al., "RNA interference in adult mice," Nature, 418:38-39 (2002).
McGarvey, T.W., et al., "PTCH gene mutations in invasive transitional cell carcinoma of the bladder," Oncogene, 17:1167-1172 (1998).
McManus, M.T., et al., "Gene silencing using micro-RNA designed hairpins," RNA, 8:842-850 (2002).
Nakano, Y., et al., "A protein with several possible membrane-spanning domains encoded by the Drosophila segment polarity gene patched," Nature, 341:508-513 (1989).
Nybakken, K., et al., "Hedgehog signal transduction: recent findings," Curr. Opin. Genet. Dev., 12:503-511 (2002).
Nybakken, K., et al., "Heparan sulfate proteoglycan modulation of developmental signaling in Drosophila," Biochim. Biophys. Acta, 1573:280-291 (2002).
Paddison, P.J., et al., "Short hairpin RNAs (shRNAs) induce sequence-specific silencing in mammalian cells," Genes & Dev., 16:948-958 (2002).
Paddison, P.J., et al., "Stable suppression of gene expression by RNAi in mammalian cells," PNAS, 99:1443-1448 (2002).
Paine-Saunders, S., et al., "GPC6, a Novel Member of the Glypican Gene Family, Encodes a Product Structurally Related to GPC4 and is Colocalized with GPC5 on Human Chromosome 13," Genomics, 57:455-458 (1999).

(56) References Cited

OTHER PUBLICATIONS

Pepicelli, C.V., et al., "Sonic hedgehog regulates branching morphogenesis in the mammalian lung," Current Biology, 8:1083-1086 (1998).
Perrimon, N., "Hedgehog and Beyond," Cell, 80:517-520 (1995).
Perrimon, N., "Serpentine Proteins Slither into the Wingless and Hedgehog Fields," Cell, 86:513-516 (1996).
Podlasek, C.A., et al., "Prostate Development Requires Sonic Hedgehog Expressed by the Urogenital Sinus Epithelium," Developmental Biology, 209:28-39 (1999).
Price, M.A., et al., "Proteolysis of the Hedgehog Signaling Effector Cubitus interruptus Requires Phosphorylation by Glycogen Synthase Kinase 3 and Casein Kinase 1," Cell, 108:823-835 (2002).
Ramalho-Santos, M., et al., "Hedgehog signals regulate multiple aspects of gastrointestinal development," Development, 127:2763-2772 (2000).
Sato, N., et al., "Induction of the hair growth phase in postnatal mice by localized transient expression of Sonic hedgehog," J. Clin. Invest., 104:855-864 (1999).
Smeets, W., et al., "Chromosomal Analysis of Bladder Cancer. III. Nonrandom Alterations," Cancer Genetics and Cytogenetics, 29:29-41 (1987).
Song, H.H., et al., "The role of glypicans in mammalian development," Biochim. Biophys. Acta, 1573:241-246 (2002).
Sui, G., et al., "A DNA vector-based RNAi technology to suppress gene expression in mammalian cells," PNAS, 8:5515-5520 (2002).
Taipale, J., et al., "The Hedgehog and Wnt signaling pathways in cancer," Nature, 411:349-354 (2001).
Tran, N., et al., "Expressing functional siRNAs in mammalian cells using convergent transcription," BMC Biotechnology, 3:21 (2003).
Watanabe, K., et al., "K-Glypican: A Novel GPI-anchored Heparan Sulfate Proteoglycan That Is Highly Expressed in Developing Brain and Kidney," J. Cell. Biol., 130:1207-1218 (1995).
Wilkin, et al., Acta Endocrinology, 94:284-288 (1980).
Wilson, et al., J. Mol. Recog., 7:89-98 (1994).
Yu, J.Y., et al., "RNA interference by expression of short-interfering RNAs and hairpin RNAs in mammalian cells," Proc. Natl. Acad. Sci. USA, 99:6047-6052 (2002).
U.S. Appl. No. 09/977,864, filed Oct. 15, 2001, Dudek et al.
U.S. Appl. No. 10/652,298, filed Aug. 29, 2003, Dudek et al.
U.S. Appl. No. 10/652,686, filed Aug. 29, 2003, Kotkow et al.
U.S. Appl. No. 12/380,583, filed Feb. 27, 2009, Ling et al.
Bian et al., "Sonic hedgehog-Gli1 Pathway in Colorectal Adenocarcinomas," World J. Gastroenterol. vol. 13(11), pp. 1659-1665 (2007).
Chatel et al., "Hedgehog signaling pathway is inactive in colorectal cancer cell lines," Int. J. Cancer, vol. 121, pp. 2622-2627 (2007).
Cherrington, J. M. et al. New paradigms for the treatment of cancer: the role of anti-angiogenesis agents. Adv. Cancer Res. 79, 1-38 (2000).
Feng et al., "Overexpression of Hedgehog Signaling Molecules and Its Involvement in the Proliferation of Endometrial Carcinoma Cells", Human Cancer Biology, vol. 13, pp. 1389-1398 (2007).
Huang et al., "Activation of the hedgehog pathway in human hepatocellular carcinomas", Carcinogenesis, vol. 27(7), pp. 1334-1340 (2006).
Reifenberger, J. et al. Missense Mutations in SMOH in Sporadic Basal Cell Carcinomas of the Skin and Primitive Neuroectodermal Tumors of the Central Nervous System. Cancer Res. 58, 1798-1803 (1998).
Ruiz I. Altaba, A: "Gli proteins and Hedgehog signaling: development and cancer", Trends in Genetics, Elsevier Science Publishers B.V. Amsterdam, NL, vol. 15, No. 10, pp. 418-425 (1999).
Schulz et al., Understanding urothelial carcinoma through cancer pathways. Int. J. Cancer. vol. 119 pp. 1513-1518 (2006).
Sheng et al., Activation of the hedgehog pathway in advanced prostate cancer. Molecular Cancer. vol. 3, No. 29 pp. 1-13 (2004).
Thievessen et al., "Hedgehog Signaling in Normal Urothelial Cells and in Urothelial Carcinoma Cell Lines", Journal of Cellular Physiology, vol. 230, pp. 372-377 (2005).
Unwin et al., "Urological malignancies and the proteomic-genomic interface", Electrophoresis, vol. 20. pp. 3629-3637 (1999).
Wang et al., "Shifting paradigms in Hedgehog signaling", Current Opinion in Cell Biology, vol. 19, pp. 159-165 (2007).
Watkins et al., "Hedgehog signalling within airway epithelial progenitors and in small-cell lung cancer", Nature, vol. 422, pp. 313-317 (2003).
Weiner, Louis M., "An Overview of Monoclonal Antibody Therapy of Cancer", Seminiars in Oncology, vol. 25:4, Suppl. 12, pp. 41-50 (Aug. 1999).
Welt et al., "Antibodies in the Therapy of Colon Cancer", Seminars in Oncology, 26(6): pp. 683-690 (1999).
Xie, J. et al. Activating Smoothened mutations in sporadic basal-cell carcinoma. Nature 391, 90-92 (1998).
Yauch et al., "A paracrine requirement for hedgehog signalling in cancer"; available online Aug. 27, 2008 in advance of publication; doi:10.1038/nature07275 (2008).
Yuan et al., "Frequent requirement of hedgehog signaling in non-small cell lung carcinoma", Oncogene, vol. 26, pp. 1046-1055 (2007).

* cited by examiner

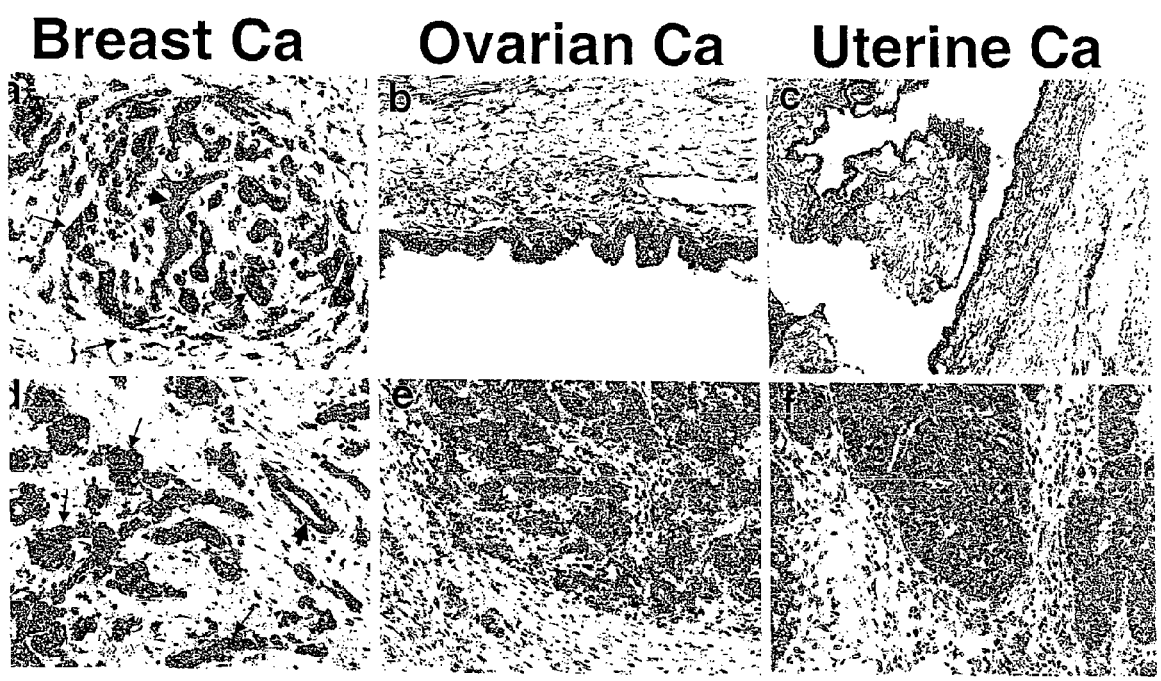

Figure55 Hedgehog expression in human cancers: (a, d) Hedgehog immunoreactivity in biopsy material taken from human breast ductal adenocarcinomas. Note the stronger immunoreactivity present on cancerous epithelium (arrows) than on the adjacent normal ductal epithelium (arrowhead) demonstrating elevated Hh levels in cancerous tissues. (b, e) Hedgehog staining in two forms of ovarian cancer, including a well differentiated borderline serous adenocarcinoma (b), and a poorly differentiated adenocarcinoma (e). (c, f) Hedgehog immunoreactivity on samples of uterine cancer demonstrating expression on both well differentiated (c), and poorly differentiated, highly invasive cancers (f).

SEQUENCE LISTING

```
<160> NUMBER OF SEQ ID NOS: 12

<210> SEQ ID NO 1
<211> LENGTH: 26
<212> TYPE: PRT
<213> ORGANISM: Artificial Sequence
<220> FEATURE:
<223> OTHER INFORMATION: Internalization polypeptide

<400> SEQUENCE: 1

Cys Phe Ile Thr Lys Ala Leu Gly Ile Ser Tyr Gly Arg Lys Lys Arg
1               5                   10                  15

Arg Gln Arg Arg Arg Pro Pro Gln Gly Ser
            20                  25

<210> SEQ ID NO 2
<211> LENGTH: 12
<212> TYPE: PRT
<213> ORGANISM: Artificial Sequence
<220> FEATURE:
<223> OTHER INFORMATION: EGF (epidermal growth factor)-derived
      internalization polypeptide

<400> SEQUENCE: 2

Cys Met His Ile Glu Ser Leu Asp Ser Tyr Thr Cys
1               5                   10

<210> SEQ ID NO 3
```

```
<211> LENGTH: 12
<212> TYPE: PRT
<213> ORGANISM: Artificial Sequence
<220> FEATURE:
<223> OTHER INFORMATION: EGF (epidermal growth factor)-derived
      internalization polypeptide

<400> SEQUENCE: 3

Cys Met Tyr Ile Glu Ala Leu Asp Lys Tyr Ala Cys
 1               5                  10

<210> SEQ ID NO 4
<211> LENGTH: 8
<212> TYPE: PRT
<213> ORGANISM: Artificial Sequence
<220> FEATURE:
<223> OTHER INFORMATION: peptide substrate for N-myristoyl transferase

<400> SEQUENCE: 4

Gly Asn Ala Ala Ala Ala Arg Arg
 1               5

<210> SEQ ID NO 5
<211> LENGTH: 21
<212> TYPE: RNA
<213> ORGANISM: Artificial Sequence
<220> FEATURE:
<223> OTHER INFORMATION: potential siRNA antagonists for human Shh

<400> SEQUENCE: 5
cgagaugucu gcugcuaguc c                                              21

<210> SEQ ID NO 6
<211> LENGTH: 21
<212> TYPE: RNA
<213> ORGANISM: Artificial Sequence
<220> FEATURE:
<223> OTHER INFORMATION: potential siRNA antagonists for human Shh

<400> SEQUENCE: 6
acuagcagca gacaucucgc c                                              21

<210> SEQ ID NO 7
<211> LENGTH: 21
<212> TYPE: RNA
<213> ORGANISM: Artificial Sequence
<220> FEATURE:
<223> OTHER INFORMATION: potential siRNA antagonists for human Shh

<400> SEQUENCE: 7
cagaguagcc cuaaccgcuc c                                              21

<210> SEQ ID NO 8
<211> LENGTH: 21
<212> TYPE: RNA
<213> ORGANISM: Artificial Sequence
<220> FEATURE:
<223> OTHER INFORMATION: potential siRNA antagonists for human Shh

<400> SEQUENCE: 8
agcgguuagg gcuacucugc c                                              21

<210> SEQ ID NO 9
<211> LENGTH: 21
<212> TYPE: RNA
<213> ORGANISM: Artificial Sequence
<220> FEATURE:
```

```
<223> OTHER INFORMATION: potential siRNA antagonists for human Shh

<400> SEQUENCE: 9
cggucaaguc cagcugaagc c                                              21

<210> SEQ ID NO 10
<211> LENGTH: 21
<212> TYPE: RNA
<213> ORGANISM: Artificial Sequence
<220> FEATURE:
<223> OTHER INFORMATION: oligomer for tagged random hexamer
      amplification

<400> SEQUENCE: 10
cuucagcugg acuugaccgc c                                              21

<210> SEQ ID NO 11
<211> LENGTH: 52
<212> TYPE: DNA
<213> ORGANISM: Artificial Sequence
<220> FEATURE:
<223> OTHER INFORMATION: short hairpin DNA oligo for siRNA synthesis

<400> SEQUENCE: 11
cgagatgtct gctgctagtt tcaagagaac tagcagcaga catctcgttt tg            52

<210> SEQ ID NO 12
<211> LENGTH: 57
<212> TYPE: DNA
<213> ORGANISM: Artificial Sequence
<220> FEATURE:
<223> OTHER INFORMATION: short hairpin DNA oligo for siRNA synthesis

<400> SEQUENCE: 12
gatccaaaaa cgagatgtct gctgctagtt ctcttgaaac tagcagcaga catctcg       57
```

RNA INTERFERENCE MODULATORS OF HEDGEHOG SIGNALING AND USES THEREOF

RELATED APPLICATIONS

This application claims the benefit of the filing date of U.S. Application Ser. No. 60/556,661, filed on Mar. 26, 2004. The entire teachings of the referenced application are incorporated by reference herein.

SEQUENCE LISTING

The instant application contains a Sequence Listing which has been submitted via EFS-Web and is hereby incorporated by reference in its entirety. Said ASCII copy, created on Dec. 23, 2013, is named CIBTP01152_Seq.txt, and is 2,987 bytes in size.

BACKGROUND OF THE INVENTION

Pattern formation is the activity by which embryonic cells form ordered spatial arrangements of differentiated tissues. The physical complexity of higher organisms arises during embryogenesis through the interplay of cell-intrinsic lineage and cell-extrinsic signaling. Inductive interactions are essential to embryonic patterning in vertebrate development from the earliest establishment of the body plan, to the patterning of the organ systems, to the generation of diverse cell types during tissue differentiation (Davidson, E., (1990) *Development* 108: 365-389; Gurdon, J. B., (1992) *Cell* 68: 185-199; Jessell, T. M. et al., (1992) *Cell* 68: 257-270). However, the generation of complexity and the refinement of cellular identity and behavior that begin in embryogenesis continues throughout adulthood. Cell-intrinsic and cell-extrinsic signaling and interactions continue to influence cell proliferation, differentiation, migration, and survival during adult development.

Members of the Hedgehog family of signaling molecules mediate many important short- and long-range patterning processes during invertebrate and vertebrate embryonic, fetal, and adult development. In the fly, a single hedgehog gene regulates segmental and imaginal disc patterning. In contrast, in vertebrates, a hedgehog gene family is involved in the control proliferation, differentiation, migration, and survival of cells and tissues derived from all three germ layers. By way of non-limiting example, hedgehog signaling is involved in left-right asymmetry, CNS development, somites and limb patterning, chondrogenesis and skeletogenesis, and spermatogenesis.

The first hedgehog gene was identified by a genetic screen in the fruit fly *Drosophila melanogaster* (Nüsslein-Volhard, C. and Wieschaus, E. (1980) *Nature* 287, 795-801). This screen identified a number of mutations affecting embryonic and larval development. In 1992 and 1993, the molecular nature of the *Drosophila* hedgehog (hh) gene was reported (C. F., Lee et al. (1992) *Cell* 71, 33-50), and since then, several hedgehog homologues have been isolated from various vertebrate species. While only one hedgehog gene has been found in *Drosophila* and other invertebrates, multiple Hedgehog genes are present in vertebrates.

The vertebrate family of hedgehog genes includes at least four members, e.g., paralogs of the single *Drosophila* hedgehog gene. Exemplary hedgehog genes and proteins are described in PCT publications WO 95/18856 and WO 96/17924. Three of these members, herein referred to as Desert hedgehog (Dhh), Sonic hedgehog (Shh) and Indian hedgehog (Ihh), apparently exist in all vertebrates, including fish, birds, and mammals. A fourth member, herein referred to as tiggie-winkle hedgehog (Thh), appears specific to fish. Desert hedgehog (Dhh) is expressed principally in the testes, both in mouse embryonic development and in the adult rodent and human; Indian hedgehog (Ihh) is involved in bone development during embryogenesis and in bone formation in the adult; and Shh, which, is involved in multiple embryonic and adult cell types derived from all three lineages. Given the critical roles of hedgehog polypeptides and hedgehog signaling through embryonic and adult development, as well as the role of aberrant hedgehog signaling in a variety of disease states, there exists a substantial need for improved methods and compositions for modulating hedgehog signaling.

The various Hedgehog proteins consist of a signal peptide, a highly conserved N-terminal region, and a more divergent C-terminal domain. In addition to signal sequence cleavage in the secretory pathway (Lee, J. J. et al. (1992) *Cell* 71:33-50; Tabata, T. et al. (1992) *Genes Dev.* 2635-2645; Chang, D. E. et al. (1994) *Development* 120:3339-3353), Hedgehog precursor proteins undergo an internal autoproteolytic cleavage which depends on conserved sequences in the C-terminal portion (Lee et al. (1994) *Science* 266:1528-1537; Porter et al. (1995) *Nature* 374:363-366). This autocleavage leads to a 19 kD N-terminal peptide and a C-terminal peptide of 26-28 kD (Lee et al. (1992) supra; Tabata et al. (1992) supra; Chang et al. (1994) supra; Lee et al. (1994) supra; Bumcrot, D. A., et al. (1995) *Mol. Cell. Biol.* 15:2294-2303; Porter et al. (1995) supra; Ekker, S. C. et al. (1995) *Curr. Biol.* 5:944-955; Lai, C. J. et al. (1995) *Development* 121:2349-2360). The N-terminal peptide stays tightly associated with the surface of cells in which it was synthesized, while the C-terminal peptide is freely diffusible both in vitro and in vivo (Porter et al. (1995) *Nature* 374:363; Lee et al. (1994) supra; Bumcrot et al. (1995) supra; Marti, E. et al. (1995) *Development* 121:2537-2547; Roelink, H. et al. (1995) *Cell* 81:445-455). Interestingly, cell surface retention of the N-terminal peptide is dependent on autocleavage, as a truncated form of HH encoded by an RNA which terminates precisely at the normal position of internal cleavage is diffusible in vitro (Porter et al. (1995) supra) and in vivo (Porter, J. A. et al. (1996) *Cell* 86, 21-34). Biochemical studies have shown that the autoproteolytic cleavage of the HH precursor protein proceeds through an internal thioester intermediate that subsequently is cleaved in a nucleophilic substitution. It is this N-terminal peptide which is both necessary and sufficient for short- and long-range Hedgehog signaling activities in *Drosophila* and vertebrates (Porter et al. (1995) supra; Ekker et al. (1995) supra; Lai et al. (1995) supra; Roelink, H. et al. (1995) *Cell* 81:445-455; Porter et al. (1996) supra; Fietz, M. J. et al. (1995) *Curr. Biol.* 5:643-651; Fan, C.-M. et al. (1995) *Cell* 81:457-465; Marti, E., et al. (1995) *Nature* 375:322-325; Lopez-Martinez et al. (1995) *Curr. Biol* 5:791-795; Ekker, S. C. et al. (1995) *Developement* 121:2337-2347; Forbes, A. J. et al. (1996) *Development* 122: 1125-1135).

As outlined briefly above and as further detailed herein, hedgehog proteins and hedgehog signaling play critical roles in modulating proliferation, differentiation, migration, and survival of numerous cell types throughout embryonic and adult development. Furthermore, aberrant hedgehog signaling (e.g., mutations in components of the hedgehog signaling pathway, misexpression of components of the hedgehog signaling pathway, etc.) has been implicated in numerous disease states.

Numerous HH signaling components have been identified to date. Mutations in many of these HH signaling components have been associated with various disease conditions such as cancer. Thus, it is desirable to modulate the function of the HH signaling pathway, by, for example, modulating the activity and/or expression of individual member proteins involved in HH signaling. However, regulating the expression of targeted genes that are implicated in important biological pathways is a major challenge of modern medicine. While overexpression of an exogenously introduced transgene in a eukaryotic cell is relatively straightforward, targeted inhibition of specific endogenous genes has been more difficult to achieve. Traditional approaches for suppressing gene expression, including site-directed gene disruption, antisense RNA or co-suppress or injection, require complex genetic manipulations or heavy dosages of suppressors that often exceed the toxicity tolerance level of the host cell.

SUMMARY OF THE INVENTION

The present invention contemplates methods and reagents for antagonizing hedgehog signaling using RNA interference (RNAi). Antagonism of hedgehog signaling can be used to decrease or inhibit at least one of undesirable proliferation, growth, differentiation, or survival of cells. Such undesirable proliferation, growth, differentiation, or survival of cells may be observed in conditions including many forms of cancer.

In certain aspects, the present invention makes available methods and reagents for inhibiting undesirable growth states that occur in cells with an active hedgehog (HH) signaling pathway. In one embodiment, the subject methods may be used to inhibit unwanted cell proliferation by determining whether cells overexpress a gli gene, and contacting cells that overexpress a gli gene with an effective amount of a hedgehog antagonist. In preferred embodiments, the unwanted cell proliferation is cancer or benign prostatic hyperplasia. Another aspect of the present invention makes available methods for determining a treatment protocol comprising obtaining a tissue sample from a patient, and determining levels of gli gene expression in said sample, wherein overexpression of a gli gene indicates that treatment with a hedgehog antagonist is appropriate.

In other preferred embodiments, hedgehog RNAi antagonists of the invention are siRNA, either transcribed from a DNA vector encoding a short hairpin (stem-loop) siRNA, a synthetic siRNA, or longer dsRNA which can be further processed to shorter siRNA (such as 21-23 nucleotides).

In certain embodiments, the RNAi antagonists of the instant invention are contemplated to be used with other non-RNAi HH antagonists selected from a small molecule of less than 2000 daltons, a hedgehog antibody, a patched antibody, a smoothened antibody, a mutant hedgehog protein, an antisense nucleic acid, and a ribozyme. In particularly preferred embodiments, these non-RNAi hedgehog antagonists are selected from one of formulae I through XXV as described in co-pending U.S. Ser. No. 10/652,298, incorporated herein by reference. In particularly preferred embodiments, the non-RNAi hedgehog antagonist is selected from cyclopamine, compound A, tomatidine, jervine, AY9944, triparanol, compound B, and functionally effective derivatives thereof as described in U.S. Ser. No. 10/652,298. In yet another preferred embodiment, the non-RNAi hedgehog antagonist is a hedgehog antibody selected from a polyclonal antibody or a monoclonal antibody. Exemplary monoclonal antibodies are specifically immunoreactive with a vertebrate hedgehog polypeptide. In a preferred embodiment, such specifically immunoreactive monoclonal antibodies do not substantially cross react with either an invertebrate hedgehog polypeptide, or with other non-hedgehog polypeptides. Exemplary hedgehog monoclonal antibodies for use as hedgehog antagonists in the subject methods include 5E1, and antibodies which recognize the same epitope as 5E1. 5E1 was deposited with the ATCC on Aug. 13, 2002. In yet another aspect, the invention provides therapeutic compositions of hedgehog RNAi antagonists for use in the subject methods. These therapeutic compositions include, but are not limited to, hedgehog RNAi antagonists alone, or used in combination with any one or more of the other non-RNAi HH antagonists, such as hedgehog monoclonal antibodies and hedgehog polyclonal antibodies. The present invention further contemplates therapeutic compositions comprising combinations of more than one hedgehog RNAi antagonist formulated with a pharmaceutically acceptable excipient or carrier. Exemplary therapeutic compositions comprise combinations of two or more hedgehog RNAi antagonists formulated with a pharmaceutically acceptable excipient or carrier. Further exemplary compositions comprise combinations of one or more hedgehog RNAi antagonists, one or more hedgehog non-RNAi antagonists (e.g., small organic molecules, antibodies, etc.), and a pharmaceutically acceptable excipient or carrier.

In still another aspect, the present invention makes available methods and reagents for inhibiting at least one of undesirable proliferation, growth, differentiation or survival of a cell with an active hedgehog signaling pathway. In one embodiment, the subject methods may be used to inhibit at least one of unwanted cell proliferation, growth, differentiation or survival by determining whether cells overexpress a gli gene, and contacting cells that overexpress a gli gene with an effective amount of a hedgehog RNAi antagonist. In still another embodiment, the subject methods may be used to inhibit at least one of unwanted cell proliferation, growth, differentiation or survival by determining whether cells overexpress a hedgehog gene, and contacting cells that overexpress a hedgehog gene with an effective amount of a hedgehog RNAi antagonist. In preferred embodiments, the unwanted cell proliferation, growth, differentiation or survival is cancer or benign prostatic hyperplasia.

Exemplary forms of cancer which may be treated by the subject methods include, but are not limited to, prostate cancer, bladder cancer, lung cancer (including either small cell or non-small cell cancer), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer. Additional exemplary forms of cancer which may be treated by the subject methods include, but are not limited to, cancer of skeletal or smooth muscle, stomach cancer, cancer of the small intestine, cancer of the salivary gland, anal cancer, rectal cancer, thyroid cancer, parathyroid cancer, pituitary cancer, and nasopharyngeal cancer. Further exemplary forms of cancer which can be treated with the hedgehog antagonists of the present invention include cancers comprising hedgehog expressing cells. Still further exemplary forms of cancer which can be treated with the hedgehog RNAi antagonists of the present invention include cancers comprising gli expressing cells. In certain such embodiments, the cancer is not characterized by a mutation in patched-1. The invention contemplates that the hedgehog RNAi antagonists of the present invention can be used alone, or can be administered as part of an overall treatment regimen including other hedgehog therapeutics and/or other traditional or non-traditional therapies.

The present invention further contemplates methods for determining the appropriate treatment regimen for a patient with cancer. Without being bound by any particular theory, cancers which express a hedgehog gene or a gli gene, or which overexpress a hedgehog gene or a gli gene in comparison to non-cancerous cells of the same tissue type, may be more amenable to treatment with the hedgehog RNAi antagonists of the present invention. Accordingly, methods of determining the expression of a hedgehog gene or a gli gene can be used to determine whether treatment with a hedgehog RNAi antagonist is appropriate (i.e., is likely to be effective).

In another aspect, the present invention provides for the use of one or more hedgehog RNAi antagonists in the manufacture of a medicament for treating cancer in a patient.

In another aspect, the present invention provides for the use of one or more hedgehog RNAi antagonists in the manufacture of a medicament for decreasing unwanted growth, proliferation, or survival of a cell.

The invention contemplates the use of any combinations of hedgehog antagonist regardless of the mechanism of action of that antagonist. Exemplary hedgehog antagonists include, but are not limited to, polypeptides, antisense oligonucleotides, antibodies, RNAi constructs, small molecules, ribozymes, and the like.

A further aspect of the invention provides methods for stimulating surfactant production in a lung cell comprising contacting said cell with an amount of hedgehog RNAi antagonist effective to stimulate surfactant production. Another aspect of the invention provides methods for stimulating lamellated body formation in a lung cell comprising contacting said cell with an amount of hedgehog RNAi antagonist effective to stimulate lamellated body formation. In preferred embodiments, the lung cell is present in the lung tissue of a premature infant.

Thus, one aspect of the invention provides a method of inhibiting at least one of unwanted growth, proliferation or survival of a cell, comprising contacting said cell with an effective amount of a hedgehog RNAi antagonist against a target sequence of the hedgehog pathway; said target sequence is a positive regulator of the hedgehog pathway, wherein contacting said cell with said hedgehog RNAi antagonist decreases at least one of cell growth, proliferation or survival.

In one embodiment, the method further comprising determining whether said cell expresses a gli gene, and contacting said cell which expresses a gli gene, if any, with an effective amount of a hedgehog RNAi antagonist against a target sequence of the hedgehog pathway.

In one embodiment, said gli gene is gli-1.

In one embodiment, said unwanted cell proliferation is cancer.

In one embodiment, said unwanted cell proliferation is benign hyperplasia.

In one embodiment, said cancer is urogenital cancer.

In one embodiment, said cancer is cancer of the neuronal system including malignant glioma, meningioma, medulloblastoma, neuroectodermal tumor, and ependymoma.

In one embodiment, said cancer is associated with one or more of lung, prostate, breast, ovary, uterus, muscle, bladder, colon, kidney, pancreas, and liver tissues.

In one embodiment, said form of cancer associated with breast tissue is selected from inferior ductal carcinoma, inferior lobular carcinoma, intraductal carcinoma, medullary carcinoma and tubular carcinoma.

In one embodiment, said cancer associated with lung tissue is selected from adenocarcinoma, broncho-alveolar adenocarcinoma and small cell carcinoma.

In one embodiment, said cancer associated with the prostate is adenocarcinoma.

In one embodiment, said unwanted cell proliferation is unwanted angiogenesis.

In one embodiment, said hedgehog antagonist is used to decrease unwanted angiogenesis Unwanted angiogenesis may occurs in any of the following: tumor growth, tumor metastases, or abnormal growths by endothelial cells, including neovascular disease, age-related macular degeneration, diabetic retinopathy, retinopathy of prematurity, corneal graft rejection, neovascular glaucoma, retrolental fibroplasia, epidemic keratoconjunctivitis, Vitamin A deficiency, contact lens overwear, atopic keratitis, superior limbic keratitis, pterygium keratitis sicca, Sjogren's syndrome, acne rosacea, phylctenulosis, syphilis, Mycobacteria infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, mariginal keratolysis, rheumatoid arthritis, systemic lupus, polyarteritis, trauma, Wegener's granulomatosis, sarcoidosis, scleritis, Stevens-Johnson syndrome, pemphigoid radial keratotomy, corneal graph rejection, rheumatoid arthritis, osteoarthritis chronic inflammation (e.g., ulcerative colitis or Crohn's disease), hemangioma, Osler-Weber-Rendu disease, and hereditary hemorrhagic telangiectasia.

In one embodiment, said unwanted angiogenesis occurs in normal physiological processes including wound healing, ovulation, and implantation of the blastula after fertilization.

In one embodiment, said unwanted growth, proliferation or survival of said cell occurs in normal hair growth, in trichosis, hypertrichosis, hirsutism, or folliculitis including folliculitis decalvans, folliculitis ulerythematosa reticulata, keloid folliculitis, and pseudofolliculitis.

In one embodiment, said unwanted cell proliferation is benign prostatic hyperplasia.

In one embodiment, said hedgehog RNAi antagonist is used to modulate proliferation, differentiation, or survival of uncommitted stem cells in culture. For example, the hedgehog RNAi antagonist can be used to modulate the differentiation of stem cells into terminally differentiated neuronal cells for use in intracerebral grafting. In one embodiment, said terminally differentiated neuronal cells include glial cells, schwann cells, chromaffin cells, cholinergic sympathetic or parasympathetic neurons, and peptidergic and serotonergic neurons. In one embodiment, hedgehog RNAi antagonist is used in combination with other neurotrophic factors that more particularly enhance a particular differentiation fate of said uncommitted stem cells.

A related aspect of the invention provides a method of stimulating at least one of desired growth, proliferation, differentiation, or survival of a cell, comprising contacting said cell with an effective amount of a hedgehog RNAi antagonist against a target sequence of the hedgehog pathway; said target sequence is a negative regulator of the hedgehog pathway, wherein contacting said cell with said hedgehog RNAi antagonist increases at least one of cell growth, proliferation, differentiation, or survival.

In one embodiment, said desired growth, proliferation, differentiation, or survival occurs in neurological conditions deriving from: (i) acute, subacute, or chronic injury to the nervous system, including traumatic injury, chemical injury, vascular injury and deficits, ischemia resulting from stroke, infectious/inflammatory and tumor-induced injury; (ii) aging of the nervous system including Alzheimer's disease; (iii) chronic neurodegenerative diseases of the nervous system, including Parkinson's disease, Huntington's chorea, amyotrophic lateral sclerosis and spinocerebellar degenerations; and (iv) chronic immunological diseases of the nervous system or affecting the nervous system, including multiple sclerosis.

In one embodiment, said desired growth, proliferation, differentiation, or survival occurs in chondrogenesis and/or osteogenesis.

In one embodiment, said chondrogenesis and/or osteogenesis occurs in a therapeutic intervention in the treatment of cartilage of a diarthroidal joint or a tempomandibular joint, or in cartilage transplantation and prosthetic device therapies.

In one embodiment, said chondrogenesis and/or osteogenesis occurs in regimen for the generation of bone (osteogenesis) at a site in the animal where such skeletal tissue is deficient.

In one embodiment, said desired growth, proliferation, differentiation, or survival occurs in hair regeneration or regrowth.

In one embodiment, said hair regeneration or regrowth occurs after chemo-therapy or radio-therapy.

In one embodiment, the RNAi antagonist is an siRNA antagonist.

In one embodiment, said siRNA antagonist is an siRNA formed after transcription from a plasmid (RNAi expression vector) or exogenous synthesis.

In one embodiment, said siRNA is a short hairpin siRNA formed after transcription from a single promoter of said plasmid (RNAi expression vector).

In one embodiment, said siRNA is a short dsRNA formed after transcription from two flanking convergent promoters on said plasmid (RNAi expression vector).

In one embodiment, said siRNA is around 19-30 nucleotides in length.

In one embodiment, said siRNA is 21-23 nucleotides in length.

In one embodiment, said siRNA is a fragment generated by nuclease dicing of longer double-stranded RNAs at least 25, 50, 100, 200, 300, 400, or 400-800 bases in length.

In one embodiment, said siRNA is double stranded, and includes short overhang(s) at one or both ends.

In one embodiment, said short overhang is 1-6 nucleotides in length at the 3' end, 2 to 4 nucleotides in length at the 3' end, or 1-3 nucleotides in length at the 3' end.

In one embodiment, one strand of said siRNA has a 3' overhang, and the other strand is blunt-ended, or also has an overhang of the same or different length.

In one embodiment, said 3' overhang is stabilized against degradation.

In one embodiment, said 3' overhang is stabilized against degradation by including purine nucleotides adenosine or guanosine.

In one embodiment, said 3' overhang is stabilized against degradation by substituting pyrimidine nucleotides by modified analogues, e.g., substitution of uridine nucleotide 3' overhangs by 2'-deoxythymidine.

In one embodiment, said siRNA is chemically synthesized.

In one embodiment, said RNAi comprise either long stretches of double stranded RNA identical or substantially identical to said target nucleic acid sequence, or short stretches of double stranded RNA identical to substantially identical to only a region of said target nucleic acid sequence.

In one embodiment, said target sequence is a positive HH signaling component listed in Table X, or a negative HH signaling component listed in Table Y.

In one embodiment, said target sequence is a human sequence.

In one embodiment, said target sequence is a non-human sequence.

In one embodiment, said target sequence is a homolog of any one of the sequences listed in Table X or Y, but is not itself listed in Table X or Y.

In one embodiment, said RNAi antagonist is specific for one member of several homologs of the same HH signaling component.

In one embodiment, said HH signaling component is a mammalian hedgehog, and said RNAi antagonist is specific for Shh.

In one embodiment, said RNAi antagonist is at least 1.5-fold, 2-fold, 3-fold, 5-fold, 10-fold, 100-fold, or 1000-fold more selective for one member over all other members of several homologs of the same HH signaling component.

In one embodiment, said RNAi antagonist is specific for the HH signaling pathway and does not significantly affect other cell signaling pathways.

In one embodiment, said other cell signaling pathway is a wingless pathway.

Another aspect of the invention provides a method of stimulating surfactant production in a lung cell comprising contacting said cell with an amount of hedgehog RNAi antagonist effective to stimulate surfactant production.

Another aspect of the invention provides a method of stimulating lamellated body formation in a lung cell comprising contacting said cell with an amount of hedgehog RNAi antagonist effective to stimulate lamellated body formation.

In one embodiment, said lung cell is present in the lung tissue of a premature infant.

Another aspect of the invention provides a method for treating a tumor in a patient, comprising administering to said patient an amount of a hedgehog RNAi antagonist sufficient to decrease at least one of the growth, proliferation or survival of the tumor, wherein the tumor expresses at least one of a hedgehog gene or a gli gene.

In one embodiment, said hedgehog RNAi antagonist is administered as part of a cancer treatment regimen.

Another aspect of the invention provides a method of inhibiting at least one of unwanted growth, proliferation or survival of a cell, comprising (a) determining whether said cell expresses a hedgehog gene, and (b) contacting said cell which expresses said hedgehog gene with an effective amount of a hedgehog RNAi antagonist; wherein contacting said cell with said hedgehog RNAi antagonist decreases at least one of cell growth, proliferation or survival.

In one embodiment, said hedgehog gene is Sonic hedgehog.

In one embodiment, said unwanted cell growth, proliferation or survival of a cell is cancer.

In one embodiment, said hedgehog RNAi antagonist is formulated in a pharmaceutically acceptable carrier.

Another aspect of the invention provides a method for treating a tumor in a patient, comprising administering to said patient an amount of a hedgehog RNAi antagonist effective to decrease at least one of the growth, proliferation or survival of said tumor.

In one embodiment, said hedgehog RNAi antagonist is administered as part of a cancer treatment regimen.

Another aspect of the invention provides a use of a hedgehog RNAi antagonist in the manufacture of a medicament for treating a tumor in a patient.

In one embodiment, the hedgehog RNAi antagonist is administered as part of a cancer treatment regimen.

Another aspect of the invention provides a use of a hedgehog RNAi antagonist in the manufacture of a medicament for inhibiting at least one of unwanted growth, proliferation or survival of a cell.

In one embodiment, the hedgehog RNAi antagonist is administered as part of a cancer treatment regimen.

It is contemplated that any one of the above embodiments may be combined with any other embodiments wherever applicable.

BRIEF DESCRIPTION OF THE DRAWINGS

FIG. 55 shows Hedgehog expression in human cancers: (a, d) Hedgehog immunoreactivity in biopsy material taken from human breast ductal adenocarcinomas. Note the stronger immunoreactivity present on cancerous epithelium (arrows) than on the adjacent normal ductal epithelium (arrowhead) demonstrating elevated Hh levels in cancerous tissues. (b, e) Hedgehog staining in two forms of ovarian cancer, including a well differentiated borderline serous adenocarcinoma (b), and a poorly differentiated adenocarcinoma (e). (c, f) Hedgehog immunoreactivity on samples of uterine cancer demonstrating expression on both well differentiated (c), and poorly differentiated, highly invasive cancers (f).

DETAILED DESCRIPTION OF THE INVENTION

I. Overview

Figure 1:
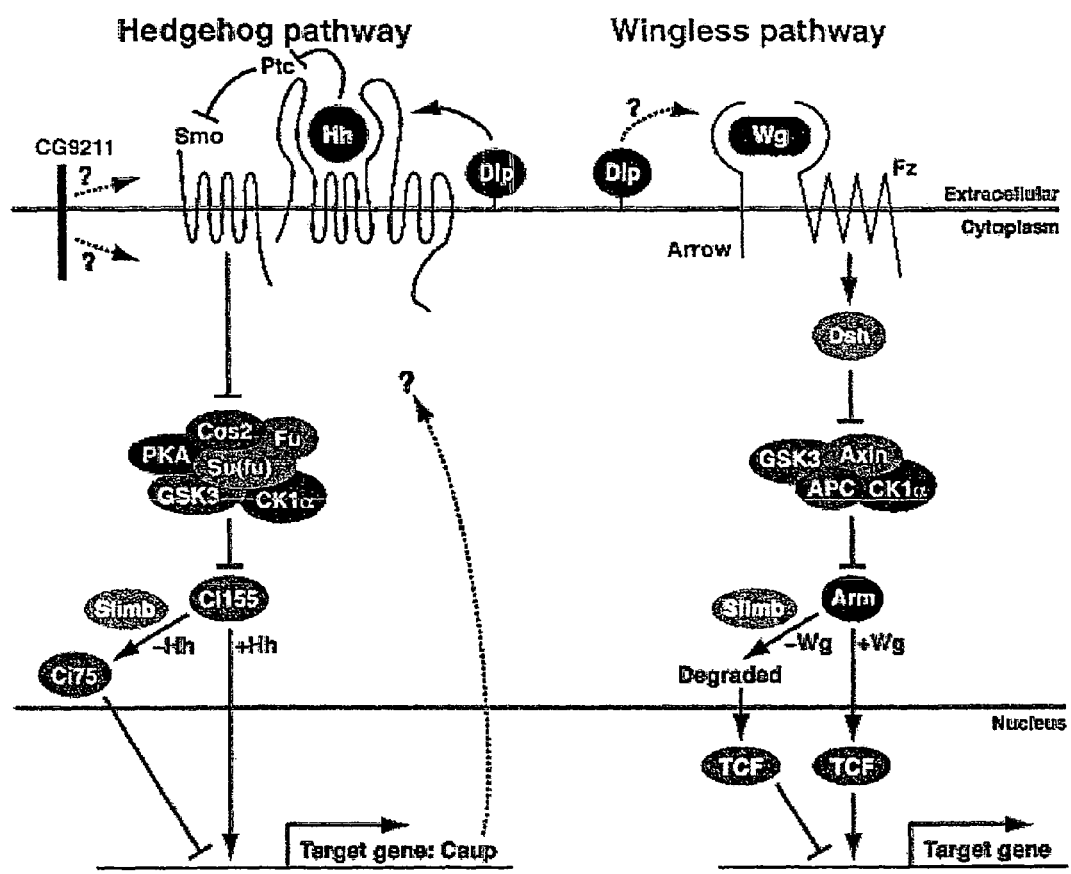
FIG. 1 Hedgehog signaling pathway (adapted from Michelson, Sci. STKE, 2003 (192): PE30, Jul. 22, 2003).

RNA interference (RNAi) is a phenomenon describing double-stranded (ds)RNA-dependent gene specific posttranscriptional silencing. Initial attempts to harness this phenomenon for experimental manipulation of mammalian cells were foiled by a robust and nonspecific antiviral defense mechanism activated in response to long dsRNA molecules. Gil et al. *Apoptosis* 2000, 5:107-114. The field was significantly advanced upon the demonstration that synthetic duplexes of 21-nucleotide RNAs could mediate gene-specific RNAi in mammalian cells, without invoking generic antiviral defense mechanisms. Elbashir et al. *Nature* 2001, 411:494-498; Caplen et al. *Proc Natl Acad Sci* 2001, 98:9742-9747. As a result, small interfering RNAs (siRNAs) have become powerful tools to dissect gene function. The chemical synthesis of small RNAs is one avenue that has produced promising results. Numerous groups have also sought the development of DNA-based vectors capable of generating such siRNA within cells. Several groups have attained this goal and published similar strategies that, in general, involve transcription of short hairpin (sh)RNAs that are efficiently processed to form siRNAs within cells. Paddison et al. *PNAS* 2002, 99:1443-1448; Paddison et al. *Genes & Dev* 2002, 16:948-958; Sui et al. *PNAS* 2002, 8:5515-5520; and Brummelkamp et al. *Science* 2002, 296:550-553. These reports describe methods to generate siRNAs capable of specifically targeting numerous endogenously and exogenously expressed genes.

The present invention relates to the discovery that signal transduction pathways regulated by hedgehog, patched (ptc), gli, smoothened, and many other HH signaling pathway proteins can be inhibited, at least in part, by specific RNAi antagonists. Since certain HH signaling proteins positively regulate the overall HH signaling, while others negatively regulate the overall HH signaling, these RNAi antagonists may either increase or decrease the overall HH signaling in an affected cell or tissue/organ. It is, therefore, specifically contemplated that these RNAi antagonists which modulate signal transduction activity of hedgehog, ptc, smoothened, etc. will likewise be capable of changing the role of a cell in tissue development from what would otherwise occur.

In preferred embodiments, the cell has a substantially wild-type hedgehog signaling pathway. It is also contemplated that hedgehog antagonists are particularly effective in treating disorders resulting from hyperactivation of the hedgehog pathway, either as a result of mutations in components of the HH signaling pathway or as a result of inappropriate activation of the HH signaling pathway in cell which does not comprise a mutation/lesion in a component of the HH signaling pathway. Therefore, it is desirable to have a method for identifying those cells in which the hedgehog pathway is hyperactive such that antagonist treatment may be efficiently targeted. One of skill in the art will readily recognize, that RNAi antagonists of the present invention can modulate hedgehog signaling at any point in the hedgehog signaling pathway. That is, an exemplary RNAi modulator can regulate HH signaling by antagonizing hedgehog itself, or any other HH signaling components such as the hedgehog receptor patched. It is contemplated that the RNAi antagonists of the present invention can be used to modulate hedgehog signaling in a wild-type cell or in a cell comprising a mutation in a component of the hedgehog signaling pathway.

Thus, the methods of the present invention include, but are not limited to, the use of RNAi antagonists that modulate HH signaling in the regulation of repair and/or functional performance of a wide range of cells, tissues and organs having the phenotype of hedgehog gain-of-function and in tissues with wild-type hedgehog activity. For instance, the subject method has therapeutic and cosmetic applications ranging from regulation of neural tissues, bone and cartilage formation and repair, regulation of spermatogenesis, regulation of smooth muscle, regulation of lung, liver and tissue of other organs arising from the primitive gut, regulation of hematopoietic function, regulation of skin and hair growth, etc. Moreover, the subject methods can be performed on cells that are provided in culture (in vitro), or on cells in a whole animal (in vivo). See, for example, PCT publications WO 95/18856 and WO 96/17924 (the specifications of which are expressly incorporated by reference herein).

In another aspect, the present invention provides pharmaceutical preparations comprising, as an active ingredient, an RNAi antagonist of any one of the HH signaling components such as described herein, formulated in an amount sufficient to inhibit, in vivo, proliferation or other biological consequences of hedgehog gain-of-function.

The subject treatments using RNAi antagonists of the HH pathway components can be effective for both human and non-human animal cells and subjects. Animal subjects to which the invention is applicable extend to both domestic animals and livestock, raised either as pets or for commercial purposes. Examples of such non-human animals include non-human primates, dogs, cats, cattle, horses, sheep, hogs, goats, mice, rats, rabbits, frogs, fish, chickens, and the like.

II. Definitions

For convenience, certain terms employed in the specification, examples, and appended claims are collected here.

The phrase "aberrant modification or mutation" of a gene refers to such genetic lesions as, for example, deletions, substitution or addition of nucleotides to a gene, as well as gross chromosomal rearrangements of the gene and/or abnormal methylation of the gene. Likewise, misexpression of a gene refers to aberrant levels of transcription of the gene relative to those levels in a normal cell under similar conditions, as well as non-wild-type splicing of mRNA transcribed from the gene.

The term "adenocarcinoma" as used herein refers to a malignant tumor originating in glandular epithelium.

The term "angiogenesis", as used herein, refers to the formation of blood vessels. Specifically, angiogenesis is a multistep process in which endothelial cells focally degrade and invade through their own basement membrane, migrate through interstitial stroma toward an angiogenic stimulus, proliferate proximal to the migrating tip, organize into blood vessels, and reattach to newly synthesized basement membrane (see Folkman et al., Adv. Cancer Res., Vol. 43, pp. 175-203 (1985)).

"Basal cell carcinomas" exist in a variety of clinical and histological forms such as nodular-ulcerative, superficial, pigmented, morphealike, fibroepithelioma and nevoid syndrome. Basal cell carcinomas are the most common cutaneous neoplasms found in humans. The majority of new cases of nonmelanoma skin cancers fall into this category.

"Benign prostatic hyperplasia", or BPH, is a benign enlargement of the prostate gland that begins normally after age 50 years probably secondary to the effects of male hormones. If significant enlargement occurs, it may pinch off the urethra making urination difficult or impossible.

"Burn wounds" refer to cases where large surface areas of skin have been removed or lost from an individual due to heat and/or chemical agents.

The term "carcinoma" refers to a malignant new growth made up of epithelial cells tending to infiltrate surrounding tissues and to give rise to metastases. Exemplary carcinomas include: "basal cell carcinoma", which is an epithelial tumor of the skin that, while seldom metastasizing, has potentialities for local invasion and destruction; "squamous cell carcinoma", which refers to carcinomas arising from squamous epithelium and having cuboid cells; "carcinosarcoma", which include malignant tumors composed of carcinomatous and sarcomatous tissues; "adenocystic carcinoma", carcinoma marked by cylinders or bands of hyaline or mucinous stroma separated or surrounded by nests or cords of small epithelial cells, occurring in the mammary and salivary glands, and mucous glands of the respiratory tract; "epidermoid carcinoma", which refers to cancerous cells which tend to differentiate in the same way as those of the epidermis; i.e., they tend to form prickle cells and undergo cornification; "nasopharyngeal carcinoma", which refers to a malignant tumor arising in the epithelial lining of the space behind the nose; and "renal cell carcinoma", which pertains to carcinoma of the renal parenchyma composed of tubular cells in varying arrangements. Other carcinomatous epithelial growths are "papillomas", which refers to benign tumors derived from epithelium and having a papillomavirus as a causative agent; and "epidermoidomas", which refers to a cerebral or meningeal tumor formed by inclusion of ectodermal elements at the time of closure of the neural groove.

The "corium" or "dermis" refers to the layer of the skin deep to the epidermis, consisting of a dense bed of vascular connective tissue, and containing the nerves and terminal organs of sensation. The hair roots, and sebaceous and sweat glands are structures of the epidermis which are deeply embedded in the dermis.

"Dental tissue" refers to tissue in the mouth that is similar to epithelial tissue, for example gum tissue. The method of the present invention is useful for treating periodontal disease.

"Dermal skin ulcers" refer to lesions on the skin caused by superficial loss of tissue, usually with inflammation. Dermal skin ulcers that can be treated by the method of the present invention include decubitus ulcers, diabetic ulcers, venous stasis ulcers and arterial ulcers. Decubitus wounds refer to chronic ulcers that result from pressure applied to areas of the skin for extended periods of time. Wounds of this type are often called bedsores or pressure sores. Venous stasis ulcers result from the stagnation of blood or other fluids from defective veins. Arterial ulcers refer to necrotic skin in the area around arteries having poor blood flow.

The term "$ED_{50}$" means the dose of a drug that produces 50% of its maximum response or effect.

An "effective amount" of, e.g., a hedgehog antagonist, with respect to the subject method of treatment, refers to an amount of the antagonist in a preparation which, when applied as part of a desired dosage regimen brings about, e.g., a change in the rate of cell proliferation and/or the state of differentiation of a cell and/or rate of survival of a cell according to clinically acceptable standards for the disorder to be treated or for the cosmetic purpose.

The terms "epithelia", "epithelial" and "epithelium" refer to the cellular covering of internal and external body surfaces (cutaneous, mucous and serous), including the glands and other structures derived therefrom, e.g., corneal, esophageal, epidermal, and hair follicle epithelial cells. Other exemplary epithelial tissue includes: olfactory epithelium, which is the pseudostratified epithelium lining the olfactory region of the nasal cavity, and containing the receptors for the sense of smell; glandular epithelium, which refers to epithelium composed of secreting cells; squamous epithelium, which refers to epithelium composed of flattened plate-like cells. The term epithelium can also refer to transitional epithelium, like that which is characteristically found lining hollow organs that are subject to great mechanical change due to contraction and distention, e.g., tissue which represents a transition between stratified squamous and columnar epithelium.

The term "epithelialization" refers to healing by the growth of epithelial tissue over a denuded surface.

The term "epidermal gland" refers to an aggregation of cells associated with the epidermis and specialized to secrete or excrete materials not related to their ordinary metabolic needs. For example, "sebaceous glands" are holocrine glands in the corium that secrete an oily substance and sebum. The term "sweat glands" refers to glands that secrete sweat, situated in the corium or subcutaneous tissue, opening by a duct on the body surface.

The term "epidermis" refers to the outermost and nonvascular layer of the skin, derived from the embryonic ectoderm, varying in thickness from 0.07-1.4 mm. On the palmar and plantar surfaces it comprises, from within outward, five layers: basal layer composed of columnar cells arranged perpendicularly; prickle-cell or spinous layer composed of flattened polyhedral cells with short processes or spines; granular layer composed of flattened granular cells; clear layer composed of several layers of clear, transparent cells in which the nuclei are indistinct or absent; and horny layer composed of flattened, cornified non-nucleated cells. In the epidermis of the general body surface, the clear layer is usually absent.

"Excisional wounds" include tears, abrasions, cuts, punctures or lacerations in the epithelial layer of the skin and may extend into the dermal layer and even into subcutaneous fat and beyond. Excisional wounds can result from surgical procedures or from accidental penetration of the skin.

The "growth state" of a cell refers to the rate of proliferation of the cell and/or the state of differentiation of the cell. An "altered growth state" is a growth state characterized by an abnormal rate of proliferation, e.g., a cell exhibiting an increased or decreased rate of proliferation relative to a normal cell.

The term "hair" refers to a threadlike structure, especially the specialized epidermal structure composed of keratin and developing from a papilla sunk in the corium, produced only by mammals and characteristic of that group of animals. Also, "hair" may refer to the aggregate of such hairs. A "hair follicle" refers to one of the tubular-invaginations of the epidermis enclosing the hairs, and from which the hairs grow. "Hair follicle epithelial cells" refers to epithelial cells that surround the dermal papilla in the hair follicle, e.g., stem cells, outer root sheath cells, matrix cells, and inner root sheath cells. Such cells may be normal non-malignant cells, or transformed/immortalized cells.

The term "hedgehog" is used to refer generically to any member of the hedgehog family, including sonic, indian, desert and tiggy winkle. The term may be used to indicate protein or gene. The term is also used to describe homolog/ortholog sequences in different animal species (see below).

The terms "hedgehog (HH) signaling pathway", "hedgehog (HH) pathway" and "hedgehog (HH) signal transduction pathway" are all used to refer to the chain of events normally mediated by hedgehog, smoothened, ptc, and gli, among others, and resulting in a changes in gene expression and other phenotypic changes typical of hedgehog activity. The hedgehog pathway can be activated even in the absence of a hedgehog protein by activating a downstream component. For example, overexpression of smoothened will activate the pathway in the absence of hedgehog. Hedgehog, gli and ptc gene expression are indicators of an active hedgehog signaling pathway.

The term "HH signaling component" refers to gene products that participate in the HH signaling pathway. An HH signaling component frequently materially or substantially affects the transmission of the HH signal in cells/tissues, typically resulting in changes in degree of downstream gene expression level and/or phenotypic changes.

Each HH signaling component, depending on their biological function and effects on the final outcome of the downstream gene activation/expression, may be divided into positive and negative regulators. A positive regulator is a HH signaling component that positively affects the transmission of the HH signal, i.e., stimulates downstream biological events when HH is present. Examples include (but are not limited to) those genes listed in Table X below. A negative regulator is a HH signaling component that negatively affects the transmission of the HH signal, i.e., inhibits downstream biological events when HH is present. Examples include (but are not limited to) those genes listed in Table Y below.

The term "hedgehog RNAi antagonist" refers to an RNAi agent that inhibits the bioactivity of an HH signaling component (such as hedgehog, patched, or gli1), such that it represses the expression of the target HH signaling component. For example, certain preferred hedgehog RNAi antagonists can be used to overcome a ptc loss-of-function and/or a smoothened gain-of-function. Other preferred RNAi antagonists can be used to overcome an inappropriate increase in hedgehog signal transduction, whether said increase in signal transduction is the result in a mutation/lesion in a component of the hedgehog signaling pathway (e.g., ptc, gli1, gli3, smoothened, etc) or whether said increase in signal transduction occurs in the context of a cell which does not comprise a mutation/lesion in a component of the hedgehog signaling pathway (e.g., a wild-type cell with respect to components of the hedgehog signaling pathway). An RNAi antagonist may be directed to a protein encoded by any of the genes in the hedgehog pathway, including (but not limited to) sonic, indian or desert hedgehog, smoothened, ptc-1, ptc-2, gli-1, gli-2, gli-3, etc. In most cases, the RNAi antagonist would inhibit the activity of the target protein by, for example, decreasing production of a protein encoded by any of the genes in the hedgehog pathway, thus either upregulating or downregulating HH signaling. When the RNAi antagonist inhibits expression of a target protein that normally functions as a positive regulator of the hedgehog signaling pathway, the overall effect is a decrease or inhibition of hedgehog signaling. When the RNAi antagonist inhibits expression of a target protein that normally functions as a negative regulator of the hedgehog signaling pathway, the overlay effect is an increase or promotion of hedgehog signaling.

Moreover, more than one antagonist, including non-RNAi antagonists of the HH signaling pathway, such as antisense nucleotides, antibodies to HH pathway proteins, small organic molecules, etc., can be administered. The co-pending U.S. application Ser. No. 10/652,298, filed on Aug. 29, 2003, describes in detail about various modulators of the HH signaling pathway, the entire contents of which is incorporated herein by reference. Thus, it is further contemplated that when more than one hedgehog antagonist is administered, said agents can inhibit hedgehog signaling through the same mechanism or through differing mechanisms.

The term "hedgehog gain-of-function" refers to an aberrant modification or mutation of a ptc gene, hedgehog gene, or smoothened gene, or a decrease (or loss) in the level of expression of such a gene, which results in a phenotype which resembles contacting a cell with a hedgehog protein, e.g., aberrant activation of a hedgehog pathway. The gain-of-function may include a loss of the ability of the ptc gene product to regulate the level of expression of Ci genes, e.g., Gli1, Gli2, and Gli3. The term 'hedgehog gain-of-function' is also used herein to refer to any similar cellular phenotype (e.g., exhibiting excess proliferation) that occurs due to an alteration anywhere in the hedgehog signal transduction pathway, including, but not limited to, a modification or mutation of hedgehog itself. For example, a tumor cell with an abnormally high proliferation rate due to activation of the hedgehog signaling pathway would have a 'hedgehog gain-of-function' phenotype, even if hedgehog is not mutated in that cell.

As used herein, "immortalized cells" refers to cells that have been altered via chemical and/or recombinant means such that the cells have the ability to grow through an indefinite number of divisions in culture.

"Internal epithelial tissue" refers to tissue inside the body that has characteristics similar to the epidermal layer in the skin. Examples include the lining of the intestine. The method of the present invention is useful for promoting the healing of certain internal wounds, for example wounds resulting from surgery.

The term "keratosis" refers to proliferative skin disorder characterized by hyperplasia of the horny layer of the epidermis. Exemplary keratotic disorders include keratosis follicularis, keratosis palmaris et plantaris, keratosis pharyngea, keratosis pilaris, and actinic keratosis.

"Lamellated bodies" refers to a subcellular structure found in lung cells that are producing surfactants. Lamellated bodies are thought to be the site of lung surfactant biosynthesis. The bodies have a multilayered membranous appearance in an electron micrograph.

The term "$LD_{50}$" means the dose of a drug that is lethal in 50% of test subjects.

The term "nail" refers to the horny cutaneous plate on the dorsal surface of the distal end of a finger or toe.

The term "overexpression" as used in reference to gene expression levels means any level of gene expression in cells of a tissue that is higher than the normal level of expression for that tissue. The normal level of expression for a tissue may be assessed by measuring gene expression in a healthy portion of that tissue.

The term "patched loss-of-function" refers to an aberrant modification or mutation of a ptc gene, or a decreased level of expression of the gene, which results in a phenotype that resembles contacting a cell with a hedgehog protein, e.g., aberrant activation of a hedgehog pathway. The loss-of-function may include a loss of the ability of the ptc gene product to regulate the level of expression of Ci genes, e.g., Gli1, Gli2 and Gli3.

The term "pharmaceutically acceptable salts" refers to physiologically and pharmaceutically acceptable salts of the compounds of the invention, i.e., salts that retain the desired biological activity of the parent compound and do not impart undesired toxicological effects thereto.

"Standard hybridization conditions" refer to salt and temperature conditions substantially equivalent to 0.5 SSC to about 5×SSC and 65° C. for both hybridization and wash. The term "standard hybridization conditions" as used herein is therefore an operational definition and encompasses a range of hybridization conditions. Nevertheless, for the purposes of this present disclosure "high stringency" conditions include hybridizing with plaque screen buffer (0.2% polyvinylpyrrolidone, 0.2% Ficoll 400; 0.2% bovine serum albumin, 50 mM Tris-HCl (pH 7.5); 1 M NaCl; 0.1% sodium pyrophosphate; 1% SDS); 10% dextran sulfate, and 100 ug/ml denatured, sonicated salmon sperm DNA at 65° C. for 12-20 hours, and washing with 75 mM NaCl/7.5 mM sodium citrate (0.5×SSC)/1% SDS at 65° C. "Low stringency" conditions include hybridizing with plaque screen buffer, 10% dextran sulfate and 110 ug/ml denatured, sonicated salmon sperm DNA at 55° C. for 12-20 hours, and washing with 300 mM NaCl/30 mM sodium citrate (2.0×SSC)/1% SDS at 55° C.

See also Current Protocols in Molecular Biology, John Wiley & Sons, Inc. New York, Sections 6.3.1-6.3.6, (1989).

A "patient" or "subject" to be treated by the subject method can mean either a human or non-human animal.

The term "prodrug" is intended to encompass compounds that, under physiological conditions, are converted into the therapeutically active agents of the present invention. A common method for making a prodrug is to include selected moieties that are hydrolyzed under physiological conditions to reveal the desired molecule. In other embodiments, the prodrug is converted by an enzymatic activity of the host animal.

As used herein, "proliferating" and "proliferation" refer to cells undergoing mitosis.

Throughout this application, the term "proliferative skin disorder" refers to any disease/disorder of the skin marked by unwanted or aberrant proliferation of cutaneous tissue. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. For example, epidermodysplasia is a form of faulty development of the epidermis. Another example is "epidermolysis", which refers to a loosened state of the epidermis with formation of blebs and bullae either spontaneously or at the site of trauma.

As used herein, the term "psoriasis" refers to a hyperproliferative skin disorder that alters the skin's regulatory mechanisms. In particular, lesions are formed which involve primary and secondary alterations in epidermal proliferation, inflammatory responses of the skin, and an expression of regulatory molecules such as lymphokines and inflammatory factors. Psoriatic skin is morphologically characterized by an increased turnover of epidermal cells, thickened epidermis, abnormal keratinization, inflammatory cell infiltrates into the dermis layer and polymorphonuclear leukocyte infiltration into the epidermis layer resulting in an increase in the basal cell cycle. Additionally, hyperkeratotic and parakeratotic cells are present.

The term "skin" refers to the outer protective covering of the body, consisting of the corium and the epidermis, and is understood to include sweat and sebaceous glands, as well as hair follicle structures. Throughout the present application, the adjective "cutaneous" may be used, and should be understood to refer generally to attributes of the skin, as appropriate to the context in which they are used.

The term "small cell carcinoma" refers to a type of malignant neoplasm, commonly of the bronchus. Cells of the tumor have endocrine like characteristics and may secrete one or more of a wide range of hormones, especially regulatory peptides like bombesin.

The term "smoothened gain-of-function" refers to an aberrant modification or mutation of a smo gene, or an increased level of expression of the gene, which results in a phenotype that resembles contacting a cell with a hedgehog protein, e.g., aberrant activation of a hedgehog pathway. While not wishing to be bound by any particular theory, it is noted that ptc may not signal directly into the cell, but rather interact with smoothened, another membrane-bound protein located downstream of ptc in hedgehog signaling (Marigo et al., (1996) *Nature* 384: 177-179). The gene smo is a segment-polarity gene required for the correct patterning of every segment in *Drosophila* (Alcedo et al., (1996) *Cell* 86: 221-232). Human homologs of smo have been identified. See, for example, Stone et al. (1996) *Nature* 384:129-134, and GenBank accession U84401. The smoothened gene encodes an integral membrane protein with characteristics of heterotrimeric G-protein-coupled receptors; i.e., 7-transmembrane regions. This protein shows homology to the *Drosophila* Frizzled (Fz) protein, a member of the wingless pathway. It was originally thought that smo encodes a receptor of the Hh signal. However, this suggestion was subsequently disproved, as evidence for ptc being the Hh receptor was obtained. Cells that express Smo fail to bind Hh, indicating that smo does not interact directly with Hh (Nusse, (1996) *Nature* 384: 119-120). Rather, the binding of Sonic hedgehog (SHH) to its receptor, PTCH, is thought to prevent normal inhibition by PTCH of smoothened (SMO), a seven-span transmembrane protein.

Recently, it has been reported that activating smoothened mutations occur in sporadic basal cell carcinoma, Xie et al. (1998) Nature 391: 90-2, and primitive neuroectodermal tumors of the central nervous system, Reifenberger et al. (1998) *Cancer Res* 58: 1798-803.

The term "therapeutic index" refers to the therapeutic index of a drug defined as $LD_{50}/ED_{50}$.

As used herein, "transformed cells" refers to cells that have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control.

"Urogenital" refers to the organs and tissues of the urogenital tract, which includes among other tissues, the prostate, ureter, kidney and bladder. A "urogenital cancer" is a cancer of a urogenital tissue.

III. Exemplary Targets of the Hedgehog Signaling Pathway

Hedgehog, which encodes a secreted signaling molecule, was originally identified in *Drosophila* as an essential embryonic patterning gene. Hh family members subsequently were discovered in diverse species, including in human, where they exert a wide range of developmental effects (see, for example, Ho and Scott, *Curr. Opin. Neurobiol.* 12, 57-63, 2002; Ingham and McMahon, *Genes Dev.* 15, 3059-3087, 2001). Of further interest, aberrant HH signaling is associated with a number of human diseases, including several types of cancer (For review, see Bale, *Annu. Rev. Genomics Hum. Genet.* 3, 47-65, 2002; Taipale and Beachy, *Nature* 411, 349-354, 2001). From intensive genetic and biochemical investigations, the following view of the Hh signaling pathway has emerged (FIG. 1) (for review, see Nybakken and Perrimon, *Curr. Opin. Genet. Dev.* 12, 503-511, 2002).

In the absence of Hh, the transmembrane receptor, Patched (Ptc), inhibits a second membrane-bound protein, Smoothened (Smo). This process enables an intracellular high-molecular-weight protein complex—which includes the kinesin-related molecule Costal2 (Cos2), the serine-threonine protein kinase Fused (Fu), and the protein Suppressor of fused [Su (fu)]—to promote the proteolytic processing of full-length Cubitus interruptus (Ci155), thereby generating a transcriptional repressor Ci75. Although not yet proven to interact directly with the inhibitory complex, protein kinase A (PKA), glycogen synthase kinase 3 (GSK3), and casein kinase 1α (CK1α) also modify Ci to regulate its cleavage. This process also depends on Slimb. Binding of Hh to Ptc relieves inhibition of Smo and, by an unknown mechanism, Smo suppresses the Ci-processing activity of the cytoplasmic complex. Unprocessed Ci155 then translocates to the nucleus, where it activates the expression of specific target genes.

Recently, Lum et al. (Science 299: 2039-2045, 2003) identified several additional members of the HH signaling pathway. Using both in vitro and in vivo assays, these authors identified four genes whose products were not previously recognized as having specific roles in Hh signaling: CK1α, dally-like (dlp), caupolican (caup), and the predicted gene, CG9211. Among them, CK1α is a negative regulator, while dlp, caup and CG9211 are all positive regulators.

All HH signaling pathway genes in various species can be routinely obtained from public and proprietary databases, such as GenBank, EMBL, FlyBase, to name but a few. In certain organisms, such as human and *Drosophila*, the whole genome is sequenced, and sequence comparison programs, such as the BLAST series of programs offered online at the NCBI website can be used to retrieve the most updated sequences of any known HH signal pathway genes. The following tables list several representative members of the known HH signaling pathway genes in various species. It is by no means exhaustive, and should not be viewed as limiting in any sense. Rather, it serves as a useful starting point for an exhaustive search, which a skilled artisan would be able to perform these searches using routine biotechniques. Some genes may have several different database entries with different accession numbers, but are nonetheless same or almost the same in sequence. Regardless, only one entry for each gene is provided in the tables below.

The genes are listed as either positive or negative regulators of the HH signaling pathway. Thus an RNAi antagonist inhibiting a positive regulator will be useful to down-regulate the HH signaling, for example, in conditions involving hyperactivity of HH signaling. In contrast, an RNAi antagonist inhibiting a negative regulator will be useful to up-regulate the HH signaling, for example, in conditions involving hypoactivity of HH signaling.

TABLE X

Positive Regulators of HH Signaling

| *Drosophila* (Acc. No.) | Other Species (Acc. No.) |
|---|---|
| Hh (NM_079735) | Human Shh (NM_000193); human Ihh (XM_050846); human Dhh (NM_021044). mouse Shh (NM_009170); rat Shh (NM_017221); cow Shh (AF144100); house shrew Shh (AB081406); chicken Shh (L28099); Japanese firebelly newt Shh (D63339); bastard halibut Shh (AB029748); smaller spotted catshark Shh (AF393835); *Eleutherodactylus coqui* Shh (AF113403); Iberian ribbed newt Shh-related protein (AF003532); *Xenopus* Shh (L39213); *Takifugu rubripes* Shh (AJ507296); Zebrafish Shh (NM_131063); mouse Ihh (NM_010544.); rat Ihh (XM_237298); chicken Ihh (U58511); *Xenopus* banded HH (U26404); zebrafish Twhh (NM_131199). |

TABLE X-continued

Positive Regulators of HH Signaling

| Drosophila (Acc. No.) | Other Species (Acc. No.) |
|---|---|
| Smo (NM_078719) | Human Smo (U84401); rat Smo (U84402); mouse Smo (XM_133018); Xenopus Smo (AF302766); zebrafish Smo (AF395809); chicken Smo (AF019977). |
| dlp (AF317090) | Human homolog (AF030186); mouse homolog (X83577); Rat homolog (L02896); Zebrafish homolog (AF354754); chicken homolog (L29089). |
| CG9211 (Protein: AAF52461; see AE003615 for nucleotide) | Human homolog (AY027658); Mouse homolog (AF388037); rat homolog (U68726); Xenopus homolog (AF388036); zebrafish homolog (AF461120). |
| Caup (X95178) | Human homolog (AF124733); mouse homolog (AF124732); Xenopus homolog (AF338157); chicken homolog (AF091504); zebrafish homolog (AY017309). |
| Ci (X54360) | Human Gli (NM_005269); human Gli2 (4 variants: NM_030379, NM_030380, NM_030381, NM_005270); human Gli3 (NM_000168); human Gli4 (NM_138465); Mouse Gli (NM_010296); rat Gli1 (XM_235221); horse Gli1 (AF510668); chicken Gli1 (U60762); Xenopus Gli1 (U57454); zebrafish Gli1 (NM_178296); mouse Gli2 (XM_196215); rat Gli2 (XM_222557); chicken Gli2 (AF022818); zebrafish Gli2 (AF085746); mouse Gli3 (NM_008130); rat Gli3 (XM_225412); chicken Gli3 (U60763); common quail Gli3 (AF231112); Xenopus Gli3 (U42461); eastern newt Gli3 (AF316110); Xenopus Gli4 (U42462). |
| Fu (Protein P23647, see X80468 for gene) | Human homolog (AF200815); Mouse homolog (AF195272, AK006827, AF124142); rat homolog (NM_019232, D49836); rabbit homolog (AF139639); Xenopus homolog (AF057138); spiny dogfish homolog (AJ223715); chicken homolog (AF039943); cow homolog (X61036); zebrafish homolog (BC052134). |

*Nucleotide sequence accession numbers from the public databases are listed in "( )."

TABLE Y

Negative Regulators of HH Signaling

| Drosophila (Acc. No.) | Other Species (Acc. No.) |
|---|---|
| Ptc (M28999) | Human PTC1 (U59464); human PTC2 (AF091501); mouse Ptc1 (U46155); rat Ptc1 (AF079162); Xenopus Ptc1 (AF302765); chicken Ptc1 (U40074); zebrafish Ptc1 (X98883); Japanese firebelly newt Ptc1 (AB000848); mouse Ptc2 (AB010833); chicken Ptc2 (AF409095); Xenopus Ptc2 (AB037688); zebrafish Ptc2 (AJ007742); Japanese firebelly newt Ptc2 (AB000846) |
| Cos2 (AF019250) | Human homolog (AY237538); rat homolog (XM_218828); mouse homolog (XM_133575); Anopheles gambiae str. PEST homolog (XM_309818). |
| Su(fu) (NM_080502) | Human SUFU (NM_016169); mouse homolog (AJ131692); rat homolog (XM_219957); chicken homolog (AF487888); Anopheles gambiae str. PEST homolog (XM_321114); zebrafish homolog (BC045348). |
| Sgg (X70862) | Human GSK3β (L33801); mouse GSK3β (AF156099); rat GSK3β (X53428); zebrafish GSK3β (AB032265); Xenopus GSK3β (U31862). |
| Pka-C1 (AY069425) | Human PKA-C1 (X07767, M34181, M34182); rat homolog (X57986); mouse homolog (BC003238); sheep homolog (AF238979); bovine homolog (X67154); pig homolog (X05998); rabbit homolog (AF367428;); hamster homolog (M63311); Xenopus homolog (AJ413219). |
| CK1α (AΨ069346) | Human homolog (X80693); mouse homolog (BC019740); rat homolog (U77582); chicken homolog (AF042862); sheep homolog (AB050945); bovine homolog (AB050944); pig homolog (F22872). |
| Slmb (AF032878) | Human homolog (AF101784; AF176022); mouse homolog (AF391190); Xenopus (M98268); chicken (AF113946). |

*Nucleotide sequence accession numbers from the public databases are listed in "( )."

Patched was originally identified in *Drosophila* as a segment polarity gene, one of a group of developmental genes that affect cell differentiation within the individual segments that occur in a homologous series along the anterior-posterior axis of the embryo. See Hooper, J. E. et al. (1989) *Cell* 59:751; and Nakano, Y. et al. (1989) *Nature* 341:508. Patterns of expression of the vertebrate homologue of patched suggest its involvement in the development of neural tube, skeleton, limbs, craniofacial structure, and skin.

Genetic and functional studies demonstrate that patched is part of the hedgehog signaling cascade, an evolutionarily conserved pathway that regulates expression of a number of downstream genes. See Perrimon, N. (1995) *Cell* 80:517; and Perrimon, N. (1996) *Cell* 86:513. Patched participates in the constitutive transcriptional repression of the target genes; its effect is opposed by a secreted glycoprotein, encoded by hedgehog, or a vertebrate homologue, which induces transcriptional activation. Genes under control of this pathway include members of the Wnt and TGF-beta families.

Patched proteins possess two large extracellular domains, twelve transmembrane segments, and several cytoplasmic segments. See Hooper, supra; Nakano, supra; Johnson, R. L. et al. (1996) *Science* 272:1668; and Hahn, H. et al. (1996) *Cell* 85:841. The biochemical role of patched in the hedgehog signaling pathway is unclear. Direct interaction with the hedgehog protein has, however, been reported (Chen, Y. et al. (1996) *Cell* 87:553), and patched may participate in a hedgehog receptor complex along with another transmembrane protein encoded by the smoothened gene. See Perrimon, supra; and Chen, supra.

The human homologue of patched was cloned and mapped to chromosome 9q22.3. See Johnson, supra; and Hahn, supra. This region has been implicated in basal cell nevus syndrome (BCNS), which is characterized by developmental abnormalities including rib and craniofacial alterations, abnormalities of the hands and feet, and spina bifida.

Sporadic tumors also demonstrated a loss of both functional alleles of patched. Of twelve tumors in which patched mutations were identified with a single strand conformational polymorphism screening assay, nine had chromosomal deletion of the second allele and the other three had inactivating mutations in both alleles (Gailani, supra). The alterations did not occur in the corresponding germ line DNA.

Most of the identified mutations resulted in premature stop codons or frame shifts (Lench, N. J., et al., *Hum. Genet.* 1997 October; 100(5-6): 497-502). Several, however, were point mutations leading to amino acid substitutions in either extracellular or cytoplasmic domains. These sites of mutation may indicate functional importance for interaction with extracellular proteins or with cytoplasmic members of the downstream signaling pathway.

The involvement of patched in the inhibition of gene expression and the occurrence of frequent allelic deletions of patched in BCC support a tumor suppressor function for this gene. Its role in the regulation of gene families known to be involved in cell signaling and intercellular communication provides a possible mechanism of tumor suppression.

CK1α is a positive regulator of Ci cleavage, a process that generates its repressor form (Price and Kalderon, *Cell* 108, 823-835, 2002, FIG. 1). Thus CK1α is a negative regulator of HH signaling. In contrast, dlp is a positive Hh signal transducer. The latter result is consistent with dlp encoding a cell-surface heparan sulfate proteoglycan (HSPG) of the glypican class, because such molecules are known to function as coreceptors for various extracellular ligands (Nybakken and Perrimon, *Biochim. Biophys. Acta* 1573, 280-291, 2002). Lum et al. presented additional evidence that Dlp acts upstream of or together with Ptc, possibly by concentrating free Hh at the cell surface or by presenting Hh to the Ptc receptor.

Of note, Lum et al. reported that dlp inhibitor had no effect in the Wg-specific cell-culture assay. This result suggests that, in contrast to its participation in Hh signaling, Dlp mediates effects of Wg that are not cell-autonomous. This model is consistent with prior genetic experiments implicating the involvement of dlp in regulating the extracellular distribution of Wg. Thus, Dlp appears to play different roles in the Hh and Wg signaling pathways, and can be used as a HH pathway-specific target.

The gene caup had previously been described as a downstream mediator of Hh signaling during wing development (Gomez-Skarmeta and Modolell, *Genes Dev.* 10, 2935-2945, 1996), thus its detection as a positive regulator of the Hh pathway was somewhat surprising. Caup, which is a homeodomain transcription factor, could conceivably be involved in a positive-feedback loop that amplifies the Hh signal, perhaps by activating the expression of proximal positive-signaling components (FIG. 1).

CG9211 is predicted to encode a cell-surface protein having immunoglobulin domain repeats and fibronectin type III repeats. It is possible that this factor could function as a positive Hh regulator by interacting with and modulating the activity of other membrane-bound components of the Hh pathway such as Ptc and Smo. Alternatively, CG9211 could mediate a parallel signaling pathway that influences Hh responses (FIG. 1).

The identification of new signaling pathway components in *Drosophila* also has implications for human disease. For example, the role of CK1α in regulating basal activity of both Wg and Hh signaling pathways suggests that it could act as a tumor suppressor in colon cancer, basal cell carcinoma, rhabdomyosarcoma, or medulloblastoma. These tumors are associated with inappropriate activity of one or the other pathway, except medulloblastoma, which is associated with the activation of either (Taipale and Beachy, *Nature* 411, 349, 2001). In the case of Dlp, GPC4 and GPC6 are the most closely related of the six mammalian glypican family members (De Cat and David, *Semin. Cell Dev. Biol.* 12, 117, 2001). GPC6 maps to 13q32 (Paine-Saunders et al., *Genomics* 57, 455, 1999), a human chromosomal locus whose deletion (13q32 syndrome) is associated with defects, including holoprosencephaly (HPE), anogenital malformations, and an absent thumb (Brown et al., *Am. J. Hum. Genet.* 57, 859, 1995); all of these malformations are consistent with loss of varying degrees of Sonic hedgehog signaling (Ramalho-Santos et al., *Development* 127, 2763, 2000; Chiang et al., *Nature* 383, 407, 1996). If GPC6 levels are limiting in mammalian Hh responsiveness, then loss of GPC6 function may play a role in 13q32 syndrome malformations, possibly alongside other HPE genes in or near this region (Brown et al., *Nature Genet.* 20, 180, 1998). Finally, mutation of CDO, the mammalian homolog of CG9211, results in a form of HPE (Cole and Krauss, *Curr. Biol.* 13, 411, 2003), consistent with a role for CDO in signaling.

IV. Method for Identifying Additional HH Signaling Pathway Components

The RNAi approach used in Lum et al. (supra) can be extended to cover the whole genome of any given organism, especially in model organisms such as worm, *Drosophila*, fish, rodents, and human where numerous established cell lines are readily available. Lum et al. (supra) provide an example of such a large-scale, kinase-phosphatase RNAi library screening, using the information provided by the sequenced *Drosophila* genome (Morrison et al., *J. Cell Biol.* 150, F57, 2000). As a result, 4 additional HH signaling components were identified. Such preliminary in vitro screen can be done in a high throughput fashion to allow quick screen of all the genes within an organism, or at least a specific subset of genes within that organism, such as all kinases, etc. (see Lum et al., supra). Results obtained from these in vitro screens can be verified in vivo, or in other independent assays to validate the role of any identified HH signaling pathway components. These validated components can then be selected for specific RNAi antagonist screens to achieve the ultimate goal of modulating HH signaling, both in vitro and in vivo. Obviously, traditional genetic, biochemical means, either alone or in combination, can also be used to identify additional HH signaling pathway components.

In theory, any biological process can be examined using this method as long as a rapid screening procedure can be developed to monitor its function. For example, fluorescence-based assays of cell proliferation, apoptosis, cell division, phagocytosis, protein-protein interactions, cell fusion or virus entry are amenable to RNAi studies. In the instant case, the biological functions of the HH signaling components are well-studied, and it is within the routine practice of a skilled artisan to develop functional assays for any of the HH signaling components. It is also feasible to adapt RNAi to study cultured primary cells, where various differentiation events could be examined. In addition, it should be possible to devise screening schemes in which synthetic phenotypes, genetic modifiers, and particular drug effects can be analyzed with RNAi methods.

Until recently, it was not possible to apply RNAi approaches to mammalian cells because long dsRNAs stimulate an antiviral response involving interferon and other intracellular pathways that together cause a generalized inhibition of protein synthesis and subsequent apoptosis. However, 21- to 23-nucleotide gene-specific dsRNAs effectively inhibit gene function in mammalian cells without stimulating the interferon response (Watanabe et al., *J. Cell. Biol.* 130, 1207, 1995; Song and Filmus, *Biochim. Biophys. Acta* 1573, 241, 2002). These short interfering or siRNAs can be synthesized in vitro and transfected directly into cells. Alternatively, mammalian cells can be stably transformed with a DNA vector that directs expression of a hairpin precursor corresponding to the coding region of interest; the resulting transcript is subsequently processed into a specific siRNA that targets the desired gene. With these advances, and appropriate siRNA libraries, it is possible to undertake informative RNAi screens in mammalian cells, including strategies designed to identify novel drug targets. However, even in the absence of direct screening in mammalian cells, information about the HH pathway gathered from studies conducted in other model organisms such as *Drosophila* can also be applied to the higher eukaryotes, due to the high degree of functional conservation in this signaling pathway.

V. Exemplary RNAi Antagonists and Synthesis Thereof

RNAi constructs comprise double stranded RNA that can specifically block expression of a target gene. Accordingly, RNAi constructs can act as antagonists by specifically blocking expression of a particular gene. "RNA interference" or "RNAi" is a term initially applied to a phenomenon observed in plants and worms where double-stranded RNA (dsRNA) blocks gene expression in a specific and post-transcriptional manner. Without being bound by theory, RNAi appears to involve mRNA degradation; however, the biochemical mechanisms are currently an active area of research. Despite some uncertainty regarding the mechanism of action, RNAi provides a useful method of inhibiting gene expression in vitro or in vivo.

As used herein, the term "dsRNA" refers to siRNA molecules, or other RNA molecules including a double stranded feature and able to be processed to siRNA in cells, such as hairpin RNA moieties.

The term "loss-of-function," as it refers to genes inhibited by the subject RNAi method, refers to a diminishment in the level of expression of a gene when compared to the level in the absence of RNAi constructs.

As used herein, the phrase "mediates RNAi" refers to (indicates) the ability to distinguish which RNAs are to be degraded by the RNAi process, e.g., degradation occurs in a sequence-specific manner rather than by a sequence-independent dsRNA response, e.g., a PKR response.

As used herein, the term "RNAi construct" is a generic term used throughout the specification to include small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo.

"RNAi expression vector" (also referred to herein as a "dsRNA-encoding plasmid") refers to replicable nucleic acid constructs used to express (transcribe) RNA which produces siRNA moieties in the cell in which the construct is expressed. Such vectors include a transcriptional unit comprising an assembly of (1) genetic element(s) having a regulatory role in gene expression, for example, promoters, operators, or enhancers, operatively linked to (2) a "coding" sequence which is transcribed to produce a double-stranded RNA (two RNA moieties that anneal in the cell to form an siRNA, or a single hairpin RNA which can be processed to an siRNA), and (3) appropriate transcription initiation and termination sequences. The choice of promoter and other regulatory elements generally varies according to the intended host cell. In general, expression vectors of utility in recombinant DNA techniques are often in the form of "plasmids" which refer to circular double stranded DNA loops which, in their vector form are not bound to the chromosome. In the present specification, "plasmid" and "vector" are used interchangeably as the plasmid is the most commonly used form of vector. However, the invention is intended to include such other forms of expression vectors which serve equivalent functions and which become known in the art subsequently hereto.

The RNAi constructs contain a nucleotide sequence that hybridizes under physiologic conditions of the cell to the nucleotide sequence of at least a portion of the mRNA transcript for the gene to be inhibited (i.e., the "target" gene). The double-stranded RNA need only be sufficiently similar to natural RNA that it has the ability to mediate RNAi. Thus, the invention has the advantage of being able to tolerate sequence variations that might be expected due to genetic mutation, strain polymorphism or evolutionary divergence. The number of tolerated nucleotide mismatches between the target sequence and the RNAi construct sequence is no more than 1 in 5 basepairs, or 1 in 10 basepairs, or 1 in 20 basepairs, or 1 in 50 basepairs. Mismatches in the center of the siRNA duplex are most critical and may essentially abolish cleavage of the target RNA. In contrast, nucleotides at the 3' end of the siRNA strand that is complementary to the target RNA do not significantly contribute to specificity of the target recognition.

Sequence identity may be optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing).

Production of RNAi constructs can be carried out by chemical synthetic methods or by recombinant nucleic acid techniques. Endogenous RNA polymerase of the treated cell may mediate transcription in vivo, or cloned RNA polymerase can be used for transcription in vitro. The RNAi constructs may include modifications to either the phosphate-sugar backbone or the nucleoside, e.g., to reduce susceptibility to cellular nucleases, improve bioavailability, improve formulation characteristics, and/or change other pharmacokinetic properties. For example, the phosphodiester linkages of natural RNA may be modified to include at least one of a nitrogen or sulfur heteroatom. Modifications in RNA structure may be tailored to allow specific genetic inhibition while avoiding a general response to dsRNA. Likewise, bases may be modified to block the activity of adenosine deaminase. The RNAi construct may be produced enzymatically or by partial/total organic synthesis, any modified ribonucleotide can be introduced by in vitro enzymatic or organic synthesis.

Methods of chemically modifying RNA molecules can be adapted for modifying RNAi constructs (see, for example, Heidenreich et al. (1997) *Nucleic Acids Res,* 25:776-780; Wilson et al. (1994) *J Mol Recog* 7:89-98; Chen et al. (1995) *Nucleic Acids Res* 23:2661-2668; Hirschbein et al. (1997) *Antisense Nucleic Acid Drug Dev* 7:55-61). Merely to illustrate, the backbone of an RNAi construct can be modified with phosphorothioates, phosphoramidate, phosphodithioates, chimeric methylphosphonate-phosphodiesters, peptide nucleic acids, 5-propynyl-pyrimidine containing oligomers or sugar modifications (e.g., 2'-substituted ribonucleosides, a-configuration).

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition, while lower doses may also be useful for specific applications. Inhibition is sequence-specific in that nucleotide sequences corresponding to the duplex region of the RNA are targeted for genetic inhibition.

In certain embodiments, the subject RNAi constructs are "small interfering RNAs" or "siRNAs." These nucleic acids are around 19-30 nucleotides in length, and even more preferably 21-23 nucleotides in length, e.g., corresponding in length to the fragments generated by nuclease "dicing" of longer double-stranded RNAs. The siRNA are double stranded, and may include short overhangs at each end. Preferably, the overhangs are 1-6 nucleotides in length at the 3' end. It is known in the art that the siRNAs can be chemically synthesized, or derived from a longer double-stranded RNA or a hairpin RNA. The siRNAs have significant sequence similarity to a target RNA so that the siRNAs can pair to the target RNA and result in sequence-specific degradation of the target RNA through an RNA interference mechanism. The siRNAs are understood to recruit nuclease complexes and guide the complexes to the target mRNA by pairing to the specific sequences. As a result, the target mRNA is degraded by the nucleases in the protein complex. In a particular embodiment, the 21-23 nucleotides siRNA molecules comprise a 3' hydroxyl group.

The siRNA molecules of the present invention can be obtained using a number of techniques known to those of skill in the art. For example, the siRNA can be chemically synthesized or recombinantly produced using methods known in the art. For example, short sense and antisense RNA oligomers can be synthesized and annealed to form double-stranded RNA structures with 2-nucleotide overhangs at each end (Caplen, et al. (2001) *Proc Natl Acad Sci USA,* 98:9742-9747; Elbashir, et al. (2001) *EMBO J,* 20:6877-88). These double-stranded siRNA structures can then be directly introduced to cells, either by passive uptake or a delivery system of choice, such as described below.

In certain embodiments, the siRNA constructs can be generated by processing of longer double-stranded RNAs, for example, in the presence of the enzyme dicer. In one embodiment, the *Drosophila* in vitro system is used. In this embodiment, dsRNA is combined with a soluble extract derived from *Drosophila* embryo, thereby producing a combination. The combination is maintained under conditions in which the dsRNA is processed to RNA molecules of about 21 to about 23 nucleotides.

The siRNA molecules can be purified using a number of techniques known to those of skill in the art. For example, gel electrophoresis can be used to purify siRNAs. Alternatively, non-denaturing methods, such as non-denaturing column chromatography, can be used to purify the siRNA. In addition, chromatography (e.g., size exclusion chromatography), glycerol gradient centrifugation, affinity purification with antibody can be used to purify siRNAs.

In certain preferred embodiments, at least one strand of the siRNA molecules has a 3' overhang from about 1 to about 6 nucleotides in length, though may be from 2 to 4 nucleotides in length. More preferably, the 3' overhangs are 1-3 nucleotides in length. In certain embodiments, one strand having a 3' overhang and the other strand being blunt-ended or also having an overhang. The length of the overhangs may be the same or different for each strand. In order to further enhance the stability of the siRNA, the 3' overhangs can be stabilized against degradation. In one embodiment, the RNA is stabilized by including purine nucleotides, such as adenosine or guanosine nucleotides. Alternatively, substitution of pyrimidine nucleotides by modified analogues, e.g., substitution of uridine nucleotide 3' overhangs by 2'-deoxythymidine is tolerated and does not affect the efficiency of RNAi. The absence of a 2' hydroxyl significantly enhances the nuclease resistance of the overhang in tissue culture medium and may be beneficial in vivo.

In other embodiments, the RNAi construct is in the form of a long double-stranded RNA. In certain embodiments, the RNAi construct is at least 25, 50, 100, 200, 300 or 400 bases. In certain embodiments, the RNAi construct is 400-800 bases in length. The double-stranded RNAs are digested intracellularly, e.g., to produce siRNA sequences in the cell. However, use of long double-stranded RNAs in vivo is not always practical, presumably because of deleterious effects which may be caused by the sequence-independent dsRNA response. In such embodiments, the use of local delivery systems and/or agents which reduce the effects of interferon or PKR are preferred.

In certain embodiments, the RNAi construct is in the form of a hairpin structure (i.e., hairpin RNA). The hairpin RNAs can be synthesized exogenously or can be formed by transcribing from RNA polymerase III promoters in vivo. Examples of making and using such hairpin RNAs for gene silencing in mammalian cells are described in, for example, Paddison et al., *Genes Dev,* 2002, 16:948-58; McCaffrey et al., *Nature,* 2002, 418:38-9; McManus et al., *RNA,* 2002, 8:842-50; Yu et al., *Proc Natl Acad Sci USA,* 2002, 99:6047-52). Preferably, such hairpin RNAs are engineered in cells or in an animal to ensure continuous and stable suppression of a desired gene. It is known in the art that siRNAs can be produced by processing a hairpin RNA in the cell.

In yet other embodiments, a plasmid is used to deliver the double-stranded RNA, e.g., as a transcriptional product. In such embodiments, the plasmid is designed to include a "coding sequence" for each of the sense and antisense strands of the RNAi construct. The coding sequences can be the same sequence, e.g., flanked by inverted promoters, or can be two separate sequences each under transcriptional control of separate promoters. After the coding sequence is transcribed, the complementary RNA transcripts base-pair to form the double-stranded RNA.

PCT application WO01/77350 describes an exemplary vector for bi-directional (or convergent) transcription of a transgene to yield both sense and antisense RNA transcripts of the same transgene in a eukaryotic cell. Accordingly, in certain embodiments, the present invention provides a recombinant vector having the following unique characteristics: it comprises a viral replicon having two overlapping transcription units arranged in an opposing orientation and flanking a transgene for an RNAi construct of interest, wherein the two overlapping transcription units yield both sense and antisense RNA transcripts from the same transgene fragment in a host cell. Also see Tran et al., BMC Biotechnology 3: 21, 2003 (incorporated herein by reference).

RNAi constructs can comprise either long stretches of double stranded RNA identical or substantially identical to the target nucleic acid sequence or short stretches of double stranded RNA identical to substantially identical to only a region of the target nucleic acid sequence. Exemplary methods of making and delivering either long or short RNAi constructs can be found, for example, in WO01/68836 and WO01/75164.

Exemplary RNAi constructs that specifically recognize a particular gene, or a particular family of genes can be selected using methodology outlined in detail above with respect to the selection of antisense oligonucleotide. Similarly, methods of delivery RNAi constructs include the methods for delivery antisense oligonucleotides outlined in detail above.

In general, it is anticipated that any of the foregoing RNAi antagonists that decrease the presence or translation of positive, activating HH signaling proteins, such as hedgehog, smoothened or gli-1, act as antagonists of HH signaling, while RNAi antagonists that decrease the production of negative, inhibitory HH signaling proteins, such as patched, will have an agonist effect to HH signaling.

In certain embodiments, the subject RNAi antagonists can be chosen on the basis of their selectively for the hedgehog pathway. This selectivity can be for the hedgehog pathway versus other pathways, such as the wingless pathway which shares certain components with the HH pathway; or for selectivity between particular hedgehog pathways using one of several homologs, e.g., ptc-1 v. ptc-2, etc.

In particular embodiments, the RNAi antagonist is chosen for use because it is more selective for one patched isoform over the next, e.g., 1.5-fold, 2-fold, 3-fold, 5-fold, 10 fold, and more preferably at least 100 or even 1000 fold more selective for one patched pathway (ptc-1, ptc-2) over another.

In certain preferred embodiments, the subject inhibitors inhibit hedgehog-mediated signal transduction with an $ED_{50}$ of 1 mM or less, more preferably of 1 µM or less, and even more preferably of 1 nM or less.

In certain embodiments, an RNAi antagonist which is an antagonist of the hedgehog pathway is chosen to selectively antagonize hedgehog activity over protein kinases other than PKA, such as PKC, e.g., the RNAi antagonist modulates the activity of the hedgehog pathway at least an order of magnitude more strongly than it modulates the activity of another protein kinase, preferably at least two orders of magnitude more strongly, even more preferably at least three orders of magnitude more strongly. Thus, for example, a preferred inhibitor of the hedgehog pathway may inhibit hedgehog activity with a $K_i$ at least an order of magnitude lower than its $K_i$ for inhibition of PKC, preferably at least two orders of magnitude lower, even more preferably at least three orders of magnitude lower. In certain embodiments, the $K_i$ for PKA inhibition is less than 10 nM, preferably less than 1 nM, even more preferably less than 0.1 nM.

VI. Exemplary Applications of Method and Compositions

Another aspect of the present invention relates to methods of modulating a differentiated state, survival, and/or proliferation of a cell.

For example, it is contemplated that the subject method could be used to inhibit angiogenesis. Hedgehog is known to stimulate angiogenesis. Matrigel plugs impregnated with hedgehog protein and inserted into mice evince substantial neovascularization, whereas Matrigel plugs not carrying hedgehog show comparatively little vascularization. Hedgehog protein is also capable of increasing vascularization of the normally avascular mouse cornea. The ptc-1 gene is expressed in normal vascular tissues, including the endothelial cells of the aorta, vascular smooth muscle cells, adventitial fibroblasts of the aorta, the coronary vasculature and cardiomyocytes of the atria and ventricles. These tissues are also sensitive to hedgehog protein. Treatment with exogenous hedgehog causes upregulation of ptc-1 expression. In addition, hedgehog proteins stimulate proliferation of vascular smooth muscle cells in vivo. Hedgehog proteins also cause fibroblasts to increase expression of angiogenic growth factors such as VEGF, bFGF, Ang-1 and Ang-2. Lastly, hedgehog proteins are known to stimulate recovery from ischemic injury and stimulate formation of collateral vessels.

Given that hedgehog promotes angiogenesis, hedgehog antagonists are expected to act as angiogenesis inhibitors, particularly in situations where some level of hedgehog signaling is necessary for angiogenesis.

Angiogenesis is fundamental to many disorders. Persistent, unregulated angiogenesis occurs in a range of disease states, tumor metastases and abnormal growths by endothelial cells. The vasculature created as a result of angiogenic processes supports the pathological damage seen in these conditions. The diverse pathological states created due to unregulated angiogenesis have been grouped together as angiogenic dependent or angiogenic associated diseases. Therapies directed at control of the angiogenic processes could lead to the abrogation or mitigation of these diseases.

Diseases caused by, supported by or associated with angiogenesis include ocular neovascular disease, age-related macular degeneration, diabetic retinopathy, retinopathy of prematurity, corneal graft rejection, neovascular glaucoma, retrolental fibroplasia, epidemic keratoconjunctivitis, Vitamin A deficiency, contact lens overwear, atopic keratitis, superior limbic keratitis, pterygium keratitis sicca, Sjogren's syndrome, acne rosacea, phylctenulosis, syphilis, Mycobacteria infections, lipid degeneration, chemical burns, bacterial ulcers, fungal ulcers, Herpes simplex infections, Herpes zoster infections, protozoan infections, Kaposi's sarcoma, Mooren's ulcer, Terrien's marginal degeneration, mariginal keratolysis, rheumatoid arthritis, systemic lupus, polyarteritis, trauma, Wegener's granulomatosis, sarcoidosis, scleritis, Stevens-Johnson syndrome, pemphigoid radial keratotomy, corneal graph rejection, rheumatoid arthritis, osteoarthritis chronic inflammation (e.g., ulcerative colitis or Crohn's disease), hemangioma, Osler-Weber-Rendu disease, and hereditary hemorrhagic telangiectasia.

In addition, angiogenesis plays a critical role in cancer. A tumor cannot expand without a blood supply to provide nutrients and remove cellular wastes. Tumors in which angiogenesis is important include solid tumors such as rhabdomyosarcomas, retinoblastoma, Ewing sarcoma, neuroblastoma, and osteosarcoma, and benign tumors such as acoustic neuroma, neurofibroma, trachoma and pyogenic granulomas. Angiogenic factors have been found associated with several solid tumors. Prevention of angiogenesis could halt the growth of these tumors and the resultant damage to the animal due to the presence of the tumor. Angiogenesis is also associated with blood-born tumors such as leukemias, any of various acute or chronic neoplastic diseases of the bone marrow in which unrestrained proliferation of white blood cells occurs, usually accompanied by anemia, impaired blood clotting, and enlargement of the lymph nodes, liver, and spleen. It is believed that angiogenesis plays a role in the abnormalities in the bone marrow that give rise to leukemia-like tumors.

In addition to tumor growth, angiogenesis is important in metastasis. Initially, angiogenesis is important in the vascularization of the tumor which allows cancerous cells to enter the blood stream and to circulate throughout the body. After the tumor cells have left the primary site, and have settled into the secondary, metastasis site, angiogenesis must occur before the new tumor can grow and expand. Therefore, prevention of angiogenesis could lead to the prevention of metastasis of tumors and possibly contain the neoplastic growth at the primary site.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

It is anticipated that the invention will be useful for the treatment and/or prevention of respiratory distress syndrome or other disorders resulting from inappropriate lung surface tension. Respiratory distress syndrome results from insufficient surfactant in the alveolae of the lungs. The lungs of vertebrates contain surfactant, a complex mixture of lipids and protein that causes surface tension to rise during lung inflation and decrease during lung deflation. During lung deflation, surfactant decreases such that there are no surface forces that would otherwise promote alveolar collapse. Aerated alveoli that have not collapsed during expiration permit continuous oxygen and carbon dioxide transport between blood and alveolar gas and require much less force to inflate during the subsequent inspiration. During inflation, lung surfactant increases surface tension as the alveolar surface area increases. A rising surface tension in expanding alveoli opposes over-inflation in those airspaces and tends to divert inspired air to less well-aerated alveoli, thereby facilitating even lung aeration.

Respiratory distress syndrome is particularly prevalent among premature infants. Lung surfactant is normally synthesized at a very low rate until the last six weeks of fetal life. Human infants born more than six weeks before the normal term of a pregnancy have a high risk of being born with inadequate amounts of lung surfactant and inadequate rates of surfactant synthesis. The more prematurely an infant is born, the more severe the surfactant deficiency is likely to be. Severe surfactant deficiency can lead to respiratory failure within a few minutes or hours of birth. The surfactant deficiency produces progressive collapse of alveoli (atelectasis) because of the decreasing ability of the lung to expand despite maximum inspiratory effort. As a result, inadequate amounts of oxygen reach the infant's blood. RDS can occur in adults as well, typically as a consequence of failure in surfactant biosynthesis.

Lung tissue of premature infants shows high activity of the hedgehog signaling pathway. Inhibition of this pathway using hedgehog antagonists increases the formation of lamellated bodies and increases the expression of genes involved in surfactant biosynthesis. Lamellar bodies are subcellular structures associated with surfactant biosynthesis. For these reasons, treatment of premature infants with a hedgehog antagonist should stimulate surfactant biosynthesis and ameliorate RDS. In cases where adult RDS is associated with hedgehog pathway activation, treatment with hedgehog antagonists should also be effective.

It is further contemplated that the use of hedgehog antagonists may be specifically targeted to disorders where the affected tissue and/or cells evince high hedgehog pathway activation. Expression of gli genes is activated by the hedgehog signaling pathway, including gli-1, gli-2 and gli-3. gli-1 expression is most consistently correlated with hedgehog signaling activity across a wide range of tissues and disorders, while gli-3 is somewhat less so. The gli genes encode transcription factors that activate expression of many genes needed to elicit the full effects of hedgehog signaling. However, the Gli-3 transcription factor can also act as a repressor of hedgehog effector genes, and therefore, expression of gli-3 can cause a decreased effect of the hedgehog signaling pathway. Whether Gli-3 acts as a transcriptional activator or repressor depends on post-translational events, and therefore it is expected that methods for detecting the activating form (versus the repressing form) of Gli-3 protein would also be a reliable measure of hedgehog pathway activation. gli-2 gene expression is expected to provide a reliable marker for hedgehog pathway activation. The gli-1 gene is strongly expressed in a wide array of cancers, hyperplasias and immature lungs, and serves as a marker for the relative activation of the hedgehog pathway. In addition, tissues, such as immature lung, that have high gli gene expression are strongly affected by hedgehog inhibitors. Accordingly, it is contemplated that the detection of gli gene expression may be used as a powerful predictive tool to identify tissues and disorders that will particularly benefit from treatment with a hedgehog antagonist.

In preferred embodiments, gli-1 expression levels are detected, either by direct detection of the transcript or by detection of protein levels or activity. Transcripts may be detected using any of a wide range of techniques that depend primarily on hybridization of probes to the gli-1 transcripts or to cDNAs synthesized therefrom. Well known techniques include Northern blotting, reverse-transcriptase PCR and microarray analysis of transcript levels. Methods for detecting Gli protein levels include Western blotting, immunoprecipitation, two-dimensional polyacrylamide gel electrophoresis (2D SDS-PAGE) (preferably compared against a standard wherein the position of the Gli proteins has been determined), and mass spectroscopy. Mass spectroscopy may be coupled with a series of purification steps to allow high-throughput identification of many different protein levels in a particular sample. Mass spectroscopy and 2D SDS-PAGE can also be used to identify post-transcriptional modifications to proteins including proteolytic events, ubiquitination, phosphorylation, lipid modification etc. Gli activity may also be assessed by analyzing binding to substrate DNA or in vitro transcriptional activation of target promoters. Gel shift assays, DNA footprinting assays and DNA-protein crosslinking assays are all methods that may be used to assess the presence of a protein capable of binding to Gli binding sites on DNA. (*J Mol Med* 1999 June; 77(6):459-68; *Cell* 2000 Feb. 18; 100(4):423-34; *Development* 2000; 127(19):4293-4301)

In certain embodiments, gli transcript levels are measured and diseased or disordered tissues showing abnormally high gli levels are treated with a hedgehog antagonist. In other embodiments, the condition being treated is known to have a significant correlation with aberrant activation of the hedgehog pathway, even though a measurement of gli expression levels is not made in the tissue being treated. Premature lung tissue, lung cancers (e.g., adenocarcinomas, broncho-alveolar adenocarcinomas, small cell carcinomas), breast cancers (e.g., inferior ductal carcinomas, inferior lobular carcinomas, tubular carcinomas), prostate cancers (e.g., adenocarcinomas), and benign prostatic hyperplasias all show strongly elevated gli-1 expression levels in certain cases. Accordingly, gli-1 expression levels are a powerful diagnostic device to determine which of these tissues should be treated with a hedgehog antagonist. In addition, there is substantial correlative evidence that cancers of urothelial cells (e.g., bladder cancer, other urogenital cancers) will also have elevated gli-1 levels in certain cases. For example, it is known that loss of heterozygosity on chromosome 9q22 is common in bladder cancers. The ptc-1 gene is located at this position and ptc-1 loss of function is probably a partial cause of hyperproliferation, as in many other cancer types. Accordingly, such cancers would also show high gli expression and would be particularly amenable to treatment with a hedgehog antagonist.

Expression of ptc-1 and ptc-2 is also activated by the hedgehog signaling pathway, but these genes are inferior to the gli genes as markers of hedgehog pathway activation. In certain tissues only one of ptc-1 or ptc-2 is expressed although the hedgehog pathway is highly active. For example, in testicular development, desert hedgehog plays an important role and the hedgehog pathway is activated, but only ptc-2 is expressed. Accordingly, these genes may be individually unreliable as markers for hedgehog pathway activation, although simultaneous measurement of both genes is contemplated as a more useful indicator for tissues to be treated with a hedgehog antagonist.

It is anticipated that any degree of gli overexpression may be useful in determining that a hedgehog antagonist will be an effective therapeutic. In preferred embodiments, gli should be expressed at a level at least twice as high as normal. In particularly preferred embodiments, expression is four, six, eight or ten times as high as normal.

For instance, it is contemplated by the invention that, in light of the findings of an apparently broad involvement of hedgehog, ptc, and smoothened in the formation of ordered spatial arrangements of differentiated tissues in vertebrates, the subject method could be used as part of a process for generating and/or maintaining an array of different vertebrate tissue both in vitro and in vivo. The hedgehog antagonist, whether inductive or anti-inductive with respect to proliferation or differentiation of a given tissue, can be, as appropriate, any of the preparations described above.

For example, the present method is applicable to cell culture techniques wherein it is desirable to reduce the level of hedgehog signaling. In vitro neuronal culture systems have proved to be fundamental and indispensable tools for the study of neural development, as well as the identification of neurotrophic factors such as nerve growth factor (NGF), ciliary trophic factors (CNTF), and brain derived neurotrophic factor (BDNF). One use of the present method may be in cultures of neuronal stem cells, such as in the use of such cultures for the generation of new neurons and glia. In such embodiments of the subject method, the cultured cells can be contacted with a hedgehog antagonist of the present invention in order to alter the rate of proliferation of neuronal stem cells in the culture and/or alter the rate of differentiation, or to maintain the integrity of a culture of certain terminally differentiated neuronal cells. In an exemplary embodiment, the subject method can be used to culture, for example, sensory neurons or, alternatively, motor neurons. Such neuronal cultures can be used as convenient assay systems as well as sources of implantable cells for therapeutic treatments.

To further illustrate other uses of the subject hedgehog antagonists, it is noted that intracerebral grafting has emerged as an additional approach to central nervous system therapies. For example, one approach to repairing damaged brain tissues involves the transplantation of cells from fetal or neonatal animals into the adult brain (Dunnett et al. (1987) *J Exp Biol* 123:265-289; and Freund et al. (1985) *J Neurosci* 5:603-616). Fetal neurons from a variety of brain regions can be successfully incorporated into the adult brain, and such grafts can alleviate behavioral defects. For example, movement disorder induced by lesions of dopaminergic projections to the basal ganglia can be prevented by grafts of embryonic dopaminergic neurons. Complex cognitive functions that are impaired after lesions of the neocortex can also be partially restored by grafts of embryonic cortical cells. The subject method can be used to regulate the growth state in the culture, or where fetal tissue is used, especially neuronal stem cells, can be used to regulate the rate of differentiation of the stem cells.

Stem cells useful in the present invention are generally known. For example, several neural crest cells have been identified, some of which are multipotent and likely represent uncommitted neural crest cells, and others of which can generate only one type of cell, such as sensory neurons, and likely represent committed progenitor cells. The role of hedgehog antagonists employed in the present method to culture such stem cells can be to regulate differentiation of the uncommitted progenitor, or to regulate further restriction of the developmental fate of a committed progenitor cell towards becoming a terminally differentiated neuronal cell. For example, the present method can be used in vitro to regulate the differentiation of neural crest cells into glial cells, schwann cells, chromaffin cells, cholinergic sympathetic or parasympathetic neurons, as well as peptidergic and serotonergic neurons. The hedgehog antagonists can be used alone, or can be used in combination with other neurotrophic factors that act to more particularly enhance a particular differentiation fate of the neuronal progenitor cell.

In addition to the implantation of cells cultured in the presence of the subject hedgehog antagonists, yet another aspect of the present invention concerns the therapeutic application of a hedgehog antagonist to regulate the growth state of neurons and other neuronal cells in both the central nervous system and the peripheral nervous system. The ability of ptc, hedgehog, and smoothened to regulate neuronal differentiation during development of the nervous system and also presumably in the adult state indicates that, in certain instances, the subject hedgehog antagonists can be expected to facilitate control of adult neurons with regard to maintenance, functional performance, and aging of normal cells; repair and regeneration processes in chemically or mechanically lesioned cells; and treatment of degeneration in certain pathological conditions. In light of this understanding, the present invention specifically contemplates applications of the subject method to the treatment protocol of (prevention and/or reduction of the severity of) neurological conditions deriving from: (i) acute, subacute, or chronic injury to the nervous system, including traumatic injury, chemical injury, vascular injury and deficits (such as the ischemia resulting from stroke), together with infectious/inflammatory and tumor-induced injury; (ii) aging of the nervous system including Alzheimer's disease; (iii) chronic neurodegenerative diseases of the nervous system, including Parkinson's disease, Huntington's chorea, amyotrophic lateral sclerosis and the like, as well as spinocerebellar degenerations; and (iv) chronic immunological diseases of the nervous system or affecting the nervous system, including multiple sclerosis.

As appropriate, the subject method can also be used in generating nerve prostheses for the repair of central and peripheral nerve damage. In particular, where a crushed or severed axon is intubated by use of a prosthetic device, hedgehog antagonists can be added to the prosthetic device to regulate the rate of growth and regeneration of the dendritic processes. Exemplary nerve guidance channels are described in U.S. Pat. Nos. 5,092,871 and 4,955,892.

In another embodiment, the subject method can be used in the treatment of neoplastic or hyperplastic transformations such as may occur in the central nervous system. For instance, the hedgehog antagonists can be utilized to cause such transformed cells to become either post-mitotic or apoptotic. The present method may, therefore, be used as part of a treatment for, e.g., malignant gliomas, meningiomas, medulloblastomas, neuroectodermal tumors, and ependymomas.

In a preferred embodiment, the subject method can be used as part of a treatment regimen for malignant medulloblastoma and other primary CNS malignant neuroectodermal tumors.

In certain embodiments, the subject method is used as part of treatment program for medulloblastoma. Medulloblastoma, a primary brain tumor, is the most common brain tumor in children. A medulloblastoma is a primitive neuroectodermal tumor arising in the posterior fossa. They account for approximately 25% of all pediatric brain tumors (Miller). Histologically, they are small round cell tumors commonly arranged in true rosettes, but may display some differentiation to astrocytes, ependymal cells or neurons (Rorke; Kleihues). PNET's may arise in other areas of the brain including the pineal gland (pineoblastoma) and cerebrum. Those arising in the supratentorial region generally fare worse than their PF counterparts.

Medulloblastoma/PNET's are known to recur anywhere in the CNS after resection, and can even metastasize to bone. Pretreatment evaluation should therefore include an examination of the spinal cord to exclude the possibility of "dropped metastases". Gadolinium-enhanced MRI has largely replaced myelography for this purpose, and CSF cytology is obtained postoperatively as a routine procedure.

In other embodiments, the subject method is used as part of treatment program for ependymomas. Ependymomas account for approximately 10% of the pediatric brain tumors in children. Grossly, they are tumors that arise from the ependymal lining of the ventricles and microscopically form rosettes, canals, and perivascular rosettes. In the CHOP series of 51 children reported with ependymomas, ¾ were histologically benign. Approximately ⅔ arose from the region of the 4th ventricle. One third presented in the supratentorial region. Age at presentation peaks between birth and 4 years, as demonstrated by SEER data as well as data from CHOP. The median age is about 5 years. Because so many children with this disease are babies, they often require multimodal therapy.

Yet another aspect of the present invention concerns the observation in the art that ptc, hedgehog, and/or smoothened are involved in morphogenic signals involved in other vertebrate organogenic pathways in addition to neuronal differentiation as described above, having apparent roles in other endodermal patterning, as well as both mesodermal and endodermal differentiation processes. Thus, it is contemplated by the invention that compositions comprising hedgehog antagonists can also be utilized for both cell culture and therapeutic methods involving generation and maintenance of non-neuronal tissue.

In one embodiment, the present invention makes use of the discovery that ptc, hedgehog, and smoothened are apparently involved in controlling the development of stem cells responsible for formation of the digestive tract, liver, lungs, and other organs which derive from the primitive gut. Shh serves as an inductive signal from the endoderm to the mesoderm, which is critical to gut morphogenesis. Therefore, for example, hedgehog antagonists of the instant method can be employed for regulating the development and maintenance of an artificial liver that can have multiple metabolic functions of a normal liver. In an exemplary embodiment, the subject method can be used to regulate the proliferation and differentiation of digestive tube stem cells to form hepatocyte cultures which can be used to populate extracellular matrices, or which can be encapsulated in biocompatible polymers, to form both implantable and extracorporeal artificial livers.

In another embodiment, therapeutic compositions of hedgehog antagonists can be utilized in conjunction with transplantation of such artificial livers, as well as embryonic liver structures, to regulate uptake of intraperitoneal implantation, vascularization, and in vivo differentiation and maintenance of the engrafted liver tissue.

In yet another embodiment, the subject method can be employed therapeutically to regulate such organs after physical, chemical or pathological insult. For instance, therapeutic compositions comprising hedgehog antagonists can be utilized in liver repair subsequent to a partial hepatectomy.

The generation of the pancreas and small intestine from the embryonic gut depends on intercellular signaling between the endodermal and mesodermal cells of the gut. In particular, the differentiation of intestinal mesoderm into smooth muscle has been suggested to depend on signals from adjacent endodermal cells. One candidate mediator of endodermally derived signals in the embryonic hindgut is Sonic hedgehog. See, for example, Apelqvist et al. (1997) *Curr Biol* 7:801-4. The Shh gene is expressed throughout the embryonic gut endoderm with the exception of the pancreatic bud endoderm, which instead expresses high levels of the homeodomain protein Ipf1/Pdx1 (insulin promoter factor 1/pancreatic and duodenal homeobox 1), an essential regulator of early pancreatic development. Apelqvist et al., supra, have examined whether the differential expression of Shh in the embryonic gut tube controls the differentiation of the surrounding mesoderm into specialised mesoderm derivatives of the small intestine and pancreas. To test this, they used the promoter of the Ipf1/Pdx1 gene to selectively express Shh in the developing pancreatic epithelium. In Ipf1/Pdx1-Shh transgenic mice, the pancreatic mesoderm developed into smooth muscle and interstitial cells of Cajal, characteristic of the intestine, rather than into pancreatic mesenchyme and spleen. Also, pancreatic explants exposed to Shh underwent a similar program of intestinal differentiation. These results provide evidence that the differential expression of endodermally derived Shh controls the fate of adjacent mesoderm at different regions of the gut tube.

In the context of the present invention, it is contemplated therefore that the subject hedgehog antagonists can be used to control or regulate the proliferation and/or differentiation of pancreatic tissue both in vivo and in vitro.

In another embodiment, hedgehog antagonists are used to generate endodermal tissue from non-endodermal stem cells including mesenchymal stem cells and stem cells derived from mesodermal tissues. Exemplary mesodermal tissues from which stem cells may be isolated include skeletal muscle, cardiac muscle, kidney, bone, cartilage, and fat.

There are a wide variety of pathological cell proliferative and differentiative conditions for which the inhibitors of the present invention may provide therapeutic benefits, with the general strategy being, for example, the correction of aberrant insulin expression, or modulation of differentiation. More generally, however, the present invention relates to a method of inducing and/or maintaining a differentiated state, enhancing survival and/or affecting proliferation of pancreatic cells, by contacting the cells with the subject inhibitors. For instance, it is contemplated by the invention that, in light of the apparent involvement of ptc, hedgehog, and smoothened in the formation of ordered spatial arrangements of pancreatic tissues, the subject method could be used as part of a technique to generate and/or maintain such tissue both in vitro and in vivo. For instance, modulation of the function of hedgehog can be employed in both cell culture and therapeutic methods involving generation and maintenance of β-cells and possibly also for non-pancreatic tissue, such as in controlling the development and maintenance of tissue from the digestive tract, spleen, lungs, urogenital organs (e.g., bladder), and other organs which derive from the primitive gut.

In an exemplary embodiment, the present method can be used in the treatment of hyperplastic and neoplastic disorders effecting pancreatic tissue, particularly those characterized by aberrant proliferation of pancreatic cells. For instance, pancreatic cancers are marked by abnormal proliferation of pancreatic cells, which can result in alterations of insulin secretory capacity of the pancreas. For instance, certain pancreatic hyperplasias, such as pancreatic carcinomas, can result in hypoinsulinemia due to dysfunction of β-cells or decreased islet cell mass.

Moreover, manipulation of hedgehog signaling properties at different points may be useful as part of a strategy for reshaping/repairing pancreatic tissue both in vivo and in vitro. In one embodiment, the present invention makes use of the apparent involvement of ptc, hedgehog, and smoothened in regulating the development of pancreatic tissue. In general, the subject method can be employed therapeutically to regulate the pancreas after physical, chemical or pathological insult. In yet another embodiment, the subject method can be applied to cell culture techniques, and in particular, may be employed to enhance the initial generation of prosthetic pancreatic tissue devices. Manipulation of proliferation and differentiation of pancreatic tissue, for example, by altering hedgehog activity, can provide a means for more carefully controlling the characteristics of a cultured tissue. In an exemplary embodiment, the subject method can be used to augment production of prosthetic devices which require β-islet cells, such as may be used in the encapsulation devices described in, for example, the Aebischer et al. U.S. Pat. No. 4,892,538, the Aebischer et al. U.S. Pat. No. 5,106,627, the Lim U.S. Pat. No. 4,391,909, and the Sefton U.S. Pat. No. 4,353,888. Early progenitor cells to the pancreatic islets are multipotential, and apparently coactivate all the islet-specific genes from the time they first appear. As development proceeds, expression of islet-specific hormones, such as insulin, becomes restricted to the pattern of expression characteristic of mature islet cells. The phenotype of mature islet cells, however, is not stable in culture, as reappearance of embryonal traits in mature β-cells can be observed. By utilizing the subject hedgehog antagonists, the differentiation path or proliferative index of the cells can be regulated.

Furthermore, manipulation of the differentiative state of pancreatic tissue can be utilized in conjunction with transplantation of artificial pancreas. For instance, manipulation of hedgehog function to affect tissue differentiation can be utilized as a means of maintaining graft viability.

Bellusci et al. (1997) *Development* 124:53 report that Sonic hedgehog regulates lung mesenchymal cell proliferation in vivo. Accordingly, the present method can be used to regulate regeneration of lung tissue, e.g., in the treatment of emphysema.

Fujita et al. (1997) *Biochem Biophys Res Commun* 238:658 reported that Sonic hedgehog is expressed in human lung squamous carcinoma and adenocarcinoma cells. The expression of Sonic hedgehog was also detected in the human lung squamous carcinoma tissues, but not in the normal lung tissue of the same patient. They also observed that Sonic hedgehog stimulates the incorporation of BrdU into the carcinoma cells and stimulates their cell growth, while anti-Shh-N inhibited their cell growth. These results suggest that a ptc, hedgehog, and/or smoothened is involved in the cell growth of such transformed lung tissue and therefore indicates that the subject method can be used as part of a treatment of lung carcinoma and adenocarcinomas, and other proliferative disorders involving the lung epithelia.

Many other tumors may, based on evidence such as involvement of the hedgehog pathway in these tumors, or detected expression of hedgehog or its receptor in these tissues during development, be affected by treatment with the subject compounds. Such tumors include, but are by no means limited to, tumors related to Gorlin's syndrome (e.g., medulloblastoma, meningioma, etc.), tumors evidenced in ptc knock-out mice (e.g., hemangioma, rhabdomyosarcoma, etc.), tumors resulting from gli-1 amplification (e.g., glioblastoma, sarcoma, etc.), tumors connected with TRC8, a ptc homolog (e.g., renal carcinoma, thyroid carcinoma, etc.), Ext-1-related tumors (e.g., bone cancer, etc.), Shh-induced tumors (e.g., lung cancer, chondrosarcomas, etc.), and other tumors (e.g., breast cancer, urogenital cancer (e.g., kidney, bladder, ureter, prostate, etc.), adrenal cancer, gastrointestinal cancer (e.g., stomach, intestine, etc.), etc.).

Exemplary forms of cancer which may be treated by the subject methods include, but are not limited to, prostate cancer, bladder cancer, lung cancer (including either small cell or non-small cell cancer), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer. Additional exemplary forms of cancer which may be treated by the subject methods include, but are not limited to, cancer of skeletal or smooth muscle, stomach cancer, cancer of the small intestine, cancer of the salivary gland, anal cancer, rectal cancer, thyroid cancer, parathyroid cancer, pituitary cancer, and nasopharyngeal cancer. Further exemplary forms of cancer which can be treated with the hedgehog antagonists of the present invention include cancers comprising hedgehog expressing cells. Still further exemplary forms of cancer which can be treated with the hedgehog antagonists of the present invention include cancers comprising gli expressing cells. In one embodiment, the cancer is not characterized by a mutation in patched-1.

In still another embodiment of the present invention, compositions comprising hedgehog antagonists can be used in the in vitro generation of skeletal tissue, such as from skeletogenic stem cells, as well as the in vivo treatment of skeletal tissue deficiencies. The present invention particularly contemplates the use of hedgehog antagonists to regulate the rate of chondrogenesis and/or osteogenesis. By "skeletal tissue deficiency", it is meant a deficiency in bone or other skeletal connective tissue at any site where it is desired to restore the bone or connective tissue, no matter how the deficiency originated, e.g., whether as a result of surgical intervention, removal of tumor, ulceration, implant, fracture, or other traumatic or degenerative conditions.

For instance, the method of the present invention can be used as part of a regimen for restoring cartilage function to a connective tissue. Such methods are useful in, for example, the repair of defects or lesions in cartilage tissue which is the result of degenerative wear such as that which results in arthritis, as well as other mechanical derangements which may be caused by trauma to the tissue, such as a displacement of torn meniscus tissue, meniscectomy, a Taxation of a joint by a torn ligament, malignment of joints, bone fracture, or by hereditary disease. The present reparative method is also useful for remodeling cartilage matrix, such as in plastic or reconstructive surgery, as well as periodontal surgery. The present method may also be applied to improving a previous reparative procedure, for example, following surgical repair of a meniscus, ligament, or cartilage. Furthermore, it may prevent the onset or exacerbation of degenerative disease if applied early enough after trauma.

In one embodiment of the present invention, the subject method comprises treating the afflicted connective tissue with a therapeutically sufficient amount of a hedgehog antagonist, particularly an antagonist selective for Indian hedgehog signal transduction, to regulate a cartilage repair response in the connective tissue by managing the rate of differentiation and/or proliferation of chondrocytes embedded in the tissue. Such connective tissues as articular cartilage, interarticular cartilage (menisci), costal cartilage (connecting the true ribs and the sternum), ligaments, and tendons are particularly amenable to treatment in reconstructive and/or regenerative therapies using the subject method. As used herein, regenerative therapies include treatment of degenerative states which have progressed to the point of which impairment of the tissue is obviously manifest, as well as preventive treatments of tissue where degeneration is in its earliest stages or imminent.

In an illustrative embodiment, the subject method can be used as part of a therapeutic intervention in the treatment of cartilage of a diarthroidal joint, such as a knee, an ankle, an elbow, a hip, a wrist, a knuckle of either a finger or toe, or a tempomandibular joint. The treatment can be directed to the meniscus of the joint, to the articular cartilage of the joint, or both. To further illustrate, the subject method can be used to treat a degenerative disorder of a knee, such as which might be the result of traumatic injury (e.g., a sports injury or excessive wear) or osteoarthritis. The subject antagonists may be administered as an injection into the joint with, for instance, an arthroscopic needle. In some instances, the injected agent can be in the form of a hydrogel or other slow release vehicle described above in order to permit a more extended and regular contact of the agent with the treated tissue.

The present invention further contemplates the use of the subject method in the field of cartilage transplantation and prosthetic device therapies. However, problems arise, for instance, because the characteristics of cartilage and fibrocartilage vary between different tissue: such as between articular, meniscal cartilage, ligaments, and tendons, and between the two ends of the same ligament or tendon, and between the superficial and deep parts of the tissue. The zonal arrangement of these tissues may reflect a gradual change in mechanical properties, and failure occurs when implanted tissue, which has not differentiated under those conditions, lacks the ability to appropriately respond. For instance, when meniscal cartilage is used to repair anterior cruciate ligaments, the tissue undergoes a metaplasia to pure fibrous tissue. By regulating the rate of chondrogenesis, the subject method can be used to particularly address this problem, by helping to adaptively control the implanted cells in the new environment and effectively resemble hypertrophic chondrocytes of an earlier developmental stage of the tissue.

In similar fashion, the subject method can be applied to enhancing both the generation of prosthetic cartilage devices and to their implantation. The need for improved treatment has motivated research aimed at creating new cartilage that is based on collagen-glycosaminoglycan templates (Stone et al. (1990) *Clin Orthop Relat Red* 252:129), isolated chondrocytes (Grande et al. (1989) *J Orthop Res* 7:208; and Takigawa et al. (1987) *Bone Miner* 2:449), and chondrocytes attached to natural or synthetic polymers (Walitani et al. (1989) *J Bone Jt Surg* 71B:74; Vacanti et al. (1991) *Plast Reconstr Surg* 88:753; von Schroeder et al. (1991) *J Biomed Mater Res* 25:329; Freed et al. (1993) *J Biomed Mater Res* 27:11; and the Vacanti et al. U.S. Pat. No. 5,041,138). For example, chondrocytes can be grown in culture on biodegradable, biocompatible highly porous scaffolds formed from polymers such as polyglycolic acid, polylactic acid, agarose gel, or other polymers that degrade over time as function of hydrolysis of the polymer backbone into innocuous monomers. The matrices are designed to allow adequate nutrient and gas exchange to the cells until engraftment occurs. The cells can be cultured in vitro until adequate cell volume and density has developed for the cells to be implanted. One advantage of the matrices is that they can be cast or molded into a desired shape on an individual basis, so that the final product closely resembles the patient's own ear or nose (by way of example), or flexible matrices can be used which allow for manipulation at the time of implantation, as in a joint.

In one embodiment of the subject method, the implants are contacted with a hedgehog antagonist during certain stages of the culturing process in order to manage the rate of differentiation of chondrocytes and the formation of hypertrophic chrondrocytes in the culture.

In another embodiment, the implanted device is treated with a hedgehog antagonist in order to actively remodel the implanted matrix and to make it more suitable for its intended function. As set out above with respect to tissue transplants, the artificial transplants suffer from the same deficiency of not being derived in a setting which is comparable to the actual mechanical environment in which the matrix is implanted. The ability to regulate the chondrocytes in the matrix by the subject method can allow the implant to acquire characteristics similar to the tissue for which it is intended to replace.

In yet another embodiment, the subject method is used to enhance attachment of prosthetic devices. To illustrate, the subject method can be used in the implantation of a periodontal prosthesis, wherein the treatment of the surrounding connective tissue stimulates formation of periodontal ligament about the prosthesis.

In still further embodiments, the subject method can be employed as part of a regimen for the generation of bone (osteogenesis) at a site in the animal where such skeletal tissue is deficient. Indian hedgehog is particularly associated with the hypertrophic chondrocytes that are ultimately replaced by osteoblasts. For instance, administration of a hedgehog antagonist of the present invention can be employed as part of a method for regulating the rate of bone loss in a subject. For example, preparations comprising hedgehog antagonists can be employed, for example, to control endochondral ossification in the formation of a "model" for ossification.

In yet another embodiment of the present invention, a hedgehog antagonist can be used to regulate spermatogenesis. The hedgehog proteins, particularly Dhh, have been shown to be involved in the differentiation and/or proliferation and maintenance of testicular germ cells. Dhh expression is initiated in Sertoli cell precursors shortly after the activation of Sry (testicular determining gene) and persists in the testis into the adult. Males are viable but infertile, owing to a complete absence of mature sperm. Examination of the developing testis in different genetic backgrounds suggests that Dhh regulates both early and late stages of spermatogenesis. Bitgood et al. (1996) Curr Biol 6:298. In a preferred embodiment, the hedgehog antagonist can be used as a contraceptive. In similar fashion, hedgehog antagonists of the subject method are potentially useful for modulating normal ovarian function.

The subject method also has wide applicability to the treatment or prophylaxis of disorders afflicting epithelial tissue, as well as in cosmetic uses. In general, the method can be characterized as including a step of administering to an animal an amount of a hedgehog antagonist effective to alter the growth state of a treated epithelial tissue. The mode of administration and dosage regimens will vary depending on the epithelial tissue(s) that is to be treated. For example, topical formulations will be preferred where the treated tissue is epidermal tissue, such as dermal or mucosal tissues.

A method that "promotes the healing of a wound" results in the wound healing more quickly as a result of the treatment than a similar wound heals in the absence of the treatment. "Promotion of wound healing" can also mean that the method regulates the proliferation and/or growth of, inter alia, keratinocytes, or that the wound heals with less scarring, less wound contraction, less collagen deposition and more superficial surface area. In certain instances, "promotion of wound healing" can also mean that certain methods of wound healing have improved success rates, (e.g., the take rates of skin grafts,) when used together with the method of the present invention.

Despite significant progress in reconstructive surgical techniques, scarring can be an important obstacle in regaining normal function and appearance of healed skin. This is particularly true when pathologic scarring such as keloids or hypertrophic scars of the hands or face causes functional disability or physical deformity. In the severest circumstances, such scarring may precipitate psychosocial distress and a life of economic deprivation. Wound repair includes the stages of hemostasis, inflammation, proliferation, and remodeling. The proliferative stage involves multiplication of fibroblasts and endothelial and epithelial cells. Through the use of the subject method, the rate of proliferation of epithelial cells in and proximal to the wound can be controlled in order to accelerate closure of the wound and/or minimize the formation of scar tissue.

The present treatment can also be effective as part of a therapeutic regimen for treating oral and paraoral ulcers, e.g., resulting from radiation and/or chemotherapy. Such ulcers commonly develop within days after chemotherapy or radiation therapy. These ulcers usually begin as small, painful irregularly shaped lesions usually covered by a delicate gray necrotic membrane and surrounded by inflammatory tissue. In many instances, lack of treatment results in proliferation of tissue around the periphery of the lesion on an inflammatory basis. For instance, the epithelium bordering the ulcer usually demonstrates proliferative activity, resulting in loss of continuity of surface epithelium. These lesions, because of their size and loss of epithelial integrity, dispose the body to potential secondary infection. Routine ingestion of food and water becomes a very painful event and, if the ulcers proliferate throughout the alimentary canal, diarrhea usually is evident with all its complicating factors. According to the present invention, a treatment for such ulcers that includes application of a hedgehog antagonist can reduce the abnormal proliferation and differentiation of the affected epithelium, helping to reduce the severity of subsequent inflammatory events.

The subject method and compositions can also be used to treat wounds resulting from dermatological diseases, such as lesions resulting from autoimmune disorders such as psoriasis. Atopic dermititis refers to skin trauma resulting from allergies associated with an immune response caused by allergens such as pollens, foods, dander, insect venoms and plant toxins.

In other embodiments, antiproliferative preparations of hedgehog antagonists can be used to inhibit lens epithelial cell proliferation to prevent post-operative complications of extracapsular cataract extraction. Cataract is an intractable eye disease and various studies on a treatment of cataract have been made. But at present, the treatment of cataract is attained by surgical operations. Cataract surgery has been applied for a long time and various operative methods have been examined. Extracapsular lens extraction has become the method of choice for removing cataracts. The major medical advantages of this technique over intracapsular extraction are lower incidence of aphakic cystoid macular edema and retinal detachment. Extracapsular extraction is also required for implantation of posterior chamber-type intraocular lenses, which are now considered to be the lenses of choice in most cases.

However, a disadvantage of extracapsular cataract extraction is the high incidence of posterior lens capsule opacification, often called after-cataract, which can occur in up to 50% of cases within three years after surgery. After-cataract is caused by proliferation of equatorial and anterior capsule lens epithelial cells that remain after extracapsular lens extraction. These cells proliferate to cause Sommerling rings, and along with fibroblasts, which also deposit and occur on the posterior capsule, cause opacification of the posterior capsule, which interferes with vision. Prevention of after-cataract would be preferable to treatment. To inhibit secondary cataract formation, the subject method provides a means for inhibiting proliferation of the remaining lens epithelial cells. For example, such cells can be induced to remain quiescent by instilling a solution containing a hedgehog antagonist preparation into the anterior chamber of the eye after lens removal. Furthermore, the solution can be osmotically balanced to provide minimal effective dosage when instilled into the anterior chamber of the eye, thereby inhibiting subcapsular epithelial growth with some specificity.

The subject method can also be used in the treatment of corneopathies marked by corneal epithelial cell proliferation, as for example in ocular epithelial disorders such as epithelial downgrowth or squamous cell carcinomas of the ocular surface.

Levine et al. (1997) J Neurosci 17:6277 show that hedgehog proteins can regulate mitogenesis and photoreceptor differentiation in the vertebrate retina, and Ihh is a candidate factor from the pigmented epithelium to promote retinal progenitor proliferation and photoreceptor differentiation. Likewise, Jensen et al. (1997) Development 124:363 demonstrated that treatment of cultures of perinatal mouse retinal cells with the amino-terminal fragment of Sonic hedgehog protein results in an increase in the proportion of cells that incorporate bromodeoxyuridine, in total cell numbers, and in rod photoreceptors, amacrine cells and Muller glial cells, suggesting that Sonic hedgehog promotes the proliferation of retinal precursor cells. Thus, the subject method can be used in the treatment of proliferative diseases of retinal cells and regulate photoreceptor differentiation.

Yet another aspect of the present invention relates to the use of the subject method to control hair growth. Hair is basically composed of keratin, a tough and insoluble protein; its chief strength lies in its disulfide bond of cystine. Each individual hair comprises a cylindrical shaft and a root, and is contained in a follicle, a flask-like depression in the skin. The bottom of the follicle contains a finger-like projection termed the papilla, which consists of connective tissue from which hair grows, and through which blood vessels supply the cells with nourishment. The shaft is the part that extends outwards from the skin surface, whilst the root has been described as the buried part of the hair. The base of the root expands into the hair bulb, which rests upon the papilla. Cells from which the hair is produced grow in the bulb of the follicle; they are extruded in the form of fibers as the cells proliferate in the follicle. Hair "growth" refers to the formation and elongation of the hair fiber by the dividing cells.

As is well known in the art, the common hair cycle is divided into three stages: anagen, catagen and telogen. During the active phase (anagen), the epidermal stem cells of the dermal papilla divide rapidly. Daughter cells move upward and differentiate to form the concentric layers of the hair itself. The transitional stage, catagen, is marked by the cessation of mitosis of the stem cells in the follicle. The resting stage is known as telogen, where the hair is retained within the scalp for several weeks before an emerging new hair developing below it dislodges the telogen-phase shaft from its follicle. From this model it has become clear that the larger the pool of dividing stem cells that differentiate into hair cells, the more hair growth occurs. Accordingly, methods for increasing or reducing hair growth can be carried out by potentiating or inhibiting, respectively, the proliferation of these stem cells.

In certain embodiments, the subject method can be employed as a way of reducing the growth of human hair as opposed to its conventional removal by cutting, shaving, or depilation. For instance, the present method can be used in the treatment of trichosis characterized by abnormally rapid or dense growth of hair, e.g., hypertrichosis. In an exemplary embodiment, hedgehog antagonists can be used to manage hirsutism, a disorder marked by abnormal hairiness. The subject method can also provide a process for extending the duration of depilation.

Moreover, because a hedgehog antagonist will often be cytostatic to epithelial cells, rather than cytotoxic, such agents can be used to protect hair follicle cells from cytotoxic agents that require progression into S-phase of the cell-cycle for efficacy, e.g., radiation-induced death. Treatment by the subject method can provide protection by causing the hair follicle cells to become quiescent, e.g., by inhibiting the cells from entering S phase, and thereby preventing the follicle cells from undergoing mitotic catastrophe or programmed cell death. For instance, hedgehog antagonists can be used for patients undergoing chemo- or radiation-therapies that ordinarily result in hair loss. By inhibiting cell-cycle progression during such therapies, the subject treatment can protect hair follicle cells from death, which might otherwise result from activation of cell death programs. After the therapy has concluded, the instant method can also be removed with concomitant relief of the inhibition of follicle cell proliferation.

The subject method can also be used in the treatment of folliculitis, such as folliculitis decalvans, folliculitis ulerythematosa reticulata or keloid folliculitis. For example, a cosmetic preparation of a hedgehog antagonist can be applied topically in the treatment of pseudofolliculitis, a chronic disorder occurring most often in the submandibular region of the neck and associated with shaving, the characteristic lesions of which are erythematous papules and pustules containing buried hairs.

In certain other embodiments, the subject method can be employed as a way of increasing the growth of human hair. Sato et al. (*J Clin Invest* 104: 855-864, October 1999) reported that upregulation of Shh activity in postnatal skin functions as a biologic switch that induces resting hair follicles to enter anagen with consequent hair growth. Sato et al. used an adenovirus vector, AdShh, to transfer the murine Shh cDNA to skin of postnatal day 19 C57BL/6 mice. The treated skin showed increased mRNA expression of Shh, Patched (the Shh receptor), and Gli 1 (a transcription factor in the Shh pathway). In mice receiving AdShh, but not in controls, acceleration into anagen was evident, since hair follicle size and melanogenesis increased and the hair-specific keratin ghHb-1 and the melanin synthesis-related tyrosinase mRNAs accumulated. Finally, C57BL/6 mice showed marked acceleration of the onset of new hair growth in the region of AdShh administration to skin 2 weeks after treatment, but not in control vector-treated or untreated areas. After 6 months, AdShh-treated skin showed normal hair and normal skin morphology. Thus, it may be useful in certain situations to stimulate hair growth by inhibiting certain negative regulators of the hh pathway (see table Y above).

In another aspect of the invention, the subject method can be used to induce differentiation and/or inhibit proliferation of epithelially derived tissue. Such forms of these molecules can provide a basis for differentiation therapy for the treatment of hyperplastic and/or neoplastic conditions involving epithelial tissue. For example, such preparations can be used for the treatment of cutaneous diseases in which there is abnormal proliferation or growth of cells of the skin.

For instance, the pharmaceutical preparations of the invention are intended for the treatment of hyperplastic epidermal conditions, such as keratosis, as well as for the treatment of neoplastic epidermal conditions such as those characterized by a high proliferation rate for various skin cancers, as for example squamous cell carcinoma. The subject method can also be used in the treatment of autoimmune diseases affecting the skin, in particular, of dermatological diseases involving morbid proliferation and/or keratinization of the epidermis, as for example, caused by psoriasis or atopic dermatosis.

Many common diseases of the skin, such as psoriasis, squamous cell carcinoma, keratoacanthoma and actinic keratosis are characterized by localized abnormal proliferation and growth. For example, in psoriasis, which is characterized by scaly, red, elevated plaques on the skin, the keratinocytes are known to proliferate much more rapidly than normal and to differentiate less completely.

In one embodiment, the preparations of the present invention are suitable for the treatment of dermatological ailments linked to keratinization disorders causing abnormal proliferation of skin cells, which disorders may be marked by either inflammatory or noninflammatory components. To illustrate, therapeutic preparations of a hedgehog antagonist, e.g., which promotes quiescence or differentiation can be used to treat varying forms of psoriasis, be they cutaneous, mucosal or ungual. Psoriasis, as described above, is typically characterized by epidermal keratinocytes that display marked proliferative activation and differentiation along a "regenerative" pathway. Treatment with an antiproliferative embodiment of the subject method can be used to reverse the pathological epidermal activation and can provide a basis for sustained remission of the disease.

A variety of other keratotic lesions are also candidates for treatment with the subject method. Actinic keratoses, for example, are superficial inflammatory premalignant tumors arising on sun-exposed and irradiated skin. The lesions are erythematous to brown with variable scaling. Current therapies include excisional and cryosurgery. These treatments are painful, however, and often produce cosmetically unacceptable scarring. Accordingly, treatment of keratosis, such as actinic keratosis, can include application, preferably topical, of a hedgehog antagonist composition in amounts sufficient to inhibit hyperproliferation of epidermal/epidermoid cells of the lesion.

Acne represents yet another dermatologic ailment which may be treated by the subject method. Acne vulgaris, for instance, is a multifactor disease most commonly occurring in teenagers and young adults, and is characterized by the appearance of inflammatory and noninflammatory lesions on the face and upper trunk. The basic defect which gives rise to acne vulgaris is hypercornification of the duct of a hyperactive sebaceous gland. Hypercornification blocks the normal mobility of skin and follicle microorganisms, and in so doing, stimulates the release of lipases by *Propinobacterium acnes* and *Staphylococcus epidermidis* bacteria and *Pitrosporum ovale*, a yeast. Treatment with an antiproliferative hedgehog antagonist, particularly topical preparations, may be useful for preventing the transitional features of the ducts, e.g., hypercornification, which lead to lesion formation. The subject treatment may further include, for example, antibiotics, retinoids and antiandrogens.

The present invention also provides a method for treating various forms of dermatitis. Dermatitis is a descriptive term referring to poorly demarcated lesions that are either pruritic, erythematous, scaly, blistered, weeping, fissured or crusted. These lesions arise from any of a wide variety of causes. The most common types of dermatitis are atopic, contact and diaper dermatitis. For instance, seborrheic dermatitis is a chronic, usually pruritic, dermatitis with erythema, dry, moist, or greasy scaling, and yellow-crusted patches on various areas, especially the scalp, with exfoliation of an excessive amount of dry scales. The subject method can also be used in the treatment of stasis dermatitis, an often chronic, usually eczematous dermatitis. Actinic dermatitis is dermatitis that due to exposure to actinic radiation such as that from the sun, ultraviolet waves, or x- or gamma-radiation. According to the present invention, the subject method can be used in the treatment and/or prevention of certain symptoms of dermatitis caused by unwanted proliferation of epithelial cells. Such therapies for these various forms of dermatitis can also include topical and systemic corticosteroids, antipruritics, and antibiotics.

Ailments that may be treated by the subject method are disorders specific to non-humans, such as mange.

In still another embodiment, the subject method can be used in the treatment of human cancers, such as tumors of epithelial tissues such as the skin. For example, hedgehog antagonists can be employed in the subject method as part of a treatment for human carcinomas, adenocarcinomas, sarcomas and the like. Exemplary forms of cancer which may be treated by the subject methods include, but are not limited to, prostate cancer, bladder cancer, lung cancer (including either small cell or non-small cell cancer), colon cancer, kidney cancer, liver cancer, breast cancer, cervical cancer, endometrial or other uterine cancer, ovarian cancer, testicular cancer, cancer of the penis, cancer of the vagina, cancer of the urethra, gall bladder cancer, esophageal cancer, or pancreatic cancer. Additional exemplary forms of cancer which may be treated by the subject methods include, but are not limited to, cancer of skeletal or smooth muscle, stomach cancer, cancer of the small intestine, cancer of the salivary gland, anal cancer, rectal cancer, thyroid cancer, parathyroid cancer, pituitary cancer, and nasopharyngeal cancer. Further exemplary forms of cancer which can be treated with the hedgehog antagonists of the present invention include cancers comprising hedgehog expressing cells. Still further exemplary forms of cancer which can be treated with the hedgehog antagonists of the present invention include cancers comprising gli expressing cells. In one embodiment, the cancer is not characterized by a mutation in patched-1.

In yet another aspect, the subject method can be used in regulating the activity in a noncanonical Shh pathway that is independent of the Patched-Smoothened receptor complex and the Gli transcription factors. In a recent report, Jarov et al. (*Dev. Biol.* 261(2): 520-536, 2003) describes that, when Shh was immobilized to the substrate (extracellular matrix) or produced by neuroepithelial cells themselves after transfection, neural plate explants failed to disperse and instead formed compact structures. Changes in the adhesive capacities of neuroepithelial cells caused by Shh could be accounted for by inactivation of surface 1-integrins combined with an increase in N-cadherin-mediated cell adhesion. This immobilized-Shh-mediated adhesion does not contradict or interfere with the previously known (soluble) Shh-mediated inductive, mitogenic, and trophic functions, since the immobilized Shh promoted differentiation of neuroepithelial cells into motor neurons and floor plate cells with the same potency as soluble Shh. Jarov et al. also demonstrated that Shh regulation of adhesion properties during neural tube morphogenesis is rapid and reversible, and it does not involve the classical Patched-Smoothened-Gli signaling pathway, and it is independent and discernible from Shh-mediated cell differentiation. Thus, modifications of the adhesive properties of neural epithelial cells induced by Shh cannot be attributed to its differentiation-promoting effect, but reveal a novel function of Shh in this tissue that has never been described before.

Therefore, the methods of the invention may be used to regulate this non-canonical hedgehog pathway that does not depend on Ptc, Smo, and/or Gli. More specifically, hedgehog antagonists (such as RNAi inhibitors of Shh) may be used to disrupt this function in neuronal or other applicable tissues, preferably at specific developmental stages.

In another aspect, the present invention provides pharmaceutical preparations comprising hedgehog antagonists. The hedgehog antagonists for use in the subject method may be conveniently formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the hedgehog antagonist, its use in the pharmaceutical preparation of the invention is contemplated. Suitable vehicles and their formulation inclusive of other proteins are described, for example, in the book *Remington's Pharmaceutical Sciences* (Remington's Pharmaceutical Sciences. Mack Publishing Company, Easton, Pa., USA 1985). These vehicles include injectable "deposit formulations".

Pharmaceutical formulations of the present invention can also include veterinary compositions, e.g., pharmaceutical preparations of the hedgehog antagonists suitable for veterinary uses, e.g., for the treatment of livestock or domestic animals, e.g., dogs.

Methods of introduction may also be provided by rechargeable or biodegradable devices. Various slow release polymeric devices have been developed and tested in vivo in recent years for the controlled delivery of drugs, including proteinaceous biopharmaceuticals. A variety of biocompatible polymers (including hydrogels), including both biodegradable and non-degradable polymers, can be used to form an implant for the sustained release of a hedgehog antagonist at a particular target site.

The preparations of the present invention may be given orally, parenterally, topically, or rectally. They are, of course, given by forms suitable for each administration route. For example, they are administered in tablets or capsule form, by injection, inhalation, eye lotion, ointment, suppository, controlled release patch, etc. administration by injection, infusion or inhalation; topical by lotion or ointment; and rectal by suppositories. Oral and topical administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the RNAi antagonists of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular hedgehog antagonist employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of an RNAi antagonist of the invention will be that amount of the compound that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms.

The term "treatment" is intended to encompass also prophylaxis, therapy and cure.

The patient receiving this treatment is any animal in need, including primates, in particular humans, and other non-human mammals such as equines, cattle, swine and sheep; and poultry and pets in general.

The RNAi antagonist of the invention can be administered as such or in admixtures with pharmaceutically acceptable and/or sterile carriers and can also be administered in conjunction with other antimicrobial agents such as penicillins, cephalosporins, aminoglycosides and glycopeptides. Conjunctive therapy thus includes sequential, simultaneous and separate administration of the active compound in a way that the therapeutic effects of the first administered one is not entirely disappeared when the subsequent is administered.

VII. Pharmacogenomics

The ability to rapidly assess gene expression in patients promises to radically change the means by which a physician selects an appropriate pharmaceutical for treating a particular disease. Gene expression profiles of diseased tissue can be obtained and therapeutic measures can be selected based on the gene expression profile. This methodology is particularly effective when the molecular mechanism of action for a given therapeutic is known. In other words, if an anti-tumor agent acts by inhibiting a particular oncoprotein, it is desirable to know whether a particular cancer expresses that oncogene before attempting to treat the cancer with the anti-tumor agent. As expression profiling becomes faster, cheaper and more reliable, such information may become a routine part of treatment selection, minimizing fruitless treatment protocols and allowing the more rapid application of appropriate therapeutics.

In addition, if a pool of patients suffering from a certain type of disorder can be segregated into subgroups based on gene expression profiles, drugs can be re-tested for their ability to affect these defined subgroups of patients. Thus drugs that appeared useless in the patient group as a whole may now be found to be useful for patient subgroups. This type of screening may allow the resurrection of failed compounds, the identification of new compounds and the identification of new uses for well-known compounds.

The expression of a particular gene can be assessed in many ways. The level of gene transcript or the level of encoded protein may be determined. The presence of a protein may be determined directly, through methods such as antibody binding, mass spectroscopy and two-dimensional gel electrophoresis, or indirectly, by detecting an activity of the protein, be it a biochemical activity or an effect on the levels of another protein or expression of one or more genes.

Methods for measuring levels of gene transcripts are well known in the art and depend for the most part on hybridization of a single stranded probe to the transcript in question (or a cDNA thereof). Such methods include Northern blotting, using a labeled probe, or PCR amplification of the cDNA (also known as RT-PCR). mRNAs and cDNAs may be labeled according to various methods and hybridized to an oligonucleotide array. Such arrays may contain ordered probes corresponding to one or more genes, and in preferred embodiments, the array contains probes corresponding to all the genes in the genome of the organism from which the RNA was obtained.

A number of methodologies are currently used for the measurement of gene expression. The most sensitive of these methodologies utilizes the polymerase chain reaction (PCR) technique, the details of which are provided in U.S. Pat. No. 4,683,195, U.S. Pat. No. 4,683,202, and U.S. Pat. No. 4,965,188, all to Mullis et al., all of which are specifically incorporated herein by reference. The details of PCR technology, thus, are not included herein. Recently, additional technologies for the amplification of nucleic acids have been described, most of which are based upon isothermal amplification strategies as opposed to the temperature cycling required for PCR. These strategies include, for example, Strand Displacement Amplification (SDA) (U.S. Pat. Nos. 5,455,166 and 5,457,027 both to Walker; Walker et al. (1992) PNAS 89:392; each of which is specifically incorporated herein by reference) and Nucleic Acid Sequence-Based Amplification (NASBA) (U.S. Pat. No. 5,130,238 to Malek et al.; European Patent 525882 to Kievits et al.; both specifically incorporated herein by reference). Each of these amplification technologies are similar in that they employ the use of short, deoxyribonucleic acid primers to define the region of amplification, regardless of the enzymes or specific conditions used.

Until recently, RNA amplification required a separate, additional step and the use of non-thermostable reverse transcriptase enzymes to generate a cDNA capable of being amplified by a thermostable DNA polymerase, such as Taq. The discovery of a recombinant thermostable enzyme (rTth) capable of coupling reverse transcription of the RNA with DNA amplification in a single enzyme: single reaction procedure greatly simplified and enhanced RNA amplification (see, Myers & Gelfand (1991) Biochemistry 30:7661-7666; U.S. Pat. No. 5,407,800 to Gelfand and Myers, both incorporated herein by reference).

In gene expression analysis with microarrays, an array of "probe" oligonucleotides is contacted with a nucleic acid sample of interest, i.e., target, such as polyA mRNA from a particular tissue type. Contact is carried out under hybridization conditions and unbound nucleic acid is then removed. The resultant pattern of hybridized nucleic acid provides information regarding the genetic profile of the sample tested. Gene expression analysis finds use in a variety of applications, including: the identification of novel expression of genes, the correlation of gene expression to a particular phenotype, screening for disease predisposition, identifying the effect of a particular agent on cellular gene expression, such as in toxicity testing; among other applications. Detailed methods for analyzing transcript levels are described in the following patents: U.S. Pat. No. 5,082,830 and WO 97/27317.

Other references of interest include: Schena et al., Science (1995) 467-470; Schena et al., P.N.A.S. U.S.A. (1996) 93: 10614-10616; Pietu et al., Genome Res. (June 1996) 6: 492-503; Zhao et al., Gene (Apr. 24, 1995) 156: 207-213; Soares, Curr. Opin. Biotechnol. (October 1997) 8: 542-546; Raval, J. Pharmacol Toxicol Methods (November 1994) 32: 125-127; Chalifour et al., Anal. Biochem (Feb. 1, 1994) 216: 299-304; Stolz & Tuan, Mol. Biotechnol. (December 19960 6: 225-230; Hong et al., Bioscience Reports (1982) 2: 907; and McGraw, Anal. Biochem. (1984) 143:298.

VIII. Pharmaceutical Compositions and Formulations

The RNAi constructs of the invention may also be admixed, encapsulated, conjugated or otherwise associated with other molecules, molecule structures or mixtures of compounds, as for example, liposomes, polymers, receptor targeted molecules, oral, rectal, topical or other formulations, for assisting in uptake, distribution and/or absorption. The subject RNAi constructs can be provided in formulations also including penetration enhancers, carrier compounds and/or transfection agents.

Representative United States patents that teach the preparation of uptake, distribution and/or absorption assisting formulations which can be adapted for delivery of RNAi constructs include, but are not limited to, U.S. Pat. Nos. 5,108,921; 5,354,844; 5,416,016; 5,459,127; 5,521,291; 51543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756.

While it is possible for a compound of the present invention to be administered alone, it is preferable to administer the compound as a pharmaceutical formulation (composition). The hedgehog antagonists according to the invention may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

Thus, another aspect of the present invention provides pharmaceutically acceptable compositions comprising a therapeutically effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin; or (4) intravaginally or intrarectally, for example, as a pessary, cream or foam. However, in certain embodiments the subject compounds may be simply dissolved or suspended in sterile water. In certain embodiments, the pharmaceutical preparation is non-pyrogenic, i.e., does not elevate the body temperature of a patient.

The phrase "therapeutically effective amount" as used herein means that amount of a compound, material, or composition comprising a compound of the present invention which is effective for producing some desired therapeutic effect by overcoming a hedgehog gain-of-function phenotype in at least a sub-population of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject antagonists from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As set out above, certain embodiments of the present hedgehog antagonists may contain a basic functional group, such as amino or alkylamino, and are, thus, capable of forming pharmaceutically acceptable salts with pharmaceutically acceptable acids. The term "pharmaceutically acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthylate, mesylate, glucoheptonate, lactobionate, and laurylsulphonate salts and the like. (See, for example, Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically acceptable salts with pharmaceutically acceptable bases. The term "pharmaceutically acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically acceptable metal cation, with ammonia, or with a pharmaceutically acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra).

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,NI-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids.

For siRNA oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene disulfonic acid, polygalacturonic acid, and the like; and (d) salts formed from elemental anions such as chlorine, bromine, and iodine.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouthwashes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions that can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

It is known that sterols, such as cholesterol, will form complexes with cyclodextrins. Thus, in preferred embodiments, where the inhibitor is a steroidal alkaloid, it may be formulated with cyclodextrins, such as α-, β- and γ-cyclodextrin, dimethyl-β cyclodextrin and 2-hydroxypropyl-β-cyclodextrin.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active hedgehog antagonist.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the hedgehog antagonists in the proper medium. Absorption enhancers can also be used to increase the flux of the hedgehog antagonists across the skin. The rate of such flux can be controlled by either providing a rate controlling membrane or dispersing the compound in a polymer matrix or gel.

Another aspect of the invention provides aerosols for the delivery of RNAi constructs to the respiratory tract. The respiratory tract includes the upper airways, including the oropharynx and larynx, followed by the lower airways, which include the trachea followed by bifurcations into the bronchi and bronchioli. The upper and lower airways are called the conductive airways. The terminal bronchioli then divide into respiratory bronchioli which then lead to the ultimate respiratory zone, the alveoli, or deep lung.

Herein, administration by inhalation may be oral and/or nasal. Examples of pharmaceutical devices for aerosol delivery include metered dose inhalers (MDIs), dry powder inhalers (DPIs), and air-jet nebulizers. Exemplary nucleic acid delivery systems by inhalation which can be readily adapted for delivery of the subject RNAi constructs are described in, for example, U.S. Pat. Nos. 5,756,353; 5,858,784; and PCT applications WO98/31346; WO98/10796; WO00/27359; WO01/54664; WO02/060412. Other aerosol formulations that may be used for delivering the double-stranded RNAs are described in U.S. Pat. Nos. 6,294,153; 6,344,194; 6,071,497, and PCT applications WO02/066078; WO02/053190; WO01/60420; WO00/66206. Further, methods for delivering RNAi constructs can be adapted from those used in delivering other oligonucleotides (e.g., an antisense oligonucleotide) by inhalation, such as described in Templin et al., *Antisense Nucleic Acid Drug Dev,* 2000, 10:359-68; Sandrasagra et al., *Expert Opin Biol Ther,* 2001, 1:979-83; Sandrasagra et al., *Antisense Nucleic Acid Drug Dev,* 2002, 12:177-81.

The human lungs can remove or rapidly degrade hydrolytically cleavable deposited aerosols over periods ranging from minutes to hours. In the upper airways, ciliated epithelia contribute to the "mucociliary excalator" by which particles are swept from the airways toward the mouth. Pavia, D., "LungMucociliary Clearance," in *Aerosols and the Lung: Clinical and Experimental Aspects,* Clarke, S. W. and Pavia, D., Eds., Butterworths, London, 1984. In the deep lungs, alveolar macrophages are capable of phagocytosing particles soon after their deposition. Warheit et al. *Microscopy Res. Tech.,* 26: 412-422 (1993); and Brain, J. D., "Physiology and Pathophysiology of Pulmonary Macrophages," in *The Reticuloendothelial System,* S. M. Reichard and J. Filkins, Eds., Plenum, New. York., pp. 315-327, 1985. The deep lung, or alveoli, are the primary target of inhaled therapeutic aerosols for systemic delivery of RNAi constructs.

In preferred embodiments, particularly where systemic dosing with the RNAi construct is desired, the aerosoled RNAi constructs are formulated as microparticles. Microparticles having a diameter of between 0.5 and ten microns can penetrate the lungs, passing through most of the natural barriers. A diameter of less than ten microns is required to bypass the throat; a diameter of 0.5 microns or greater is required to avoid being exhaled.

Another aspect of the invention relates to coated medical devices. For instance, in certain embodiments, the subject invention provides a medical device having a coating adhered to at least one surface, wherein the coating includes the subject polymer matrix and an RNAi construct containing modifications as disclosed herein. Optionally the coating further comprises protein noncovalently associated with the RNAi construct (or selected to interact with the RNAi construct upon release from the coating). Such coatings can be applied to surgical implements such as screws, plates, washers, sutures, prosthesis anchors, tacks, staples, electrical leads, valves, membranes. The devices can be catheters, intraluminal devices, wires, implantable vascular access ports, blood storage bags, blood tubing, central venous catheters, arterial catheters, vascular grafts, intraaortic balloon pumps, heart valves, cardiovascular sutures, artificial hearts, a pacemaker, ventricular assist pumps, extracorporeal devices, blood filters, hemodialysis units, hemoperfasion units, plasmapheresis units, and filters adapted for deployment in a blood vessel.

In some embodiments according to the present invention, monomers for forming a polymer are combined with an RNAi construct and are mixed to make a homogeneous dispersion of the RNAi construct in the monomer solution. The dispersion is then applied to a stent or other device according to a conventional coating process, after which the crosslinking process is initiated by a conventional initiator, such as UV light. In other embodiments according to the present invention, a polymer composition is combined with an RNAi construct to form a dispersion. The dispersion is then applied to a surface of a medical device and the polymer is cross-linked to form a solid coating. In other embodiments according to the present invention, a polymer and an RNAi construct are combined with a suitable solvent to form a dispersion, which is then applied to a stent in a conventional fashion. The solvent is then removed by a conventional process, such as heat evaporation, with the result that the polymer and RNAi construct (together forming a sustained-release drug delivery system) remain on the stent as a coating. An analogous process may be used where the RNAi construct is dissolved in the polymer composition. Where the RNAi is to be pre-mixed with a protein, solvents are preferably selected so as to preserve the tertiary structure of the protein.

In some embodiments according to the invention, the system comprises a polymer that is relatively rigid. In other embodiments, the system comprises a polymer that is soft and malleable. In still other embodiments, the system includes a polymer that has an adhesive character. Hardness, elasticity, adhesive, and other characteristics of the polymer are widely variable, depending upon the particular final physical form of the system, as discussed in more detail below.

Embodiments of the system according to the present invention take many different forms. In some embodiments, the system consists of the RNAi construct suspended or dispersed in the polymer. In certain other embodiments, the system consists of an RNAi construct and a semi solid or gel polymer, which is adapted to be injected via a syringe into a body. In other embodiments according to the present invention, the system consists of an RNAi construct and a soft flexible polymer, which is adapted to be inserted or implanted into a body by a suitable surgical method. In still further embodiments according to the present invention, the system consists of a hard, solid polymer, which is adapted to be inserted or implanted into a body by a suitable surgical method. In further embodiments, the system comprises a polymer having the RNAi construct suspended or dispersed therein, wherein the RNAi construct and polymer mixture forms a coating on a surgical implement, such as a screw, stent, pacemaker, etc. In particular embodiments according to the present invention, the device consists of a hard, solid polymer, which is shaped in the form of a surgical implement such as a surgical screw, plate, stent, etc., or some part thereof. In other embodiments according to the present invention, the system includes a polymer that is in the form of a suture having the RNAi construct dispersed or suspended therein.

In some embodiments according to the present invention, provided is a medical device comprising a substrate having a surface, such as an exterior surface, and a coating on the exterior surface. The coating comprises a polymer and an RNAi construct dispersed in the polymer, wherein the polymer is permeable to the RNAi construct or biodegrades to release the RNAi construct. Optionally, the coating further comprises a protein that associates with the RNAi construct. In certain embodiments according to the present invention, the device comprises an RNAi construct suspended or dispersed in a suitable polymer, wherein the RNAi construct and polymer are coated onto an entire substrate, e.g., a surgical implement. Such coating may be accomplished by spray coating or dip coating.

In other embodiments according to the present invention, the device comprises an RNAi construct and polymer suspension or dispersion, wherein the polymer is rigid, and forms a constituent part of a device to be inserted or implanted into a body. Optionally, the suspension or dispersion further comprises a polypeptide that non-covalently interacts with the RNAi construct. For instance, in particular embodiments according to the present invention, the device is a surgical screw, stent, pacemaker, etc. coated with the RNAi construct suspended or dispersed in the polymer. In other particular embodiments according to the present invention, the polymer in which the RNAi construct is suspended forms a tip or a head, or part thereof, of a surgical screw. In other embodiments according to the present invention, the polymer in which RNAi construct is suspended or dispersed is coated onto a surgical implement such as surgical tubing (such as colostomy, peritoneal lavage, catheter, and intravenous tubing). In still further embodiments according to the present invention, the device is an intravenous needle having the polymer and RNAi construct coated thereon.

As discussed above, the coating according to the present invention comprises a polymer that is bioerodible or non bioerodible. The choice of bioerodible versus non-bioerodible polymer is made based upon the intended end use of the system or device. In some embodiments according to the present invention, the polymer is advantageously bioerodible. For instance, where the system is a coating on a surgically implantable device, such as a screw, stent, pacemaker, etc., the polymer is advantageously bioerodible. Other embodiments according to the present invention in which the polymer is advantageously bioerodible include devices that are implantable, inhalable, or injectable suspensions or dispersions of RNAi construct in a polymer, wherein the further elements (such as screws or anchors) are not utilized.

In some embodiments according to the present invention wherein the polymer is poorly permeable and bioerodible, the rate of bioerosion of the polymer is advantageously sufficiently slower than the rate of RNAi construct release so that the polymer remains in place for a substantial period of time after the RNAi construct has been released, but is eventually bioeroded and resorbed into the surrounding tissue. For example, where the device is a bioerodible suture comprising the RNAi construct suspended or dispersed in a bioerodible polymer, the rate of bioerosion of the polymer is advantageously slow enough that the RNAi construct is released in a linear manner over a period of about three to about 14 days, but the sutures persist for a period of about three weeks to about six months. Similar devices according to the present invention include surgical staples comprising an RNAi construct suspended or dispersed in a bioerodible polymer.

In other embodiments according to the present invention, the rate of bioerosion of the polymer is advantageously on the same order as the rate of RNAi construct release. For instance, where the system comprises an RNAi construct suspended or dispersed in a polymer that is coated onto a surgical implement, such as an orthopedic screw, a stent, a pacemaker, or a non-bioerodible suture, the polymer advantageously bioerodes at such a rate that the surface area of the RNAi construct that is directly exposed to the surrounding body tissue remains substantially constant over time.

In other embodiments according to the present invention, the polymer vehicle is permeable to water in the surrounding tissue, e.g. in blood plasma. In such cases, water solution may permeate the polymer, thereby contacting the RNAi construct. The rate of dissolution may be governed by a complex set of variables, such as the polymer's permeability, the solubility of the RNAi construct, the pH, ionic strength, and protein composition, etc. of the physiologic fluid.

In some embodiments according to the present invention, the polymer is non-bioerodible. Non bioerodible polymers are especially useful where the system includes a polymer intended to be coated onto, or form a constituent part of, a surgical implement that is adapted to be permanently, or semi permanently, inserted or implanted into a body. Exemplary devices in which the polymer advantageously forms a permanent coating on a surgical implement include an orthopedic screw, a stent, a prosthetic joint, an artificial valve, a permanent suture, a pacemaker, etc.

There are a multiplicity of different stents that may be utilized following percutaneous transluminal coronary angioplasty. Although any number of stents may be utilized in accordance with the present invention, for simplicity, a limited number of stents will be described in exemplary embodiments of the present invention. The skilled artisan will recognize that any number of stents may be utilized in connection with the present invention. In addition, as stated above, other medical devices may be utilized.

A stent is commonly used as a tubular structure left inside the lumen of a duct to relieve an obstruction. Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen.

The stents of the present invention may be fabricated utilizing any number of methods. For example, the stent may be fabricated from a hollow or formed stainless steel tube that may be machined using lasers, electric discharge milling, chemical etching or other means. The stent is inserted into the body and placed at the desired site in an unexpanded form. In one exemplary embodiment, expansion may be effected in a blood vessel by a balloon catheter, where the final diameter of the stent is a function of the diameter of the balloon catheter used.

It should be appreciated that a stent in accordance with the present invention may be embodied in a shape-memory material, including, for example, an appropriate alloy of nickel and titanium or stainless steel.

Structures formed from stainless steel may be made self-expanding by configuring the stainless steel in a predetermined manner, for example, by twisting it into a braided configuration. In this embodiment after the stent has been formed it may be compressed so as to occupy a space sufficiently small as to permit its insertion in a blood vessel or other tissue by insertion means, wherein the insertion means include a suitable catheter, or flexible rod.

On emerging from the catheter, the stent may be configured to expand into the desired configuration where the expansion is automatic or triggered by a change in pressure, temperature or electrical stimulation.

Regardless of the design of the stent, it is preferable to have the RNAi construct applied with enough specificity and a sufficient concentration to provide an effective dosage in the lesion area. In this regard, the "reservoir size" in the coating is preferably sized to adequately apply the RNAi construct at the desired location and in the desired amount.

In an alternate exemplary embodiment, the entire inner and outer surface of the stent may be coated with the RNAi construct in therapeutic dosage amounts. It is, however, important to note that the coating techniques may vary depending on the RNAi construct and any included protein. Also, the coating techniques may vary depending on the material comprising the stent or other intraluminal medical device.

The intraluminal medical device comprises the sustained release drug delivery coating. The RNAi construct coating may be applied to the stent via a conventional coating process, such as impregnating coating, spray coating and dip coating.

In one embodiment, an intraluminal medical device comprises an elongate radially expandable tubular stent having an interior luminal surface and an opposite exterior surface extending along a longitudinal stent axis. The stent may include a permanent implantable stent, an implantable grafted stent, or a temporary stent, wherein the temporary stent is defined as a stent that is expandable inside a vessel and is thereafter retractable from the vessel. The stent configuration may comprise a coil stent, a memory coil stent, a Nitinol stent, a mesh stent, a scaffold stent, a sleeve stent, a permeable stent, a stent having a temperature sensor, a porous stent, and the like. The stent may be deployed according to conventional methodology, such as by an inflatable balloon catheter, by a self-deployment mechanism (after release from a catheter), or by other appropriate means. The elongate radially expandable tubular stent may be a grafted stent, wherein the grafted stent is a composite device having a stent inside or outside of a graft. The graft may be a vascular graft, such as an ePTFE graft, a biological graft, or a woven graft.

The RNAi construct, and any associated molecules, may be incorporated onto or affixed to the stent in a number of ways. In the exemplary embodiment, the RNAi construct is directly incorporated into a polymeric matrix and sprayed onto the outer surface of the stent. The RNAi construct elutes from the polymeric matrix over time and enters the surrounding tissue. The RNAi construct preferably remains on the stent for at least three days up to approximately six months, and more preferably between seven and thirty days.

In certain embodiments, the polymer according to the present invention comprises any biologically tolerated polymer that is permeable to the RNAi construct and while having a permeability such that it is not the principal rate determining factor in the rate of release of the RNAi construct from the polymer.

In some embodiments according to the present invention, the polymer is non-bioerodible. Examples of non-bioerodible polymers useful in the present invention include poly(ethylene-co-vinyl acetate) (EVA), polyvinylalcohol and polyurethanes, such as polycarbonate-based polyurethanes. In other embodiments of the present invention, the polymer is bioerodible. Examples of bioerodible polymers useful in the present invention include polyanhydride, polylactic acid, polyglycolic acid, polyorthoester, polyalkylcyanoacrylate or derivatives and copolymers thereof. The skilled artisan will recognize that the choice of bioerodibility or non-bioerodibility of the polymer depends upon the final physical form of the system, as described in greater detail below. Other exemplary polymers include polysilicone and polymers derived from hyaluronic acid. The skilled artisan will understand that the polymer according to the present invention is prepared under conditions suitable to impart permeability such that it is not the principal rate determining factor in the release of the RNAi construct from the polymer.

Moreover, suitable polymers include naturally occurring (collagen, hyaluronic acid, etc.) or synthetic materials that are biologically compatible with bodily fluids and mammalian tissues, and essentially insoluble in bodily fluids with which the polymer will come in contact. In addition, the suitable polymers essentially prevent interaction between the RNAi construct dispersed/suspended in the polymer and proteinaceous components in the bodily fluid. The use of rapidly dissolving polymers or polymers highly soluble in bodily fluid or which permit interaction between the RNAi construct and endogenous proteinaceous components are to be avoided in certain instances since dissolution of the polymer or interaction with proteinaceous components would affect the constancy of drug release. The selection of polymers may differ where the RNAi construct is pre-associated with protein in the coating.

Other suitable polymers include polypropylene, polyester, polyethylene vinyl acetate (PVA or EVA), polyethylene oxide (PEO), polypropylene oxide, polycarboxylic acids, polyalkylacrylates, cellulose ethers, silicone, poly(dl-lactide-co glycolide), various Eudragits (for example, NE30D, RS PO and RL PO), polyalkyl-alkyacrylate copolymers, polyester-polyurethane block copolymers, polyether-polyurethane block copolymers, polydioxanone, poly-(β-hydroxybutyrate), polylactic acid (PLA), polycaprolactone, polyglycolic acid, and PEO-PLA copolymers.

The coating of the present invention may be formed by mixing one or more suitable monomers and a suitable RNAi construct, then polymerizing the monomer to form the polymer system. In this way, the RNAi construct, and any associated protein, is dissolved or dispersed in the polymer. In other embodiments, the RNAi construct, and any associated protein, is mixed into a liquid polymer or polymer dispersion and then the polymer is further processed to form the inventive coating. Suitable further processing may include crosslinking with suitable crosslinking RNAi constructs, further polymerization of the liquid polymer or polymer dispersion, copolymerization with a suitable monomer, block copolymerization with suitable polymer blocks, etc. The further processing traps the RNAi construct in the polymer so that the RNAi construct is suspended or dispersed in the polymer vehicle.

Any number of non-erodible polymers may be utilized in conjunction with the RNAi construct. Film-forming polymers that can be used for coatings in this application can be absorbable or non-absorbable and must be biocompatible to minimize irritation to the vessel wall. The polymer may be either biostable or bioabsorbable depending on the desired rate of release or the desired degree of polymer stability, but a bioabsorbable polymer may be preferred since, unlike biostable polymer, it will not be present long after implantation to cause any adverse, chronic local response. Furthermore, bioabsorbable polymers do not present the risk that over extended periods of time there could be an adhesion loss between the stent and coating caused by the stresses of the biological environment that could dislodge the coating and introduce further problems even after the stent is encapsulated in tissue.

Suitable film-forming bioabsorbable polymers that could be used include polymers selected from the group consisting of aliphatic polyesters, poly(amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, biomolecules and blends thereof. For the purpose of this invention aliphatic polyesters include homopolymers and copolymers of lactide (which includes lactic acid d-, l- and meso lactide), ε-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, 6,6-dimethyl-1,4-dioxan-2-one and polymer blends thereof. Poly(iminocarbonate) for the purpose of this invention include as described by Kemnitzer and Kohn, in the Handbook of Biodegradable Polymers, edited by Domb, Kost and Wisemen, Hardwood Academic Press, 1997, pages 251-272. Copoly(ether-esters) for the purpose of this invention include those copolyester-ethers described in Journal of Biomaterials Research, Vol. 22, pages 993-1009, 1988 by Cohn and Younes and Cohn, Polymer Preprints (ACS Division of Polymer Chemistry) Vol. 30(1), page 498, 1989 (e.g. PEO/PLA). Polyalkylene oxalates for the purpose of this invention include U.S. Pat. Nos. 4,208,511; 4,141,087; 4,130,639; 4,140,678; 4,105,034; and 4,205,399 (incorporated by reference herein). Polyphosphazenes, co-, ter- and higher order mixed monomer based polymers made from L-lactide, D,L-lactide, lactic acid, glycolide, glycolic acid, para-dioxanone, trimethylene carbonate and ε-caprolactone such as are described by Allcock in The Encyclopedia of Polymer Science, Vol. 13, pages 31-41, Wiley Intersciences, John Wiley & Sons, 1988 and by Vandorpe, Schacht, Dejardin and Lemmouchi in the Handbook of Biodegradable Polymers, edited by Domb, Kost and Wisemen, Hardwood Academic Press, 1997, pages 161-182 (which are hereby incorporated by reference herein). Polyanhydrides from diacids of the form $HOOC-C_6H_4-O-(CH_2)_m-O-C_6H_4-COOH$ where m is an integer in the range of from 2 to 8 and copolymers thereof with aliphatic alpha-omega diacids of up to 12 carbons. Polyoxaesters polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213 and 5,700,583; (which are incorporated herein by reference). Polyorthoesters such as those described by Heller in Handbook of Biodegradable Polymers, edited by Domb, Kost and Wisemen, Hardwood Academic Press, 1997, pages 99-118 (hereby incorporated herein by reference). Film-forming polymeric biomolecules for the purpose of this invention include naturally occurring materials that may be enzymatically degraded in the human body or are hydrolytically unstable in the human body such as fibrin, fibrinogen, collagen, elastin, and absorbable biocompatable polysaccharides such as chitosan, starch, fatty acids (and esters thereof), glucoso-glycans and hyaluronic acid.

Suitable film-forming biostable polymers with relatively low chronic tissue response, such as polyurethanes, silicones, poly(meth)acrylates, polyesters, polyalkyl oxides (polyethylene oxide), polyvinyl alcohols, polyethylene glycols and polyvinyl pyrrolidone, as well as, hydrogels such as those formed from crosslinked polyvinyl pyrrolidinone and polyesters could also be used. Other polymers could also be used if they can be dissolved, cured or polymerized on the stent. These include polyolefins, polyisobutylene and ethylene-alphaolefin copolymers; acrylic polymers (including methacrylate) and copolymers, vinyl halide polymers and copolymers, such as polyvinyl chloride; polyvinyl ethers, such as polyvinyl methyl ether; polyvinylidene halides such as polyvinylidene fluoride and polyvinylidene chloride; polyacrylonitrile, polyvinyl ketones; polyvinyl aromatics such as polystyrene; polyvinyl esters such as polyvinyl acetate; copolymers of vinyl monomers with each other and olefins, such as etheylene-methyl methacrylate copolymers, acrylonitrile-styrene copolymers, ABS resins and ethylene-vinyl acetate copolymers; polyamides, such as Nylon 66 and polycaprolactam; alkyd resins; polycarbonates; polyoxymethylenes; polyimides; polyethers; epoxy resins, polyurethanes; rayon; rayon-triacetate, cellulose, cellulose acetate, cellulose acetate butyrate; cellophane; cellulose nitrate; cellulose propionate; cellulose ethers (i.e. carboxymethyl cellulose and hydoxyalkyl celluloses); and combinations thereof. Polyamides for the purpose of this application would also include polyamides of the form $-NH-(CH_2)_n-CO-$ and $NH-(CH_2)_x-NH-CO-(CH_2)_y-CO$, wherein n is preferably an integer in from 6 to 13; x is an integer in the range of form 6 to 12; and y is an integer in the range of from 4 to 16. The list provided above is illustrative but not limiting.

The polymers used for coatings can be film-forming polymers that have molecular weight high enough as to not be waxy or tacky. The polymers also should adhere to the stent and should not be so readily deformable after deposition on the stent as to be able to be displaced by hemodynamic stresses. The polymer's molecular weight is preferably high enough to provide sufficient toughness so that the polymers will not be rubbed off during handling or deployment of the stent or crack during expansion of the stent. In certain embodiments, the polymer has a melting temperature above 40° C., preferably above about 45° C., more preferably above 50° C. and most preferably above 55° C.

Coating may be formulated by mixing one or more of the therapeutic RNAi constructs with the coating polymers in a coating mixture. The RNAi construct may be present as a liquid, a finely divided solid, or any other appropriate physical form. Optionally, the mixture may include one or more proteins that associate with the RNAi construct. Optionally, the mixture may include one or more additives, e.g., nontoxic auxiliary substances such as diluents, carriers, excipients, stabilizers or the like. Other suitable additives may be formulated with the polymer and RNAi construct. For example, hydrophilic polymers selected from the previously described lists of biocompatible film forming polymers may be added to a biocompatible hydrophobic coating to modify the release profile (or a hydrophobic polymer may be added to a hydrophilic coating to modify the release profile). One example would be adding a hydrophilic polymer selected from the group consisting of polyethylene oxide, polyvinyl pyrrolidone, polyethylene glycol, carboxymethyl cellulose, hydroxymethyl cellulose and combination thereof to an aliphatic polyester coating to modify the release profile. Appropriate relative amounts can be determined by monitoring the in vitro and/or in vivo release profiles for the therapeutic RNAi constructs.

The thickness of the coating can determine the rate at which the RNAi construct elutes from the matrix. Essentially, the RNAi construct elutes from the matrix by diffusion through the polymer matrix. Polymers are permeable, thereby allowing solids, liquids and gases to escape therefrom. The total thickness of the polymeric matrix is in the range from about one micron to about twenty microns or greater. It is important to note that primer layers and metal surface treatments may be utilized before the polymeric matrix is affixed to the medical device. For example, acid cleaning, alkaline (base) cleaning, salinization and parylene deposition may be used as part of the overall process described.

To further illustrate, a poly(ethylene-co-vinylacetate), polybutylmethacrylate and RNAi construct solution may be incorporated into or onto the stent in a number of ways. For example, the solution may be sprayed onto the stent or the stent may be dipped into the solution. Other methods include spin coating and RF plasma polymerization. In one exemplary embodiment, the solution is sprayed onto the stent and then allowed to dry. In another exemplary embodiment, the solution may be electrically charged to one polarity and the stent electrically changed to the opposite polarity. In this manner, the solution and stent will be attracted to one another. In using this type of spraying process, waste may be reduced and more precise control over the thickness of the coat may be achieved.

In another exemplary embodiment, the RNAi construct may be incorporated into a film-forming polyfluoro copolymer comprising an amount of a first moiety selected from the group consisting of polymerized vinylidenefluoride and polymerized tetrafluoroethylene, and an amount of a second moiety other than the first moiety and which is copolymerized with the first moiety, thereby producing the polyfluoro copolymer, the second moiety being capable of providing toughness or elastomeric properties to the polyfluoro copolymer, wherein the relative amounts of the first moiety and the second moiety are effective to provide the coating and film produced therefrom with properties effective for use in treating implantable medical devices.

In one embodiment according to the present invention, the exterior surface of the expandable tubular stent of the intraluminal medical device of the present invention comprises a coating according to the present invention. The exterior surface of a stent having a coating is the tissue-contacting surface and is biocompatible. The "sustained release RNAi construct delivery system coated surface" is synonymous with "coated surface", which surface is coated, covered or impregnated with a sustained release RNAi construct delivery system according to the present invention.

In an alternate embodiment, the interior luminal surface or entire surface (i.e. both interior and exterior surfaces) of the elongate radially expandable tubular stent of the intraluminal medical device of the present invention has the coated surface. The interior luminal surface having the inventive sustained release RNAi construct delivery system coating is also the fluid contacting surface, and is biocompatible and blood compatible.

In certain embodiments, the polymeric complexes of the subject invention can be associated with one or more ligands effective to bind to specific cell surface proteins or matrix on the target cell, thereby facilitating sequestration of the complex to target cells, and in some instances, enhancing uptake of the RNAi construct by the cell. Merely to illustrate, examples of ligands suitable for use in targeting the supramolecular complexes and liposomes of the present invention to specific cell types are listed in the Table below.

| Ligand | Receptor | Cell type |
| --- | --- | --- |
| folate | folate receptor | epithelial carcinomas, bone marrow stem cells |
| water soluble vitamins | vitamin receptor | various cells |
| pyridoxyl phosphate | CD4 | CD4 + lymphocytes |
| apolipoproteins | LDL | liver hepatocytes, vascular endothelial cells |
| insulin | insulin receptor | |
| transferrin | transferrin receptor | endothelial cells |
| galactose | asialoglycoprotein receptor | liver hepatocytes |
| sialyl-Lewis$_X$ | E, P selectin | activated endothelial cells |
| Mac-1 | L selectin | neutrophils, leukocytes |
| VEGF | Flk-1, 2 | tumor epithelial cells |
| basic FGF | FGF receptor | tumor epithelial cells |
| EGF | EGF receptor | epithelial cells |
| VCAM-1 | $a_4b_1$ integrin | vascular endothelial cells |
| ICAM-1 | $a_Lb_2$ integrin | vascular endothelial cells |
| PECAM-1/CD31 | $a_vb_3$ integrin | vascular endothelial cells, activated platelets |
| osteopontin | $a_vb_1$ integrin $a_vb_5$ integrin | endothelial cells and smooth muscle cells in atherosclerotic plaques |
| RGD sequences | $a_vb_3$ integrin | tumor endothelial cells, vascular smooth muscle cells |
| HIV GP 120/41 or GP120 | CD4 | CD4 + lymphocytes |

The present invention also contemplates the derivatization of the subject polymeric complexes with ligands that promote transcytosis of the complexes. To further illustrate, a polymeric complex can be covalently linked to an internalizing peptide which drives the translocation of the complex across a cell membrane in order to facilitate intracellular localization of the RNAi construct. In this regard, the internalizing peptide, by itself, is capable of crossing a cellular membrane by, e.g., transcytosis, at a relatively high rate. The internalizing peptide is conjugated, e.g., as covalent pendant group, to the polymer.

In one embodiment, the internalizing peptide is derived from the *Drosophila* antepennepedia protein, or homologs thereof. The 60 amino acid long homeodomain of the homeoprotein antepennepedia has been demonstrated to translocate through biological membranes and can facilitate the translocation of heterologous polypeptides to which it is couples. See for example Derossi et al. (1994) *J Biol Chem* 269:10444-10450; and Perez et al. (1992) *J Cell Sci* 102:717-722. Recently, it has been demonstrated that fragments as small as 16 amino acids long of this protein are sufficient to drive internalization. See Derossi et al. (1996) *J Biol Chem* 271: 18188-18193. The present invention contemplates a RNAi-containing polymeric complex that is decorated with at least a portion of the antepennepedia protein (or homolog thereof) sufficient to increase the transmembrane transport of the decorated complex, relative to the undecorated complex, by a statistically significant amount.

Another example of an internalizing peptide is the HIV transactivator (TAT) protein. This protein appears to be divided into four domains (Kuppuswamy et al. (1989) *Nucl. Acids Res.* 17:3551-3561). Purified TAT protein is taken up by cells in tissue culture (Frankel and Pabo, (1989) *Cell* 55:1189-1193), and peptides, such as the fragment corresponding to residues 37-62 of TAT, are rapidly taken up by cell in vitro (Green and Loewenstein, (1989) *Cell* 55:1179-1188). The highly basic region mediates internalization and targeting of the internalizing moiety to the nucleus (Ruben et al., (1989) *J. Virol.* 63:1-8). Peptides or analogs that include a sequence present in the highly basic region, such as CFITKALGISYGRKKRRQRRRPPQGS (SEQ ID NO: 1), are conjugated to the polymer to aid in internalization and targeting those complexes to the intracellular milleau.

Another exemplary transcellular polypeptide can be generated to include a sufficient portion of mastoparan (T. Higashijima et al., (1990) *J. Biol. Chem.* 265:14176) to increase the transmembrane transport of the RNAi complexes.

Other suitable internalizing peptides can be generated using all or a portion of, e.g., a histone, insulin, transferrin, basic albumin, prolactin and insulin-like growth factor I (IGF-I), insulin-like growth factor II (IGF-II) or other growth factors. For instance, it has been found that an insulin fragment, showing affinity for the insulin receptor on capillary cells, and being less effective than insulin in blood sugar reduction, is capable of transmembrane transport by receptor-mediated transcytosis and can therefore serve as an internalizing peptide for the subject transcellular polypeptides. Preferred growth factor-derived internalizing peptides include EGF (epidermal growth factor)-derived peptides, such as CMHIESLDSYTC (SEQ ID NO: 2) and CMYIEALDKYAC (SEQ ID NO: 3); TGF-beta (transforming growth factor beta)-derived peptides; peptides derived from PDGF (platelet-derived growth factor) or PDGF-2; peptides derived from IGF-I (insulin-like growth factor) or IGF-II; and FGF (fibroblast growth factor)-derived peptides.

Another class of translocating/internalizing peptides exhibits pH-dependent membrane binding. For an internalizing peptide that assumes a helical conformation at an acidic pH, the internalizing peptide acquires the property of amphiphilicity, e.g., it has both hydrophobic and hydrophilic interfaces. More specifically, within a pH range of approximately 5.0-5.5, an internalizing peptide forms an alpha-helical, amphiphilic structure that facilitates insertion of the moiety into a target membrane. An alpha-helix-inducing acidic pH environment may be found, for example, in the low pH environment present within cellular endosomes. Such internalizing peptides can be used to facilitate transport of RNAi-complexes, taken up by an endocytic mechanism, from endosomal compartments to the cytoplasm.

Yet other preferred internalizing peptides include peptides of apo-lipoprotein A-1 and B; peptide toxins, such as melittin, bombolittin, delta hemolysin and the pardaxins; antibiotic peptides, such as alamethicin; peptide hormones, such as calcitonin, corticotrophin releasing factor, beta endorphin, glucagon, parathyroid hormone, pancreatic polypeptide; and peptides corresponding to signal sequences of numerous secreted proteins. In addition, exemplary internalizing peptides may be modified through attachment of substituents that enhance the alpha-helical character of the internalizing peptide at acidic pH.

Yet another class of internalizing peptides suitable for use within the present invention include hydrophobic domains that are "hidden" at physiological pH, but are exposed in the low pH environment of the target cell endosome. Upon pH-induced unfolding and exposure of the hydrophobic domain, the moiety binds to lipid bilayers and effects translocation of the covalently linked complexes into the cell cytoplasm. Such internalizing peptides may be modeled after sequences identified in, e.g., *Pseudomonas* exotoxin A, clathrin, or Diphtheria toxin.

Pore-forming proteins or peptides may also serve as internalizing peptides herein. Pore-forming proteins or peptides may be obtained or derived from, for example, C9 complement protein, cytolytic T-cell molecules or NK-cell molecules. These moieties are capable of forming ring-like structures in membranes, thereby allowing transport of attached complexes through the membrane and into the cell interior.

Mere membrane intercalation of an internalizing peptide may be sufficient for translocation of the RNAi-complexes across cell membranes. However, translocation may be improved by attaching to the internalizing peptide a substrate for intracellular enzymes (i.e., an "accessory peptide"). It is preferred that an accessory peptide be attached to a portion(s) of the internalizing peptide that protrudes through the cell membrane to the cytoplasmic face. The accessory peptide may be advantageously attached to one terminus of a trans-locating/internalizing moiety or anchoring peptide. An accessory moiety of the present invention may contain one or more amino acid residues. In one embodiment, an accessory moiety may provide a substrate for cellular phosphorylation (for instance, the accessory peptide may contain a tyrosine residue).

An exemplary accessory moiety in this regard would be a peptide substrate for N-myristoyl transferase, such as GNAAAARR, SEQ ID NO: 4 (Eubanks et al., in: *Peptides. Chemistry and Biology*, Garland Marshall (ed.), ESCOM, Leiden, 1988, pp. 566-69) In this construct, an internalizing, peptide would be attached to the C-terminus of the accessory peptide, since the N-terminal glycine is critical for the accessory moiety's activity. This hybrid peptide, attached to a RNAi-containing polymer complex, is N-myristylated and further anchored to the target cell membrane, e.g., it serves to increase the local concentration of the complex at the cell membrane.

Suitable accessory peptides include peptides that are kinase substrates, peptides that possess a single positive charge, and peptides that contain sequences which are glycosylated by membrane-bound glycotransferases. Accessory peptides that are glycosylated by membrane-bound glycotransferases may include the sequence x-NLT-x, where "x" may be another peptide, an amino acid, coupling agent or hydrophobic molecule, for example. When this hydrophobic tripeptide is incubated with microsomal vesicles, it crosses vesicular membranes, is glycosylated on the luminal side, and is entrapped within the vesicles due to its hydrophilicity (C. Hirschberg et al., (1987) *Ann. Rev. Biochem.* 56:63-87).

Accessory peptides that contain the sequence x-NLT-x thus will enhance target cell retention of corresponding complexes.

As described above, the internalizing and accessory peptides can each, independently, be added to an RNAi construct-containing complex or liposome by chemical cross-linking or through non-covalent interaction (e.g., use of streptavidin-biotin conjugates, $His_6$-Ni interactions, etc). In certain instances, unstructured polypeptide linkers can be included between the peptide moieties and the polymeric complex or liposome.

It is also contemplates that such internalizing and accessory peptides can be associated directly with an RNAi construct, such as through a covalent linkage to a hydroxyl group on the backbone of the nucleic acid. In certain embodiments, the linkage is susceptible to cleavage under physiological conditions, such as by exposure to esterases, or simple hydrolysis reactions. Such compositions can be used alone ("naked RNAi" constructs) or formulated in polymeric complexes or liposomes.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions that are compatible with body tissue.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The addition of the active compound of the invention to animal feed is preferably accomplished by preparing an appropriate feed premix containing the active compound in an effective amount and incorporating the premix into the complete ration.

Alternatively, an intermediate concentrate or feed supplement containing the active ingredient can be blended into the feed. The way in which such feed premixes and complete rations can be prepared and administered are described in reference books (such as "Applied Animal Nutrition", W.H. Freedman and CO., San Francisco, U.S.A., 1969 or "Livestock Feeds and Feeding" O and B books, Corvallis, Ore., U.S.A., 1977).

In any of the foregoing embodiments, the invention contemplates that the pharmaceutical preparations may be non-pyrogenic.

The pharmaceutical preparations for use in the methods of the present invention may comprises combinations of two or more hedgehog antagonists. For example, two different HH pathway RNAi antagonists may be combined with a pharmaceutically acceptable carrier or excipient. The two RNAi antagonists may act additively or synergistically. In another example, one or more RNAi antagonists may be combined with one or more non-RNAi hedgehog antagonists (e.g., one or more small organic molecules), and with a pharmaceutically acceptable carrier or excipients. Said combination of hedgehog antagonists may act additively or synergistically.

EXAMPLES

The invention now being generally described, it will be more readily understood by reference to the following examples, which are included merely for purposes of illustration of certain aspects and embodiments of the present invention, and are not intended to limit the invention.

Example 1

Hedgehog, Lung Development and Surfactant Production

Respiratory distress syndrome results from insufficient surfactant in the alveolae of the lungs. The lungs of vertebrates contain surfactant, a complex mixture of lipids and protein that causes surface tension to rise during lung inflation and decrease during lung deflation. During lung deflation, surfactant decreases such that there are no surface forces that would otherwise promote alveolar collapse. Aerated alveoli that have not collapsed during expiration permit continuous oxygen and carbon dioxide transport between blood and alveolar gas and require much less force to inflate during the subsequent inspiration. During inflation, lung surfactant increases surface tension as the alveolar surface area increases. A rising surface tension in expanding alveoli opposes over-inflation in those airspaces and tends to divert inspired air to less well-aerated alveoli, thereby facilitating even lung aeration.

Respiratory distress syndrome is particularly prevalent among premature infants. Lung surfactant is normally synthesized at a very low rate until the last six weeks of fetal life. Human infants born more than six weeks before the normal term of a pregnancy have a high risk of being born with inadequate amounts of lung surfactant and inadequate rates of surfactant synthesis. The more prematurely an infant is born, the more severe the surfactant deficiency is likely to be. Severe surfactant deficiency can lead to respiratory failure within a few minutes or hours of birth. The surfactant deficiency produces progressive collapse of alveoli (atelectasis) because of the decreasing ability of the lung to expand despite maximum inspiratory effort. As a result, inadequate amounts of oxygen reach the infant's blood. RDS can occur in adults as well, typically as a consequence of failure in surfactant biosynthesis.

The role of the hedgehog signaling pathway in lung maturation and surfactant production was investigated, with the finding that inhibition of the hedgehog signaling pathway stimulated surfactant production.

Figure 4:
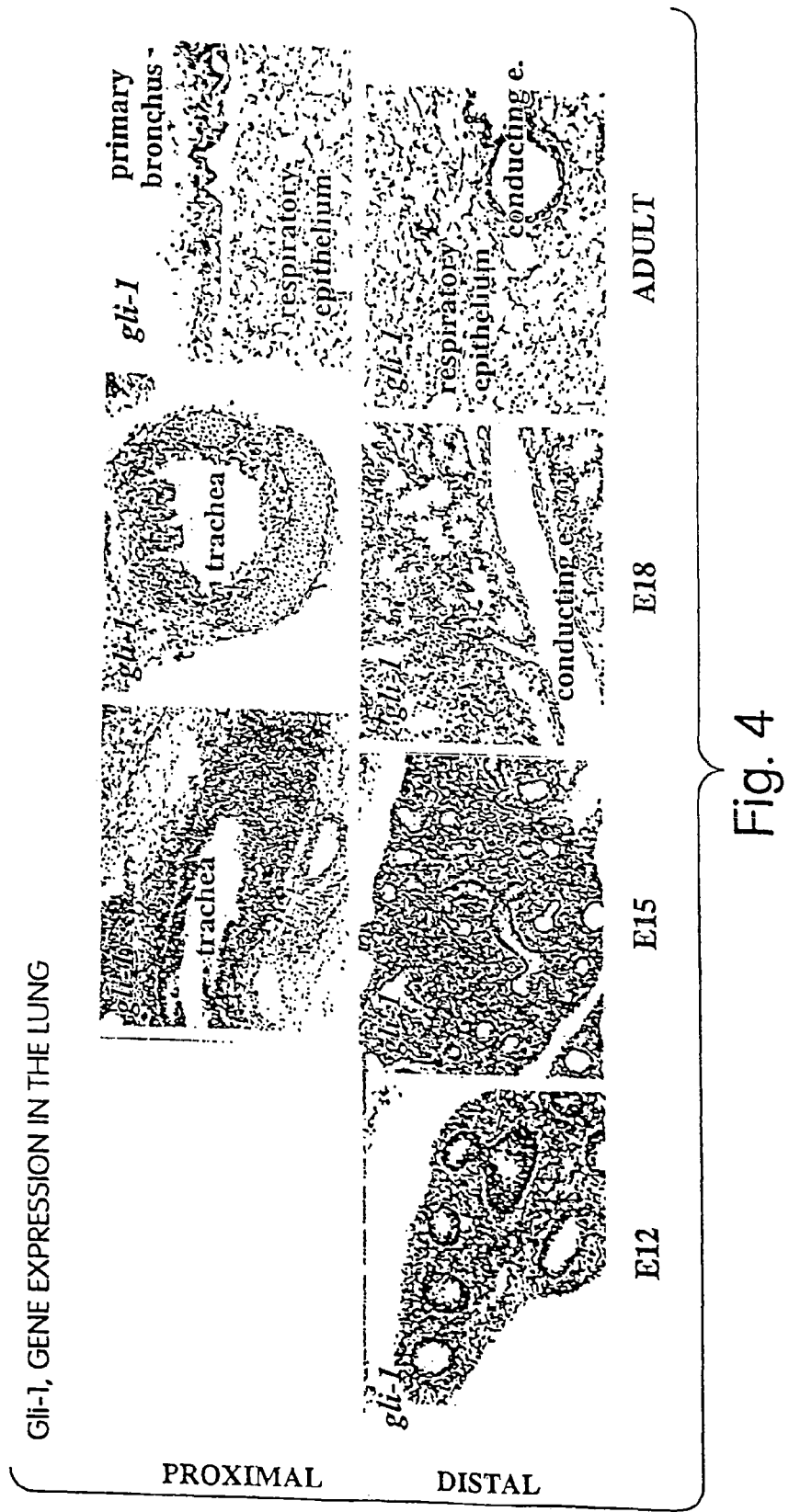
FIG. 4 depicts gli-1 gene expression in embryonic and adult mouse lung.

The expression of a hedgehog-regulated gene, Gli-1, was assessed in embryonic mouse lung tissue. Gli-1 was strongly expressed in the embryonic lung, however this expression decreases during lung maturation (FIG. 4). Note that the decline in hedgehog signaling towards the end of embryogenesis correlates with the maturation of the distal lung epithelium into respiratory pneumocytes. Gli-1, a transcription factor indicative of hedgehog signaling, continues to be expressed in the conducting, but not respiratory airways in the adult.

METHODS: Sections of paraformaldehyde-fixed, paraffin-embedded tissue were cleared, re-hydrated, digested with proteinase K, acetylated and hybridized with [$^{33}$P]-labeled sonic hedgehog and gli-1 RNA probes over night, respectively. After high stringency post-hybridization washes, slides were dipped in photo-emulsion, incubated for up to three weeks, developed, and imaged using dark field illumination. Dark-field signals were filled in with artificial color (red) and superimposed with bright-field images.

Figure 5:
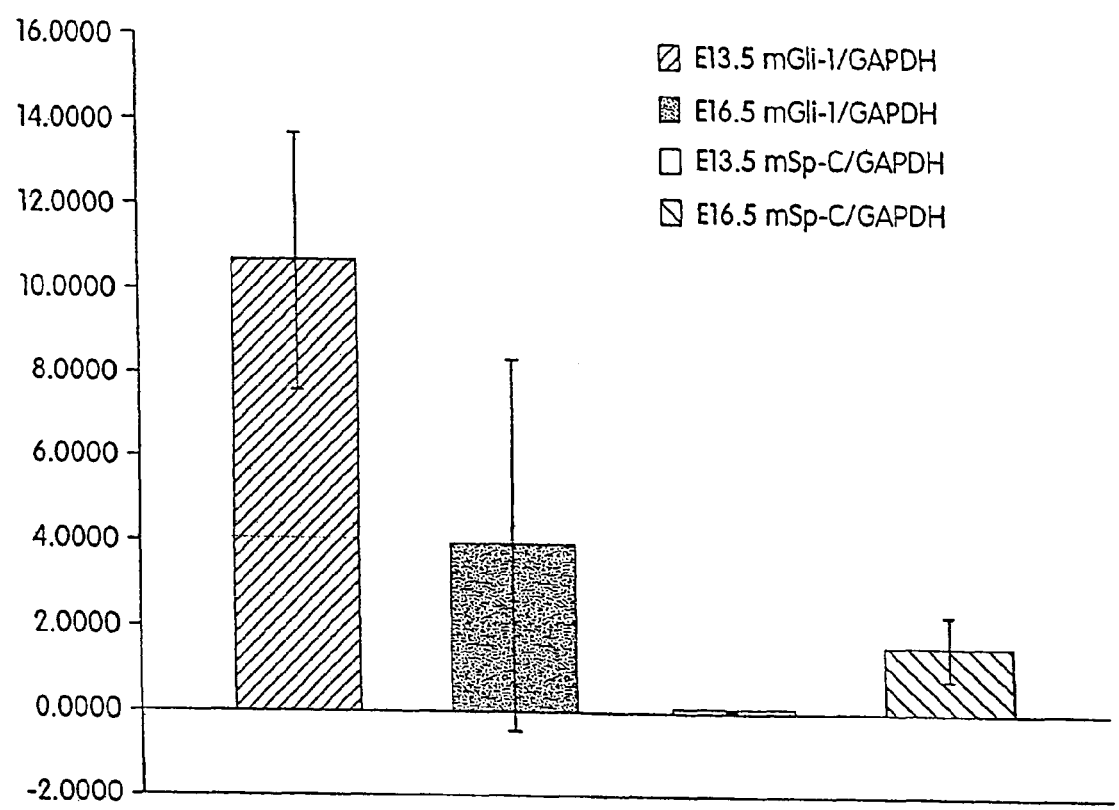
FIG. 5 shows the inverse relationship between gli-1 expression and the expression of markers of lung maturation. Between E13.5 and E16.5, the expression of gli-1 decreases while the expression of the maturation marker, surfactant type C (Sp-C), increases.

To further correlate the decrease in gli-1 expression with lung maturation, expression of gli-1 was compared to expression of the lung maturation marker, surfactant type C (Sp-C) (FIG. 5). This analysis demonstrates that as expression of gli-1 decreases between E13.5-E16.5, the expression of Sp-C increases.

METHODS: E13.5 and E16.5 mouse lung explants were dissected and analyzed by Quantatative Real-Time PCR (Q-RT-PCR). Briefly, total ribonucleic acid (RNA) is isolated from the tissue and subjected to reverse transcription to generate DNA. This DNA is amplified in a polymerase chain reaction using gene-specific primers as well as primers for the ubiquitously expressed housekeeping gene GAPDH. The two primer sets are labeled with different fluorophores, allowing for quantification of both signals in the same reaction tube in a real-time PCR machine (TaqMan). When calculating the expression levels of gli-1 and Sp-C, the specific signal is normalized to the GAPDH signal, which serves as a measure of the total DNA used in the reaction.

As Gli-1 expression is a marker for hedgehog signaling, it appears that the hedgehog signaling pathway is active in immature lung tissue. Accordingly, it was hypothesized that inhibition of the hedgehog signaling pathway would permit more rapid lung maturation and, particularly, stimulate surfactant production.

Figure 6:
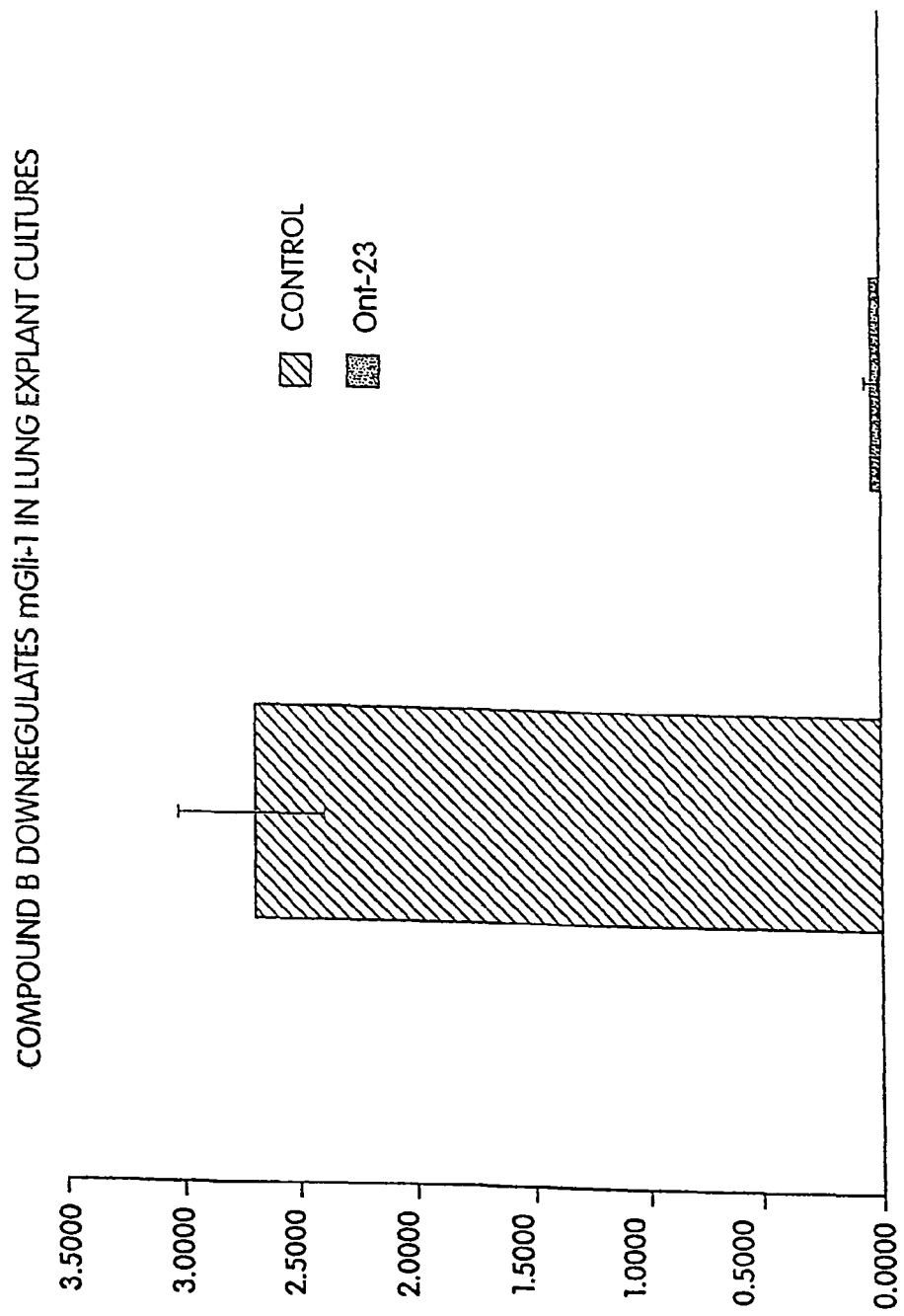
FIG. 6 shows the effect of compound B treatment of embryonic mouse lungs on gli-1 expression.

Treatment of embryonic mouse lungs with hedgehog antagonist compound B downregulates Gli-1 expression (FIG. 6). METHODS: E13.5 embryonic mouse lungs were dissected. Explants were grown exposed to the air-liquid interface in lung explant medium (DMEM based, additives optimized for the culture of mouse lungs) for 67 hrs. They were then processed for quantitative real-time PCR (Q-RT-PCR). Briefly, total ribonucleic acid (RNA) is isolated from the tissue and subjected to reverse transcription to generate DNA. This DNA is amplified in a polymerase chain reaction using gene-specific primers as well as primers for the ubiquitously expressed housekeeping gene GAPDH. The two primer sets are labeled with different fluorophores, allowing for quantification of both signals in the same reaction tube in a real-time PCR machine (TaqMan). When calculating the expression level of gli-1, the specific signal is normalized to the GAPDH signal, which serves as a measure of the total DNA used in the reaction.

Figure 7:
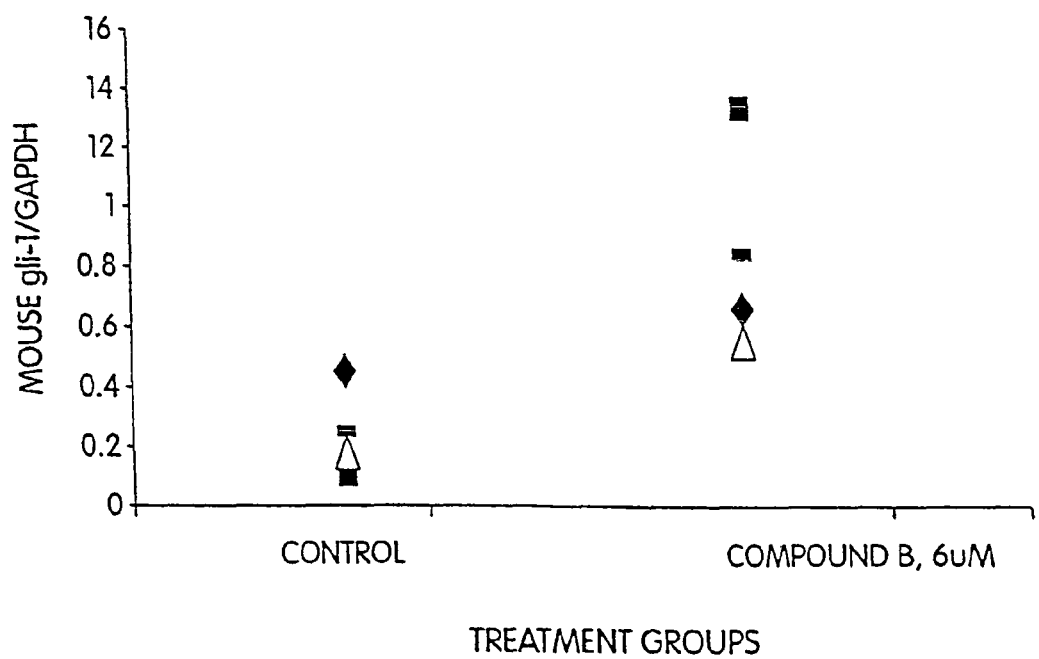
FIG. 7 shows compound B treatment increases surfactant type C production in embryonic mouse lungs.

Compound B treatment increases surfactant type C production in embryonic mouse lungs (FIG. 7). Surfactant production is a measure of lung maturity, and the inability to produce surfactant is the primary cause of adult and infant respiratory distress syndrome. The increase in surfactant type C production was assessed by measuring expression of Sp-C, which encodes a protein critical for the production of surfactant.

METHODS: E13.5 old embryonic mouse lungs were dissected. Explants were grown submerged in lung explant medium (DMEM based, additives optimized for the culture of mouse lungs) for 50 hrs. They were then processed for Q-RT-PCR. Briefly, total ribonucleic acid (RNA) is isolated from the tissue and subjected to reverse transcription to generate DNA. This DNA is amplified in a polymerase chain reaction using gene-specific primers as well as primers for the ubiquitously expressed housekeeping gene GAPDH. The two primer sets are labeled with different fluorophores, allowing for quantification of both signals in the same reaction tube in a real-time PCR machine (TaqMan). When calculating the expression level of Sp-C, the specific signal is normalized to the GAPDH signal, which serves as a measure of the total DNA used in the reaction.

Figure 8:
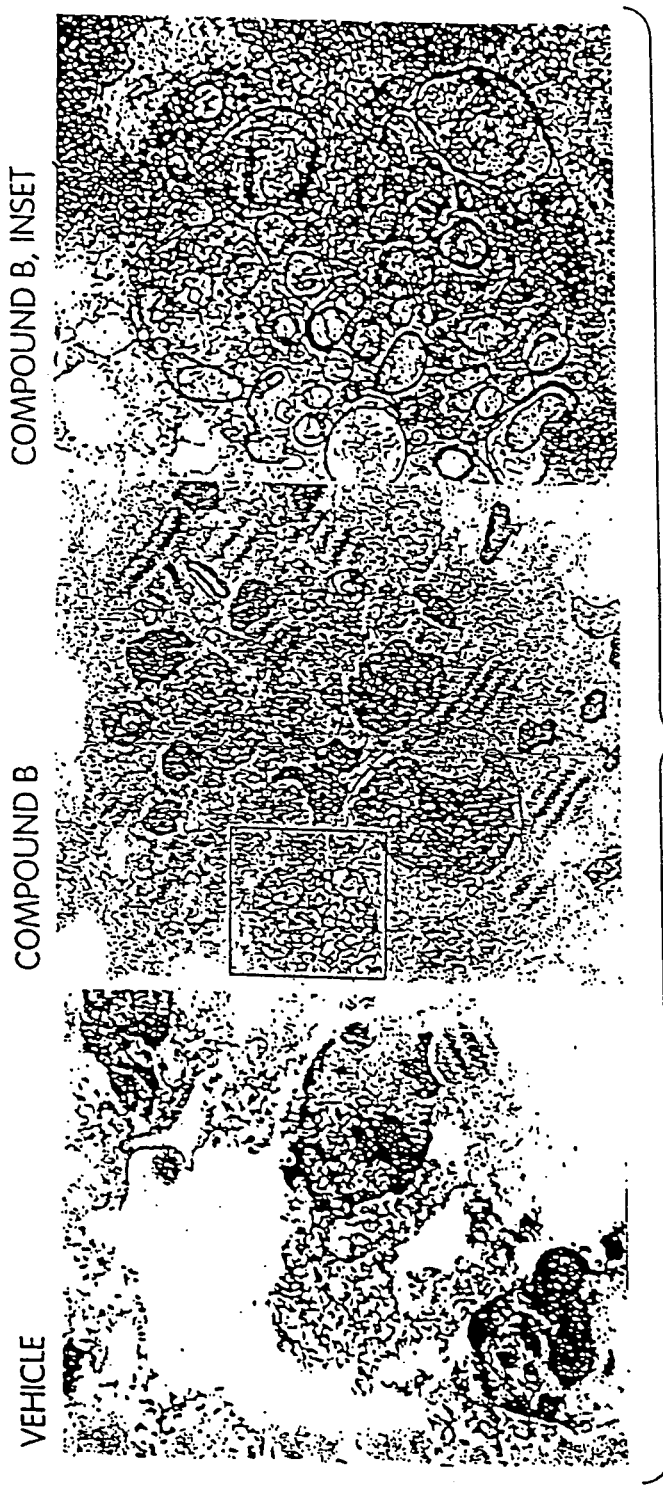
FIG. 8 shows that type II pneumocytes in compound B-treated lungs differentiate prematurely, as evidenced by the presence of surfactant producing lamellated bodies.

Lamellated bodies are subcellular structures found in surfactin-producing lung cells and are thought to be a site of surfactin production. Type II pneumocytes in compound B-treated lungs differentiate prematurely, as evidenced by the presence of surfactant producing lamellated bodies. No such structures could be observed in the vehicle-treated controls (FIG. 8). METHODS: E13.5 old embryonic mouse lungs were dissected. Explants were grown exposed to the air-liquid interface in lung explant medium (DMEM based, additives optimized for the culture of mouse lungs) for 67 hrs. They were then processed for transmission electron microscopy and photographed at a magnification of 62,000.

Figure 9:
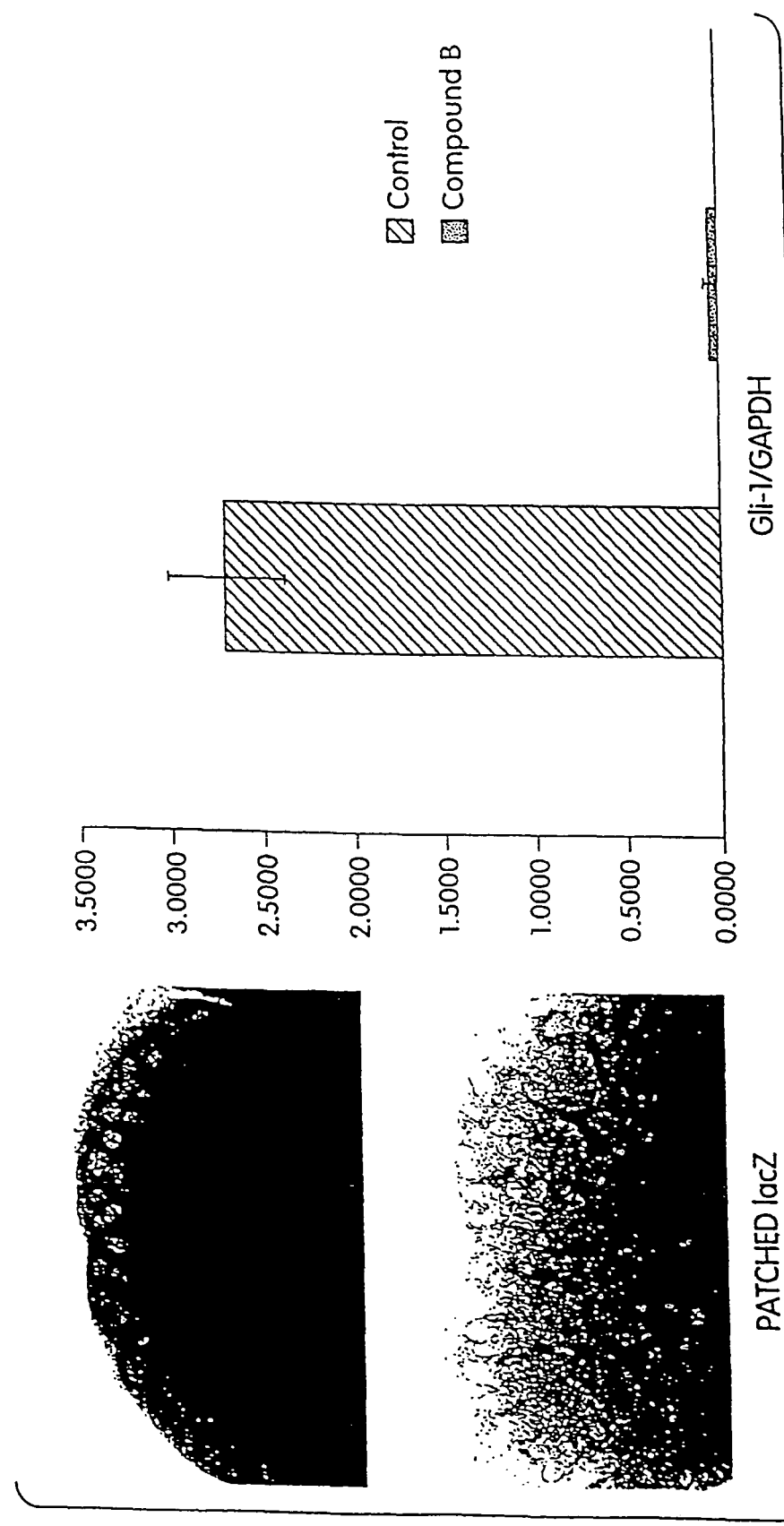
FIG. 9 shows that treatment of embryonic lung cultures with compound B decreases expression of gli-1.
Figure 10:
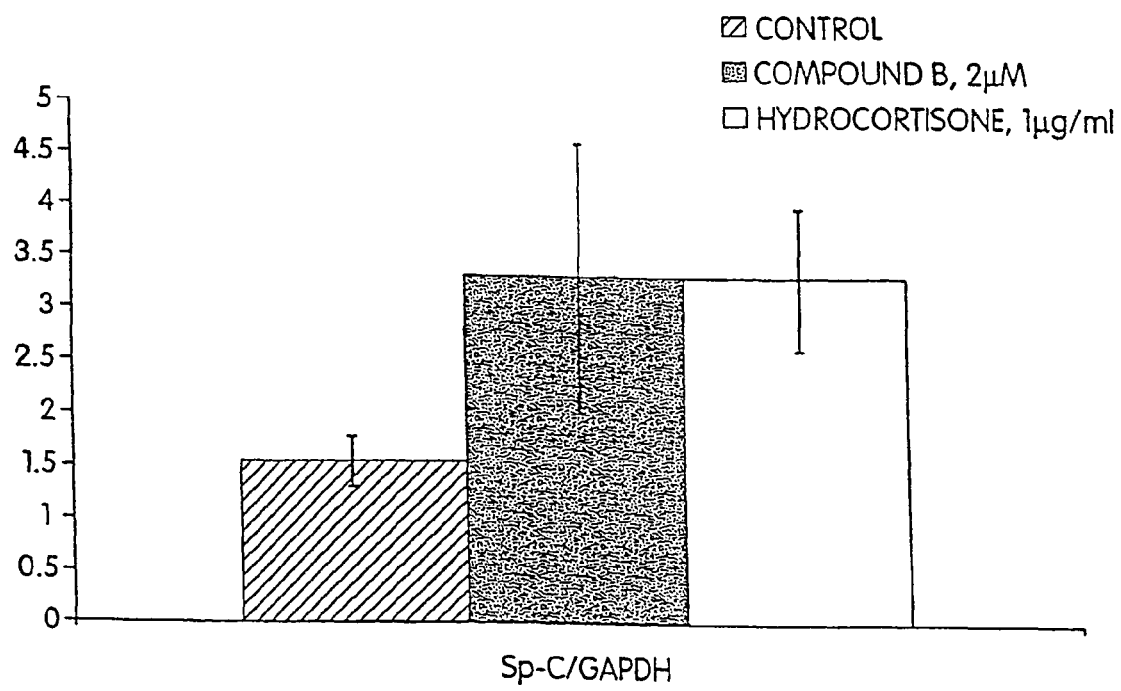
FIG. 10 shows that treatment of embryonic lung cultures with compound B increases expression of the maturation marker Sp-C. The induction of Sp-C observed following treatment is comparable to that observed following treatment with known lung maturation factor hydrocortisone.

FIGS. 9 and 10 show similar results as obtained above upon treatment of embryonic lung cultures with Compound B (FIG. 9-10). The increase in Sp-C expression observed following Compound B treatment is comparable to that observed when embryonic lung explants are treated with the steroid hormone hydrocortisone. Steroids are known to increase lung maturation and surfactant production in animals, including humans.

Figure 11:
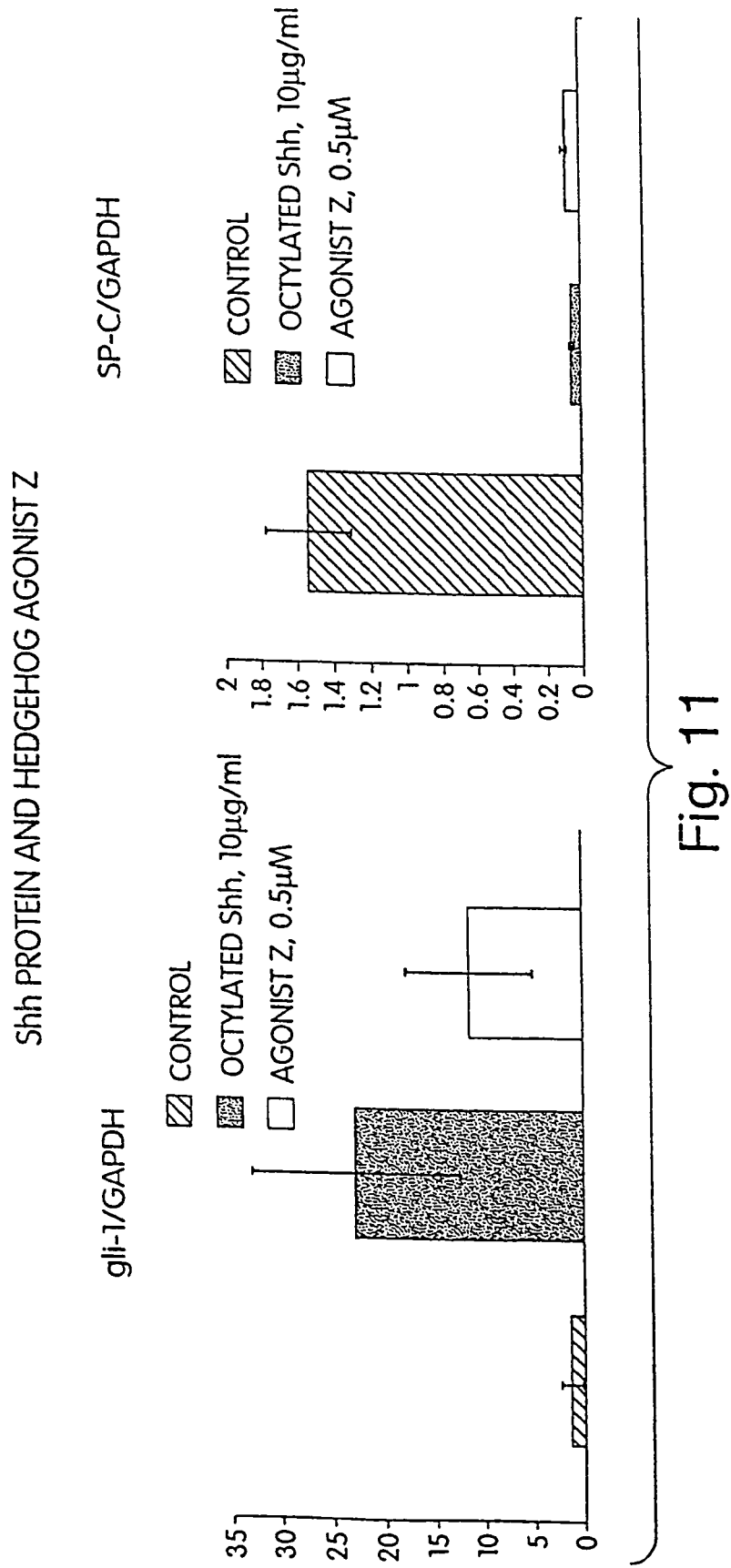
FIG. 11 shows that treatment of embryonic lung cultures with hedgehog agonists has the opposite effect. Treatment with either sonic hedgehog or with agonist Z increases gli-1 expression and decreases Sp-C expression.
Figure 12:
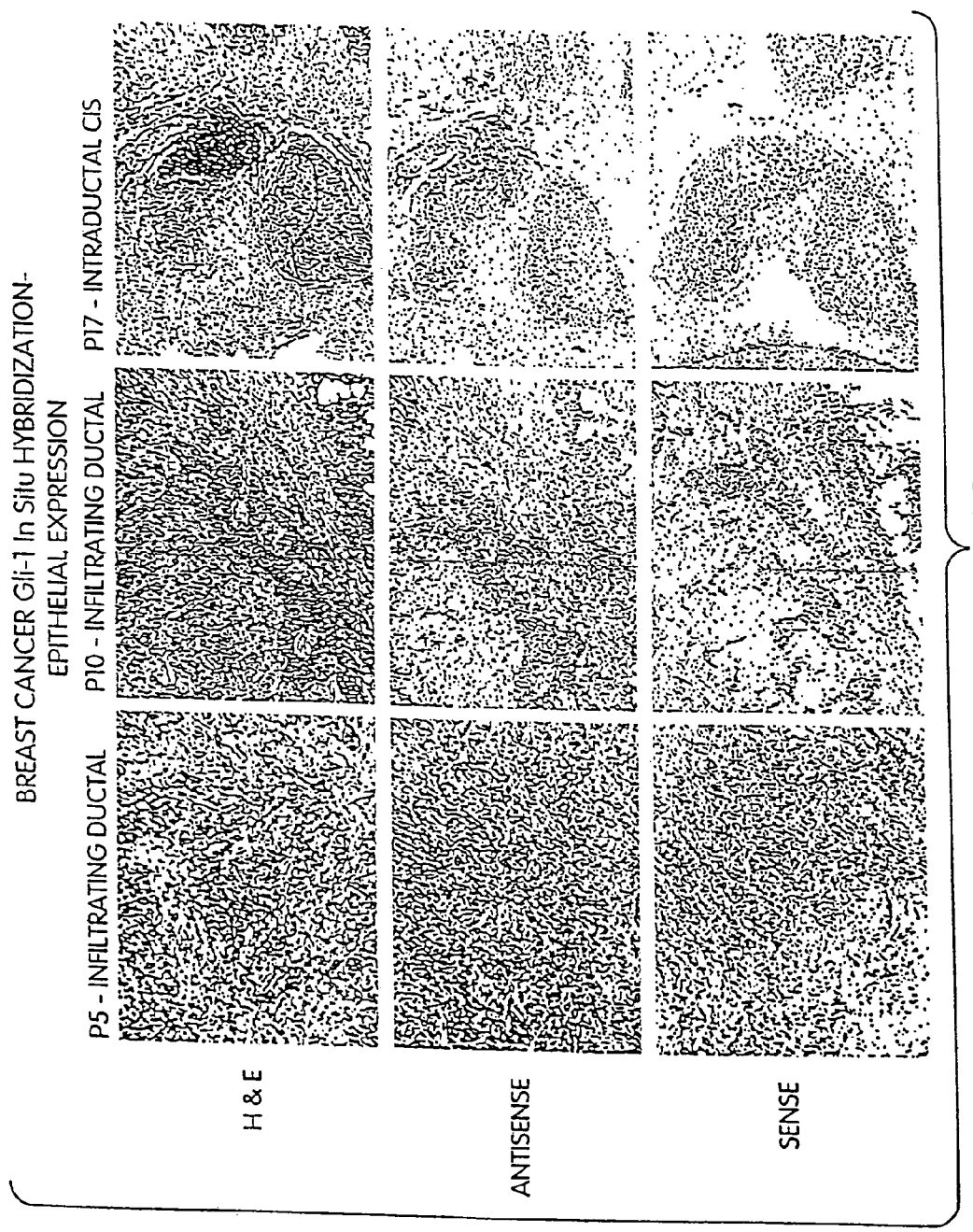
FIG. 12 illustrates gli-1 expression in breast cancer tissue as visualized by in situ hybridization.
Figure 13:
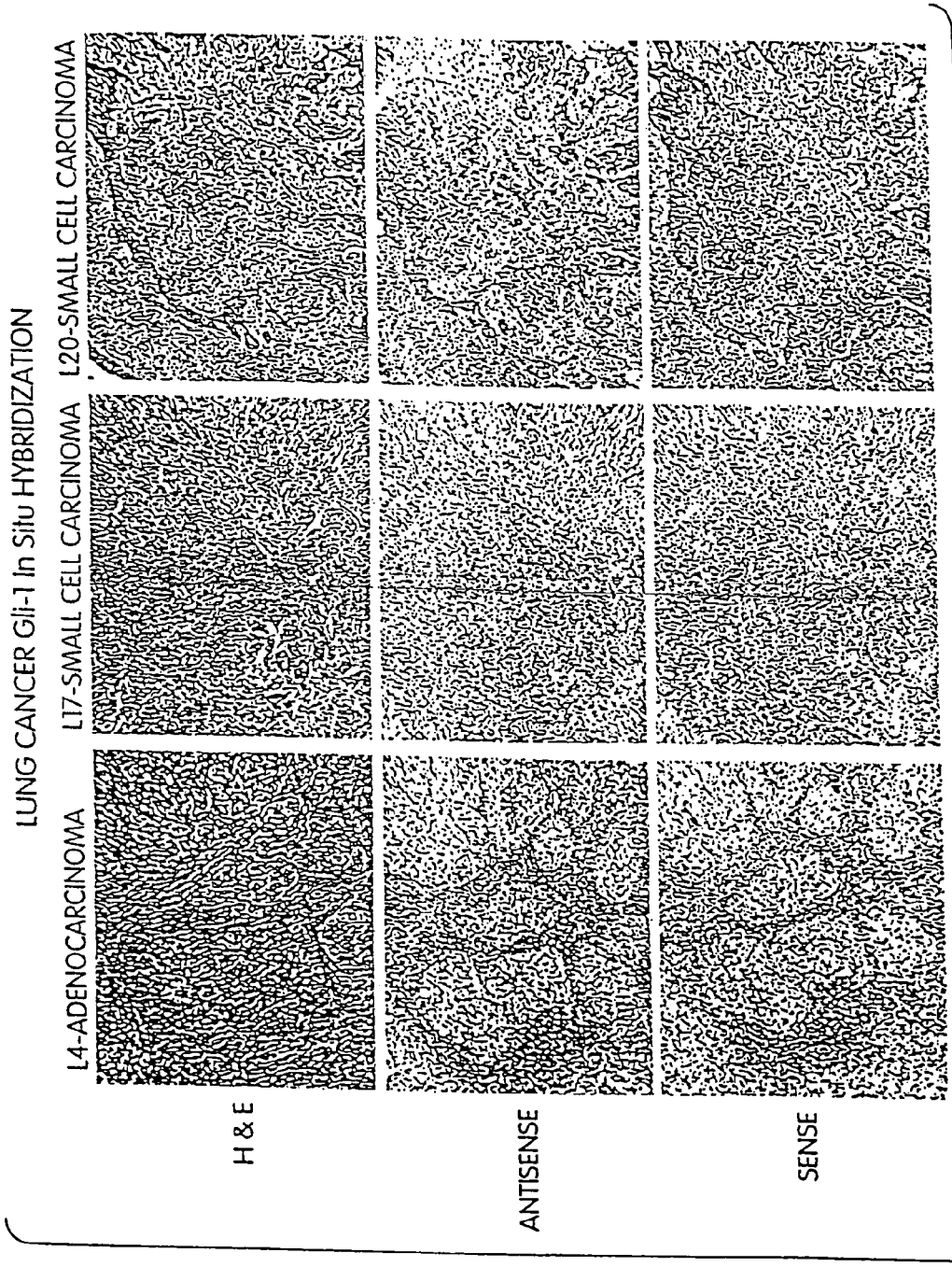
FIG. 13 shows gli-1 expression in lung cancer visualized by in situ hybridization
Figure 14:
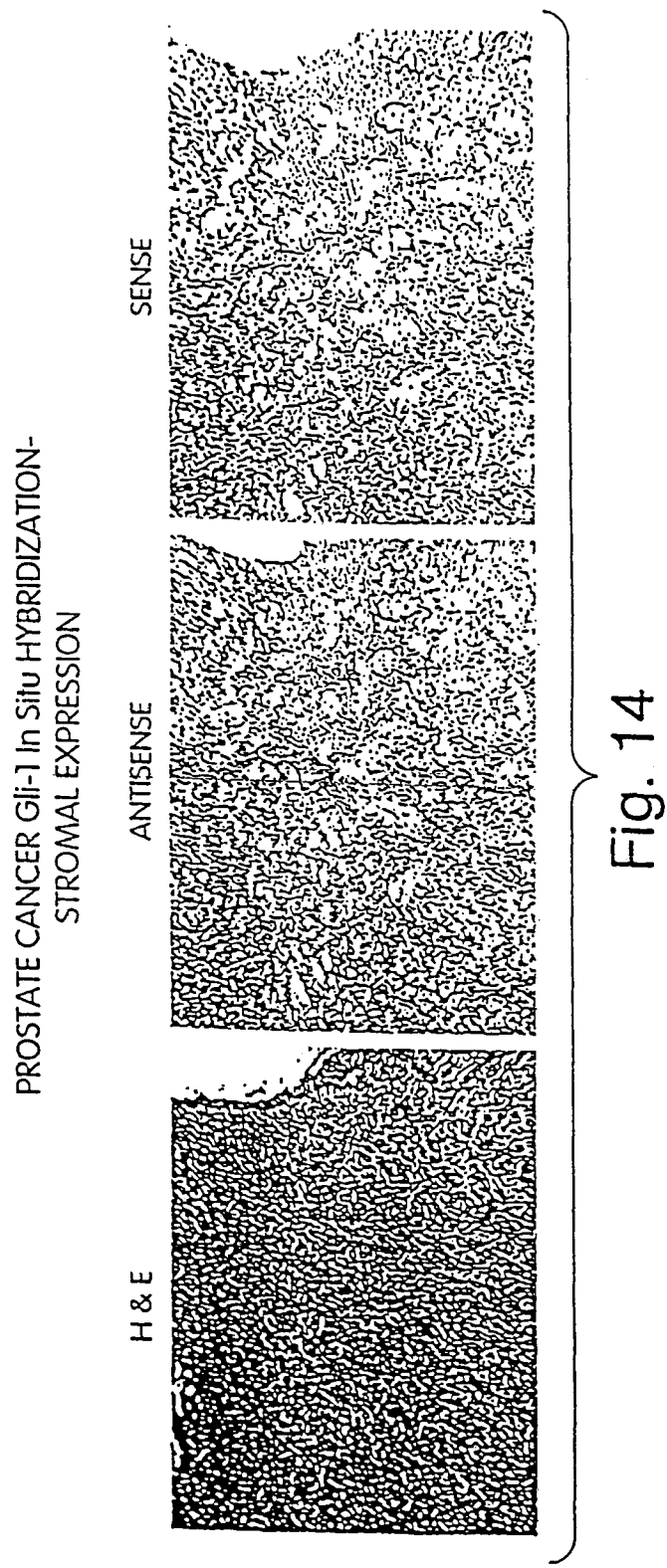
FIG. 14 illustrates gli-1 expression in prostate cancer as visualized by in situ hybridization
Figure 15:
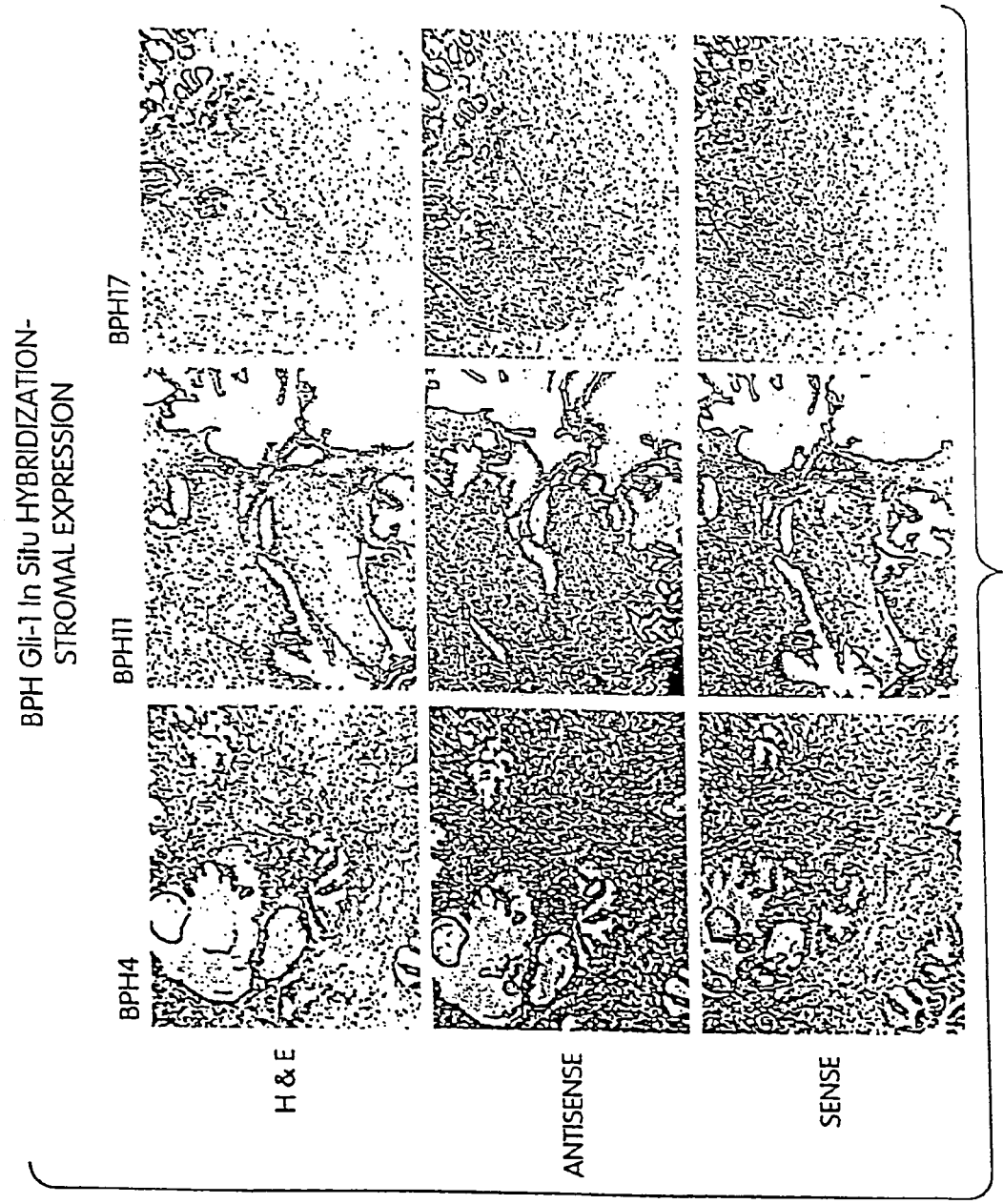
FIG. 15 depicts gli-1 expression in benign prostatic hyperplasia as visualized by in situ hybridization

The specificity of the effects of hedgehog antagonists on lung maturation is demonstrated by examining the effects of agonists of hedgehog signaling on lung maturation. Treatment of embryonic lung cultures with either a lipid modified sonic hedgehog or with a hedgehog agonist compound result in increased expression of gli-1 and decreased expression of Sp-C (FIG. 11).

In summary, these results demonstrate that hedgehog inhibitors can stimulate maturation and surfactin production in immature lung tissue. The hedgehog signaling pathway is active in immature lung tissues, where surfactins are not produced in substantial levels, while the hedgehog pathway is relatively inactive in the adult respiratory airway, where surfactins are produced. Treatment of immature lung tissue with antagonists of the hedgehog signaling pathway causes rapid maturation and the increased presence of molecular and cytological markers associated with surfactin production. Opposite results obtained upon the treatment of lung explants with hedgehog antagonists and agonists demonstrate the specificity of these results.

Example 2

Gli-1 Expression in Human Tumors

Hedgehog Pathway Activation in Human Tumors

Hedgehog signaling plays a causative role in the generation of basal cell carcinoma (BCC). Hedgehog signaling was analyzed to determine whether this pathway is active in other human tumors, more specifically prostate, lung and breast cancer, as well as benign prostate hyperplasia. Hedgehog proteins are known proliferative agents for a variety of cell types. Since hedgehogs have a known proliferative effect on a variety of cell types, hedgehog antagonists may be valuable therapeutics for cancers in which high level hedgehog signaling is present.

The question of hedgehog activation in the tumor types was addressed by conducting radioactive in situ hybridization experiments with gli-1, a known transcriptional effector gene of hedgehog signaling.

Briefly, sections of paraformaldehyde-fixed, paraffin-embedded tissue were cleared, re-hydrated, digested with proteinase K, acetylated and hybridized with [$^{33}$P]-labeled RNA probes over night. After high stringency post-hybridization washes, slides were dipped in photo-emulsion, incubated for up to three weeks, developed, and imaged using dark field illumination. Dark-field signals were filled in with artificial color (red) and superimposed with bright-field images. Gli-1 expression was graded on a scale from "−" to "+" through "++++". Gli-1 expression was rated "−" when expression was no higher in hyperproliferative cells than in other non-proliferative cells present in the slide. Ratings of "+" through "++++" were given for increased expression levels, with any cell rated "++" or above considered to have substantially increased gli-1 expression. When the signal was not interpretable, a sample is indicated as "ND".

The data for these experiments are summarized in table 1-4 below. In brief, 8 out of 18 breast cancer samples showed substantially increased gli-1 expression. 7 out of 11 lung cancer samples, 11 of 19 benign prostatic hypertrophy samples (BPH), and 6 of 15 prostate cancer samples all showed strong gli-1 expression.

TABLE 1

Results of Gli-1 in situ hybridization in breast cancer tissue

| Tissue | Diagnosis | Sample Number | Age/Sex | Signal |
| --- | --- | --- | --- | --- |
| Breast | Inf Ductal Carcinoma | 1 | 93F | ND |
| Breast | Inf Ductal Carcinoma | 2 | 37F | +++ |
| Breast | Inf Ductal Carcinoma | 3 | 54F | + |
| Breast | Inf Ductal Carcinoma | 4 | 39F | ++ |
| Breast | Inf Ductal Carcinoma | 5 | 73F | +++ |
| Breast | Inf Ductal Carcinoma | 6 | 65F | ++++ |
| Breast | Inf Ductal Carcinoma | 7 | 58F | ND |
| Breast | Inf Ductal Carcinoma | 8 | 48F | + |
| Breast | Inf Ductal Carcinoma | 9 | 27F | ++ |
| Breast | Inf Ductal Carcinoma | 10 | NA | +++ |
| Breast | Inf Ductal Carcinoma | 11 | 34F | + |
| Breast | Inf Lobular Carcinoma | 12 | 46F | + |
| Breast | Inf Lobular Carcinoma | 13 | F | − |
| Breast | Inf Lobular Carcinoma | 14 | 56F | + |
| Breast | Inf Lobular Carcinoma | 15 | 70F | − |
| Breast | Intraductal Carcinoma | 16 | 40F | +++ |
| Breast | Intraductal Carcinoma | 17 | 55F | +++ |
| Breast | Medullary Carcinoma | 18 | NA | + |
| Breast | Tubular Carcinoma | 19 | 75F | − |
| Breast | Tubular Carcinoma | 20 | 60F | − |

TABLE 2

Results of Gli-1 in situ hybridization in lung cancer tissue

| Tissue | Diagnosis | Sample Number | Age/Sex | Signal |
| --- | --- | --- | --- | --- |
| Lung | Adenocarcinoma | 1 | 54F | +++++ |
| Lung | Adenocarcinoma | 2 | 61M | ND |
| Lung | Adenocarcinoma | 3 | 61F | ++++ |
| Lung | Adenocarcinoma | 4 | 58F | +++ |
| Lung | Adenocarcinoma | 5 | 77M | ND |
| Lung | Adenocarcinoma | 6 | 65M | ++ |
| Lung | Adenocarcinoma | 7 | 73M | ND |
| Lung | Adenocarcinoma | 8 | 69M | ND |
| Lung | Adenocarcinoma | 9 | 82M | ND |
| Lung | Adenocarcinoma | 10 | NA | − |
| Lung | Adenocarcinoma | 11 | F | ND |
| Lung | Adenocarcinoma | 12 | 56F | + |
| Lung | Broncho-alveolar adenocar | 13 | 70F | + |
| Lung | Broncho-alveolar adenocar | 14 | 76F | − |
| Lung | Small Cell Carcinoma | 15 | 68M | ++ |
| Lung | Small Cell Carcinoma | 16 | 61M | ND |
| Lung | Small Cell Carcinoma | 17 | 70M | +++++ |
| Lung | Small Cell Carcinoma | 18 | NA | ND |
| Lung | SCC | 19 | 60F | ND |
| Lung | SCC | 20 | 63M | +++++ |

TABLE 3

Results of Gli-1 in situ hybridization in benign prostate hyperplasia

| Tissue | Diagnosis | Sample Number | Age/Sex | Signal |
| --- | --- | --- | --- | --- |
| Prostate | BPH | 1 | 65M | + |
| Prostate | BPH | 2 | 86M | ++++ |
| Prostate | BPH | 3 | 53M | + |
| Prostate | BPH | 4 | 65M | ++++ |
| Prostate | BPH | 5 | 68M | ++ |
| Prostate | BPH | 6 | 70M | ++ |
| Prostate | BPH | 7 | 54M | − |
| Prostate | BPH | 8 | M | ++ |
| Prostate | BPH | 9 | 69M | − |
| Prostate | BPH | 10 | M | − |
| Prostate | BPH | 11 | 73M | +++ |
| Prostate | BPH | 12 | 53M | ++++ |
| Prostate | BPH | 13 | 84M | − |
| Prostate | BPH | 14 | 67M | − |
| Prostate | BPH | 15 | 66M | ++ |
| Prostate | BPH | 16 | 69M | ++ |
| Prostate | BPH | 17 | 72M | ++++ |
| Prostate | BPH | 18 | M | ++ |

TABLE 3-continued

Results of Gli-1 in situ hybridization in benign prostate hyperplasia

| Tissue | Diagnosis | Sample Number | Age/Sex | Signal |
|---|---|---|---|---|
| Prostate | BPH | 19 | 60M | − |
| Prostate | BPH | 20 | 60M | − |

TABLE 4

Results of Gli-1 in situ hybridization in prostate cancer tissue

| Tissue | Diagnosis | Sample Number | Age/Sex | Signal |
|---|---|---|---|---|
| Prostate | Adenocarcinoma | 1 | 79M | + |
| Prostate | Adenocarcinoma | 2 | 72M | + |
| Prostate | BPH next to Adenocarcinoma | 3 | 81M | ND |
| Prostate | Adenocarcinoma | 4 | 79M | ++ |
| Prostate | Adenocarcinoma | 5 | 81M | ND |
| Prostate | Adenocarcinoma | 6 | 73M | − |
| Prostate | Adenocarcinoma | 7 | 79M | ++ |
| Prostate | Adenocarcinoma | 8 | M | +++ |
| Prostate | Adenocarcinoma | 9 | 69M | ND |
| Prostate | Adenocarcinoma | 10 | 53M | +++ |
| Prostate | Adenocarcinoma | 11 | 65M | + |
| Prostate | Adenocarcinoma | 12 | 60M | ++ |
| Prostate | Adenocarcinoma | 13 | 66M | ND |
| Prostate | Adenocarcinoma | 14 | 66M | + |
| Prostate | Adenocarcinoma | 15 | 92M | − |
| Prostate | Adenocarcinoma | 16 | 80M | − |
| Prostate | Adenocarcinoma | 17 | 78M | ND |
| Prostate | Adenocarcinoma | 18 | 85M | − |
| Prostate | Adenocarcinoma | 19 | 78M | − |
| Prostate | Adenocarcinoma | 20 | 93M | +++ |

In summary, high level Gli-1 expression, i.e., hedgehog signaling activation, can be observed in human prostate cancer and benign prostatic hyperplasia, lung cancer and breast cancer (FIGS. 12-15). Hedgehog pathway activation in these tumor types has never before been described. The presence of an exceptionally active hedgehog pathway in these proliferating cells strongly suggests a causal link between the hedgehog pathway and hyperproliferation in these disorders. It is expected that hedgehog antagonists will be effective as antiproliferative agents in these cancer types.

Example 3

Bladder Cancer

Cytogenetic and Mutational Data Suggest Hedgehog Activation Plays a Causative Role in Bladder Cancer The cytogenetic and molecular alterations found in bladder cancer are heterogeneous. In establishing the primary, specific mutations in cancers, it is often useful to examine near-diploid cancers, which do not yet have complex, multiple chromosome changes accompanied by hyperdiploidy. Gibas et al., found monosomy of chromosome 9 in 4 out of 9 cases of transitional cell carcinoma of the bladder (Gibas et al. (1984) *Cancer Research* 44:1257-1264). In three of these, the karyotype was near diploid, and in one, monosomy 9 was the only abnormality observed. Therefore, monosomy of chromosome 9 may initiate malignant transformation in a subgroup of such cancers.

More evidence that this change appears as an early event was presented by two other group who reported that deletions of chromosome 9 are the only genetic changes present frequently in superficial papillary tumors (Dalbagni et al. (1993) *Lancet* 342: 469-471). In fact, 9q deletions are estimated to occur in approximately 60-70 percent of bladder tumors (Cairns et al. (1992) *Oncogene* 8: 1083-1085; Dalbagni et al., supra). One study reported that deletion of 9q22 occurs in 35% of informative cases (Simoneau et al. 1999). The hedgehog signaling pathway component patched-1 is located on 9q22.

LOH of all other chromosomes is infrequent (less than 10%) in low-grade, non-invasive cancers. Likewise, alteration in bladder-cancer associated oncogenes (ERBB2, EGFR) are also rare in superficial, low-grade tumors (Cairns et al., supra).

On the basis of these cytogenetic findings, the following model for bladder carcinogenesis has been proposed: Initiation occurs by deletion of tumor-suppressor genes on chromosome 9, leading to superficial papillary or occasionally flat tumors, a few of which may then acquire further mutations (e.g., p53) and progress to invasion.

Three groups observed trisomy 7 in a low percentage of bladder cancers (Sandberg, supra; Berger et al. supra; Smeets et al., supra). Shh, which according to our own experiments continues to be expressed in bladder epithelium throughout adult life, localizes to chromosome 7. Berger et al. also observed deletions of 10q24, the locus of su(fu) (Berger et al (1986) *Cancer Genetics and Cytogenetics* 23: 1-24). Likewise, Smeets et al. suggested that 10q loss may be a primary event in the development of bladder cancer (Smeets et al. (1987) *Cancer Genetics and Cytogenetics* 29: 29-41).

This data suggests mechanisms by which the baseline expression of hedgehog signaling present in the adult bladder epithelium may be increased, thus leading to increased proliferation of urothelial cells. This hypothesis is supported by the cytological data, as well as by the finding of McGarvey et al. that described ptc-1, smo and gli-3 expression in normal human urothelium and two transitional cell carcinoma lines (McGarvey et al. (1998) *Oncogene* 17: 1167-1172).

Figure 16:
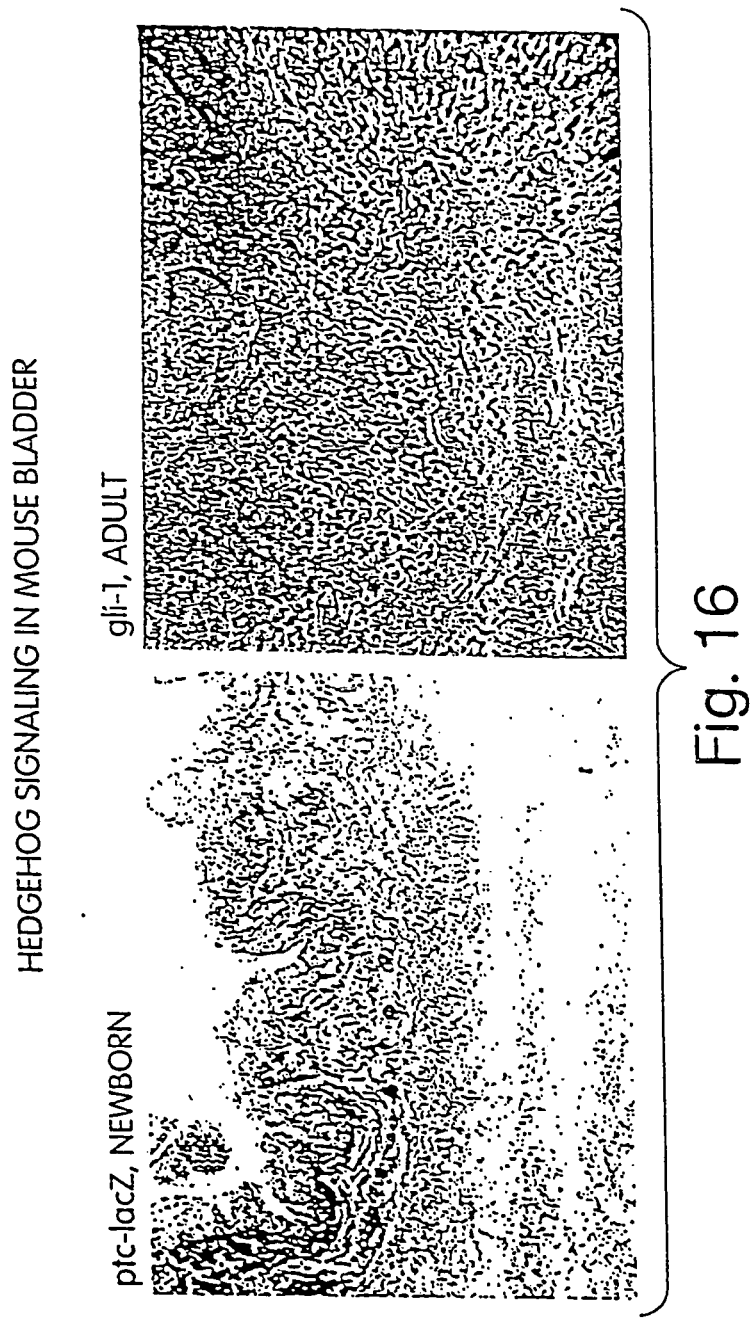
FIG. 16 shows: (A) Ptc-lacZ transgene expression in newborn mouse ptc-1 (d11) lacZ bladder epithelium. LacZ expression can be detected in the proliferating urothelial cells and, more weakly, in adjacent mesenchymal cells. (B) Gli-1 expression in adult mouse bladder epithelium. Gli-1 expression can be detected in the proliferating urothelial cells.

Hedgehog signaling was examined in the mouse bladder, and found to be present in normal bladder. In Ptc-lacZ transgenic newborn mice (ptc-1 (d11) lacZ), LacZ expression can be detected in the proliferating urothelial cells of the bladder epithelium, and more weakly, in adjacent mesenchymal cells (FIG. 16A). Additional in situ hybridization analysis of adult mouse bladder indicates expression of gli-1 in the bladder epithelium, and specifically in the proliferating urothelial cells (FIG. 16B).

METHODS: For lacZ staining, ptc-1 (d11) lacZ bladder was harvested from the transgenic newborn mouse pups identified by lacZ detection using tails. Bladders were fixed in lacZ fixative, rinsed and stained for lacZ O/N at 37° C., then processed for standard histology. Sections were counterstained with eosin. For in situ hybridization, sections of paraformaldehyde-fixed, paraffin-embedded tissue were cleared, re-hydrated, digested with proteinase K, acetylated and hybridized with [$^{33}$P]-labeled gli-1 RNA probe over night. After high stringency post-hybridization washes, slides were dipped in photo-emulsion, incubated for up to three weeks, developed, and imaged using dark field illumination. Dark-field signals were filled in with artificial color (red) and superimposed with bright-field images.

Hedgehog Signaling in Bladder Cancer

Hedgehog signaling and hedgehog pathway gene expression was analyzed in a human bladder cancer, and in several bladder cancer cell lines. Gene expression in these tissues was measured using Quantitative Real-Time PCR (Q-RT-PCR). These results are summarized in FIGS. 17-19, and demonstrate that hedgehog pathway genes are expressed in bladder cancer cell lines.

Figure 17:
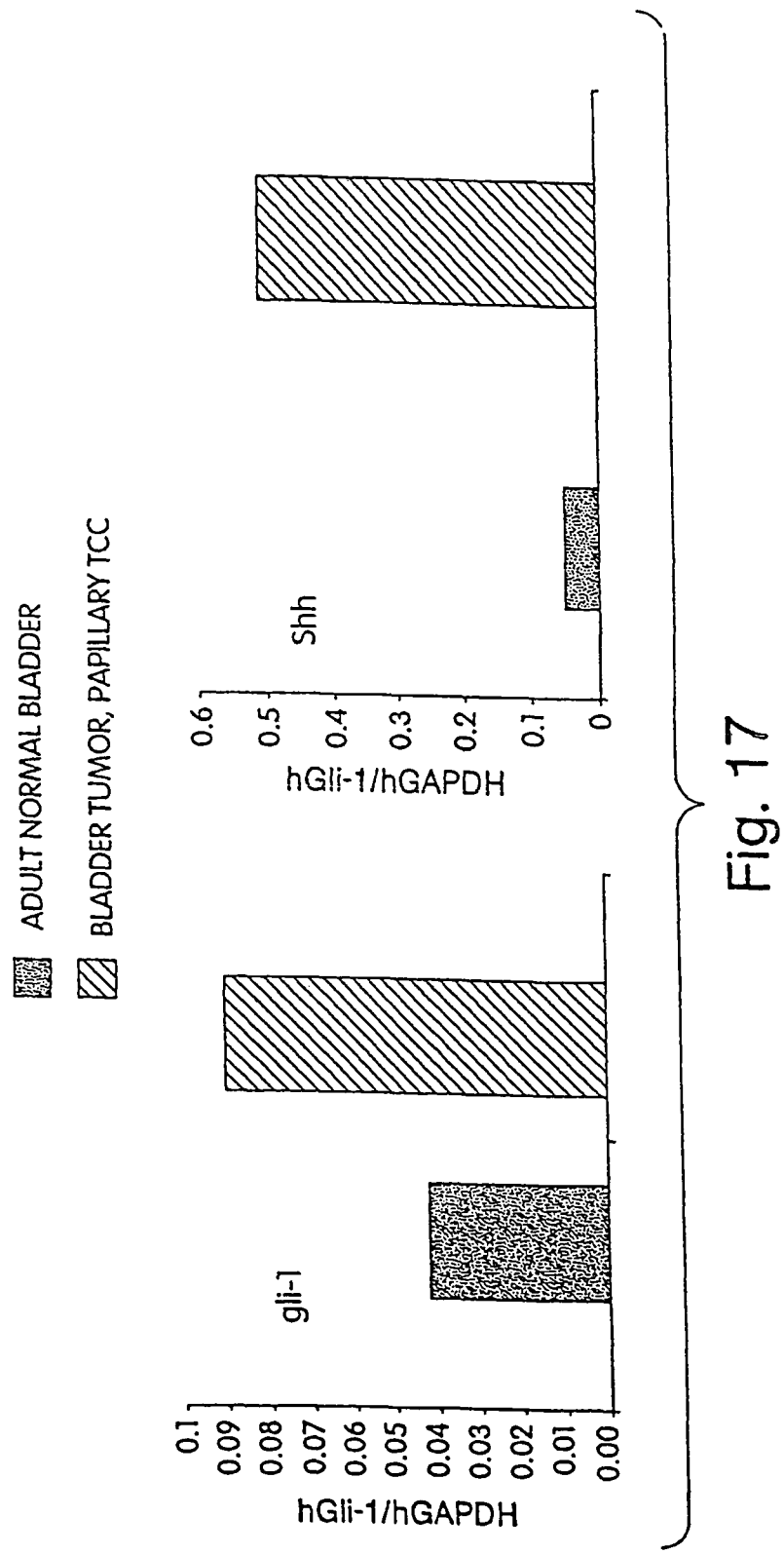
FIG. 17 shows the expression of gli-1 and shh in normal adult bladder and in a commercially available bladder tumor.
Figure 18:
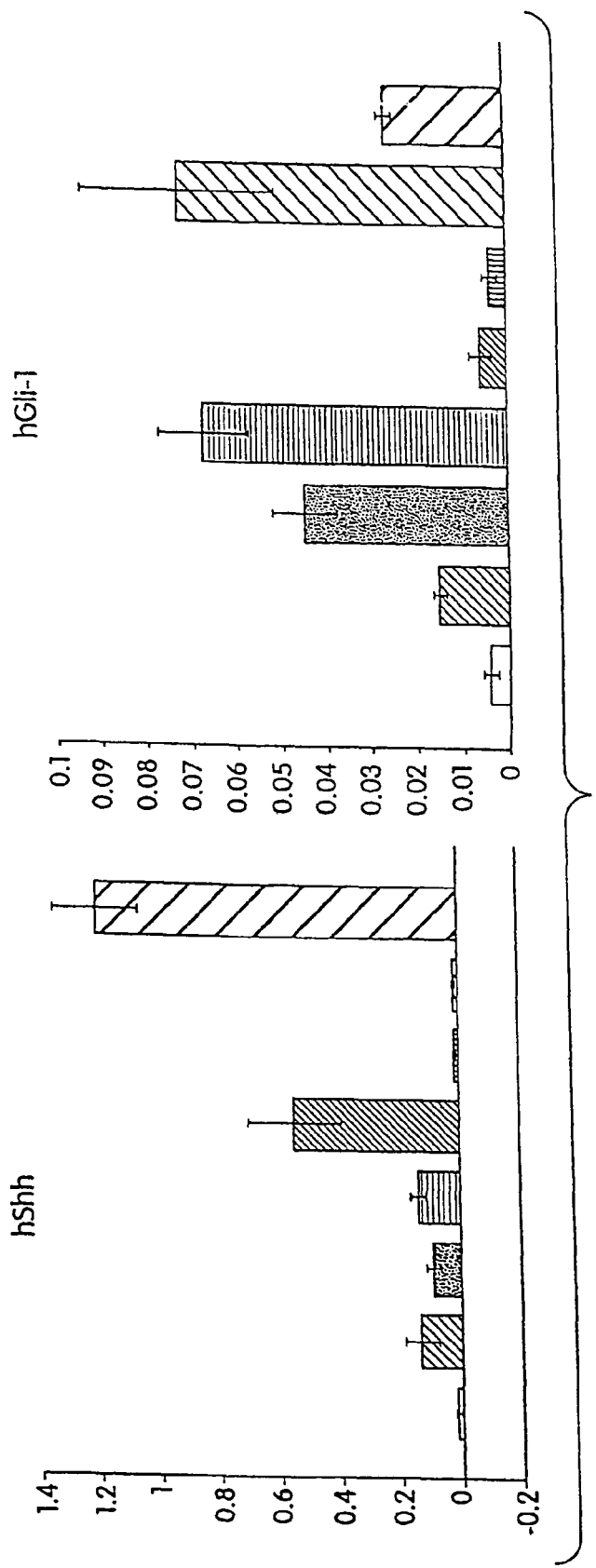
FIG. 18 shows the expression of shh and gli-1 in eight commercially available bladder cancer cell lines. All eight cell lines examined express genes involved in hedgehog signaling.
Figure 19:
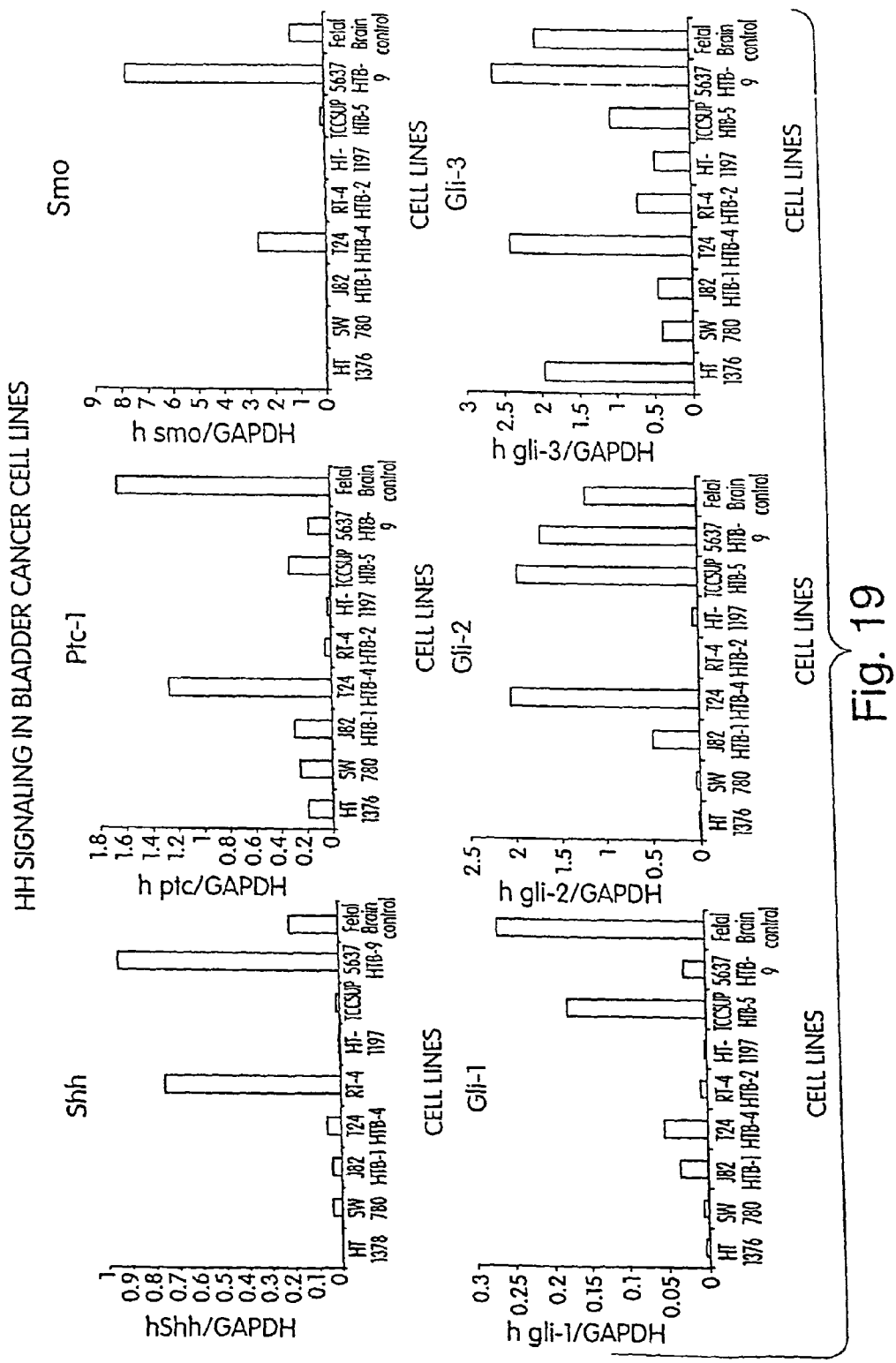
FIG. 19 shows the expression of shh, ptc-1, smo, gli-1, gli-2, and gli-3 in eight commercially available bladder cancer cell lines, as well as in fetal brain.

FIG. 17 demonstrates that shh expression is increased 12-fold and gli-1 expression is increased 2.5 fold in a bladder tumor sample when compared to normal adult bladder. FIG. 18 examines shh and gli-1 expression in eight human bladder cancer cell lines, and FIG. 19 examines expression of shh, ptc-1, smo, gli-1, gli-2, and gli-3 in the same eight human bladder cancer cell lines. These results indicate that components of the hedgehog pathway are expressed in eight out of eight cell lines examined.

METHODS: Experiment 1 (FIG. 17)—evaluation of hedgehog signaling in a bladder tumor.

For Quantitative Real-Time Polymerase Chain Reaction (Q-RT-PCR) experiments, commercially available cDNA (Clontech) was amplified using an ABI Prism 7700 Sequence Detection System (TaqMan) from Perkin Elmer and gene-specific primers. The housekeeping gene GAPDH was used to normalize RNA concentration and PCR efficiency, and GAPDH primers were added to the same reactions. Since probes for both genes are labeled with different fluorophores, the specific signal and that of GAPDH can be detected in the same tube. Signal intensities were calculated using the algorithms provided in Sequence Detector v1.7, the software provided by the manufacturer.

Experiment 2 (FIGS. 18-19)—hedgehog signaling in eight bladder cancer cell lines.

Bladder cancer cell lines were purchased from ATCC (American Type Culture Collection) and maintained as recommended in the product description. At confluency, cells were rinsed and switched to medium containing 1% serum, a treatment that increases hedgehog signaling. Cells were then grown 2 more days, collected in Trizol (GIBCO-BRL) and RNA isolated according to the manufacturer's protocol. The RNA was then transcribed into first strand cDNA according to standard protocols, and amplified using an ABI Prism 7700 Sequence Detection System (TaqMan) from Perkin Elmer and gene-specific primers. The housekeeping gene GAPDH was used to normalize RNA concentration and PCR efficiency, and GAPDH primers were added to the same reactions. Since probes for both genes are labeled with different fluorophores, the specific signal and that of GAPDH can be detected in the same tube. Signal intensities were calculated using the algorithms provided in Sequence Detector v1.7, the software provided by the manufacturer.

In Vitro Assay to Examine Hedgehog Signaling in Bladder Cancer Cell Lines

Figure 20:
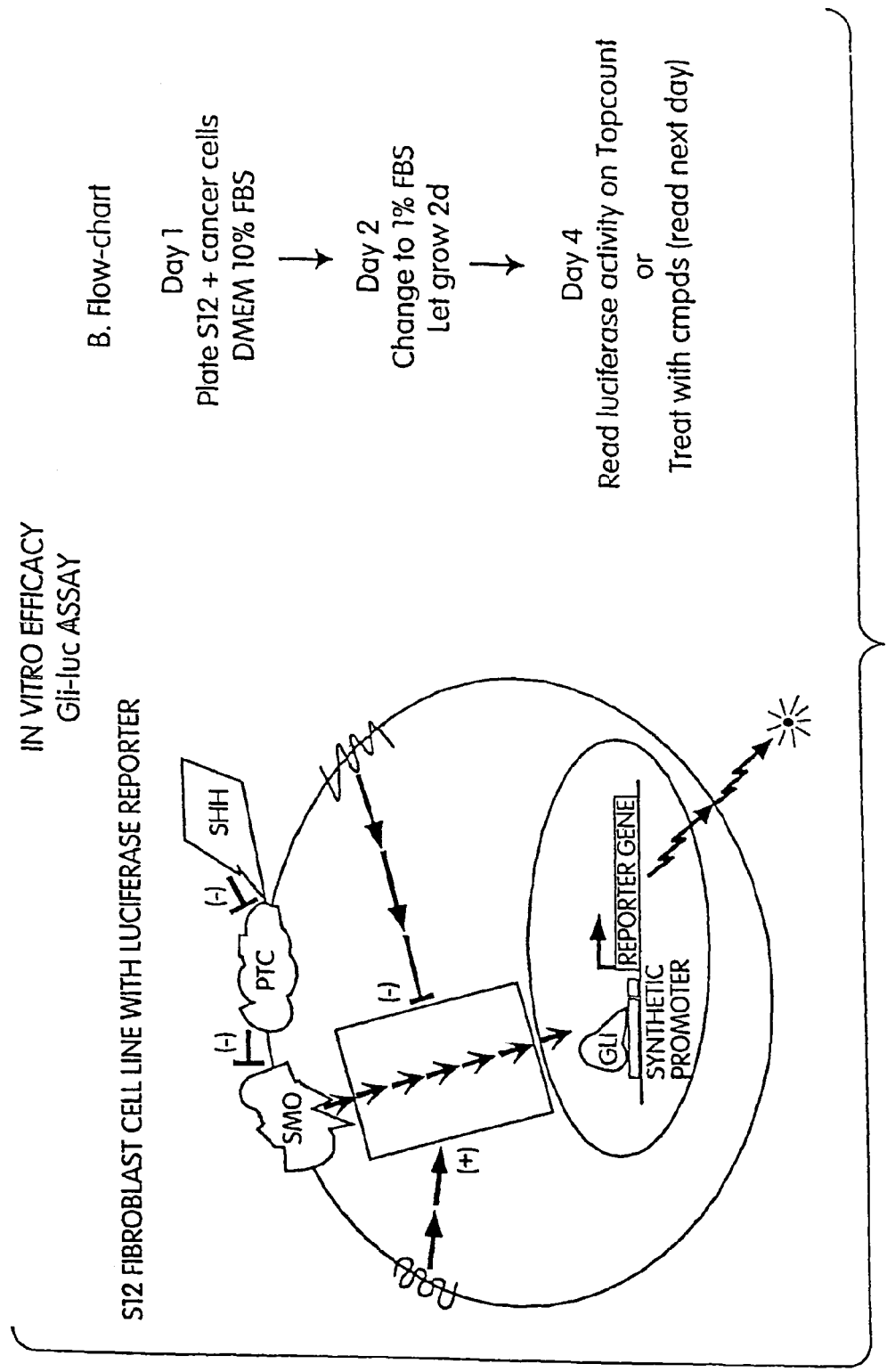
FIG. 20 shows a schematic representation of the gli-Luc assay.

The expression of components of the hedgehog signaling pathway in the eight bladder cancer cell lines examined suggested that hedgehog signaling is active in bladder cancer cells. However the gene expression observed may not be indicative of functional signaling. To assess whether functional hedgehog signaling occurs in bladder cancer cell lines, a gli-Luc in vitro assay was used. This assay is summarized schematically in FIG. 20. Briefly, 10T ½ (S12) fibroblasts expressing a luciferase reporter gene responsive to hedgehog serve as an indicator of hedgehog signaling. When these cells are contacted with functional hedgehog protein, the hedgehog signaling pathway is activated in the S12 cells, and luciferase is expressed. In the experiments presented here, S12 cells are co-cultured with bladder cancer cells. If the bladder cancer cell line secretes functional hedgehog protein, luciferase expression will be activated in the adjacent S12 cells.

Figure 21:
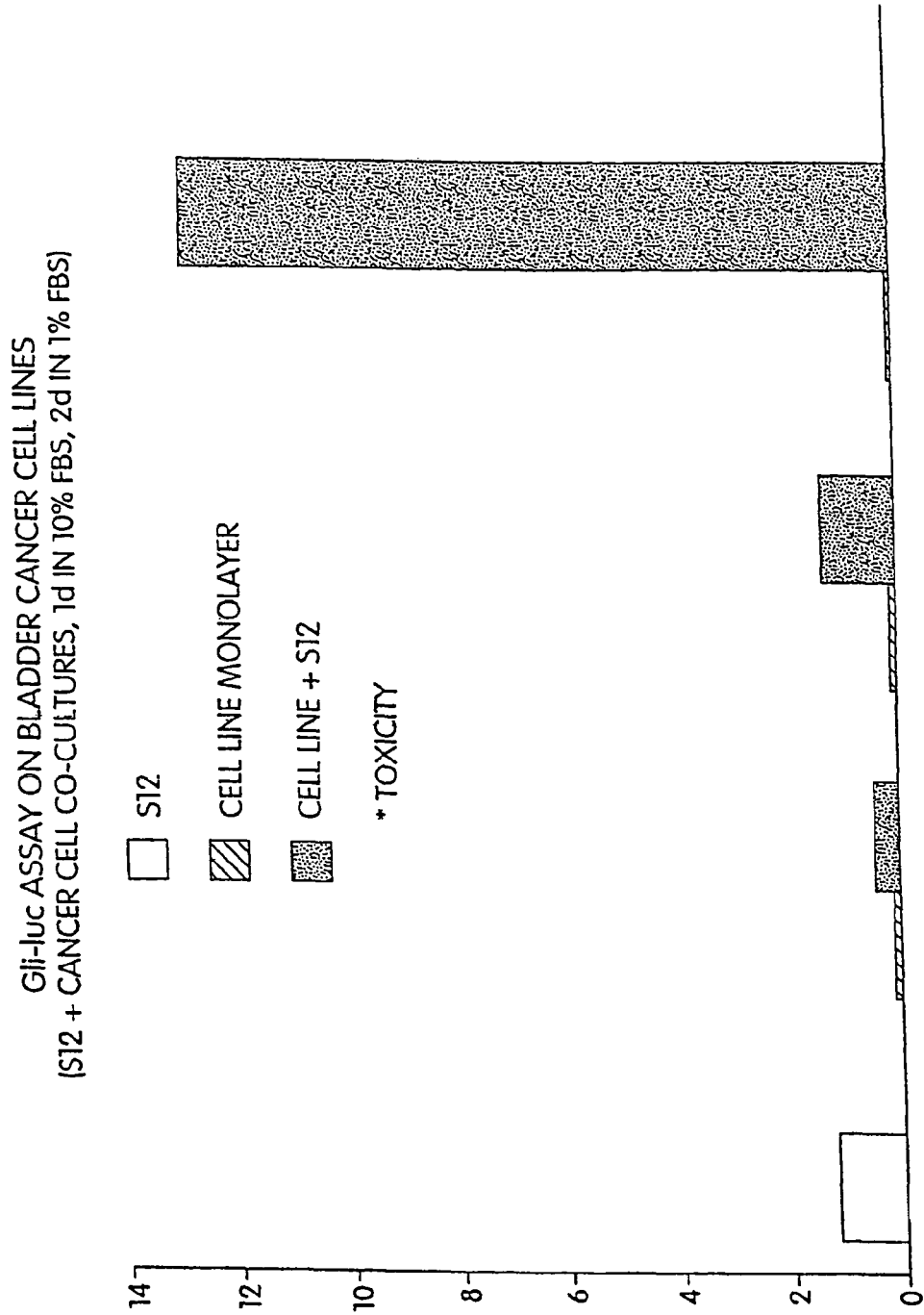
FIG. 21 shows the results of the gli-Luc assay on bladder cancer cell co-cultures. Co-culture of S12 cells with either cell line 5637 or cell line RT4 results in activation of the reporter gene indicating that these cell lines can activate hedgehog signaling.

FIG. 21 shows luciferase induction in S12 cells alone, and in S12 cells co-cultured with three bladder cancer cell lines. Two of the three cell lines examined induced expression of luciferase in S12 cells indicating that these bladder cancer cell lines secrete functional hedgehog protein.

Figure 22:
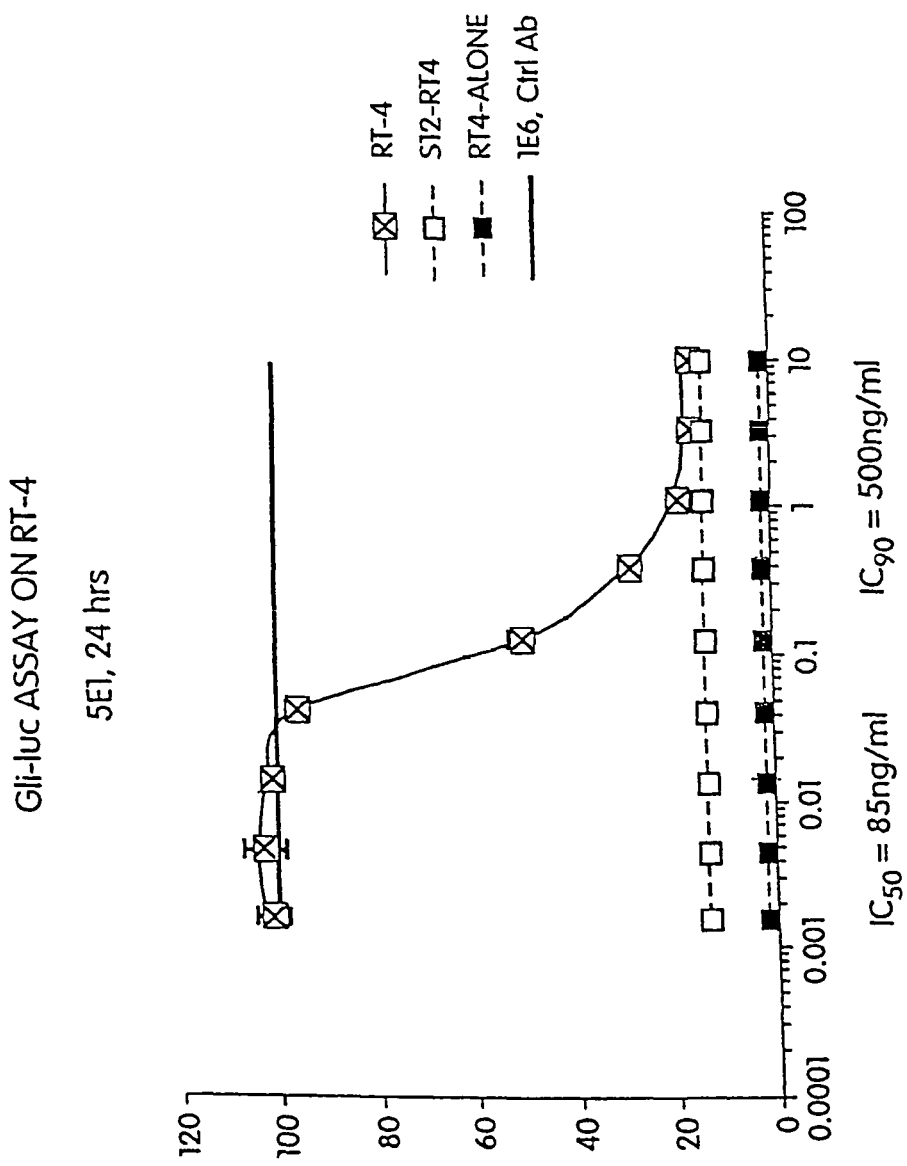
FIG. 22 shows that the Shh antibody 5E1 inhibits activation of the reporter gene in RT-4/S12 co-cultures.

To confirm the specificity of this activation of hedgehog signaling by bladder cancer cell lines, S12/RT-4 co-cultures were treated with the Shh blocking antibody (5E1). FIG. 22 demonstrates that 5E1 treatment of co-cultures inhibits expression of luciferase in S12 cells with an $IC_{50}$ of 85 ng/ml and an $IC_{90}$ of 500 ng/ml. It should be noted that this model also provides a means for evaluating the in vitro efficacy of other hedgehog antagonists including small molecule and polypeptide antagonists.

Hedgehog Signaling in an In Vivo Mouse Bladder Tumor Model

Figure 23:
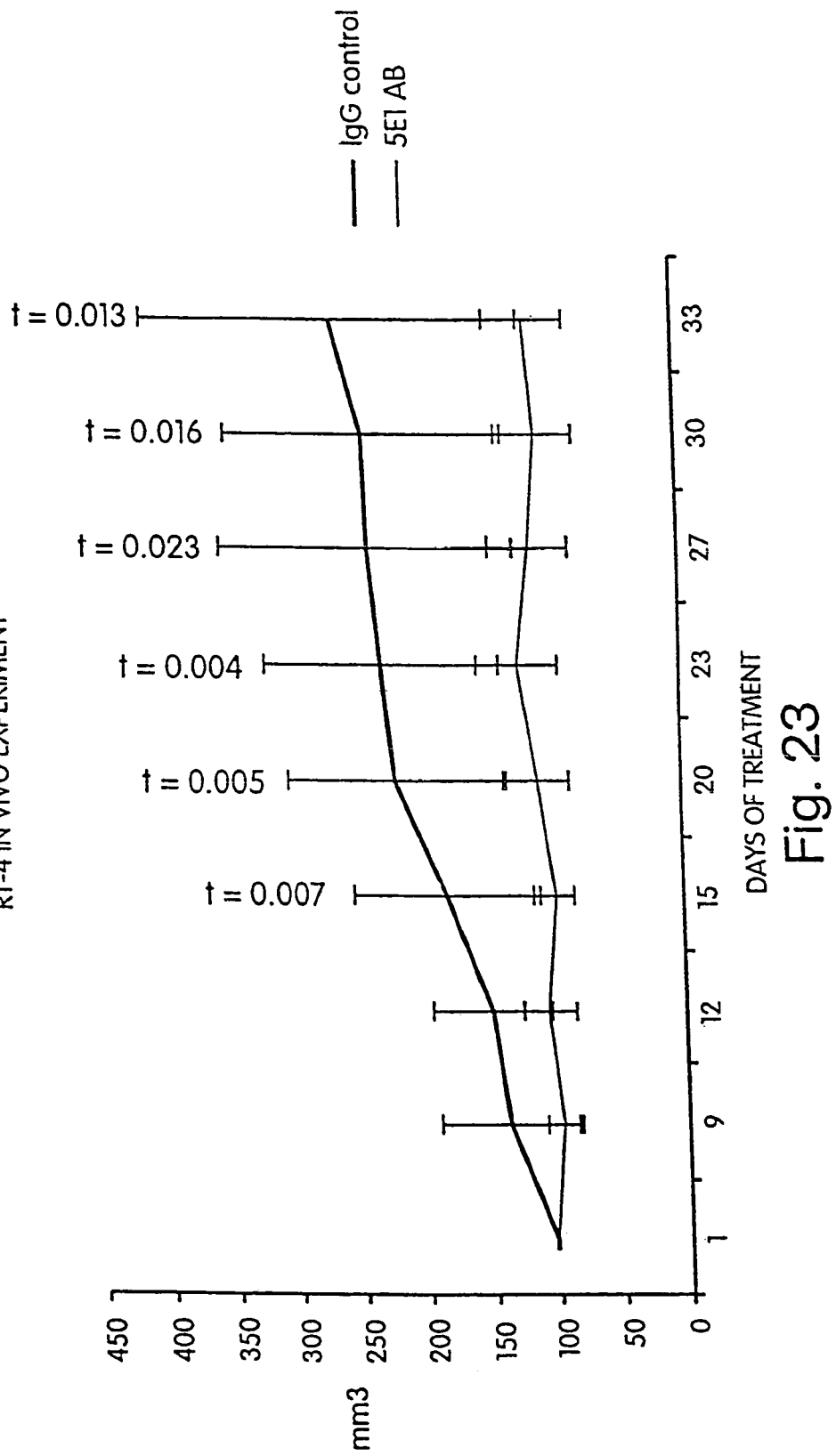
FIGS. 23 and 24 show that administration of the Shh antibody 5E1 inhibits tumor growth in vivo in a nude mouse bladder cancer model.
Figure 24:
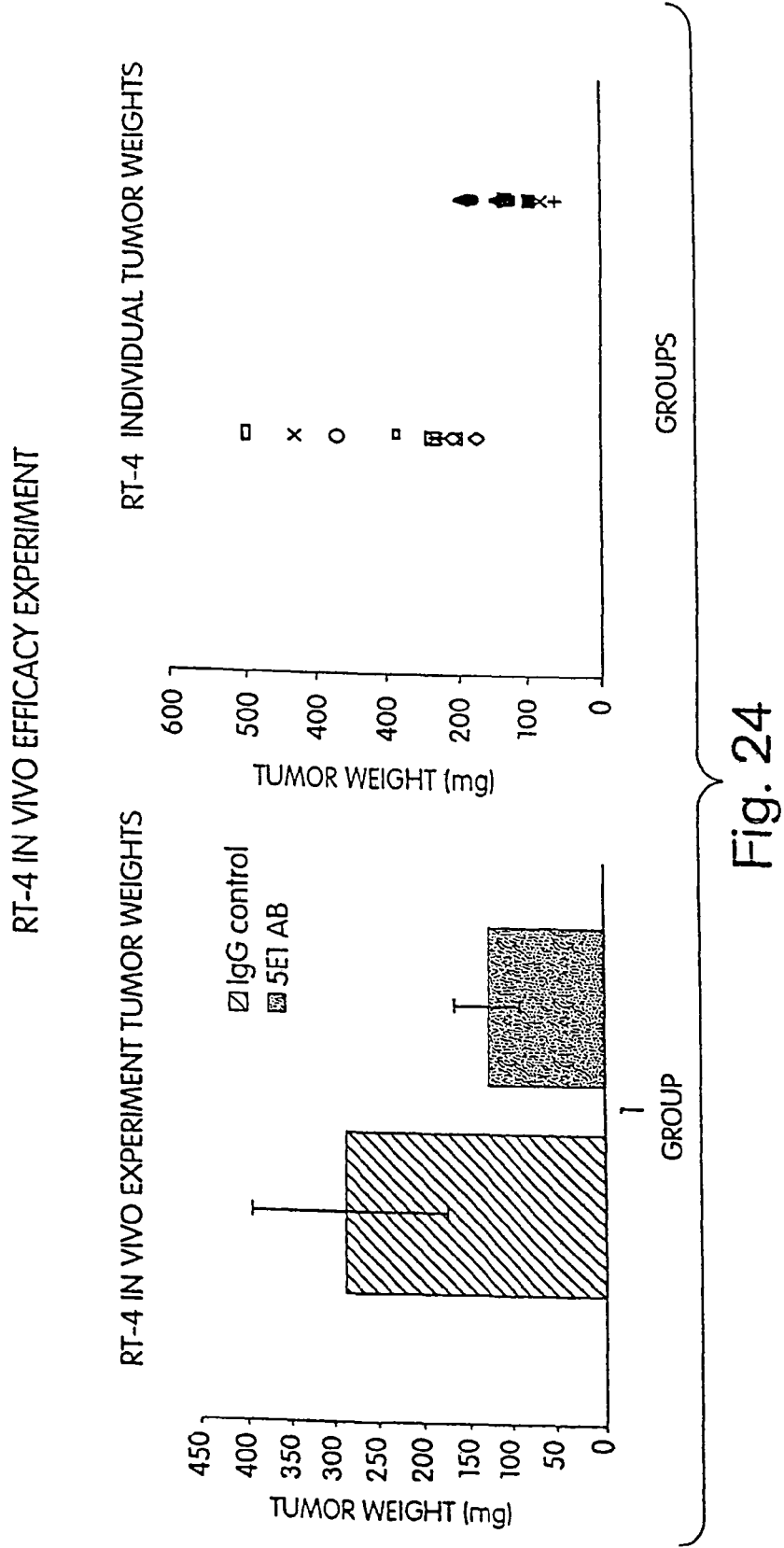

Injection of bladder tumor cells into nude mice induces tumor formation. Based on the ability of the Shh antibody 5E1 to inhibit hedgehog signaling in the in vitro gli-Luc assay described in detail above, the ability of 5E1 to inhibit bladder cell tumor growth in vivo was examined. Briefly, nude mice were injected subcutaneously with $10^7$ RT-4 cells. The mice were divided into two groups and treated with either 5E1 or with a control IgG antibody. FIGS. 23 and 24 show that treatment with 5E1 significantly decreased the size of the tumor in comparison to treatment with the IgG control. It is important to note that due to the procedure used in this particular experiment (injection of tumor cells with Matrigel) the tumors start out with an average size of 100 mm$^3$ due to the Matrigel matrix (=100 μl injection volume). Matrigel is a liquid when kept on wet ice, but solidifies upon injection. Thus, the average tumor size in the 5E1 group at the end of the experiment is roughly equal to that at the beginning of treatment. Results are highly statistically significant (Student's t-test: p=0.017). It should be noted that this model also provides a means for evaluating the in vivo efficacy of other hedgehog antagonists including small molecule and polypeptide antagonists.

Figure 25:
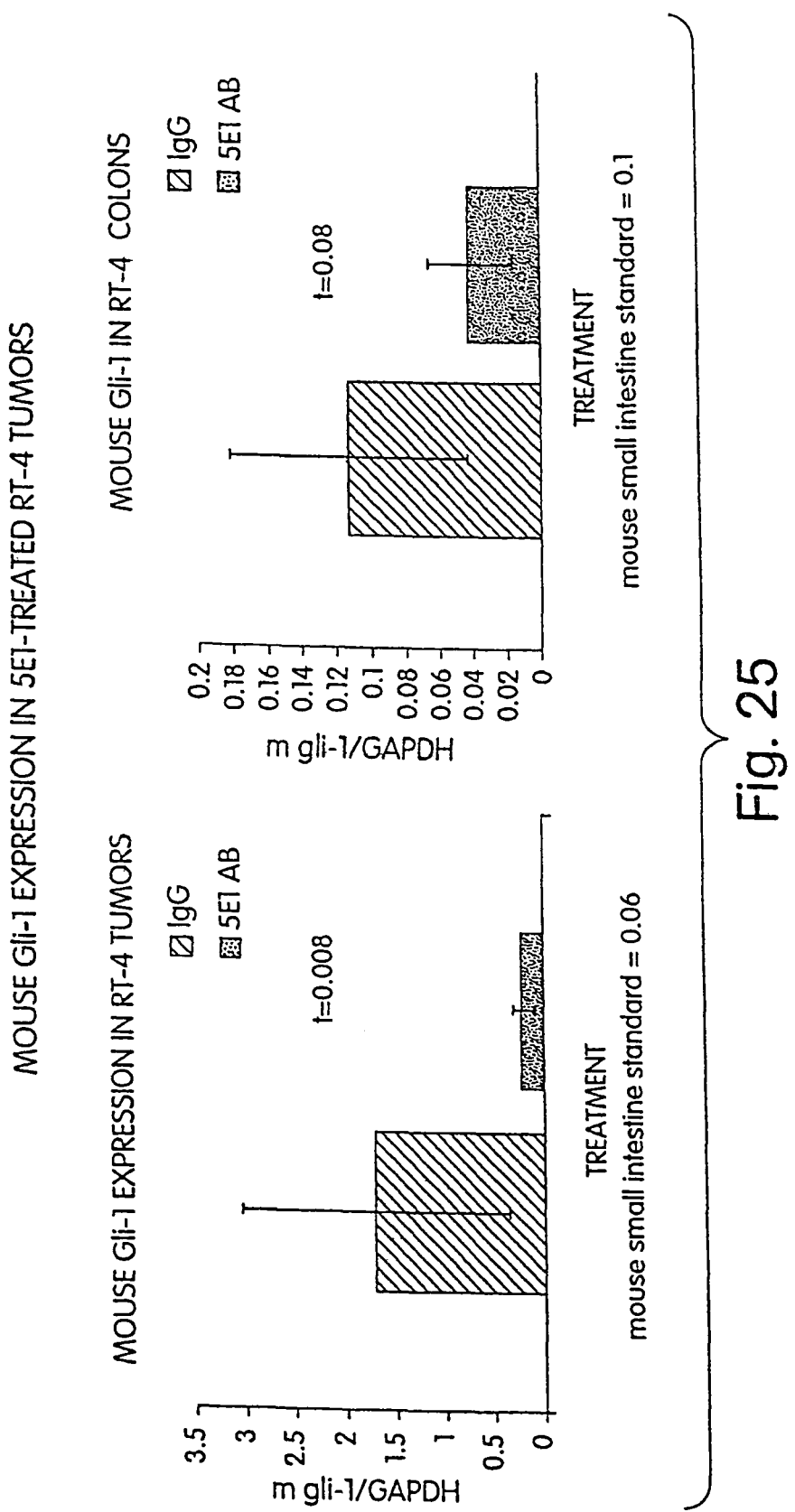
FIG. 25 shows that administration of the Shh antibody 5E1 decreases expression of gli-1 in vivo in a nude mouse bladder cancer model.

In addition to evaluating the effect of 5E1 treatment on tumor size, expression of gli-1 in both the RT-4 tumors and in the surrounding tissue was also evaluated. 5E1 treatment decreased expression of gli-1 in both the RT-4 tumors and in adjacent tissue (FIG. 25). This finding is significant because the in vitro experiments outlined above indicate that these hedgehog-expressing cells can activate hedgehog signaling in adjacent cell. Given the complex nature of cancer progression, it is possible that hedgehog signaling influences cancer both directly and indirectly. The indirect effects may include the induction of proliferative factors, angiogenic factors, or anti-apoptotic factors, to name a few. The induction of such factors may occur within the cancer cells themselves or in adjacent cells. Thus, the demonstration that a hedgehog antagonist 5E1 can inhibit hedgehog signaling in both cancer cells and in surrounding cells has significant implications.

METHODS: Exponentially growing RT-4 cultures were trypsinized, spun down, and resuspended in a small volume of culture medium. The proportion of viable tumor cells was determined by trypan blue exclusion. $10^7$ cells/animal were resuspended in 100 μl Matrigel (a commercially available preparation of basement membrane components) and injected subcutaneously in the right side of the flank of 6-8 week-old athymic male BALB/c nu/nu nude mice. Treatment was begun the day after injection of the cells. Mice were divided into two groups containing 16 animals/group. The control group (IgG control antibody) and the 5E1-treated group were injected 3×/week intraperitoneally with 10 mg/kg antibody. Tumors were measured 2×/week by caliper in 2 dimensions and measurements converted to tumor mass using the formula for a prolate ellipsoid (a×b$^2$×½). As noted above, in this particular example the tumors were injected in combination with Matrigel. Therefore, the tumors have an initial size of 100 mm$^3$ and the inhibition of tumor size observed following 5E1 treatment is nearly a complete inhibition of tumor growth.

Expression of gli-1 was measured using Q-RT-PCR as described throughout the application.

The inhibition of tumor growth by the hedgehog antagonist 5E1 supports the utility of the claimed invention. It is expected that antagonism of hedgehog signaling using a range of agents would have similar effects in decreasing tumor growth, and the efficacy of any candidate compound could be easily assessed using the in vitro and in vivo methods described above.

Example 4

Prostate Cancer

Hedgehog signaling plays an important role in normal prostate development. Sonic hedgehog is required for prostate growth, and expression of Shh is strongly correlated with prostate ductal branching (Podlasek et al. (1999) *Developmental Biology* 209: 28-39). Recent evidence supporting the essential role of shh in proper prostate branching demonstrates that treatment of embryonic prostate with the hedgehog antagonist cyclopamine inhibits growth and branching (W. Bushman, unpublished result). Additionally, the maintenance of low levels of hedgehog signaling in the adult mouse prostate suggests additional roles for hedgehog signaling beyond this early role in the initial growth and branching of the embryonic prostate.

Recent studies have examined the correlation between the expression of components of the hedgehog pathway and prostate cancer. These results show a correlation between increased expression of shh and/or gli-1 and prostate cancer. Additional cytological data supports the idea that mis-regulation of the hedgehog pathway plays a role in prostate cancer. Two studies have described deletions of a fragment of chromosome 10 containing the Su(fu) locus in prostate cancers (Carter et al. (1990) *PNAS* 87: 8751-8755; Li et al. (1997) *Science* 275: 1943-1947). Given the evidence in the literature suggestive of a role for hedgehog signaling in prostate cancer, hedgehog signaling in several prostate cancer cell lines was examined. Additionally, the ability of hedgehog antagonists to decrease activation of hedgehog signaling in prostate tumor cell lines was demonstrated. These results suggest that, like in bladder cancer cells, antagonism of hedgehog signaling has utility in decreasing growth and proliferation of prostate cancer cells.

Hedgehog Signaling in Prostate Cancer

Figure 26:
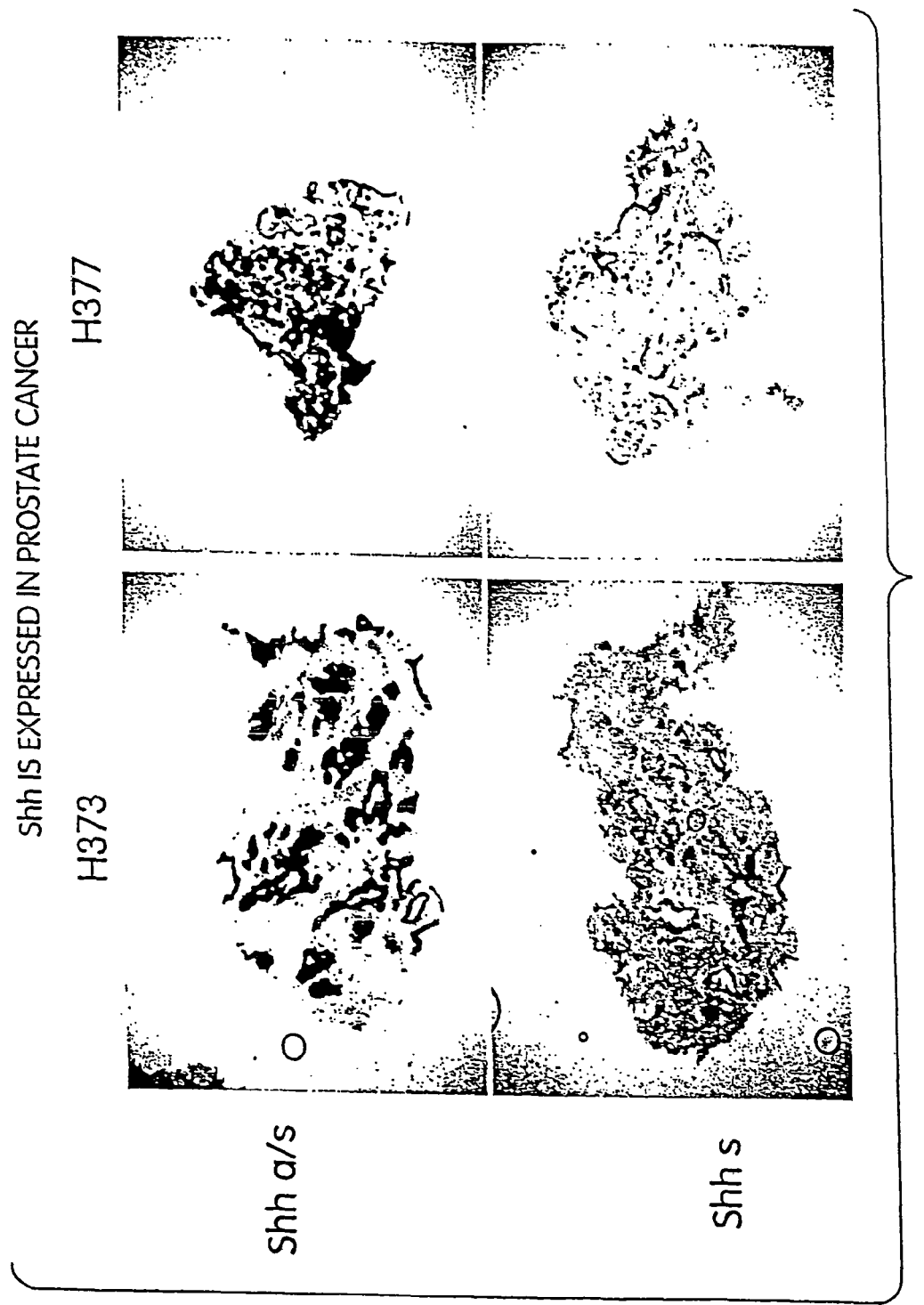
FIG. 26 shows that shh is expressed in prostate cancer samples as visualized by in situ hybridization.
Figure 27:
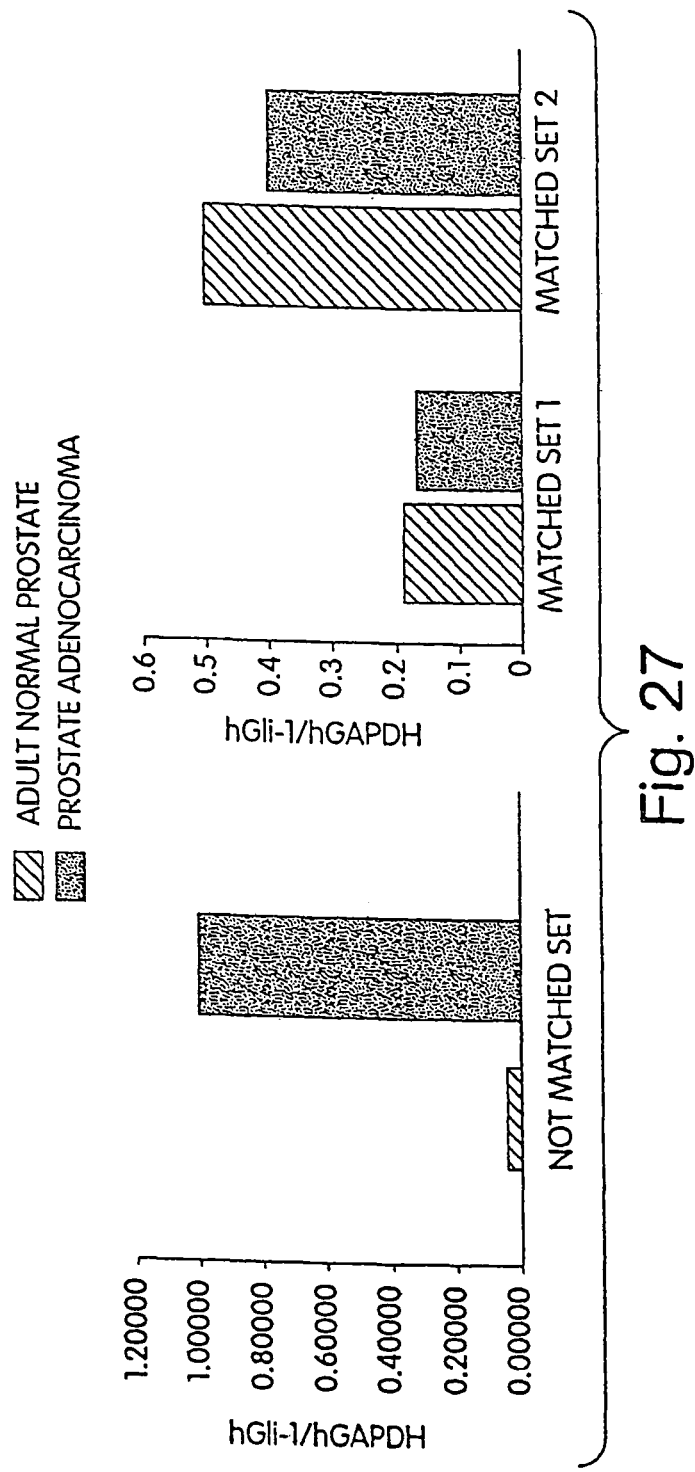
FIG. 27 shows by Q-RT-PCR the expression of gli-1 in normal adult prostate and in a prostate adenocarcinoma.
Figure 28:
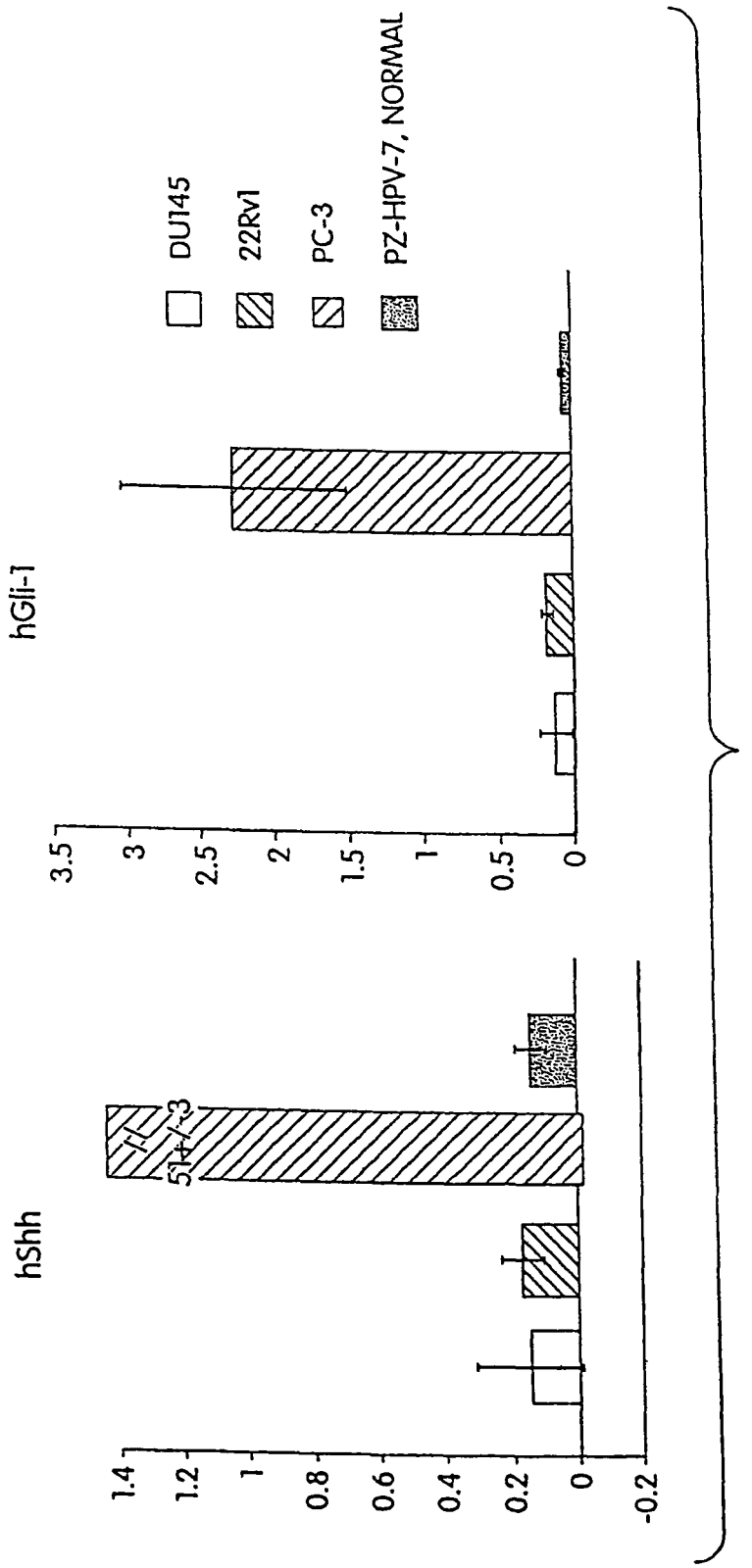
FIG. 28 shows the expression of shh and gli-1 in three prostate cancer cell lines in comparison with expression in a normal prostate cell line.

Expression of shh and gli-1 in both human prostate cancer samples and in commercially available prostate cancer cell lines was examined. FIG. 26 shows in situ hybridization analysis of human prostate cancer samples, and demonstrates the abundant expression of shh. Similarly, FIG. 27 demonstrates high levels of gli-1 expression in prostate cancer cells as measured by Q-RT-PCR. Finally, FIG. 28 examined expression of both shh and gli-1 by Q-RT-PCR in three commercially available prostate cancer cell lines. These results indicate hedgehog signaling occurs in all three commercially available cell lines.

METHODS: In situ hybridization: Paraformaldehyde-fixed tissue is cryo-sectioned into 30 µm sections, digested with proteinase K, hybridized overnight with digoxigenin-labeled RNA probe. After high stringency post-hybridization washes, sections are incubated with an anti-digoxigenin antibody which is labeled with alkaline phosphatase. The signal is visualized by addition of BM purple, a commercially available chromagen solution that reacts with the alkaline phosphatase to form a purple precipitate.

Prostate cancer cell lines were purchased from ATCC (American Type Culture Collection) and maintained as recommended in the product description. At confluency, cells were rinsed and switched to medium containing 1% serum, a treatment that increases hedgehog signaling. Cells were then grown 2 more days, collected in Trizol (GIBCO-BRL) and RNA isolated according to the manufacturer's protocol. The RNA was then transcribed into first strand cDNA according to standard protocols, and amplified using an ABI Prism 7700 Sequence Detection System (TaqMan) from Perkin Elmer and gene-specific primers. The housekeeping gene GAPDH was used to normalize RNA concentration and PCR efficiency, and GAPDH primers were added to the same reactions. Since probes for both genes are labeled with different fluorophores, the specific signal and that of GAPDH can be detected in the same tube. Signal intensities were calculated using the algorithms provided in Sequence Detector v1.7, the software provided by the manufacturer.

In Vitro Assay to Examine Hedgehog Signaling in Prostate Cancer Cell Lines

The expression of components of the hedgehog signaling pathway in prostate cancer samples and cell lines suggests that hedgehog signaling is active in prostate cancer. However the gene expression observed may not be indicative of functional signaling. To assess whether functional hedgehog signaling occurs in prostate cancer cell lines, the gli-Luc in vitro assay was employed. This assay was summarized above, and is represented schematically in FIG. 20. Briefly, 10T ½(S12) fibroblasts expressing a luciferase reporter gene responsive to hedgehog serves as an indicator of hedgehog signaling. When these cells are contacted with functional hedgehog protein, the hedgehog signaling pathway is activated in the S12 cells, and luciferase is expressed. In the experiments presented here, S12 cells are co-cultured with prostate cancer cells. If the prostate cancer cell line secretes functional hedgehog protein, luciferase expression will be activated in the adjacent S12 cells.

Figure 29:
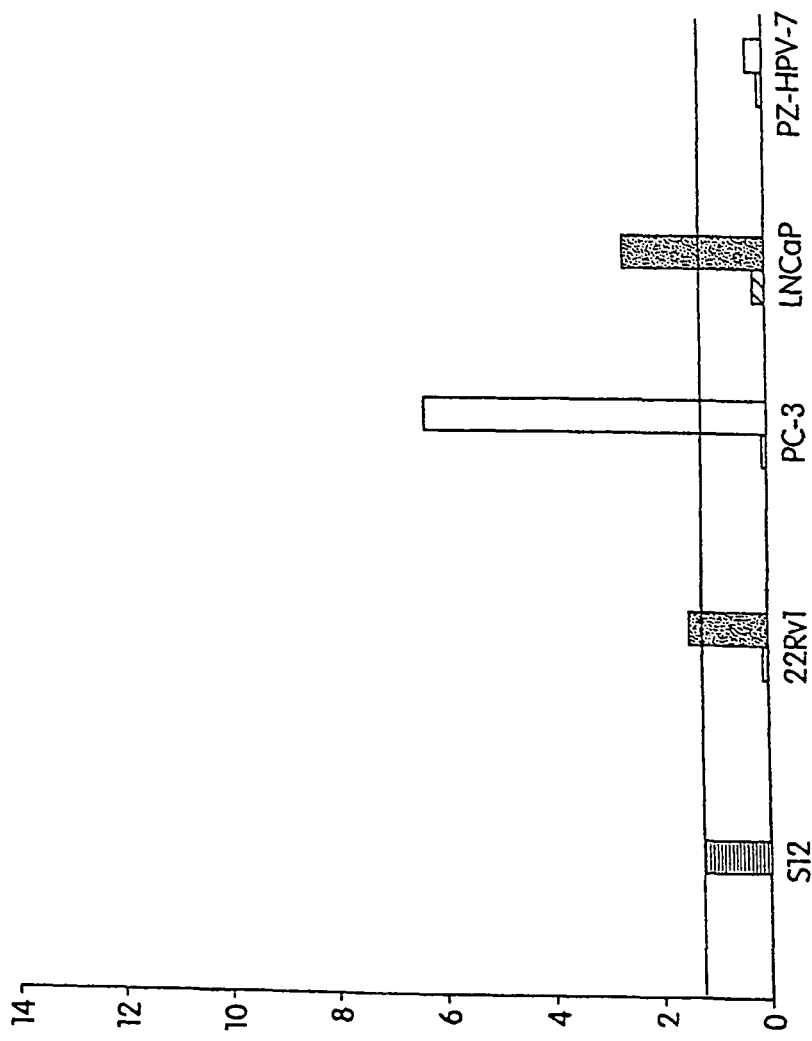
FIG. 29 shows that prostate cancer cell lines induce expression of luciferase when co-cultured with S12 cells in the gli-Luc in vitro assay.

FIG. 29 shows no induction of luciferase in S12 cells cultured alone, or in S12 cells cultured with PZ-HPV-7 (normal) cells. However, luciferase induction is observed when S12 cells are cultured with any of three prostate cancer cell lines: 22Rv1, PC-3, or LNCaP. This result indicates that these prostate cancer cell lines secrete functional hedgehog protein.

Figure 30:
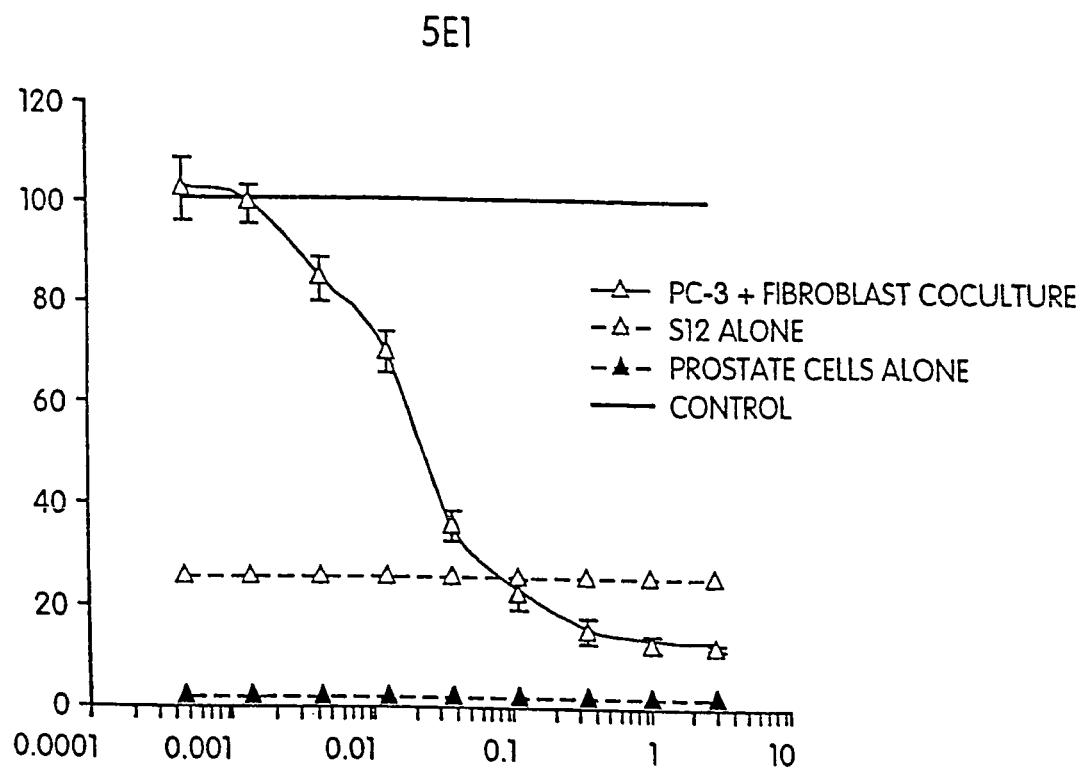
FIG. 30 shows that the antagonizing antibody 5E1 inhibits the induction of luciferase in by prostate cancer cells in the gli-Luc in vitro assay.

To confirm the specificity of this activation of hedgehog signaling by prostate cancer cell lines, S12/prostate cancer co-cultures were treated with the Shh blocking antibody (5E1). FIG. 30 demonstrates that 5E1 treatment of co-cultures inhibits expression of luciferase in S12 cells.

METHODS: S12 cultures and co-cultures, and luciferase assays were performed as detailed above.

Example 5

Benign Prostatic Hyperplasia (BPH)

As detailed above, hedgehog signaling appears to have both an important role in early prostate patterning, and a role in maintenance of the adult prostate. Although prostate cancer is one potential affect of misregulation of hedgehog signaling in the adult prostate, another common condition of the prostate that seems to correlate with hedgehog expression is benign prostatic hyperplasia (BPH).

BPH is a disease of the central prostate, and is characterized by increased smooth muscle around the prostatic urethra. Interestingly, shh is expressed in a gradient in the adult prostate with highest expression in the central zone of the prostate. Additionally, shh is involved in smooth muscle differentiation in other tissues including the gut and lung (Apelqvist et al. (1997) Current Biology 7: 801-804; Pepicelli et al. (1998) Current Biology 8: 1083-1086). This evidence identified hedgehog signaling as a good candidate for involvement in the etiology of BPH. Finally, transcription of shh is increased by exposure to dihydro-testosterone (DHT) (Podlasek et al., supra). This is significant because the concentration of 5-alpha-reductase, an enzyme which converts testosterone to DHT, is elevated in BPH stroma (Wilkin et al. (1980) *Acta Endocrinology* 94: 284-288). This data suggests that misregulation of hedgehog signaling may be involved in BPH, and thus that the present invention provides utility for the treatment of BPH.

Hedgehog Signaling in BPH

Figure 31:
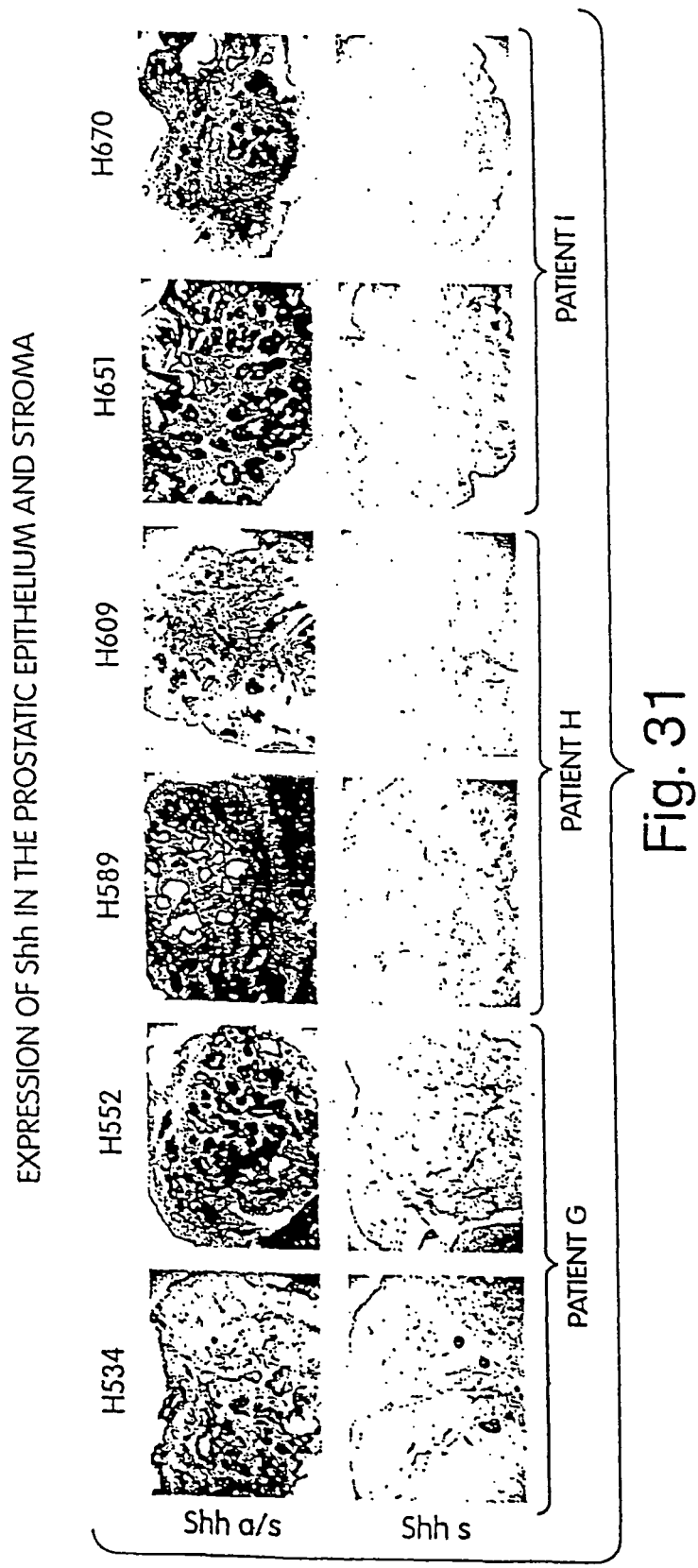
FIG. 31 shows the expression of shh in prostatic epithelium and stroma in human BPH samples.
Figure 32:
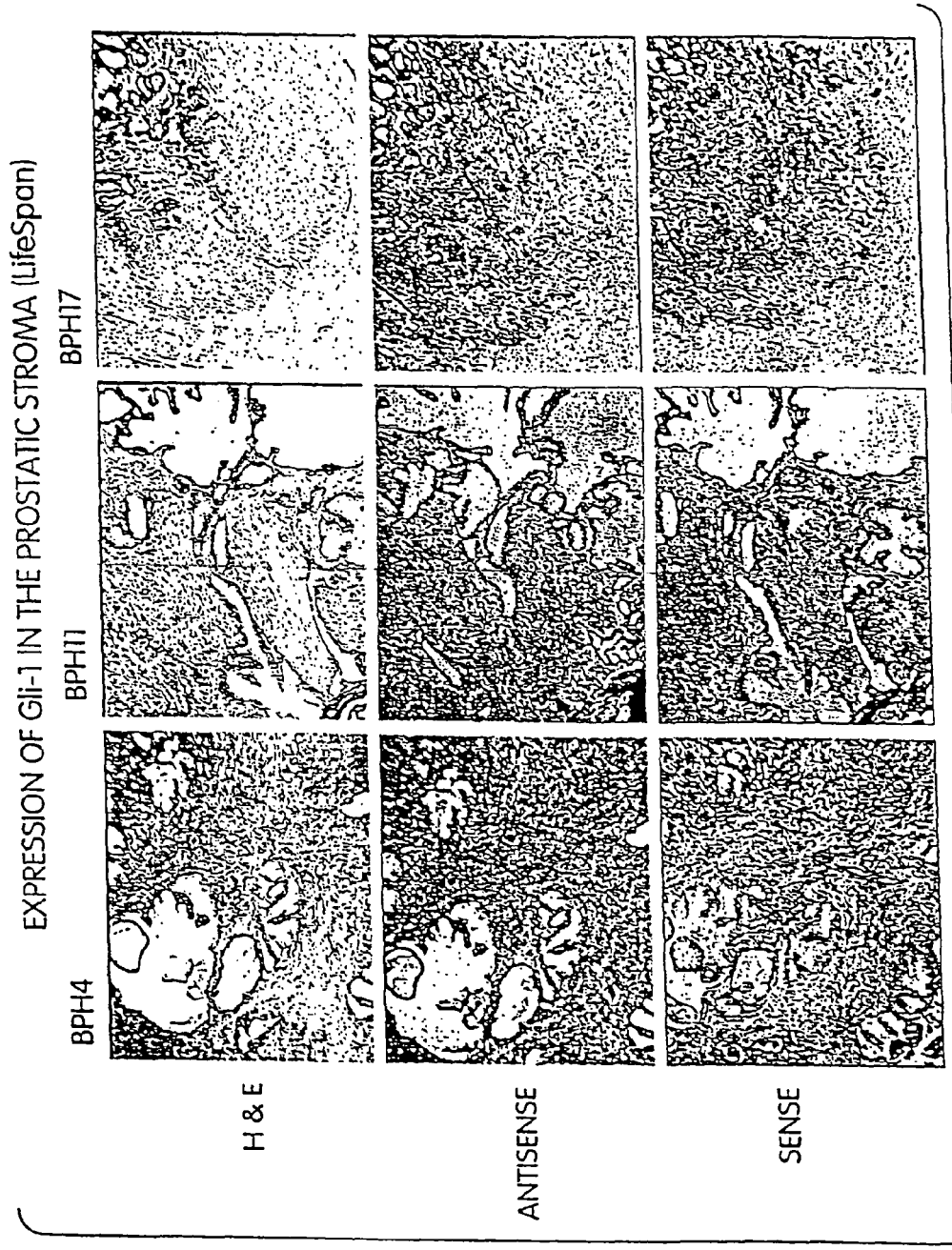
FIG. 32 shows the expression of gli-1 in the prostatic stroma of human BPH samples as measured by radioactive in situ hybridization.
Figure 33:
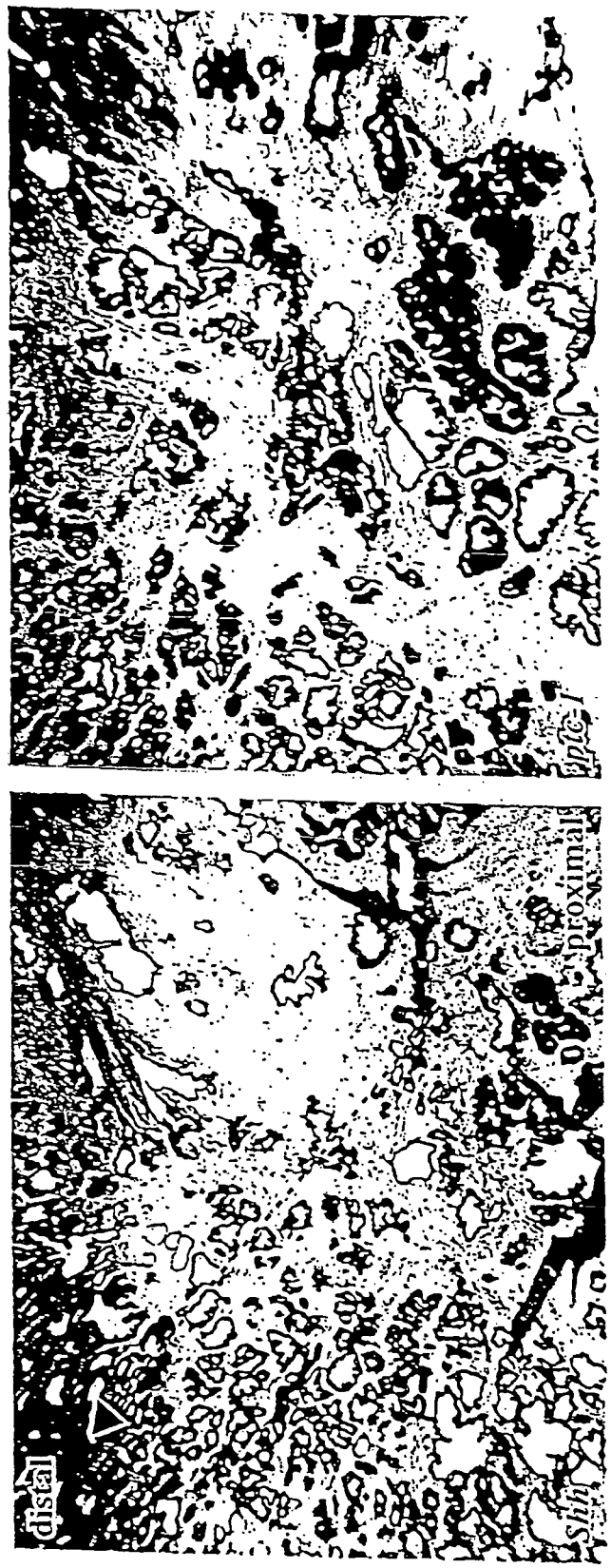
FIG. 33 shows that shh and patched-1 are expressed in a proximo-distal pattern in normal prostate tissue with the highest levels of gene expression occurring in the proximo or central region.

Expression of sonic hedgehog and gli-1 expression in human BPH samples was examined. FIGS. 31 and 32 show in situ hybridization analysis of human BPH samples, and demonstrate that both shh and gli-1 are abundantly expressed in BPH. Furthermore, FIG. 33 demonstrates that shh is not ubiquitously expressed throughout the prostate, but is instead present in a gradient with the highest level of both hedgehog and ptc-1 transcripts present in the proximal central zone of the prostate.

Figure 34:
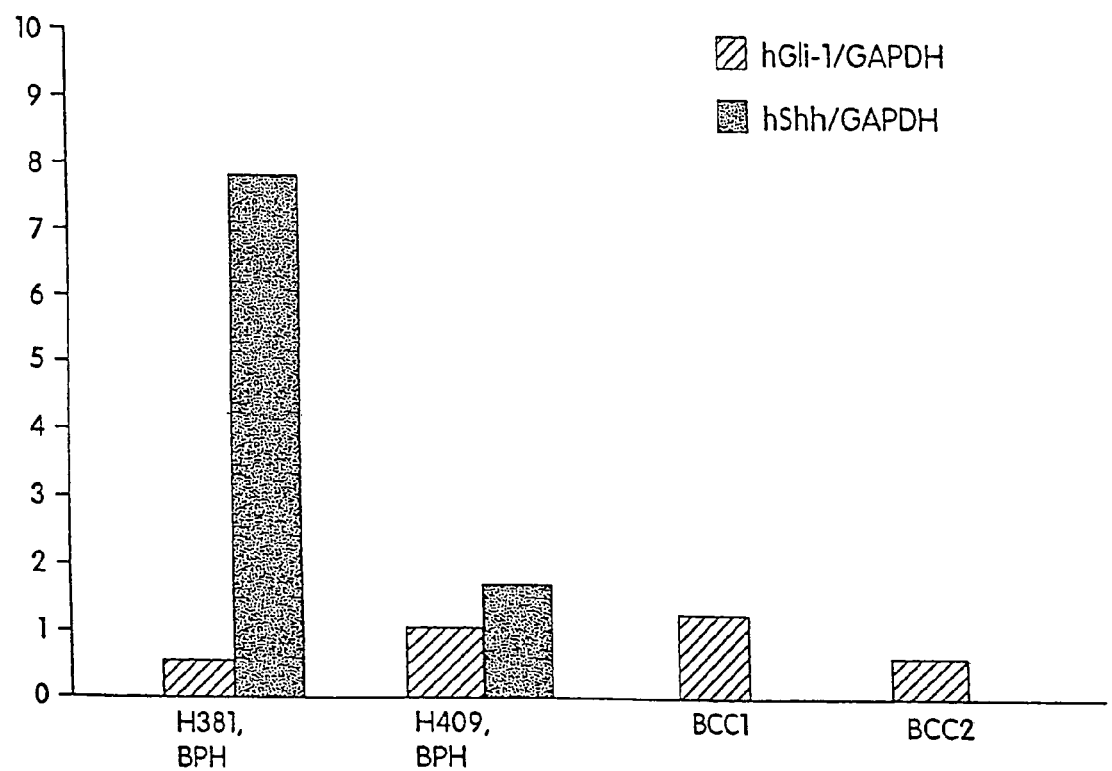
FIG. 34 shows the expression of shh and gli-1 in BPH samples, and compares the levels of gene expression to BCC samples.
Figure 35:
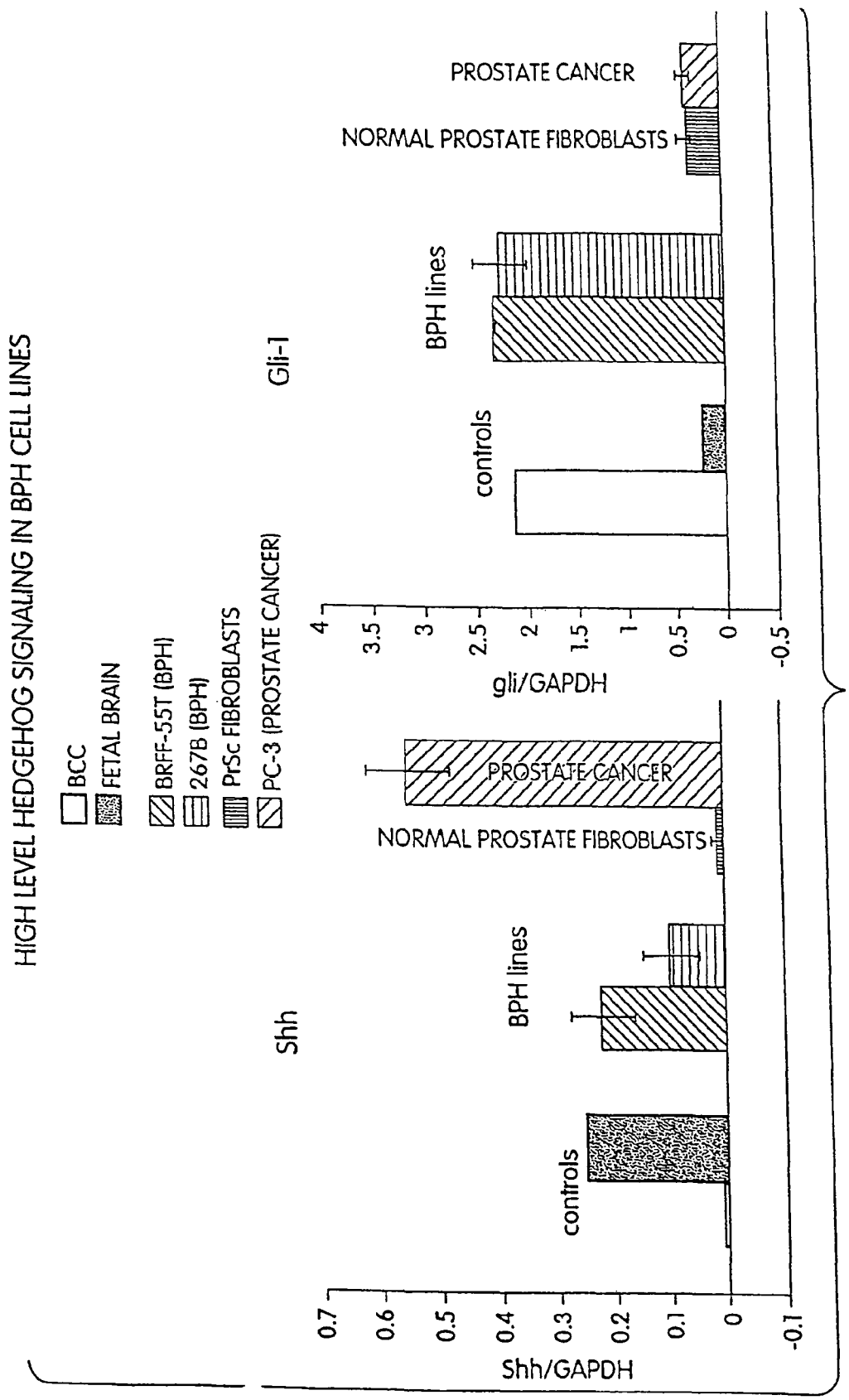
FIG. 35 shows the expression of shh and gli-1 in BPH cell lines, and compares the levels of gene expression to that of BCC samples, normal prostate, and prostate cancer.

Additionally, the expression of shh and gli-1 by Q-RT-PCR was analyzed. FIG. 34 shows that both shh and gli-1 are expressed in BPH samples. Expression of shh and gli-1 in basal cell carcinoma (BCC) samples is provided for comparison. These results demonstrate that gli-1 is expressed in BPH samples at a level similar to that found in a cancer type known to be caused by a hedgehog pathway mutation. Finally, FIG. 35 shows the expression of shh and gli-1 in BPH cell lines, and compares expression to that observed in BCC, prostate cancer cell lines, and normal prostate fibroblasts. Note that gli-1 is expressed at similar levels in both BPH cell lines and in BCC samples. These results are suggestive of a role for hedgehog signaling in BPH and further suggests that antagonism of hedgehog signaling has significant utility in the treatment of BPH.

METHODS: In situ hybridization (FIGS. 31 and 33): Paraformaldehyde-fixed tissue is cryo-sectioned into 30 μm sections, digested with proteinase K, hybridized overnight with digoxigenin-labeled RNA probe. After high stringency post-hybridization washes, sections are incubated with an anti-digoxigenin antibody which is labeled with alkaline phosphatase. The signal is visualized by addition of BM purple, a commercially available chromagen solution that reacts with the alkaline phosphatase to form a purple precipitate.

Radioactive In situ hybridization (FIG. 32): Briefly, 7 mm sections of paraformaldehyde-fixed, paraffin-embedded tissue containing large basal cell islands are cleared, re-hydrated, digested with proteinase K, acetylated and hybridized overnight with 33P-labeled RNA probes. After high stringency post-hybridization washes, slides were dipped in photo emulsion and incubated in the dark for 14 days at 4° C. After developing, slides were counter-stained with hematoxylin and eosin and imaged using dark-field illumination. Dark-field images were converted to red artificial color and superimposed with bright-field images. Q-RT-PCR: Samples were collected in Trizol (GIBCO-BRL) and RNA isolated according to the manufacturer's protocol. The RNA was then transcribed into first strand cDNA according to standard protocols, and amplified using an ABI Prism 7700 Sequence Detection System (TaqMan) from Perkin Elmer and gene-specific primers. The housekeeping gene GAPDH was used to normalize RNA concentration and PCR efficiency, and GAPDH primers were added to the same reactions. Since probes for both genes are labeled with different fluorophores, the specific signal and that of GAPDH can be detected in the same tube. Signal intensities were calculated using the algorithms provided in Sequence Detector v1.7, the software provided by the manufacturer.

Example 6

Additional Analysis of Hedgehog Expression in Normal and Hyperproliferative Tissue To further access the range of tissues in which the methods and compositions of the present invention may be useful in inhibiting the proliferation, growth, differentiation or survival of cells, hedgehog expression was analyzed in a range of normal and cancerous human tissues. Expression was examined at both the level of hedgehog mRNA using quantitative RT-PCR and at the level of hedgehog protein by immunohistochemistry.

Figure 36:
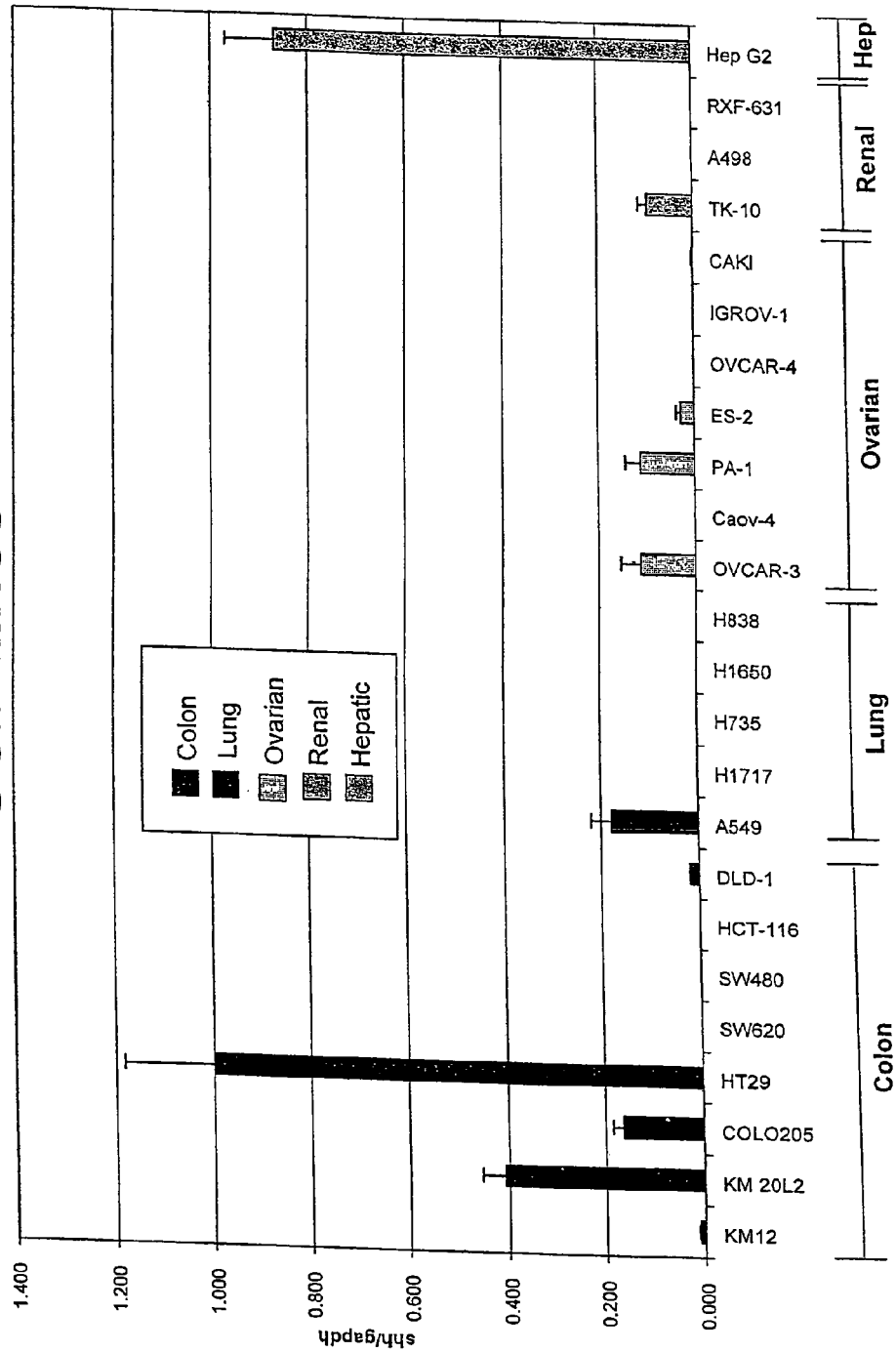
FIG. 36 shows the expression of shh in a variety of colon, lung, ovarian, renal and hepatic human cancer cell lines. Expression of shh is measured using Q-RT-PCR which demonstrates that shh is expressed, to a varying degree, in human cancer cell lines derived from several diverse tissue types.

FIG. 36 presents Q-RT-PCR analysis of Sonic hedgehog (shh) expression in a variety of human cancer cell lines. Shh expression was examined in human colon, lung, ovarian, renal and hepatic cell lines, and these results indicate that shh is expressed, at varying concentrations, in cell lines derived from each of these tissues.

Figure 37:
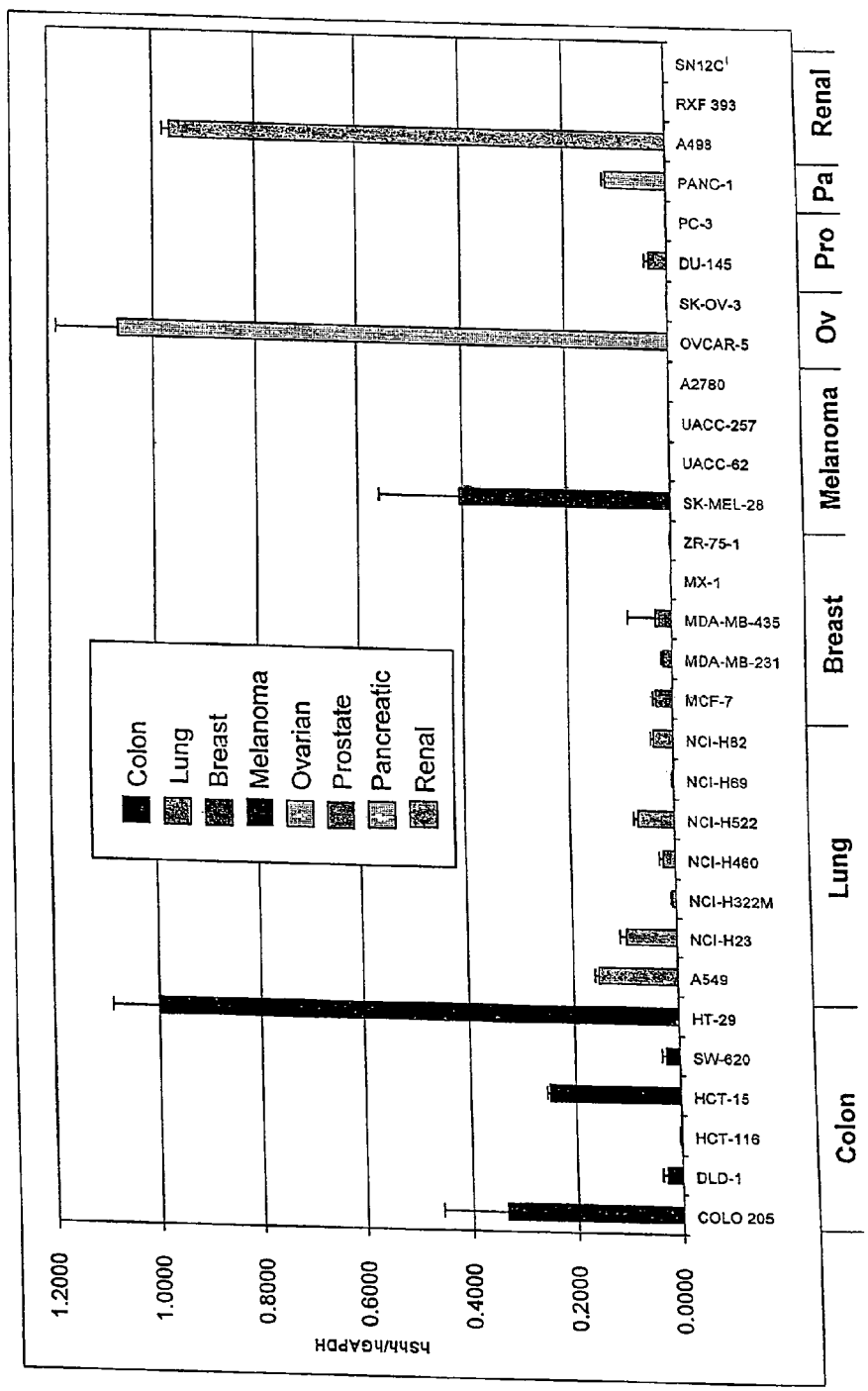
FIG. 37 shows the expression of shh in a variety of passaged tumors derived from colon, lung, breast, melanoma, ovarian, prostate, pancreatic and renal tissue. Expression of shh is measured using Q-RT-PCR which demonstrates that shh is expressed, to a varying degree, in passaged tumors derived from several diverse tissue types.

FIG. 37 presents Q-RT-PCR analysis of shh expression in passaged colon, lung, breast, melanoma, ovarian, prostate, pancreatic and renal tumors. The results demonstrate that shh is expressed, at varying levels, in passaged tumors derived from each of these tissues.

Figure 38:
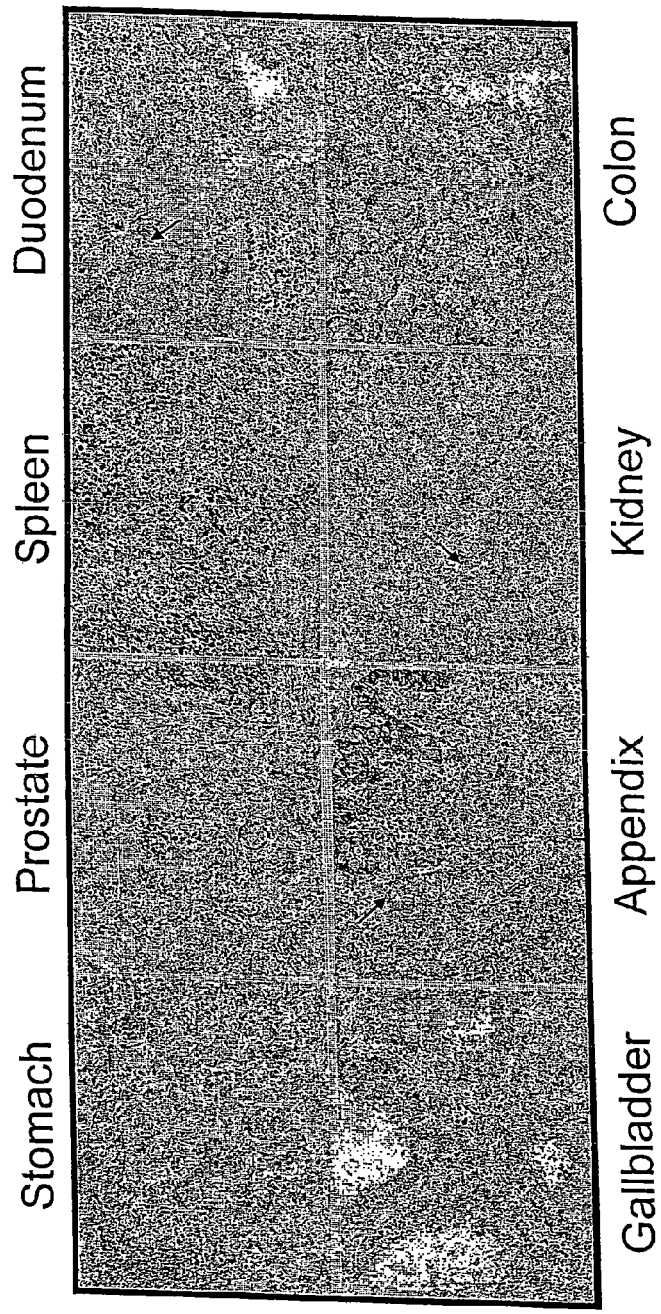
FIG. 38 shows the expression of hedgehog protein in normal human stomach, prostate, spleen, small intestine, large intestine, gall bladder, appendix and kidney tissue. Hedgehog protein expression was examined by immunohistochemistry using a polyclonal anti-hedgehog antibody.

Although the expression of shh RNA in a sample provides evidence that hedgehog signaling may be active in a cell, further information may be gleaned by examining the expression of hedgehog protein in a cell. In order to address this question, immunohistochemistry using a polyclonal antihedgehog primary antibody was performed on both normal and cancerous human tissue samples. FIG. 38 shows that hedgehog protein is expressed in normal human tissue harvested from a variety of sources including the stomach, prostate, spleen, small intestine, large intestine, gall bladder, kidney and appendix. It is interesting to note that hedgehog expression is observed in normal adult tissue derived from either the mesoderm or endoderm.

Figure 39:
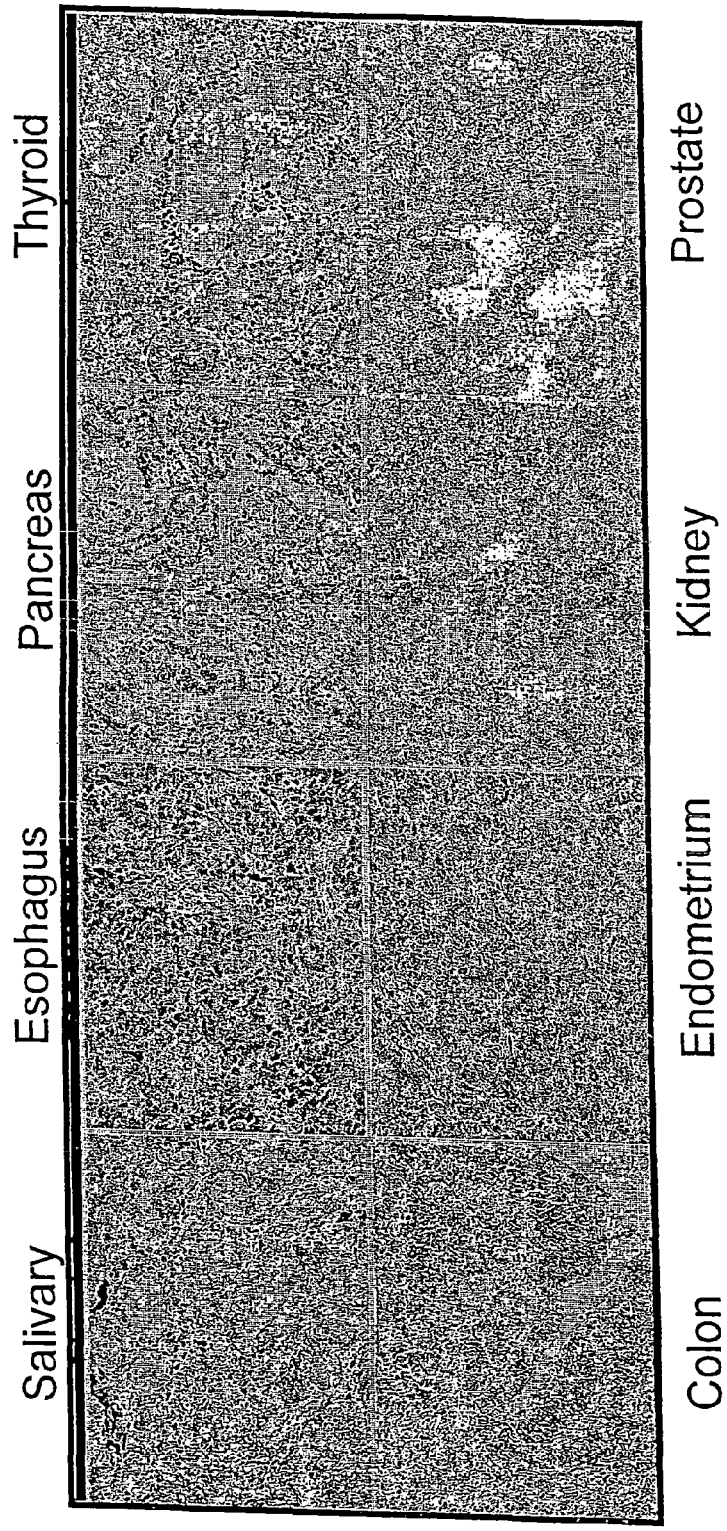
FIG. 39 shows the expression of hedgehog protein in human tumors derived from salivary, esophageal, pancreatic, thyroid, colon, endometrial, kidney and prostate tissue. Hedgehog protein expression was examined by immunohistochemistry using a polyclonal anti-hedgehog antibody.
Figure 40:
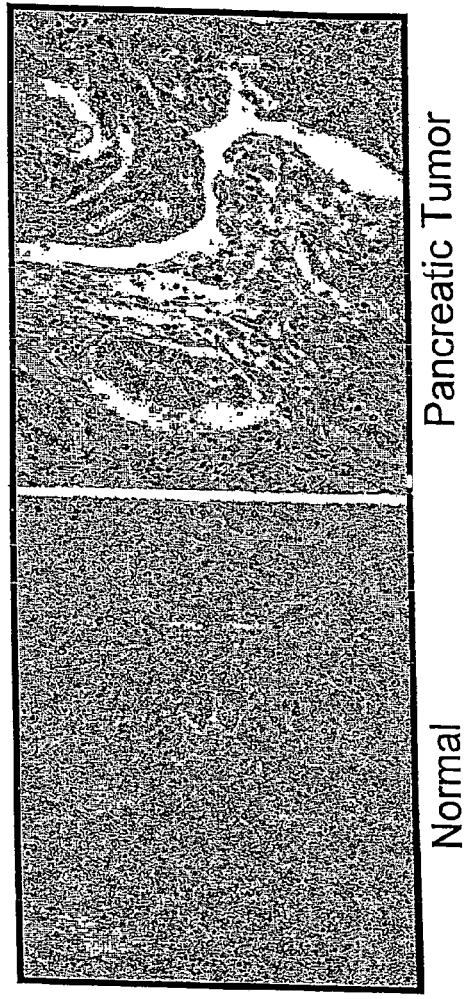
FIG. 40 shows increased expression of hedgehog protein in a sample of pancreatic tumor in comparison to hedgehog protein expression in normal pancreatic tissue. Hedgehog protein expression was measured by immunohistochemistry using a polyclonal anti-hedgehog antibody.

Expression of hedgehog protein was additionally observed in human tumors harvested from a range of tissues. FIGS. 39 and 40 demonstrate that hedgehog protein is detectable by immunohistochemistry in tumors derived from salivary esophageal, pancreatic, thyroid, colon, endometrial, kidney and prostate tissue.

These results indicate that hedgehog is expressed, at both the mRNA and protein level, in a wide range of both normal and hyperproliferative tissues. Further analysis is needed to ascertain, for a given tissue type, the differences in the level of hedgehog expression between normal tissue and hyperproliferative tissue. Such analysis will help provide a better understanding of the mechanistic role of increased hedgehog expression in hyperproliferative conditions including cancer.

METHODS: Q-RT-PCR: Samples were collected in Trizol (GIBCO-BRL) and RNA isolated according to the manufacturer's protocol. The RNA was then transcribed into first strand cDNA according to standard protocols, and amplified using an ABI Prism 7700 Sequence Detection System (TaqMan) from Perkin Elmer and gene-specific primers. The housekeeping gene GAPDH was used to normalize RNA concentration and PCR efficiency, and GAPDH primers were added to the same reactions. Since probes for both genes are labeled with different fluorophores, the specific signal and that of GAPDH can be detected in the same tube. Signal intensities were calculated using the algorithms provided in Sequence Detector v1.7, the software provided by the manufacturer.

Immunohistochemistry: Samples were harvested and processed for immunohistochemistry using standard methods. Samples were incubated overnight with a polyclonal anti-hedgehog primary antibody.

Example 7

Antagonism of Hedgehog Signaling in Colon Cancer

The growth of tumors is a complex process that requires proliferation, angiogenesis, the inhibition of cell death, and many other complex interactions between the cancer cells and the surrounding tissue. An additional mechanism by which hedgehog signaling may influence tumor growth and progression is through the induction of factors that enhance proliferation, angiogenesis, and the inhibition of cell death. For example, sonic hedgehog has been shown to induce VEGF in fibroblasts. Thus, the use of hedgehog antagonists may prevent hedgehog signaling from inducing factors that promote tumor formation, and therefore inhibit tumor formation or progression.

Given the complex interplay which likely exists between tumor cells and the surrounding tissue, we have used two models to analyze the effects of hedgehog antagonists in inhibiting the proliferation, growth, differentiation and survival of hyperproliferative tissues. In the first model, mice are injected with a combination of hedgehog expressing cancer cells and fibroblasts, and the effects of hedgehog antagonists on the growth of this mixed-tumor are examined over time. In the second model, mice are injected with hedgehog expressing cancer cells which have not been previously combined with fibroblast cells. Without wishing to be bound by any particular theory, both models appear to recapitulate at least to some degree the complex interactions which occur during tumor formation. In the mixed tumor model, cancer cells and fibroblast cells interact—much like cancer cells and stromal cells interact during the development of many forms of cancer. In the second model however, it appears that surrounding endogenous cells invade and interact with the injected hedgehog expressing cancer cells similarly recapitulating the interactions which occur in both the mixed-tumor model and during the development of many forms of cancer. Accordingly, results obtained using either model help to address the use of hedgehog antagonists in inhibiting the proliferation, growth, differentiation and survival of hyperproliferative cells.

Model I: Mixed Tumor Model

Figure 41:
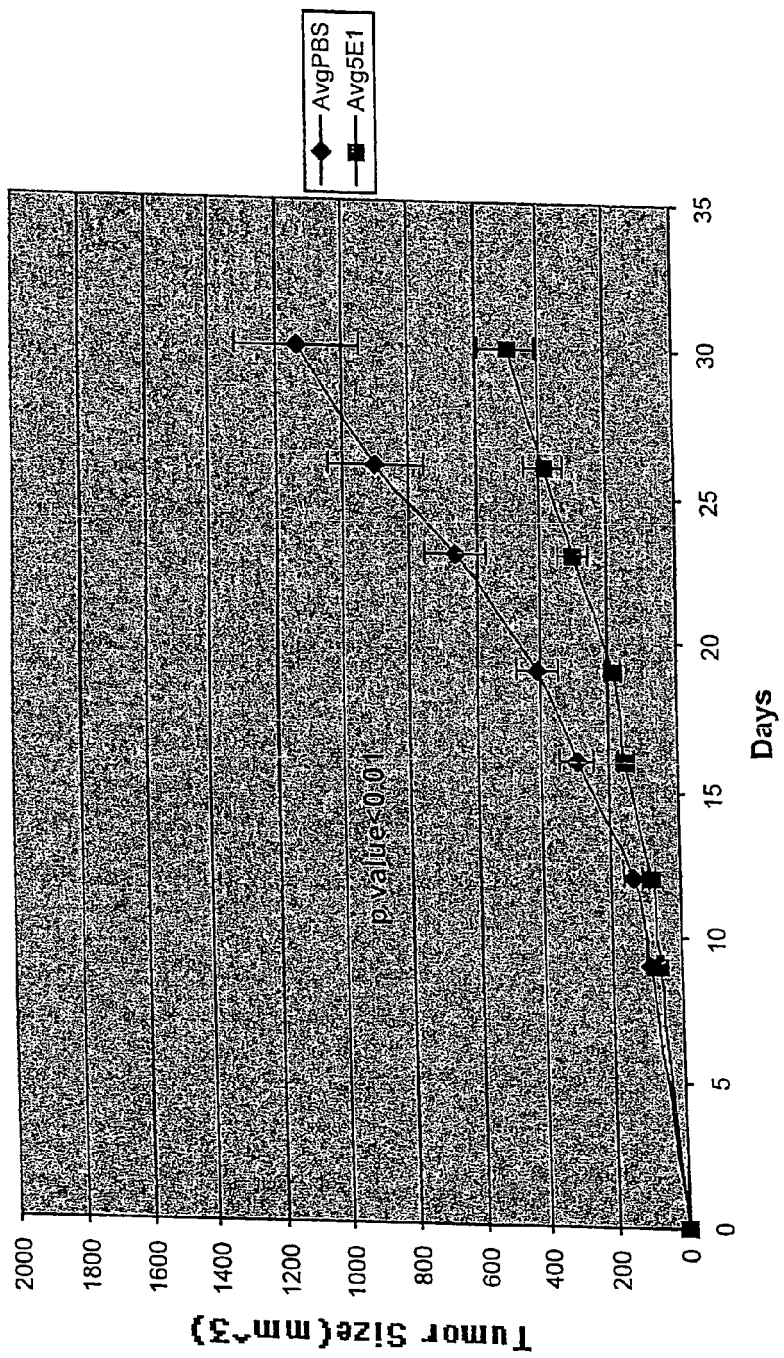
FIG. 41 shows that the Shh blocking antibody 5E1 decreases tumor size when administered to mice injected with a combination of the Shh expressing colon cancer cell line HT-29 and fibroblasts.
Figure 42:
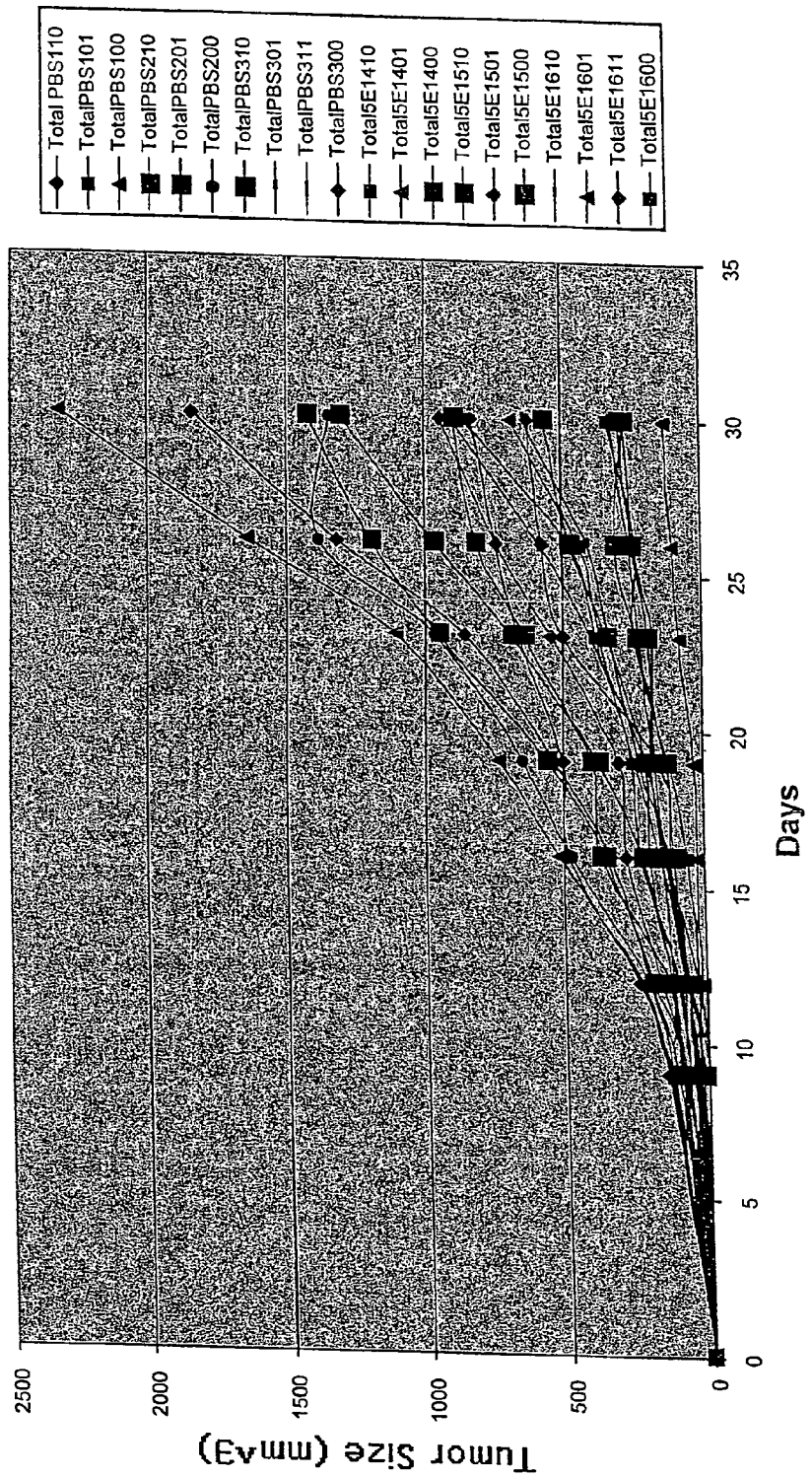
FIG. 42 shows that the Shh blocking antibody 5E1 decreases tumor size when administered to mice injected with a combination of the Shh expressing colon cancer cell line HT-29 and fibroblasts.

To help address this model, the ability of the antagonistic hedgehog antibody 5E1 to inhibit tumor growth in mice injected with a combination of hedgehog expressing colon cancer cells and fibroblasts was investigated. Two experiments were performed to assess the effects of 5E1 treatment on tumor size in mice injected with hedgehog expressing colon cancer cells. In the first experiment, treatment with 5E1, or PBS control, was initiated on the same day as injection with the tumor cells. The results are summarized in FIGS. 41 and 42, and demonstrate that treatment with 5E1 significantly decreases tumor size, weight, and rate of growth in comparison to that of mice treated with PBS (FIGS. 41 and 42). The experiment was performed using two separate colon cancer cell lines with similar affects.

Figure 43:
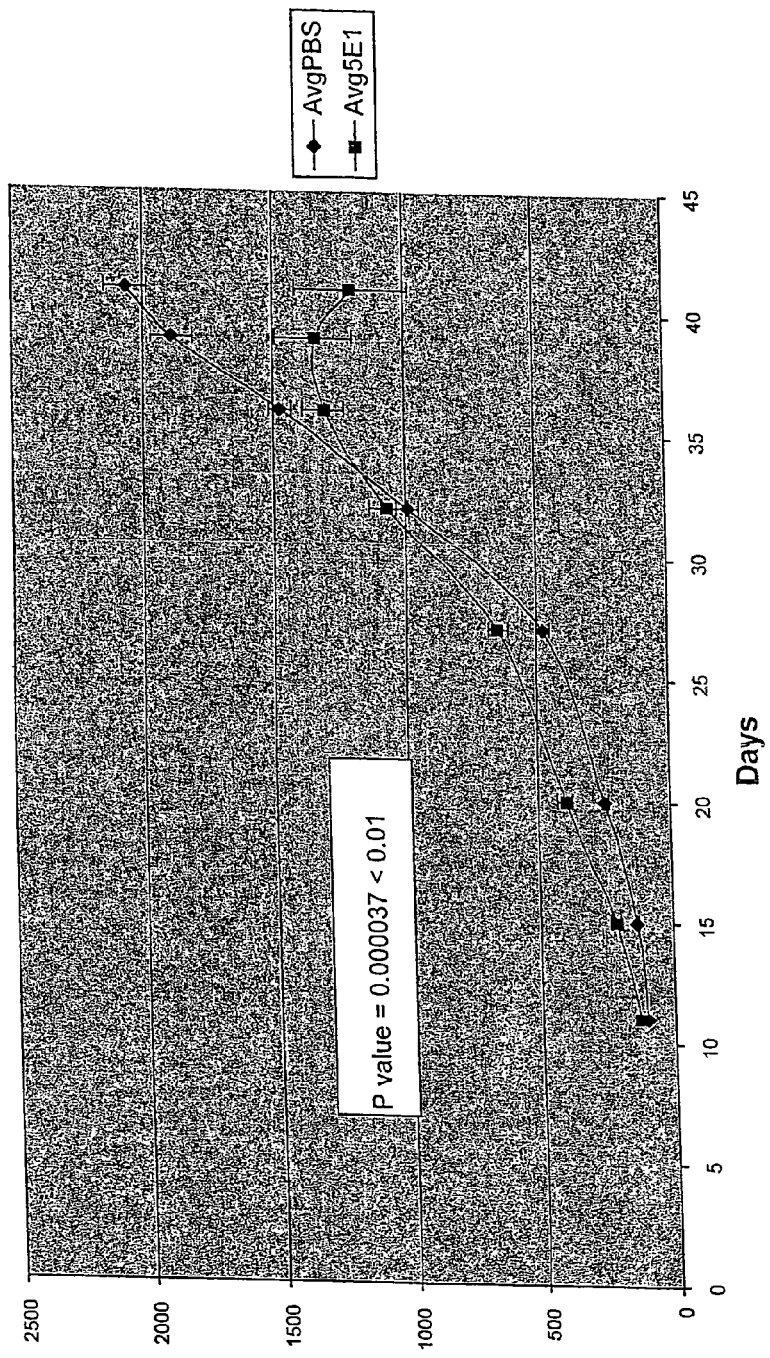
FIG. 43 shows that delayed administration of the Shh blocking antibody 5E1 decreases tumor size when administered to mice injected with a combination of the Shh expressing colon cancer cell line HT-29 and fibroblasts.
Figure 44:
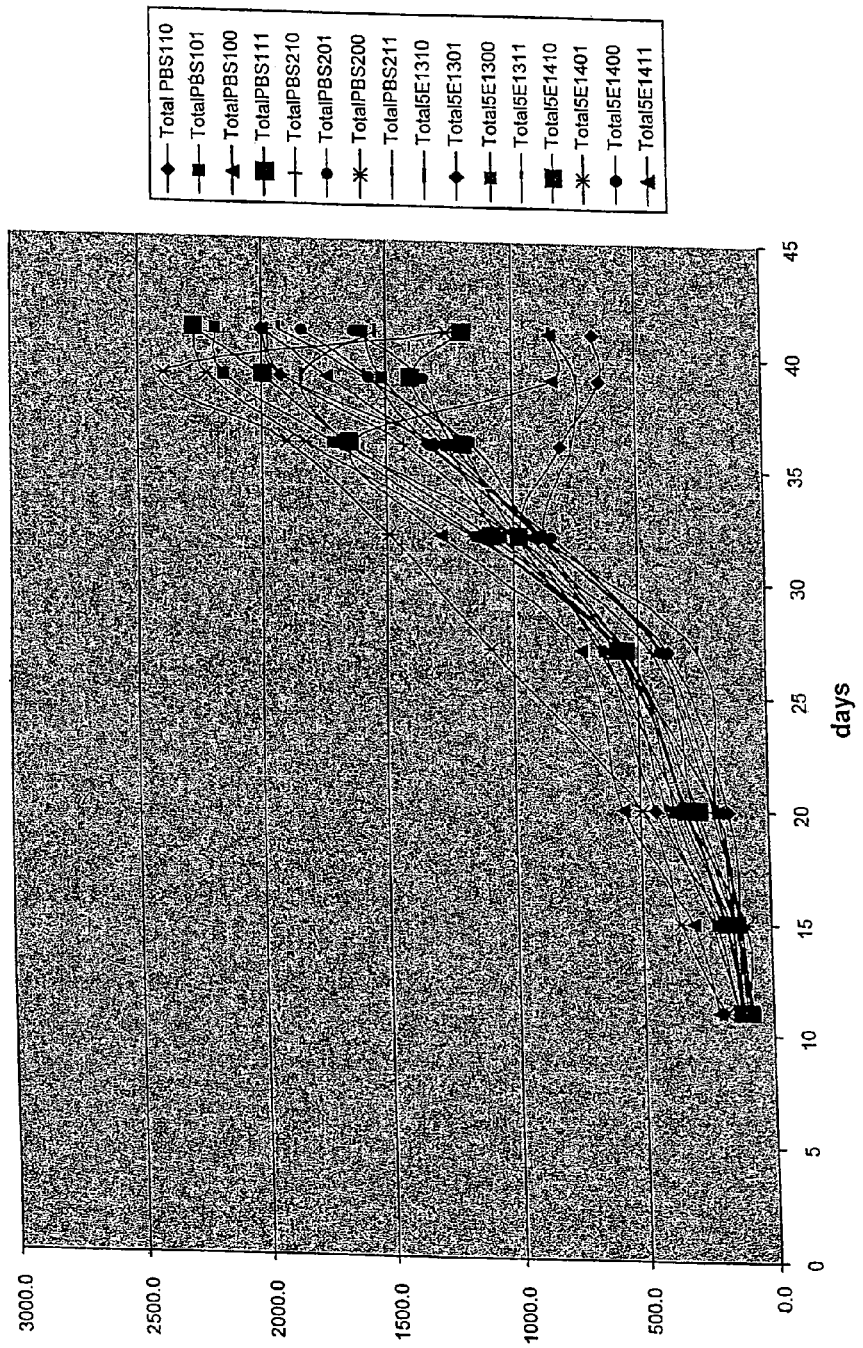
FIG. 44 shows that delayed administration of the Shh blocking antibody 5E1 decreases tumor size when administered to mice injected with a combination of the Shh expressing colon cancer cell line HT-29 and fibroblasts.

In the second experiment, treatment with 5E1 was delayed until the eleventh day of tumor growth. The results are summarized in FIGS. 43 and 44, and demonstrate that treatment with 5E1 significantly decreases the size and rate of growth of the tumor when compared to control mice (FIGS. 43 and 44). The experiment was performed using two separate colon cancer cell lines with similar affects.

Figure 45:
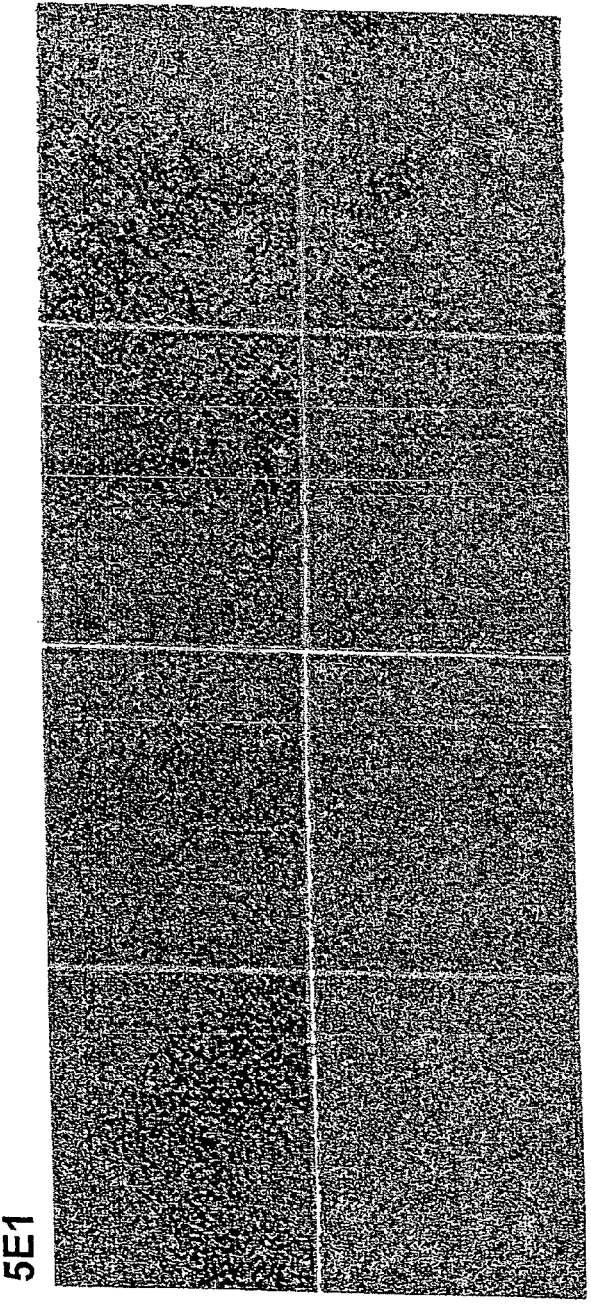
FIG. 45 shows that administration of the Shh blocking antibody 5E1 induces apoptosis in HT-29/fibroblast mixed tumors.

To further understand the mechanism by which administration of a hedgehog antagonist inhibits the growth of tumors in vivo, TUNEL analysis was performed on mixed tumors treated with either 5E1 or with the PBS control. FIG. 45 demonstrates that at least a portion of the cells in the HT-29/fibroblast mixed tumor die apoptotically following administration of the hedgehog antagonist 5E1. This result demonstrates that treatment of these hyperproliferative cells with a hedgehog antagonist inhibits the proliferation, growth and survival of the mixed tumor cells in vivo, and that at least some of this effect is due to the apoptotic death of cells in the mixed tumor following treatment.

These results demonstrate the utility of hedgehog antagonists in the inhibition of proliferation and growth of cancer cells. Additionally, this model provides an in vivo method for easily evaluating the efficacy of candidate hedgehog antagonists.

METHODS: Experiment 1. Twenty nude mice were injected subcutaneously with a combination of $10^6$ HT-29 cells (a Shh expressing colon cancer cell line) and $10^6$ 10T ½ cells (a fibroblast cell line) in a volume of 100 µl. The mice were randomized into two groups. Group A was treated with PBS, and group B was treated with 5E1. The treatments were initiated on the same day as injection of the tumor cells. Treatment was administered IP, 3 times/week over a period of thirty days, and at a dose of 6 mg/kg. Additionally, this experiment was carried out under an identical protocol using another Shh expressing colon cancer cell line (Colo205) with similar results.

Experiment 2—delayed administration. Twenty nude mice were injected subcutaneously with a combination of $10^6$ HT-29 cells (a Shh expressing colon cancer cell line) and $10^6$ 10T ½ cells (a fibroblast cell line) in a volume of 100 µl. The mice were randomized into two groups. Group A was treated with PBS, and group B was treated with 5E1. Treatment was initiated after the tumor had grown to day 11. Such tumors had a volume of approximately 90-210 mm$^3$. Treatment was administered IP, 3 times/week over a period of twenty-nine days (until day 40 of total tumor growth), and at a dose of 6 mg/kg. Additionally, this experiment was carried out under an identical protocol using another Shh expressing colon cancer cell line (Colo205) with similar results.

Model II

Figure 46:
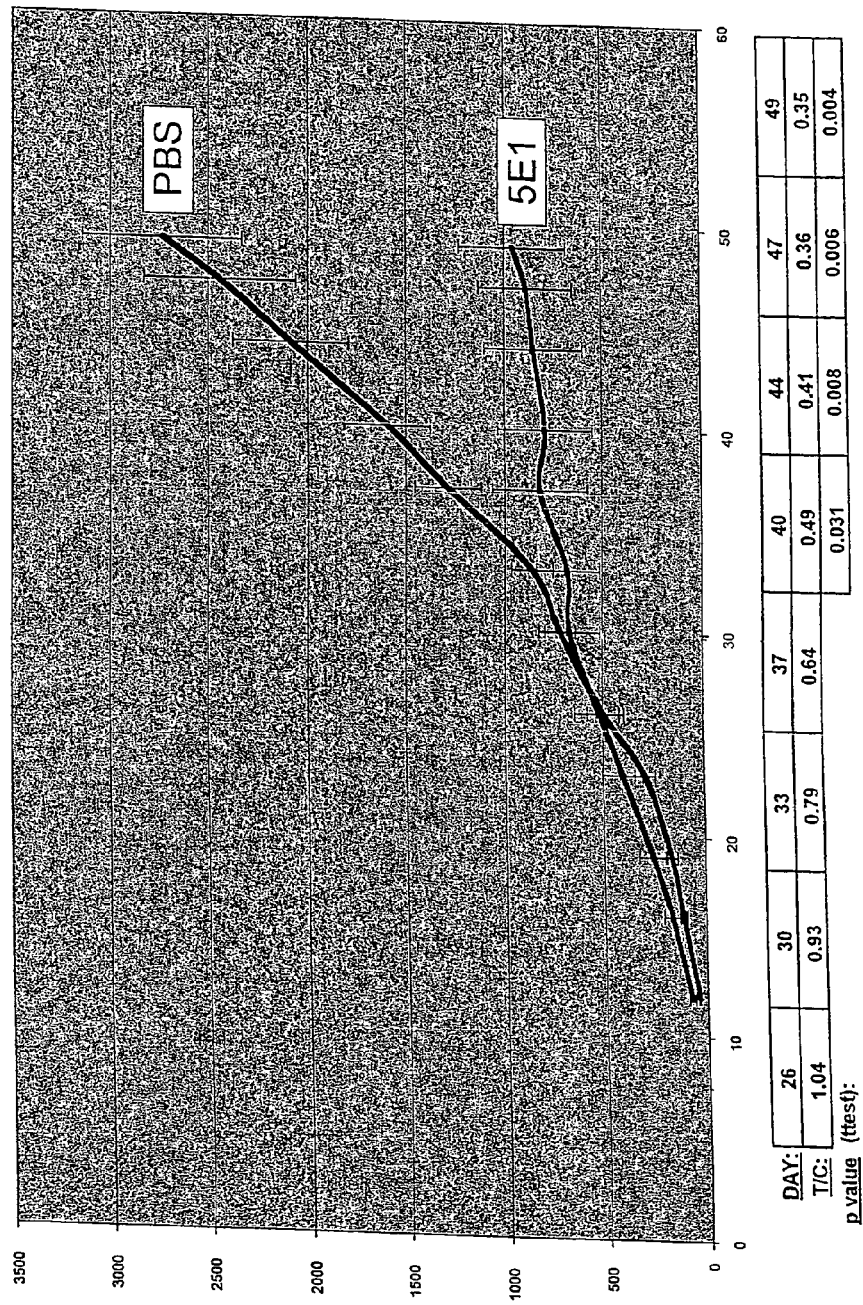
FIG. 46 shows that delayed administration of the Shh blocking antibody 5E1 decreases tumor size when administered to mice injected with the Shh expressing colon cancer cell line HT-29.
Figure 47:
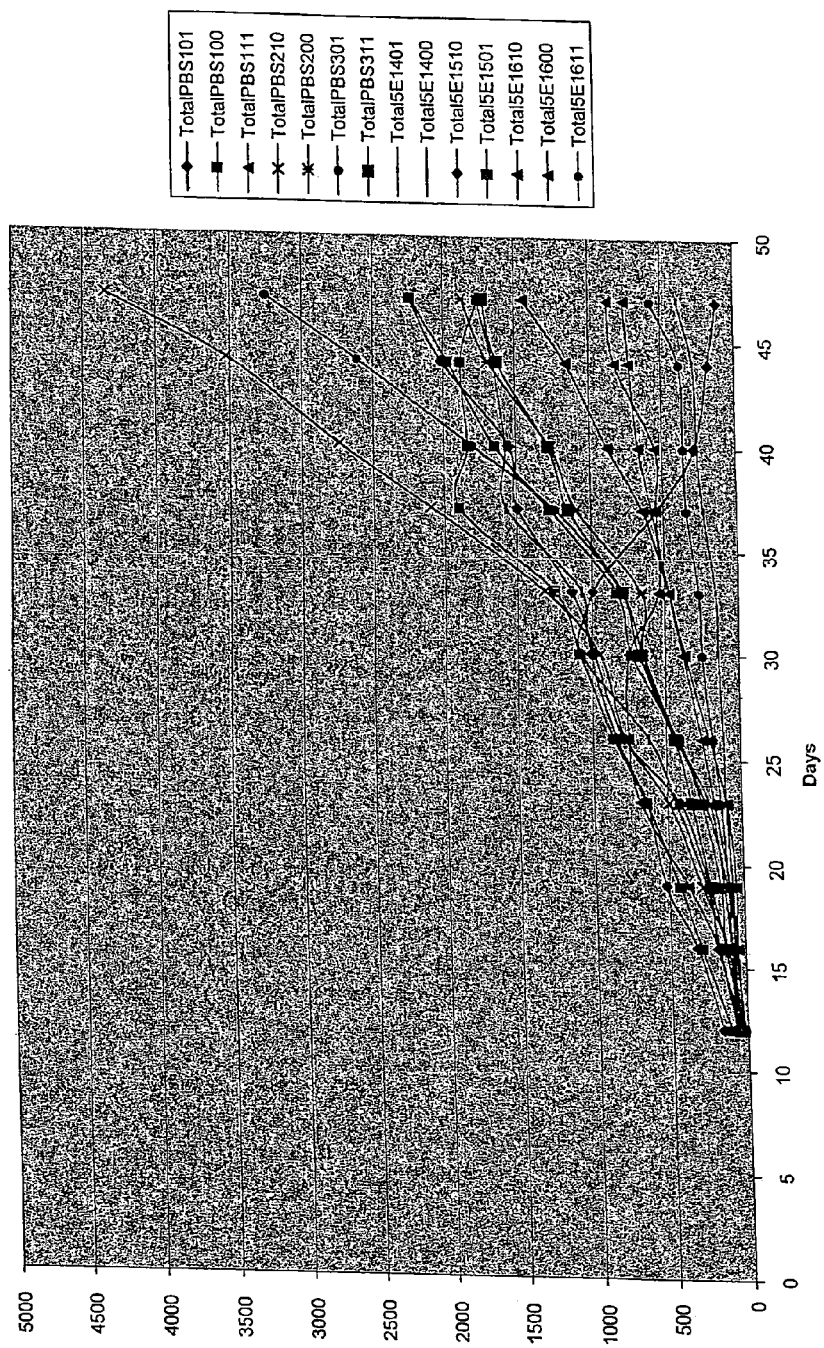
FIG. 47 shows that delayed administration of the Shh blocking antibody 5E1 decreases tumor size when administered to mice injected with the Shh expressing colon cancer cell line HT-29.
Figure 48:
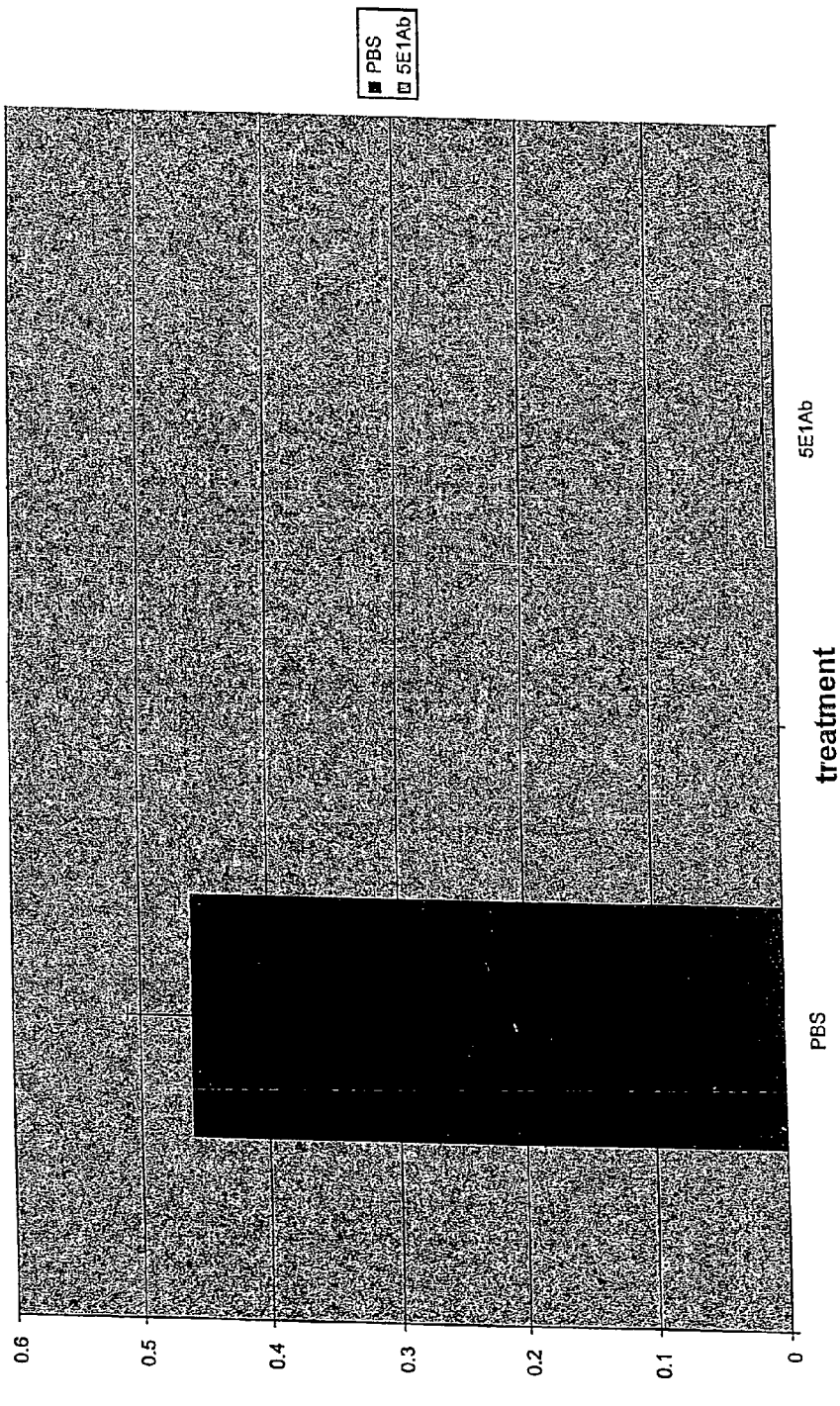
FIG. 48 shows that delayed administration of the Shh blocking antibody 5E1 to mice injected with the Shh expressing colon cancer cell line HT-29 decreases expression of gli-1 mRNA.

Similar experiments were conducted to assess the efficacy of a hedgehog antagonist in decreasing the growth, proliferation and survival of tumors derived from the transplantation of HT-29 cells alone. Hedgehog expressing HT-29 colon cancer cells were injected subcutaneously into nude mice as described in detail above. FIGS. 46 and 47 show that delayed administration of the hedgehog antagonist, 5E1, significantly reduces the growth of such tumors in vivo when compared to tumors treated with the PBS control. Consistent with these results, treatment with 5E1 also significantly reduces the expression of gli-1 in these tumors when compared to tumors treated with the PBS control (FIG. 48).

The results obtained using the two in vivo models described in detail above demonstrate that the antagonism of hedgehog signaling can significantly inhibit the growth, proliferation, and survival of hedgehog expressing tumors.

METHODS: Nude mice were injected subcutaneously with $10^6$ HT-29 cells (a Shh expressing colon cancer cell line) in a volume of 100 µl. The mice were randomized into two groups. Group A was treated with PBS, and group B was treated with 5E1. Treatment was initiated after the tumor had grown to day 11. Treatment was administered IP, 3 times/week over a period of fifty days, and at a dose of 6 mg/kg. Tumor volumes were measured over time. Additionally, expression of gli-1 mRNA was analyzed by Q-RT-PCR in PBS treated versus 5E1 treated tumors.

Example 8

Antagonism of Hedgehog Signaling in Pancreatic Cancer

We had previously demonstrated that hedgehog mRNA and protein are expressed in several pancreatic cancer cell lines, as well as in primary human pancreatic tissue samples. Given the existence of hedgehog expressing pancreatic cancer cell lines, we examined the ability of antagonism of hedgehog signaling to decrease growth, proliferation, and survival of pancreatic cancel cells in xenografts in nude mice. Similar to the results observed with xenografts of hedgehog expressing bladder, prostate and colon cancer cell lines, administration of a hedgehog antagonist decrease the size and survival of tumors generated by xenografts of hedgehog expressing pancreatic cancer cells.

SW1990 Xenograft

SW-1990 is a hedgehog expressing pancreatic ductal adenocarcinoma cell line. To assess the potential efficacy of administration of hedgehog antagonists to treat pancreatic tumors, tumors were generated in nude mice by subcutaneous injection of SW-1990 cells. In these experiments, SW-1990 cells were injected in the absence of fibroblasts. Animals that received the SW-1990 cells were divided into two groups, and immediately began receiving treatment with either the hedgehog blocking antibody 5E1 or PBS. Animals receiving 5E1 received a dose of 2 mg/kg, intravenously, once per week.

The effects of treatment with the hedgehog antagonist 5E1 were evaluated by measuring tumor volume and weight, as well as by visual inspection of the tumors. Interestingly, tumor volume was variable due to inflammation, and thus visual analysis and tumor weight appear to be a more accurate measure of the effects of hedgehog antagonism on these tumors.

Figure 49:
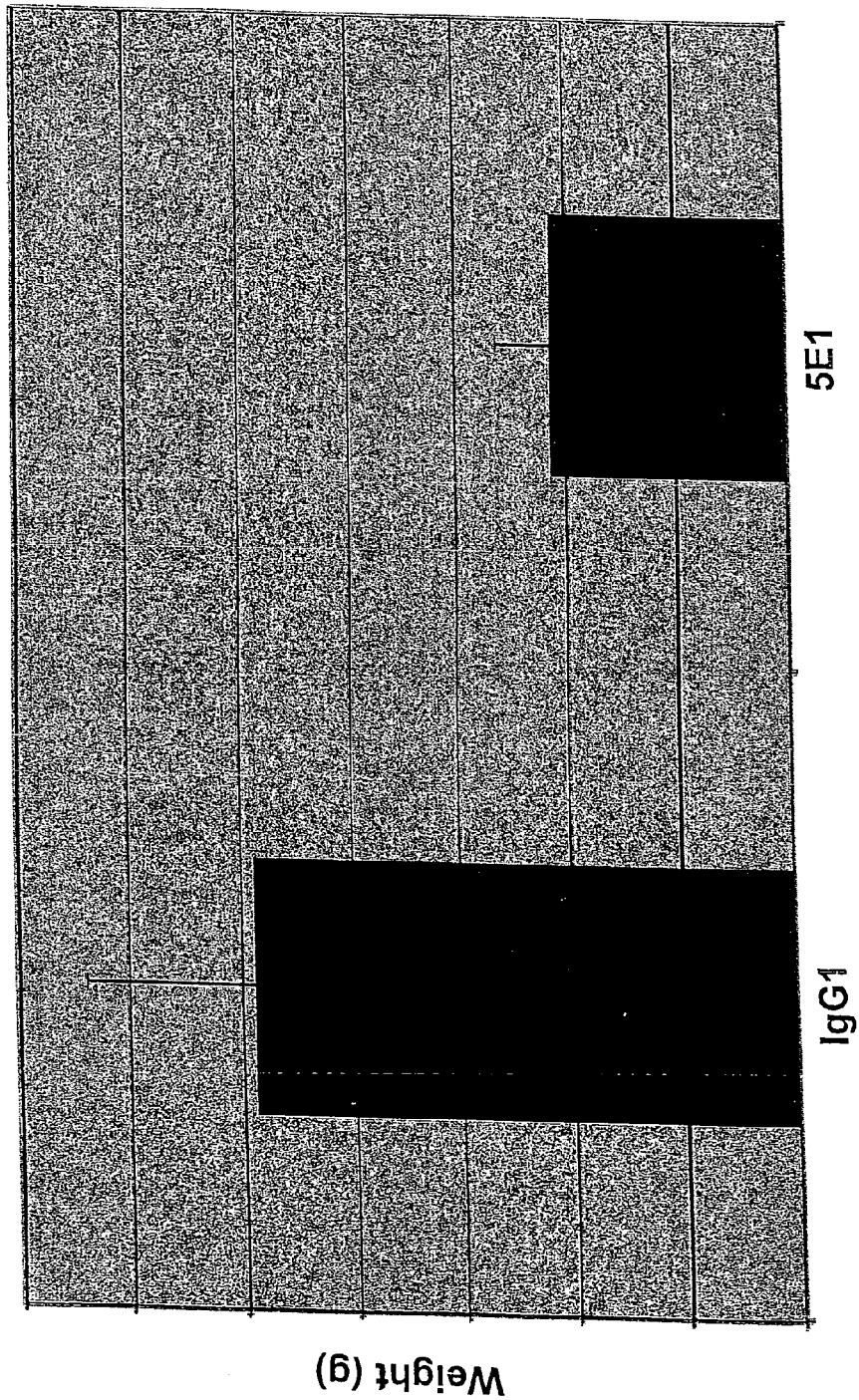
FIG. 49 shows that administration of the Shh blocking antibody 5E1 to mice injected with the hedgehog expressing pancreatic cancer cell line SW1990 decreases tumor weight.
Figure 50:
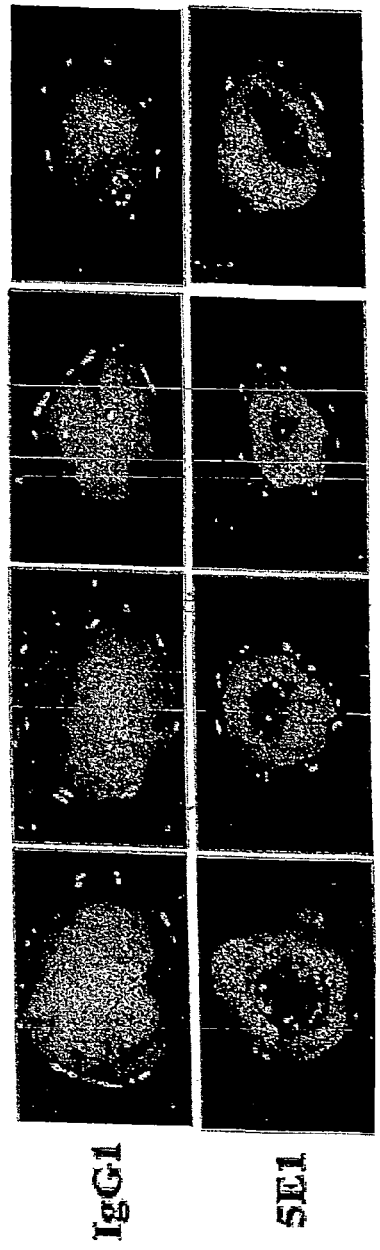
FIG. 50 shows that administration of the Shh blocking antibody 5E1 to mice injected with the hedgehog expressing pancreatic cancer cell line SW1990 decreases tumor size, and results in extensive domains of necrosis within said tumors.
Figure 51:
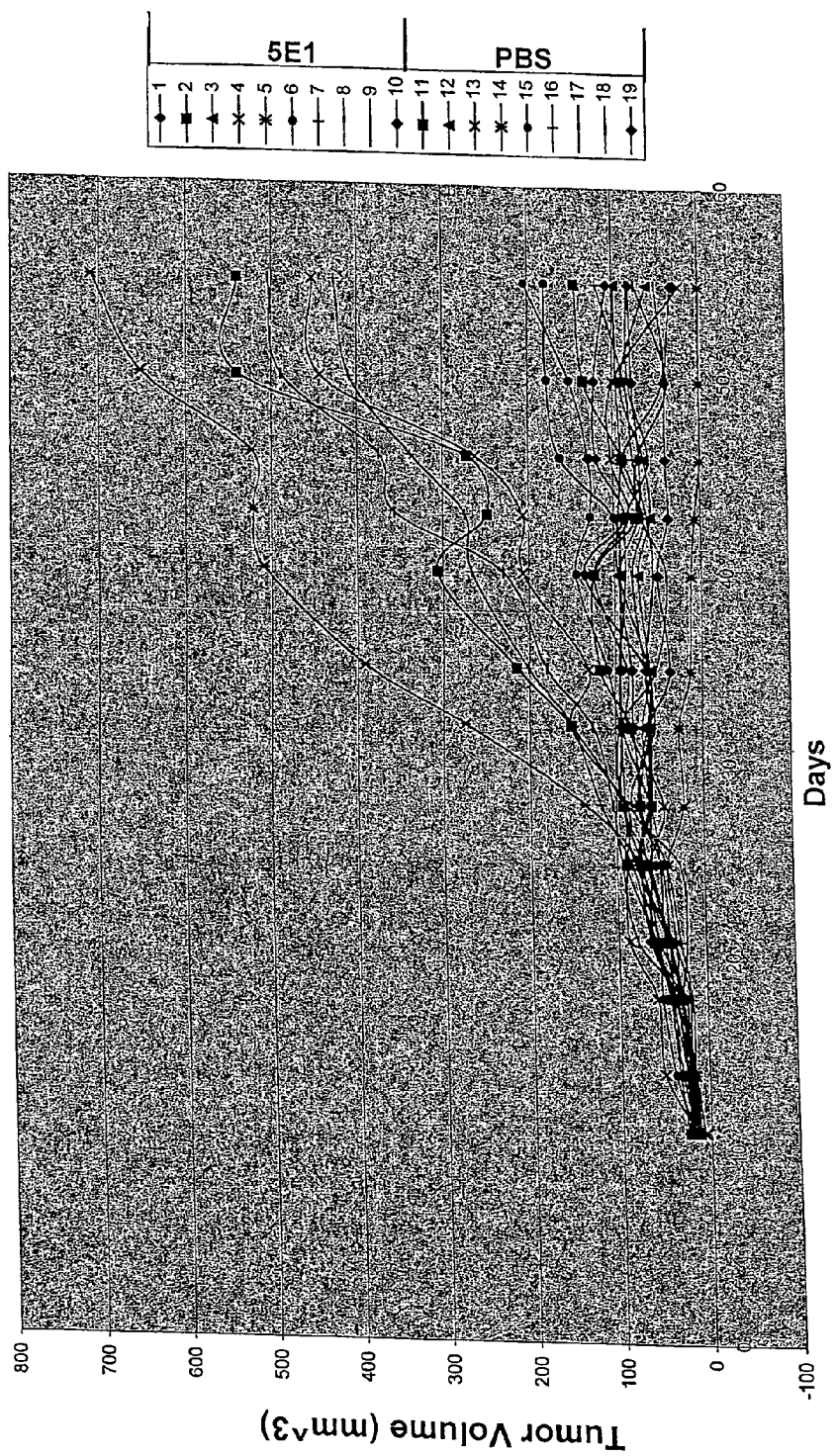
FIG. 51 shows that administration of the Shh blocking antibody 5E1 to mice injected with the hedgehog expressing pancreatic cancer cell line SW1990 decreases tumor volume.

FIG. 49 demonstrates that administration of the blocking antibody 5E1 results in a significant decrease in the weigh of SW1990 xenograft tumors. The effects of 5E1 treatment are most dramatically related through visual inspection of the tumors. FIG. 50 shows that 5E1 treated tumors are smaller than control tumors, and that the 5E1 treated tumors contain extensive regions of necrosis. Although volume of SW1990 xenograft tumors was variable, owing to inflammation, FIG. 51 indicates the overall trend of decreased volume of xenograft tumors following administration of the hedgehog antagonist 5E1.

CF PAC Xenograft

To further confirm the results demonstrating that inhibition of hedgehog signaling has efficacy in inhibiting growth, proliferation and survival of hedgehog expressing pancreatic tumors, similar experiments were conducted with another hedgehog expressing pancreatic tumor cell line, CF PAC. Like SW1990, CF PAC is a hedgehog expressing pancreatic ductal adenocarcinoma cell line. Experiments were performed using similar methods for generating SW1990 xenografts, and for testing the efficacy of the hedgehog antagonist 5E1 in said xenografts. The only difference in the two experiments is that 5E1 treatment was delayed until approximately 11 days following administration of CF-PAC cells The effects of treatment with the hedgehog antagonist 5E1 were evaluated by measuring tumor volume and weight. Interestingly, tumor volume was variable due to inflammation, and thus visual analysis and tumor weight appear to be a more accurate measure of the effects of hedgehog antagonism on these tumors.

Figure 52:
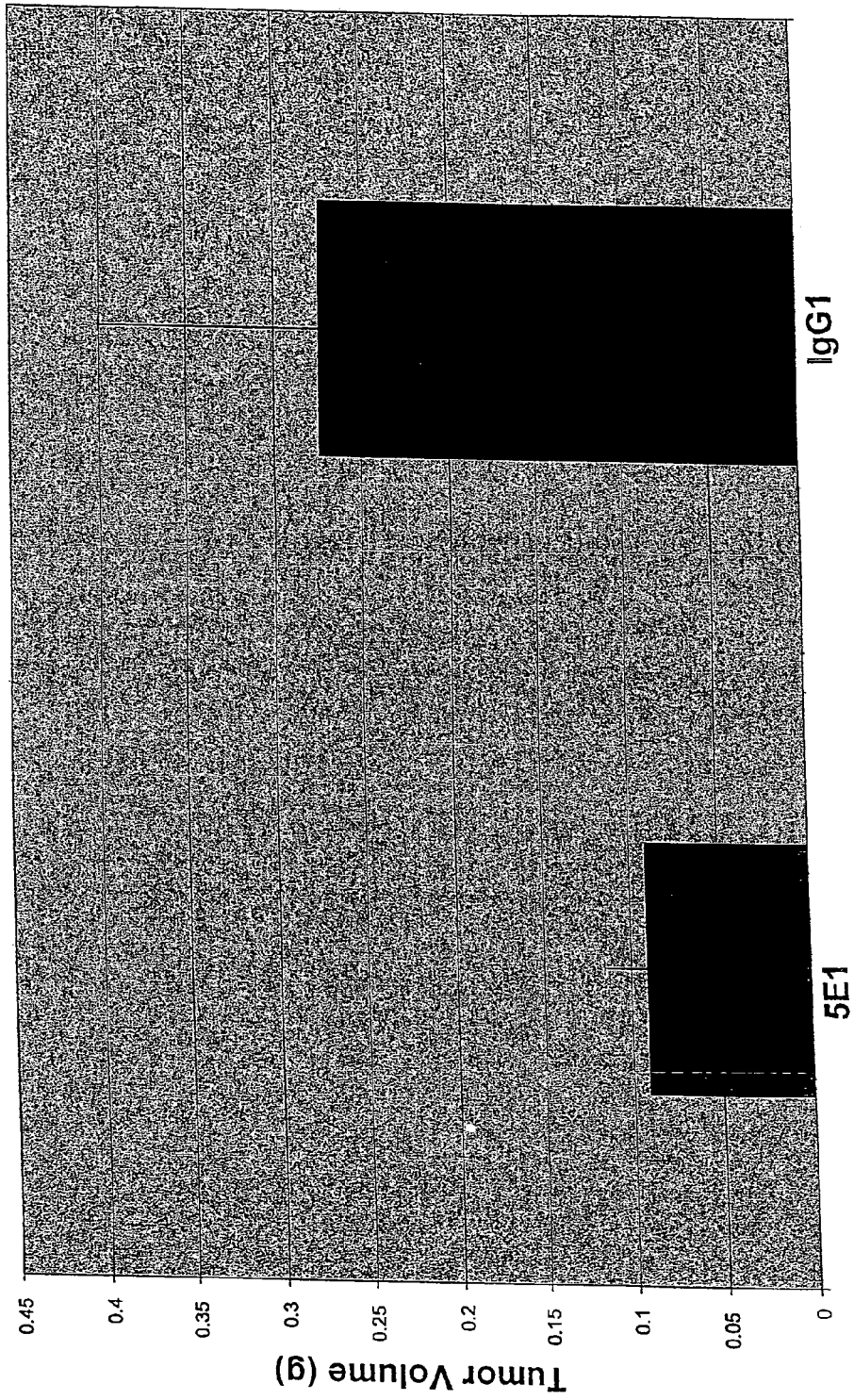
FIG. 52 shows that administration of the Shh blocking antibody 5E1 to mice injected with the hedgehog expressing pancreatic cancer cell line CF PAC decreases tumor weight.
Figure 53:
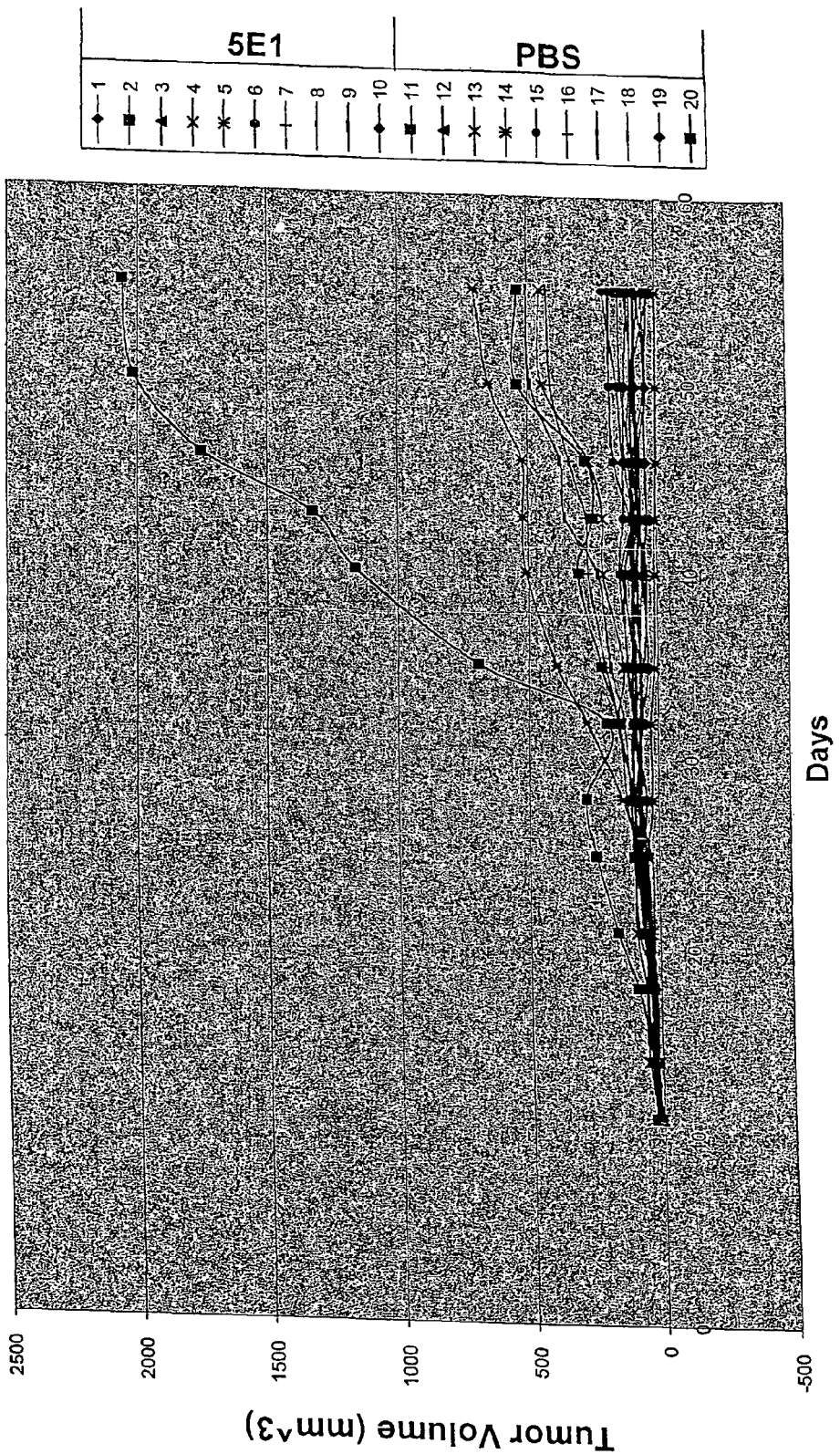
FIG. 53 shows that administration of the Shh blocking antibody 5E1 to mice injected with the hedgehog expressing pancreatic cancer cell line CF PAC decreases tumor volume.

FIG. 52 demonstrates that administration of the blocking antibody 5E1 results in a significant decrease in the weight of CF PAC xenograft tumors. Although the volume of CF PAC xenograft tumors was variable, owing to inflammation, FIG. 53 indicates the overall trend of decreased volume of xenograft tumors following administration of the hedgehog antagonist 5E1.

Additional hedgehog expression in human cancers, such as human breast ductal adenocarcinoma, ovarian cancer, uterine cancer, are shown in FIG. 55.

Example 9

Non-Hedgehog Expressing Cancer Cell Line

Efficacy of antagonism of hedgehog signaling in regulating the growth, proliferation and survival of hyperproliferative cells was examined using a cancer cell line which does not express hedgehog. Without being bound by any particular theory, it is possible that the antagonism of hedgehog signaling is most effective in regulating cell growth, proliferation and survival in cells in which hedgehog signaling is already hyper-activated. Such cells would include, for example, cells comprising a mutation in a component of the hedgehog signaling pathway wherein the mutation results in at least one of gain-of-function of an activator of hedgehog signaling or loss-of-function of a repressor of hedgehog signaling (e.g, patched).

Figure 54:
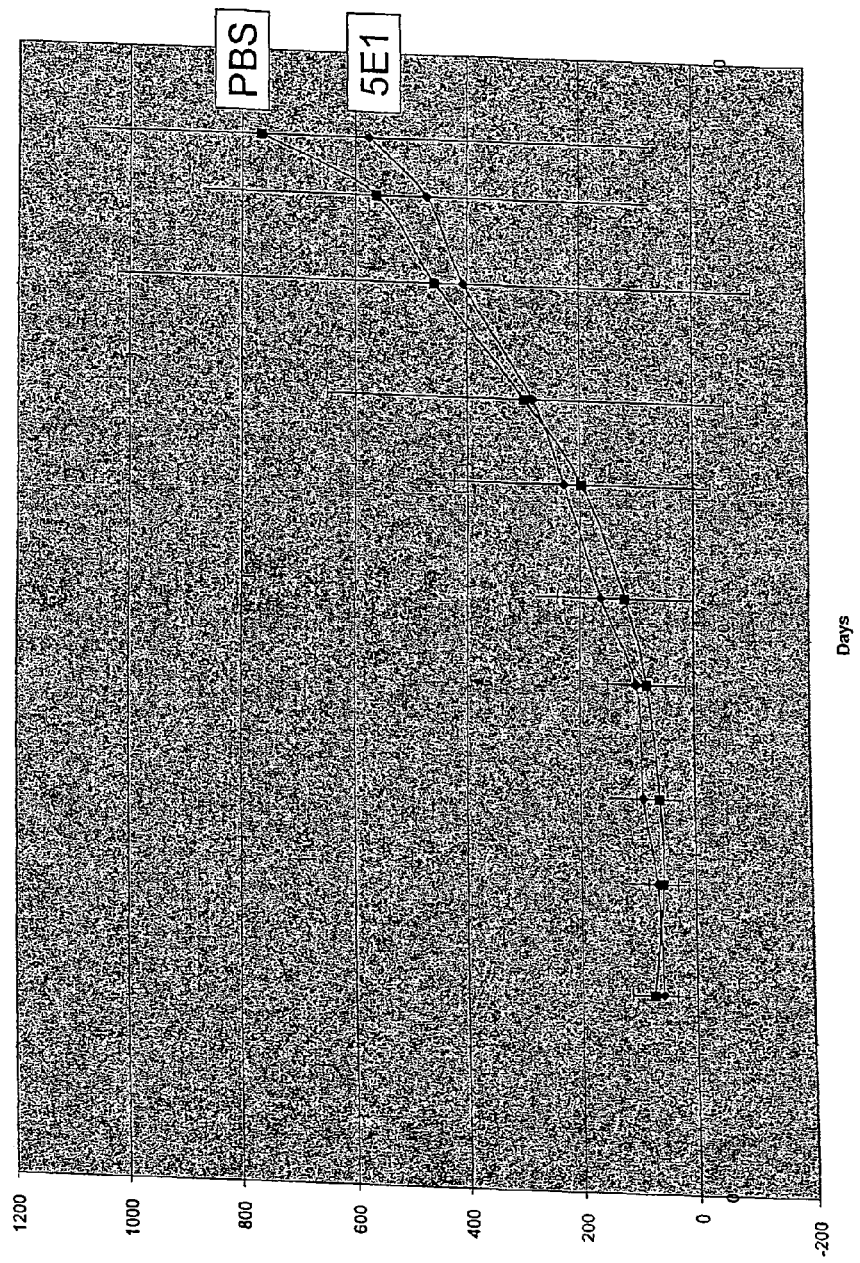
FIG. 54 shows that administration of the Shh blocking antibody 5E1 to mice injected with the non-hedgehog expressing colon cancer cell line SW480 has no effect on tumor volume.

SW-480 is a colon adenocarcinoma cell line which does not express hedgehog. SW-480 cells were administered subcutaneously to nude mice to generate xenografts, as previously described. Approximately seven days after administration of the SW-480 cells, treatment with either 5E1 or PBS control was initiated (delayed administration). In 5E1 treated animals, administration was at a dose of 2 mg/kg, intravenously, once per week. Tumor volumes were measured regularly throughout treatment. FIG. 54 demonstrates that administration of 5E1 appears to have no effect on tumor volume in SW-480 xenografts.

The results of these experiments further underscore that unregulated hedgehog signaling can result in hyper-proliferation and/or inappropriate cell survival. These results demonstrate the utility of inhibition of inappropriate hedgehog signaling as a method of inhibiting inappropriate cell proliferation, growth and survival. Examples of conditions which can be treated by these methods include, but are not limited to, various forms of cancer.

Additionally, the observation that hedgehog antagonism is most effective in regulating cell proliferation, growth and survival in cells which express hedgehog, or cells in which the hedgehog signaling pathway is hyperactivated, suggest diagnostic methods for predicting which conditions and which patients (e.g., which forms of cancer) are most likely to respond to treatment regimens which include a hedgehog antagonist.

Example 10

Screens for RNAi Inhibitors of HH Signaling Components

The foregoing examples present both in vitro and in vivo models for examining the effects of hedgehog RNAi antagonist on cell proliferation. The models provide assays for testing a range of RNAi antagonists for the ability to inhibit cell growth and proliferation. Such screens can be used in initial assays to identify lead RNAi constructs, and can also be used to evaluate the relative efficacies of candidate RNAi antagonists.

RNAi antagonistic agents that can be analyzed in this way may interfere with hedgehog signaling at any point(s) along the signal transduction pathway. For example, preferred RNAi antagonists may interact with hedgehog, patched-1, or smoothened, alone or in combination. Additional preferred agents may interact with an intracellular component of the hedgehog pathway including gli-1, gli-2, or gli-3.

The in vitro and in vivo methods described above are not specific for the cancer cell lines explicitly described herein. Any cell type or cell line could be similarly tested, and these methods could be easily used to assess the ability of hedgehog RNAi antagonists to inhibit tumor growth and proliferation in other types of cancer cells. Additionally, the in vitro assay could be employed to analyze hedgehog signaling and the ability of hedgehog RNAi antagonists to block hedgehog signaling in other non-cancerous hyperproliferative cell types. For example, hyperproliferative conditions include many other classes of disorders including skin maladies such as psoriasis. The effects of candidate hedgehog RNAi antagonists on these cell types can be easily assessed using the methods described here.

Example 11 siRNA Inhibition of Shh Expression in Cancer Cell Lines

The following experiments demonstrates the effectiveness and specificity of certain siRNA constructs, such as short haripin siRNA (sh siRNA) transcribed off plasmids transfected into target cells.

Five potential siRNA antagonists of the human Shh were designed according to the teaching of the instant specification, and three of the five pairs were selected for initial testing. Specifically, for each of the three selected siRNA antagonist, two 21-base polyribonucleotide (RNA) oligoes were ordered and synthesized as 5'-phosphorylated, de-salted, de-protected pairs of RNA oligoes (Dharmacon Research, Inc., Lafayette, Colo.). The sequences for the three oligo pairs are:

```
                                      (SEQ ID NO: 5)
1 sense:       5'-P cga gau guc ugc ugc uag ucc (SEQ ID NO: 6)
1 antisense:   5'-P acu agc agc aga cau cuc gcc (SEQ ID NO: 7)
4 sense:       5'-P cag agu agc ccu aac cgc ucc (SEQ ID NO: 8)
4 antisense:   5'-P agc ggu uag ggc uac ucu gcc (SEQ ID NO: 9)
5 sense:       5'-P cgg uca agu cca gcu gaa gcc (SEQ ID NO: 10)
5 antisense:   5'-P cuu cag cug gac uug acc gcc
```

The RNA oligoes were then dissolved in 10 mM Tris-HCl (pH 8.0) to a final concentration of 100 μM. For each siRNA antagonist, 10 μL of each of the two RNA oligoes were then mixed and annealed very slowly using a PCR block in ABI 7700 PCR machine.

Figure 2:
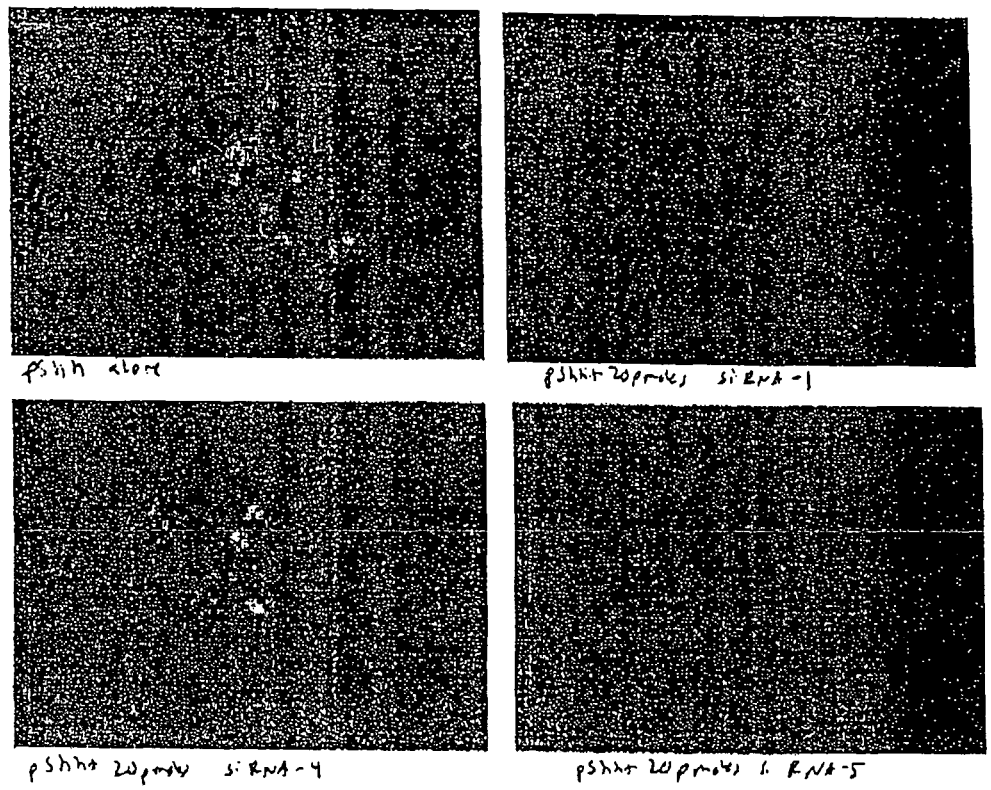
FIG. 2 shows short hairpin siRNA antagonists against human Shh inhibits Shh expression in HEK-293 cells.

To test the effectiveness of the three siRNA antagonists, a confluent plate of HEK-293 cells were splited 1:3 and plated onto a 24-well tissue culture plate. The final density of cells was about 14,000 cells/well. Lipofectamine infection was carried out according to manufacturer's instruction. Specifically, 0.4 μg phShh$^{FL}$ (a human Shh-encoding plasmid "pcDNA3.1-hShh") and either 0, 20, 100, or 500 pmole of each annealed Shh siRNA antagonist were mixed in 25 μL of serum-free DMEM (no Pen./Strep.) with 4 μL of "Plus Reagent" for 15 minutes. At the same time, 1 μL of Lipofectamine was mixed in 25 μL of serum-free DMEM (no Pen./Strep.) with 4 μL of "Plus Reagent" for 15 minutes. At the end of the incubation, the two mixtures were combined to form complexes for 15 minutes. For each well of HEK-293 cells, the medium was changed to 200 μL of serum-free DMEM (no Pen./Strp.), and the formed complexes were then added to the respective test wells. After 3 hours of incubation at 37° C. in a 5% $CO_2$ tissue culture incubator, 250 μL of DMEM (no Pen./Strep.) with 20% FBS were added to each well. The plate of cells were then returned to the incubator. After about 68 hours of incubation, cells in each well were fixed in 4% PFA/PAS, and stained with 1:200 dilution of rabbit anti-Shh antibody and Cy3-labeled anti-rabbit secondary antibody. The results shown in FIG. 2 indicated that siRNA #1 nearly completely inhibits Shh expression in transfected cells, even at the lowest amount of siRNA (20 pmoles). The inhibitory effect of siRNA #4 is less pronounced, although it cannot be ruled out that experimental error is not the main reason why this siRNA is less effective based on a single experiment. The inhibitory effect of #5 is slightly less effective than #1. Therefore, #1 siRNA was used for future experiments.

Next, the specificity of the inhibitory effects #1 Shh siRNA antagonist was tested against two other related Hh proteins, Ihh and Dhh. Specifically, the same HEK-293 cells were splited and seeded to a final density of about 14,000 cells/well in a 24-well tissue culture plate. The same Lipofectamine transfection as described above were carried out for each of the following combinations:

0.4 μg of pcDNA3.1-hShh+0, 50, or 250 pmoles of siRNA #1;

0.4 μg of pcDNA3.1-hIhh+0, 50, or 250 pmoles of siRNA #1;

0.4 μg of pcDNA3.1-hDhh+0, 50, or 250 pmoles of siRNA #1; and, 0.4 μg of pcDNA3.1-hShh+250 pmoles of siRNA #1 reverse strand only control.

Figure 3:
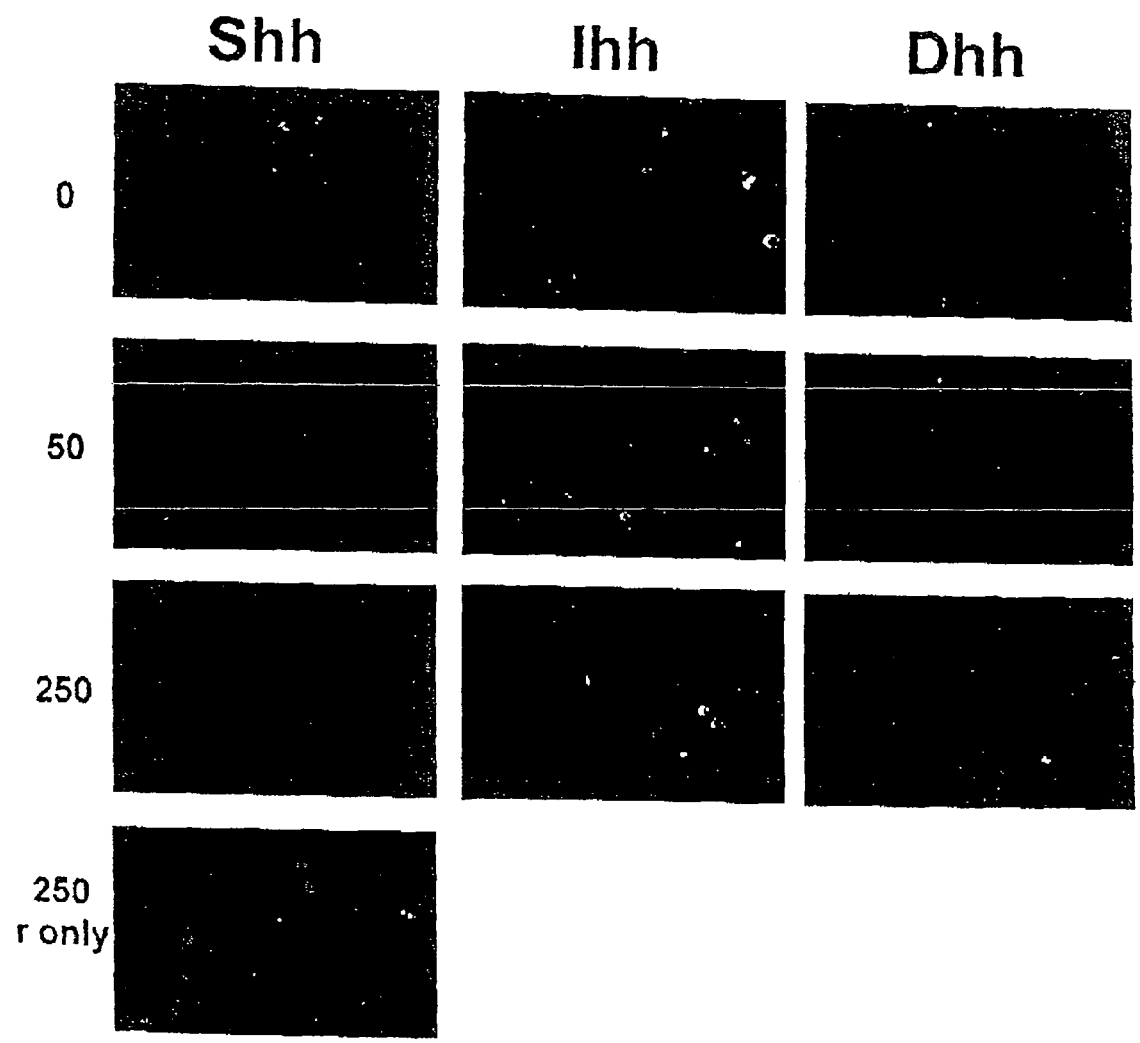
FIG. 3 shows short hairpin siRNA is specific against human Shh as compared to Ihh and Dhh.

After 2 hours of incubation with each of the complexes, the medium in each transfection well was replaced with 1 mL of fresh DMEM (no Pen./Strep.)+10% FBS, for the purpose of getting healthier cells at the end of the experiment. After 2 more days of incubation, all cells were fixed as described above, and stained with H-160 pan-Hh rabbit polyclonal antibody (Cat. No. sc-9024, Santa Cruz Biotechnology, CA) and Cy3-labeled anti-rabbit secondary antibody. The results shown in FIG. 3 indicated that #1 siRNA for Shh is very specific for Shh, and did not obviously inhibit Ihh or Dhh expression. The experiment also confirms that 50 pmoles of

1 siRNA almost completely inhibited expression of human Shh. In addition, the negative control, 250 pmoles of reverse-strand-only #1 siRNA was completely ineffective under the same conditions.

To confirm the reduced Hh mRNA transcription in transfected cells, HEK-293 cells were transfected in 6-well tissue culture plates (final seeding density about 100,000 cells/well) using similar methods as described above (result not shown).

The siRNA antagonist sequence selected by the methods above can then be used to derive a short hairpin siRNA sequence, which can then be cloned into a plasmid vector. The plasmid can be stably transfected into a host cell to establish a stable cell line. The established stable cell line may constitutively or inducibly express siRNA for human Shh, or any other HH signaling components. These stable cell lines are very useful for a number of purposes. For example, if the stable cell line is based on a well-established cancer cell line such as HT-29, they can be used to study the effects of attenuating HH signaling on cancer cell growth. They are also useful for in vitro studies, such as expression profiling in co-culture with HH-responsive fibroblasts to understand paracrine signaling via HH in cancer. The stable cell lines can also be used to evaluate efficiency of other HH inhibitors, such as the 5E1 antibody, in xenograph animal models using these stable lines.

One such plasmid with a derived short hairpin sequence of the #1 siRNA of human Shh was constructed, and used to stably transfect HEK-293 cells.

Briefly, based on the #1 siRNA sequence of human Shh, the following short hairpin oligoes were designed:

```
#1 top strand:      5'-P cga gat gtc tgc tgc tag
                    t ttc aag aga act agc agc aga
                    cat ctc g TTTT g;
(SEQ ID NO: 11)
```

```
#1 bottom strand:   5'-P gat cca aaa acg aga tgt
                    ctg ctg cta gtt ctc ttg aaa
                    cta gca gca gac atc tcg
(SEQ ID NO: 12)
```

The oligoes were dissolved in TE as 100 μM stock. These two oligoes were then mixed in a 1:1 ratio to make 50 μL of 10 μM stock, which was heated to 100° C. for 5 minutes in a PCR block. The PCR block was turned off to allow temperature to drop slowly to 40° C. over the course of about 1 hour.

The annealed oligo was subcloned into the multicloning sites (between Apa I and Bam HI sites) in pcDNA3.1-U6-hygro(-) vector using standard molecular biology techniques. This type of vector expresses the insert sequence off its U6 snRNA promoter for RNA Polymerase III, and the RNA transcript starts precisely at the 5'-end "cag" of the top strand, and terminates precisely at the 3'-end TTTT sequence (Paddison, *Genes and Dev.* 16: 948-958, 2002). The resulting single strand RNA transcript forms a stem-loop structure, or short hairpin structure, with the stem of the hairpin matching the sequence of the #1 siRNA. Similar vectors with different mammalian selectable markers, such as Zeomycin and puromycin, are also available.

All publications, patents and patent applications are herein incorporated by reference in their entirety to the same extent as if each individual publication, patent or patent application was specifically and individually indicated to be incorporated by reference in its entirety.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A method of inhibiting at least one of unwanted growth, proliferation or survival of a cell, comprising contacting said cell with an effective amount of a hedgehog RNAi antagonist against a Sonic hedgehog (Shh) gene, wherein said RNAi antagonist comprises a sequence that is at least 90% identical to a nucleic acid sequence set forth in any of SEQ ID NOs: 5, 6, 9, or 10, wherein said RNAi antagonist is 19-30 nucleotides in length, wherein contacting said cell with said hedgehog RNAi antagonist decreases at least one of cell growth, proliferation or survival, wherein said cell is a cancer cell, and wherein said cancer cell is a colon cancer cell.

2. The method of claim 1, further comprising determining whether said cell expresses a gli gene, and contacting said cell which expresses a gli gene with an effective amount of the hedgehog RNAi antagonist against the Shh gene.

3. The method of claim 2, wherein said gli gene is gli-1.

4. The method of claim 1, wherein the RNAi antagonist is an siRNA antagonist.

5. The method of claim 4, wherein said siRNA antagonist is an siRNA formed after transcription from a plasmid (RNAi expression vector) or exogenous synthesis.

6. The method of claim 5, wherein said siRNA is a short hairpin siRNA formed after transcription from a single promoter of said plasmid (RNAi expression vector).

7. The method of claim 5, wherein said siRNA is a short dsRNA formed after transcription from two flanking convergent promoters on said plasmid (RNAi expression vector).

8. The method of claim 4, wherein said siRNA is 21-23 nucleotides in length.

9. The method of claim 4, wherein said siRNA is a fragment generated by nuclease dicing of longer double-stranded RNAs at least 25, 50, 100, 200, 300, 400, or 400-800 bases in length.

10. The method of claim 4, wherein said siRNA is double stranded, and includes short overhang(s) at one or both ends.

11. The method of claim 10, wherein said short overhang is 1-6 nucleotides in length at the 3' end, 2 to 4 nucleotides in length at the 3' end, or 1-3 nucleotides in length at the 3' end.

12. The method of claim 11, wherein one strand of said siRNA has a 3' overhang, and the other strand is blunt-ended, or also has an overhang of the same or different length.

13. The method of claim 10, wherein said 3' overhang is stabilized against degradation.

14. The method of claim 13, wherein said 3' overhang is stabilized against degradation by including purine nucleotides adenosine or guanosine.

15. The method of claim 13, wherein said 3' overhang is stabilized against degradation by substituting pyrimidine nucleotides by modified analogues.

16. The method of claim 4, wherein said siRNA is chemically synthesized.

17. The method of claim 1, wherein said Shh gene is human.

18. The method of claim 1, wherein said Shh gene is hyperactive in the cell.

19. A method of inhibiting at least one of unwanted growth, proliferation or survival of a cell, comprising contacting said cell with an effective amount of a hedgehog RNAi antagonist against a Sonic hedgehog (Shh) gene, wherein said RNAi antagonist comprises a sequence that is at least 90% identical to a nucleic acid sequence set forth in any of SEQ ID NOs: 5, 6, 9, or 10, wherein said RNAi antagonist is 19-30 nucleotides in length, wherein contacting said cell with said hedgehog RNAi antagonist decreases at least one of cell growth, proliferation or survival, wherein said cell is a cancer cell, wherein said cancer is selected from the group of cancers consisting of ovarian cancer, colon cancer, salivary cancer, esophageal cancer and endometrial cancer.

20. The method of claim 1, wherein the RNAi antagonist comprises the nucleic acid sequence set forth in any of SEQ ID NOs: 5, 6, 9, or 10, wherein said RNAi antagonist is 19-30 nucleotides in length.

21. The method of claim 19, wherein the RNAi antagonist comprises the nucleic acid sequence set forth in any of SEQ ID NOs: 5, 6, 9, or 10, wherein said RNAi antagonist is 19-30 nucleotides in length.

22. The method of claim 1, wherein the RNAi comprises a double stranded molecule comprising SEQ ID NO: 5 and SEQ ID NO: 6.

* * * * *